United States Patent [19]
Hirschmann et al.

[11] Patent Number: 5,552,534
[45] Date of Patent: Sep. 3, 1996

[54] NON-PEPTIDE PEPTIDOMIMETICS

[75] Inventors: Ralph F. Hirschmann, Blue Bell, Pa.; Kyriacos C. Nicolaou, LaJolla, Calif.; Sherrie Pietranico; T. R. Reisine, both of Philadelphia, Pa.; Joseph M. Salvino, Media, Pa.; Paul Sprengeler, Philadelphia, Pa.; Catherine D. Strader, Verona, N.J.

[73] Assignee: The Trustees of the University of Pennsylvania, Philadelphia, Pa.

[21] Appl. No.: 144,660

[22] Filed: Oct. 28, 1993

Related U.S. Application Data

[63] Continuation-in-part of Ser. No. 748,826, Aug. 22, 1991, abandoned.

[51] Int. Cl.$^6$ .......................... C07H 15/00; C07H 17/00
[52] U.S. Cl. ...................... 536/17.4; 536/4.1; 536/17.2; 536/17.3
[58] Field of Search .................... 536/4.1, 17.2, 536/17.3, 17.4; 514/25

[56] References Cited

U.S. PATENT DOCUMENTS

| | | | |
|---|---|---|---|
| 3,721,633 | 3/1973 | Ranauto | 252/527 |
| 3,723,617 | 3/1973 | Sutton | 424/180 |

OTHER PUBLICATIONS

Joniak et al., "Benzyl ethers of methyl alphs-D-glucopyroanoside," *Chemical Abstracts*, 93:557–558, No. 221012c, 1980.

Kosikova et al., "Thermal degradation of 4-O-benzyl ethers of methyl alpha-D-glucopyranoside," *Chemical Abstracts*, 90:77, No. 139232d, 1979.

*The Merck Index*, 9th Ed., Windholz et al., eds., New Jersey: Merck & Co., Inc., 576, No. 4290.

Nicolaou et al., "Design and synthesis of a peptidomimetic employing beta-D-glucose for scaffolding," *Peptides*, River et al., Eds., ESCOM, 1990.

Raynor et al., "Analogs of Somatostatin Selectively Label Distinct Subtypes of Somatostatin Receptors in Rat Brain," *Journal of Pharmacology and Experimental Therapeutics*, 251:510–517, 1989.

Reisine et al., "The Localization of Receptor Binding Sites in teh Substantia Nigra and Striatum of the Rat," *Brain Research*,117:241–252, 1979.

Rich, D. H., *Protease Inhibitors*, Barrett et al., eds., Elsevier, 1986.

Sherman et al., "Compatibility of Thioamides with Reverse Turn Features: Synthesis and Conformational Analysis of Two Model Cyclic Pseudopeptides Containing Thioamides as Backbone Modifications," *J. Am. Chem. Soc.*, 112:433–441, 1990.

Thorsett et al., "Dipeptide Mimics. Conformationally Restricted Inhibitors of Angiotensin–Converting Enzyme," *Biochem. Biophys. Res. Comm.*, 111:166–171, 1983.

Veber et al., "Conformationally restricted bicyclic analogs of somatostatin," *Proc. Natl. Acad. Sci. USA*, 75:2636–2640, 1978.

Veber et al., "A Super Active Cyclic Hexapeptide Analog of Somatostatin," *Life Sciences*, 34:1371–1378, 1984.

Veber et al., "A potent cyclic hexapeptide analogue of somatostatin," *Nature*, 292:55–58, 1981.

Nicolaou et al., Chemical Abstract, vol. 114 (1991) No. 102793a.

*Primary Examiner*—Douglas W. Robinson
*Assistant Examiner*—Elli Peselev
*Attorney, Agent, or Firm*—Woodcock Washburn Kurtz Mackiewicz & Norris

[57] ABSTRACT

Compounds are provided which are crossreactive with peptides such as those which bind G-protein-linked receptors, together with preparative and therapeutic methods therefor. The compounds have the general structure:

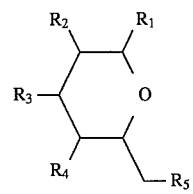

wherein at least one of $R_1$, $R_2$, $R_3$, $R_4$, or $R_5$ comprises a functional group which is chemically similar to that found in the peptide of interest.

16 Claims, 19 Drawing Sheets

NON-PEPTIDE PEPTIDOMIMETICS

GOVERNMENT SUPPORT

Certain of the inventors have been supported by National Institute of Mental Health Grant 45533 and National Institutes of Health Grant GM-41821.

CROSS REFERENCE TO RELATED APPLICATION

This application is a Continuation in Part of patent application Ser. No. 07/748,826, filed Aug. 22, 1991, now abandoned, incorporated by reference herein.

FIELD OF THE INVENTION

This invention relates to synthetic compounds which mimic or inhibit the biological and/or chemical activity of peptides, including compounds which bind G-protein-linked receptors.

BACKGROUND OF THE INVENTION

Peptides are implicated in a wide variety of biochemical processes in humans and other mammals. For example, it is known that a number of hormones and neurotransmitters are controlled by receptor-mediated stimulation of one or more of a family of guanine nucleotide-binding regulatory proteins, known as G-proteins. G-proteins activate or inhibit different effector enzymes, modulating the levels of intracellular second messengers. At least 50 sub-types of G-protein-linked receptors have been identified, among them the α-adrenergic, β-adrenergic, muscarinic, cholinergic, dopamine, histamine, adenosine, serotonin, prostaglandin, leukotriene, thromboxane, prostacyclin, PAF, cAMP, enkephalin, endorphin, cholecystokinin, bombesin, substance K, substance P, neuromedin, bradykinin, FMLP, C5a, C3a, vasopressin, oxytocin, angiotensin, VIP, parathyroid hormone, calcitonin, neurotensin, TRH, somatostatin, rhodopsin, epinephrine, norepinephrine, acetylcholine, S-hydroxytryptamine, thyrotropin, thyrotropin releasing hormone, follicle stimulating, lutropin, choriogonadotropin, thrombin, retinal, and olfactory receptors. Nine or more G-proteins and at least seven effector systems have also been described. All of the G-protein-linked receptors analyzed to date contain from one to three potential sites of asparagine-linked glycosylation.

The transmembrane signaling pathway used by G-protein-linked receptors represents one of the major mechanism of signal transduction in cellular systems. It is known, for example, that substance P acts as a vasodilator, a depressant, stimulates salivation, and produces increased capillary permeability. Substance P is a naturally occurring undecapeptide belonging to the tachykinin family of peptides, the latter being so-named because of their prompt contractile action on extravascular smooth muscle tissue. In addition to substance P (neurokinin-1, NK-1), the known mammalian tachykinins include neurokinin A (NK-2) and neurokinin B (NK-2). The tachykinins have been implicated in gastrointestinal (GI) disorders and diseases of the GI tract, such as inflammatory bowel disease, ulcerative colitis and Crohn's disease.

Substance P is known to produce both analgesia and hyperalgesia in animals, depending on dose and pain responsiveness of the animal and plays a role in sensory transmission and pain perception. Substance P also is believed to be involved in the inflammatory response in diseases such as rheumatoid arthritis and osteoarthritis. Other disease areas where the tachykinins are believed to be involved include allergic conditions, immunoregulation, bronchospasm, reflex or neuronal control of the viscera, and Alzheimer's disease and Downs Syndrome.

To date, there have been limited therapeutic applications involving peptides, due in considerable part to lack of oral bioavailability and to proteolytic degradation. Typically, for example, peptides are rapidly degraded in vivo by exo- and endopeptidases, resulting in generally very short biological half-lives. Another deficiency of peptides as potential therapeutic agents is their lack of bioavailability via oral administration. Degradation of the peptides by proteolytic enzymes in the gastrointestinal tract is likely an important contributing factor. The problem is, however, more complicated, because it has been recognized that even small, cyclic peptides which are not subject to rapid metabolic inactivation nevertheless exhibit poor oral bioavailability. This likely is due to poor transport across the intestinal membrane and rapid clearance from the blood by hepatic extraction with subsequent excretion into the intestine. These observations suggest that multiple amide bonds may interfere with oral bioavailability.

The design of peptide mimics which are resistant to degradation by proteolytic enzymes has become of increasing interest to peptide chemists, both for hormone agonist/ antagonist and for enzyme inhibitor design. A primary goal has been to reduce the susceptibility of mimics to cleavage and inactivation by peptidases. In one approach, such as disclosed by Sherman and Spatola, *J. Am. Chem. Soc.*, 112, 1990, 433, one or more amide bonds have been replaced in an essentially isosteric manner by a variety of chemical functional groups. This stepwise approach has met with some success in that active analogs have been obtained. In some instances, these analogs have been shown to possess longer biological half-lives than their naturally-occurring counterparts. Nevertheless, this approach has limitations. Successful replacement of more than one amide bond has been rare. Consequently, the resulting analogs have remained susceptible to enzymatic inactivation elsewhere in the molecule. Moreover, this approach does not permit generalizations between chemically unrelated peptides concerning permissible amide mimic substitutions.

In another approach, a variety of uncoded or modified amino acids such as D-amino acids and N-methyl amino acids have been used to modify mammalian peptides. Alternatively, a presumed bioactive conformation has been stabilized by a covalent modification, such as cyclization or by incorporation of γ-lactam or other types of bridges. See, e.g., Veber and Hirschmann, et al., *Proc. Natl. Acad. Sci. USA*, 1978 75 2636 and Thorsett, et al., *Biochem Biophys. Res. Comm.*, 1983 111 166. The primary purpose of such manipulations has not been to avoid metabolism or to enhance oral bioavailability but rather to constrain a bioactive conformation to enhance potency or to induce greater specificity for a receptor subtype.

Another approach, disclosed by Rich, D. H. in *Protease Inhibitors*, Barrett and Selveson, eds., Elsevier (1986), has been to design peptide mimics through the application of the transition state analog concept in enzyme inhibitor design. For example, it is known that the secondary alcohol of statine mimics the tetrahedral transition state of the scissile amide bond of the pepsin substrate. Again, increased potency rather than decreased susceptibility to peptidases or increased bioavailability was the principal objective. Moreover, the transition state analog concept has no apparent relevance to hormone agonist/antagonist design.

Nicolaou and Hirschmann, et al., *Design and synthesis of a peptidomimetic employing β-D-glucose for scaffolding*, in Peptides, Rivier and Marshall, eds., ESCOM (1990), disclosed non-peptide somatostatin mimics having structures (1) and (2), wherein Bn is benzyl.

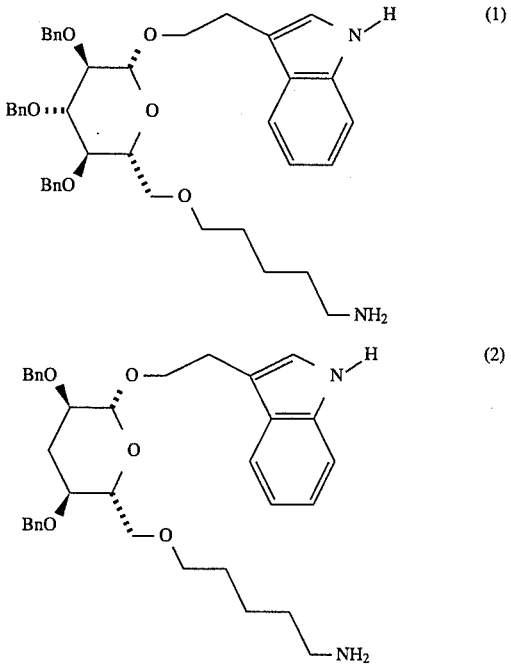

These mimics bound somatostatin receptors of AtT-20 cells with $IC_{50}$ of about $9.5 \times 10^{-6}M$ and about $1 \times 10^{-6}M$, respectively, compared with an $IC_{50}$ of about 9.3 nM ($9.3 \times 10^{-9}M$) for somatostatin itself. Significantly, the mimics failed to bind other G-protein-linked receptors at clinically acceptable concentrations. For example, while it was found that the β-adrenergic receptor, which is also found in AtT-20 cells, bound mimic (1), it required a five fold higher concentration to do so than was required for the somatostatin receptor. The goal of the authors was to increase the specificity of the mimics for the somatostatin receptor, not to develop compounds which would be bound by G-protein-linked receptors. Indeed, the authors suggested increasing the potency of the compounds as a means for enhancing this specificity.

Accordingly, there remains a long-felt need for metabolically stable chemical compounds which exhibit both good bioavailability and the capacity to bind a variety of G-protein-linked receptors.

OBJECTS OF THE INVENTION

It is one object of the present invention to provide compositions of matter which mimic or inhibit the biological and/or chemical activity of peptides.

It is another object to provide compositions which are chemically more stable than naturally-occurring peptides, particularly under conditions such as found in the human body.

It is a further object to provide compositions which function as hormone agonists or hormone antagonists.

It is a further object to provide compositions which effectively bind G-protein-linked receptors, especially the substance P receptor.

It is still a further object to provide prophylactic, diagnostic, and therapeutic uses for peptide analogs.

SUMMARY OF THE INVENTION

These and other objects are accomplished by the present invention, which provides compounds, known as peptide analogs, which contain no peptide bonds yet which mimic or inhibit the chemical and/or biological activity of peptides. In general, the peptide analogs of the invention have structure (3):

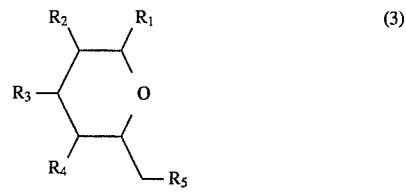

wherein at least one of $R_1$, $R_2$, $R_3$, $R_4$, or $R_5$ comprises a chemical functional group which causes the compounds to be crossreactive with the peptide of interest. In preferred embodiments, peptide analogs of the invention have the structure (4) and, more preferably, the structure (5):

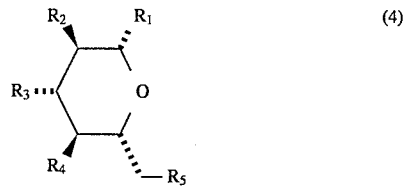

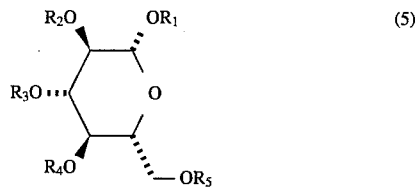

Compounds having these structures have been found to effectively bind a number of G-protein-linked receptors. Indeed, it has even been discovered in accordance with the present invention that the compound of having structures (1) and (2) are is able to bind G-protein-linked receptors other than the SRIF receptor.

The peptide analogs of the invention can be employed to mediate the chemical and/or biological effects of hormone agonists/antagonists or other peptides. These compounds are believed to possess beneficial properties such as increased half-life, lack of immunogenicity, and the ability to cross the blood-brain barrier; they are believed to be useful for the development of pharmaceutical, therapeutic, and diagnostic techniques. Accordingly, the invention also provides methods for producing a prophylactic or therapeutic response in a mammal by administering to the mammal a pharmaceutically effective amount of one or more peptide analogs of the invention. In accordance with preferred embodiments, the present invention provides methods for producing such responses by modulating the activity of at least one mammalian G-protein-linked receptor by administering an effective amount of one or more peptide analogs of the invention.

DETAILED DESCRIPTION OF THE INVENTION

Figure 1:
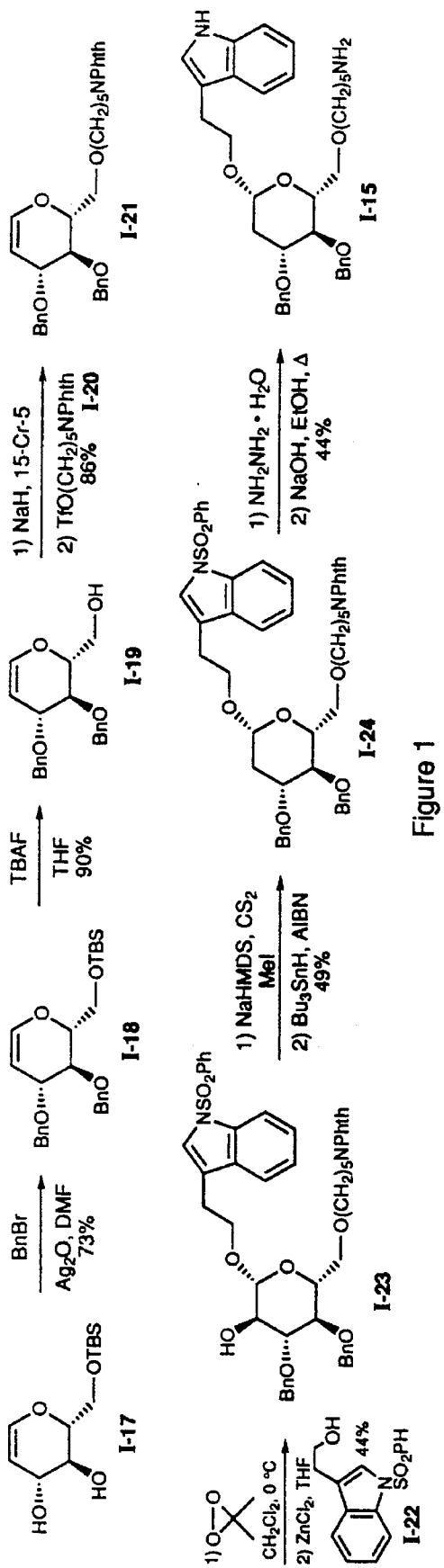
FIGS. 1–7 depict synthetic schemes for the Imidazol compounds of Example 9.

It has been found in accordance with the present invention that non-peptide compounds which mimic or inhibit the chemical and/or biological activity of a variety of peptides can be produced by appending to certain core species such as the tetrahydropyranyl ring of structure (3) chemical functional groups which cause the compounds to be at least partially crossreactive with the peptide. As will be recognized, compounds which mimic or inhibit peptides are to varying degrees crossreactive therewith. In accordance with the present invention, crossreactive moieties are those which compete with one another in binding G-protein-linked receptors through one of the many chemical reaction phenomena known in the art such as, for example, complexation, crystallization, or ionic, hydrogen, or covalent bonding. Thus, it is intended that the term "crossreactive" include both agonism and antagonism. Those skilled in the art recognize that a substance which competes with a G-protein in binding to a cell receptor is described as an agonist if the response of the cell is the same as or mimics the action of the peptide ligand. A substance that competes with the G-protein in binding to a receptor is referred to as antagonist if it blocks or inhibits the action of the cell to the action of the G-protein.

There exist a wide variety of useful analytical techniques for elucidating the precise structure of a peptide. These techniques include amino acid sequencing, x-ray crystallography, mass spectroscopy, nuclear magnetic resonance spectroscopy, computer-assisted molecular modeling, peptide mapping, and combinations thereof. Structural analysis of a peptide generally provides a large body of data which in preferred embodiments comprises the amino acid sequence of the peptide as well as the three-dimensional positioning of its atomic components. It is believed that only certain of these components, which are known both individually and collectively as chemical functionality, participate in any given reaction phenomena. It will be appreciated that the participation of a chemical functional group in peptide reactivity is manifested by the linkage or coordination of the functional group with at least a portion of a complementary reactive moiety such as a hormone receptor. Such linkage or binding may be effected through a covalent, ionic, or hydrogen bond or some weaker atomic coordination effect such as complexation or crystallization.

In accordance with the present invention, peptide chemical functionality which participates in binding is identified by one of the many techniques known in the art. For example, such identification can be effected through a stepwise process wherein one or more peptide analogs are prepared. For example, peptide analogs having structure (3) can be prepared by substitution at certain of the positions $R_1$–$R_5$ with chemical functionalities which are crossreactive with functionalities found in the peptide. The activity of the analog in a binding assay is then compared with that of the peptide. The degree to which the binding of the analog corresponds with that of the peptide indicates the degree to which the substituents participate in the binding phenomena. Accordingly, one important criterion in preparing peptide analogs according to the present invention is the respective chemical similarity of the side chains found in the peptide and any potential substitutes therefor appended to the core structure in the analog. In general, it is desired that the chemical functional group in the peptide of interest and its substitute in at least one of the peptide analogs be somewhat chemically dissimilar. Where the substitute is chemically dissimilar from the peptide side chain, it will generally be easier to elucidate the contribution, if any, of side chain to activity of the peptide.

For example, it is believed that the bioactive conformation of somatostatin (also known as somatotropin release inhibiting factor or SRIF) includes a β-turn involving residues 7–10 ($Phe^7$-$Trp^8$-$Lys^9$-$Thr^{10}$). These four amino acids have been shown to be necessary and sufficient for receptor recognition and activation, so long as they are held in the proper orientation. Somatostatin accomplishes this proper orientation through its ten remaining amino acids and the cystine bridge contained therein. In a number of active cyclic hexapeptide analogs for somatostatin, proper orientation of the four amino acids is maintained via dipeptide segments. For example, the cyclic hexapeptide L-363,301 (structure (6a)), disclosed by Veber and Hirschmann, et al., *Life Sciences*, 1984, 34, 1371 and the cyclic hexapeptide MK-678 (structure (6b)), disclosed by Veber and Hirschmann, et al., *Nature*, 1981, 292, accomplish the proper orientation via the segments Phe-N-Me-Ala or Phe-Pro, respectively.

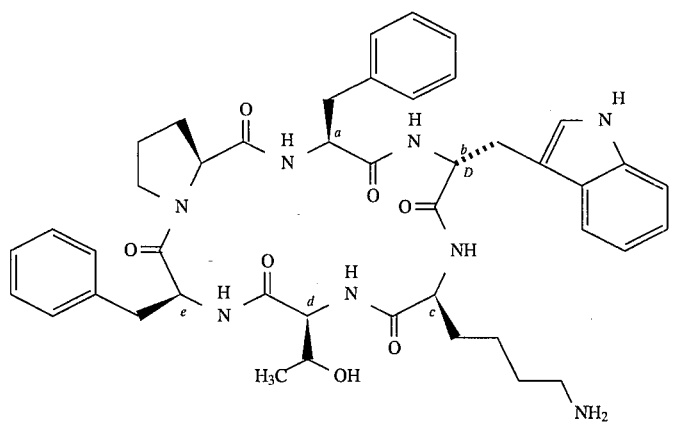

(6a)

-continued

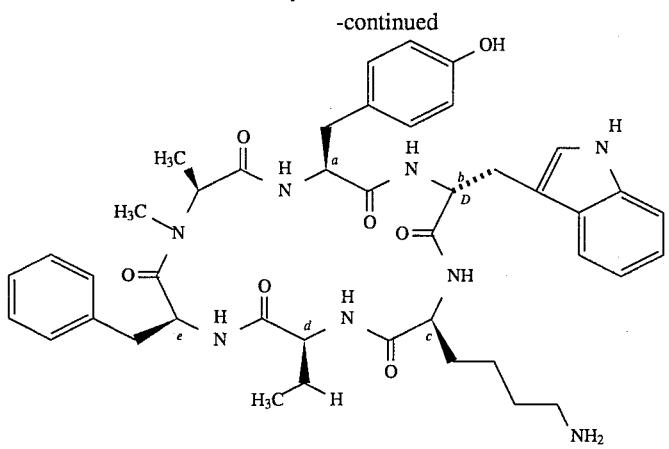

(6b)

It is believed that the solution conformation of somatostatin involves a type I β-turn for residues 7–10 and that of the significantly more potent D-TRP diastereomer involves a type II' β-turn. While these two turns differ in the Φ and ψ angles of the amide backbone, they are believed to assume similar orientations of the side chains at the receptor. In the cyclic hexapeptides, the Phe-N-Me-Ala sequence and the Phe-Pro sequence are believed to be part of a type VI β-turn. Of particular significance is the high activity found for a modified retro-enantiomeric cyclic hexapeptide wherein the amide backbone is reversed. This demonstrates that proper side chain topography is important for activity but that the amide backbone may not be.

In accordance with the present invention, peptide analogs having structure (3) were further simplified by including only three adjacent side chains of the four amino acids of the β-turn. These side chains are attached to rigid frameworks devoid of peptide bonds. The frameworks were developed through molecular modeling to orient the side chains appropriately and/or to permit the receptor to induce the proper fit.

While a proper β-turn requires the fourth amino acid of the β-turn—Thr in somatostatin and several cyclic hexapeptides and Val in the superactive cyclic hexapeptide—it is believed that neither the Thr nor the Val side chains are required for binding. This assumption is based on the fact that highly active somatostatin analogs are known which have either Val, Thr, Ser, α-aminobutyric acid, or Gly in the fourth position of the β-turn. Such non-specificity suggests a conformational rather than a binding role for that amino acid of the β-turn.

The phenylalanine residue in the dipeptide segments Phe-N-Me-Ala or Phe-Pro appears to add an important hydrophobic binding element. For this reason, the present synthetic analogs of somatostatin contain a corresponding aromatic residue. Increased hydrophobicity also should prove helpful in improving the duration of action and activity via oral administration of such compounds.

It is now believed that for the L-363,301 hexapeptide, structure (6a), the β-turn is important and the three groups extending from carbons a, b, and c—benzyl, indole, and alkylamino, respectively—are necessary for binding. Whereas the substituent at carbon d appears to be required to stabilize the β-turn rather than be required for binding, a benzyl group attached at carbon e of the skeleton is believed to be an important binding ligand which improves the activity of analogs.

It has now been discovered that a new class of therapeutic agents can be formulated having activity in a broad spectrum of utilities, especially those related to the G-protein-linked receptors. One member of the class is represented by structure (7).

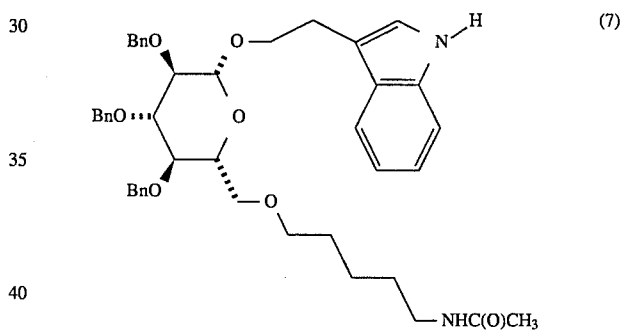

The calculated bond distances for structure (7) and the cyclic hexapeptide suggest close geometrical similarities. Furthermore, overlaying models of the designed structure (7) and the cyclic hexapeptide (6a) shows close correspondence of the important functionalities, particularly the phenylalanine, tryptophan and lysine residues.

The present invention, however, is not limited to embodiments wherein benzyl, indole, or alkylamino groups participate in binding. Participatory chemical functionality according to the present invention includes any of the wide variety of functional groups known in the art. The side chains of naturally-occurring amino acids provide examples of suitable participatory functionality. Representative participatory chemical functionality which may be contained within groups $R_1$–$R_5$ is set forth in Table 1. For example, one or more of $R_1$–$R_5$ can have the structure Z—$(CH_2)y$— or Z—O—, where y is from 0 to about 5 and Z is one of the side chains of Table 1.

TABLE 1

| | |
|---|---|
| $CH_3$— | $CH_3$—$CH_2$—S—$CH_2$—$CH_2$—HO—$CH_2$—$CH_2$— |
| HO—$CH_2$— | $CH_3$—$CH_2(OH)$— |

TABLE 1-continued

| | |
|---|---|
| $C_6H_5-CH_2-$ | $HO_2C-CH_2-NH_2C(O)-CH_2-$ |
| $HO-C_6H_5-CH_2-$ | |
| 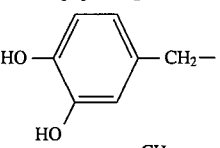 | 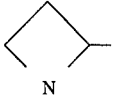 |
| 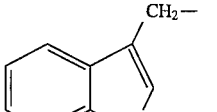 | $HCO_2-CH_2-CH_2-$ |
| | $NH_2C(O)-CH_2-CH_2-$ |
| | $(CH_3)_2-CH-$ |
| | $(CH_3)_2-CH-CH_2-$ |
| | $CH_3-CH_2-CH_2-$ |
| | $H_2N-CH_2-CH_2-CH_2-$ |
| | $H_2N-C(NH)-NH-CH_2-CH_2-CH_2-$ |
| 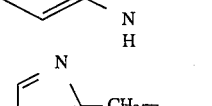 | $H_2N-C(O)-NH-CH_2-CH_2-CH_2-$ |
| | $CH_3-CH_2-CH(CH_3)-$ |
| | $CH_3-CH_2-CH_2-CH_2-$ |
| | $H_2N-CH_3-CH_2-CH_2-CH_2-$ |
| $HS-CH_2-$ | |
| $HO_2C-CH(NH_2)-CH_2-S-S-CH_2-$ | |
| $CH_3-CH_2-$ | |
| $CH_3-S-CH_2-CH_2-$ | |

In accordance with the present invention, non-peptide analogs preferably possess the general structure (3):

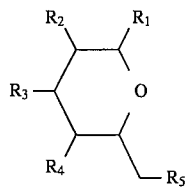 (3)

wherein:

R$_1$ is —O(CH$_2$)$_n$R$_A$, —OC(O)(CH$_2$)$_n$R$_A$, —(CH$_2$)$_n$R$_A$, or —C(O)(CH$_2$)$_n$R$_A$ where R$_A$ is —H, alkyl or alkenyl having from about 1 to about 14 carbon atoms and up to about 4 nitrogen atoms, or aryl having from about 6 to about 14 carbon atoms and up to about 4 nitrogen atoms, and n is an integer from 0 to about 12;

at least one of R$_2$, R$_3$, and R$_4$, independently, is —O(CH$_2$)$_m$R$_B$, —OC(O)(CH$_2$)$_m$R$_B$, —(CH$_2$)$_m$R$_B$ or —C(O)(CH$_2$)$_m$R$_B$ where R$_B$ is —H or aryl, and m is an integer from 0 to about 5; and R$_5$ is —O(CH$_2$)$_p$NHR$_C$, —OC(O)(CH$_2$)$_p$NHR$_C$, —O(CH$_2$)$_p$R$_D$, —OC(O)(CH$_2$)$_p$R$_D$, —(CH$_2$)$_p$NHR$_C$, —C(O)(CH$_2$)$_p$NHR$_C$, —(CH$_2$)$_p$R$_D$ or —C(O)(CH$_2$)$_p$R$_D$, where:

p is an integer from 0 to about 10;
R$_C$ is —R$_E$ or —C(O)R$_E$;
R$_D$ is —H, —OR$_E$, or —C(O)R$_E$;
R$_E$ is —H, alkyl or alkenyl having from about 1 to about 14 carbon atoms and up to about 4 nitrogen atoms, or aryl having from about 6 to about 14 carbon atoms and up to about 4 nitrogen atoms; or a pharmaceutically acceptable salt thereof.

It will be understood that the terms "alkyl" and "alkenyl" as employed herein are intended to include cyclic as well as straight chain moieties. In certain embodiments, the chemical structure and stereochemistry of the peptide analogs of the invention roughly correspond to that of β-D-glucose. Hence, the analogs can possess structures (4) and (5), with R$_1$-R$_5$ defined as above.

As will be recognized, the precise identity of R$_1$-R$_5$ depends intimately upon the peptide of interest whose biological and/or chemical activity is to be mimicked or inhibited. For example, in the case of compounds which are bound by G-protein-linked receptors such as the substance P receptor, R$_A$ should be an aryl functional group, preferably an nitrogen-substituted aryl group such as pyridine or indole. More preferably, R$_A$ is a 3-substituted indole. For such compounds, n should be 2 and R$_B$ should be phenyl. The integer m should be zero or, preferably, 1. Also, R$_5$ should be —O(CH$_2$)$_p$NH$_2$ or —O(CH$_2$)$_p$NHR$_C$, where p is from about 2 to about 8, preferably 3 to about 6, more preferably 5. R$_C$ can be, for example, a phenyl, benzyl or nitrogen heterocyclic moiety. Where substitution is possible at more than one position of these and other R$_C$, it is intended that the present invention include each of the resulting peptide analogs. For example, it is intended that the invention include analogs wherein R$_C$ is a pyridine or isonicotinic acid residue having one of the following structures:

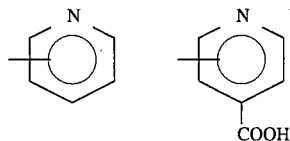

Preferably, however, R$_C$ is —CH$_3$.

In general, preferred peptide analogs have structures (8)–(13).

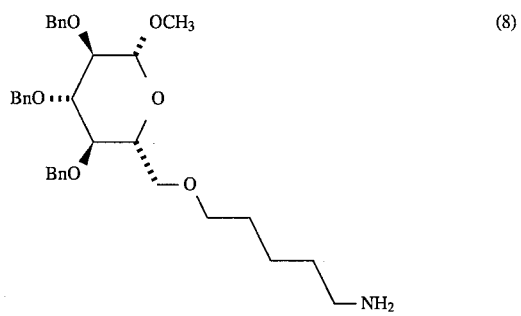 (8)

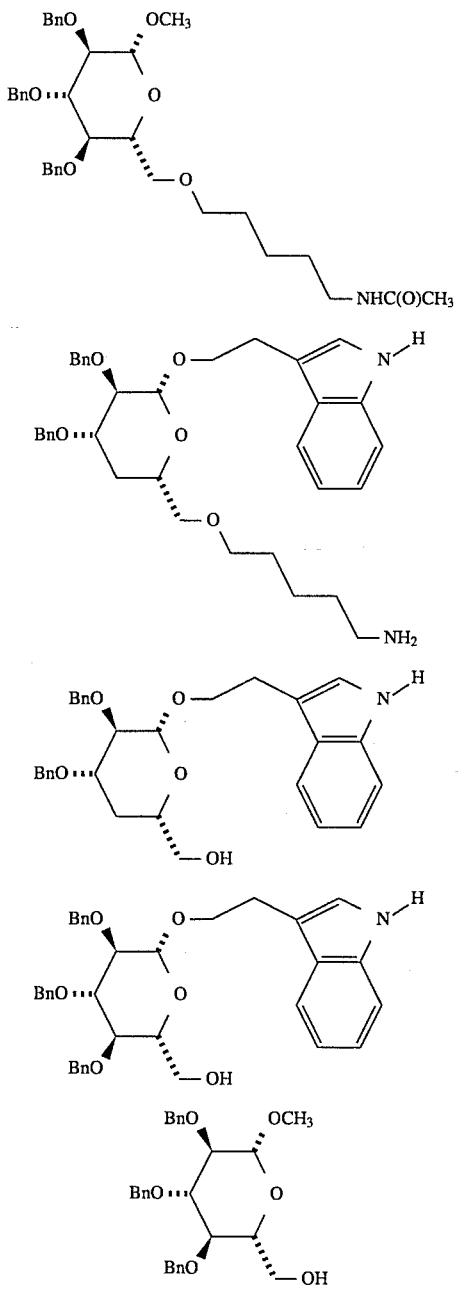

These peptide analogs are preferred to the extent that they selectively and effectively bind G-proteins-linked receptors such as the somatostatin receptor, the β-adrenergic receptor, and the substance P receptor. It will be recognized that the degree to which a compound binds a receptor is known as its binding activity or potency. The potency of a compound commonly is expressed as its inhibitory concentration (IC), the concentration at which the compound is able to displace a predetermined portion—typically 50%—of another compound which is already bound to a particular receptor. In the case of ligand-binding studies, the compound that is displaced is a radioactive agonist or antagonist at the receptor under study. It is preferred in accordance with the present invention that a peptide analog possess a clinically effective $IC_{50}$ in at least one mammal, that is, a concentration which is low enough to inhibit binding of radioactive agonist or antagonist of a given G-protein-linked receptor while causing a minimum of unacceptable side effects in the mammal.

As will be recognized, clinically effective inhibitory concentrations vary depending on a number of factors, such as the pharmacokinetic characteristics and stability of the compound under study and thus must be determined empirically for each analog and each factor. For example, the clinically effective concentration for the human somatostatin receptor is about 50–500 nm, but for the in vitro system the potency is about 1–10 nM. In general, it is desired that the potency of a compound of the invention be as great as possible, preferably greater than or equal to the native Lormone.

Selectivity or specificity is manifested for a compound of the present invention by its tendency to bind one particular G-protein-linked receptor but not other G-protein-linked receptors. In an experimental context, selectivity is manifested where a compound is bound by a particular receptor when placed in contact or close proximity with a medium containing at least one other receptor. Typically, specificity is expressed as a ratio of the potency or activity of a compound for two different receptors. Thus, a compound having an $IC_{50}$ of 100 μm for compound A and $IC_{50}$ of 200 μM for compound B can be said be two times more selective for compound A. In general, the selectivity of the peptide analogs of the present invention should be as great as possible. Selectivities greater than about 50–100 fold are preferred and selectivities greater than about 500 fold even more preferred.

As can be seen, the present invention provides a wide variety of peptide analogs which effectively and selectively are bound by individual G-protein-linked receptors. The peptide analogs which bear amino groups are capable of forming salts with various inorganic and organic acids and such salts are also within the scope of this invention. Examples of such acid addition salts include acetate, adipate, benzoate, benzenesulfonte, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-napthalenesulfonate, nitrate, oxalate, pamoate, persulfate, picrate, pivalate, propionate, succinate, sulfate, tartrate, tosylate, and undecanoate. The salts may be formed by conventional means, such as by reacting the free base form of the product with one or more equivalents of the appropriate acid in a solvent or medium in which the salt is insoluble, or in a solvent such as water which is later removed in vacuo or by freeze drying. The salts also may be formed by exchanging the anions of an existing salt for another anion on a suitable ion exchange resin.

The present invention also provides compositions which comprise one or more peptide analogs. To the extent that the compositions comprise individual peptide analogs which are bound by certain receptors, the compositions will likely also be bound by the same receptors. The analogs themselves may be present in the compositions in any of a wide variety of forms. For example, two or more peptide analogs may be merely mixed together or may be more closely associated through complexation, crystallization, or ionic or covalent bonding.

Those skilled in the art will appreciate that a wide variety of prophylactic, diagnostic, and therapeutic treatments may be prepared from the synthetic compounds and compositions of the invention, due in large part to the crossreactivity—that is, agonism or antagonism—of these moieties with one or more naturally-occurring peptides. For example, by administering an effective amount of a peptide analog, prophylactic or therapeutic responses can be produced in a human or some other type of mammal. Preferred responses are produced by modulating—that is, increasing, decreasing or otherwise modifying—the activity of at least one G-protein-linked receptor. It will be appreciated that the production of prophylactic or therapeutic responses includes the initiation or enhancement of desirable responses, as well as the cessation or suppression of undesirable responses.

Certain preferred peptide analogs of the present invention exhibit significant substance P receptor-binding activity and therefore, are of value in the treatment of a wide variety of clinical conditions which are characterized by the presence of an excess of tachykinin, in particular substance P, activity. These include disorders of the central nervous system such as anxiety, psychosis and schizophrenia; neurodegenerative disorders such as senile dementia of the Alzheimer type, Alzheimer's disease and Down's syndrome; respiratory diseases such as bronchospasm and asthma; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine. Hence, these compounds are readily adapted to therapeutic use as substance P antagonists for the control and/or treatment of any of the aforesaid clinical conditions in mammals, including humans.

Compositions for use in the methods of this invention can be in the form of a solid, semisolid or liquid form and can include one or more of peptide analogs as an active ingredient in a mixture with an organic or inorganic carrier or excipient suitble for external, enteral or parenteral applications. The active ingredient may be compounded, for example, with the usual non-toxic, pharmaceutically acceptale carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manuacturing preparations, in solid, semisolid, or liquid form, and in addition auxiliary, stabilizing, thickening and coloring agents and perfumes may be used. The active ingredient is included in the pharmaceutical composition in an amount sufficient to produce the desired effect upon the process or condition of diseases.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water ethanol, propylene glycol, glycerin and various like combinations thereof.

For parenteral administration, solutions of said compounds in either sesame or peanut oil in aqueous proplyene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

A compound of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Dosage levels of the compounds within the present invention on the order from about 0.01 mg to about 50 mg per kilogram of body weight per day, preferably from about 0.1 mg to about 10 mg per kilogram body weight per day, are believed to be useful in the treatment of the above-indicated conditions (i.e., from about 0.7 mg to about 3.5 g per patient per day, assuming a 70 kg patient). In addition, the compounds of the present invention may be administered on an intermittent basis; i.e. at semi-weekly, weekly, semi-monthly or monthly intervals.

The amount of active ingredient that may be combined with the carrier materials to produce a single dosage form will vary depending upon the host treated and the particular mode of administration. For example, a formulation intended anisaldehyde solution (sugars), ninhydrin (primary amines), phosphomolybdic acid (secondary amines), or Erlich's reagent (incoles). Flash column chromatography was performed using Merck 60–200 mesh silica gel. All yields reflect purified isolated product after flash column chromatography or recrystallization unless otherwise noted.

EXAMPLE 1

Preparation of Analog Having Structure (1), 2-(1H-Indol-3yl)ethyl-6-O-(5-aminopentyl)-2,3,4-tri-O-benzyl-β-D-glucopyranoside A. 1-Bromo α-D glucose tetraacetate Hydrobromic acid (30% in acetic acid, 11.85 ml, 55.4 mmol) was added to β-D-glucose pentaacetate (12.01 g, 30.8 mmol) at 0° C. After 10 minutes, the resulting solution was warmed to room temperature and stirred for 4 hours. The reaction mixture was slowly poured, with stirring, into ice water (250 ml) and was stirred until the product solidified. The product was collected by vacuum filtration and washed with cold water. The white solid was dissolved in carbon tetrachloride (60 ml) and washed with $H_2O$ (1×20 ml), saturated aqueous $NaHCO_3$ (3×20 ml, until pH=7), $H_2O$ (1×20 ml), dried with $CaCl_2$, and poured into cold petroleum ether (250 ml). After 30 min, the crystalline product was collected by vacuum filtration to give the target compound as a white solid (10.0 g, 80%).

B. N-phenylsulfonyl tryptophol (a) 1-O-tert-butyldimethylsillyl-2-3-indolyl)ethanol To a solution of tryptophol (5.0 g, 31 mmol) in dimethylformamide (DMF, 30 ml) was added imidazole (4.64 g, 68 mmol) and the reaction cooled to 0° C. To the cooled solution was added tert-butyldimethylsilyl chloride (5.14 g, 34.1 mmol) and the reaction was stirred at room temperature overnight. The reaction was diluted with ethyl acetate (100 ml) and extracted with water (2×100 ml). The aqueous layer was extracted with ethyl acetate (1×200 ml.) The organic layers were combined and dried over anhydrous sodium sulfate. The solvents were removed under reduced pressure to yield a pale orange oil. Purification by flash column chromatography using 30% ether in petroleum ether yielded the target compound as a colorless oil (8.43 g, 99%).

(b) 1-0-tert-butyldimethylsilyl-2-[3-(1-N-phenylsulfonyl)indolyl]ethanol

Sodium hydride (1.91 g, 60% oil dispersion) was placed in a flame dried flask under argon. Dry DMF (64 ml) was added and the suspension cooled to 0° C. A solution of 1-O-tert-butyldimethylsilyl- 2-3-indotyl)ethanol (8.43 g, 30.6 mmol) in dry DMF (30 ml) was added to the suspension and the reaction stirred to room temperature for 30 minutes. After cooling to 0° C., benzenesulfonyl chloride (5.30 ml, 39.7 mmol) was added dropwise. The reaction was stirred at room temperature overnight. A solution of ammonium chloride (100 ml) was added and the reaction was extracted with ether (3×200 ml). The organic layers were combined, extracted with saturated sodium chloride, and dried over anhydrous sodium sulfate. Removal of the solvents under reduced pressure yield a pale yellow oil. Purification by flash column chromatography using 30% ether in petroleum ether yielded the target compound as a colorless oil (7.37 g, 79%).

(c) N-phenylsulfonyl tryptophol

To a solution of 1-0-tert-butyldimethylsillyl-2-[3-(1-N-phenylsulfonyl)indolyl]ethanol (6.6 g, 21.9 mmol) in tetrahydrofuran (THF, 100 ml ) was added tetrabutylammonium fluoride (21 ml, 1M in THF) and the solution stirred at room temperature overnight. The reaction was diluted with ethyl acetate (100 ml) and extracted with water (2×100 ml). The organic layer was re-extracted with saturated sodium chloride solution, dried over anhydrous sodium sulfate and the solvents removed under reduced pressure to yield a pale yellow oil. Purification by flash column chromatography using 40% ethyl acetate in petroleum ether yielded the target compound as a pale yellow oil which crystallized upon standing (4.00 g, 84%).

C. 2-(1-Phenylsulfonyl-3-yl)ethyl-2,3,4,6-tetra-O-acetyl-β-D-glucopyranoside

To a suspension of crushed, flame dried 4 Å sieves (0.89 g) and silver (I) oxide (412 mg. 17.8 mmol) in 9 ml of dry hexane at room temperature, was added a solution of the above N-phenyl sulfonyl tryptophol (537 mg, 1.78 mmol) in 3 ml of dry benzene followed by a solution of 1-bromo α-D glucose tetraacetate (804 mg, 1.95 mmol) in 3 ml of dry benzene. The reaction vessel was covered with aluminum foil and allowed to stir for 2 days at room temperature. Thin layer chromatography (TLC, 5% ether in methylene chloride) revealed product and some unchanged starting material. Silver (I) oxide (206 mg, 8.9 mmol) was added followed by 1 ml of dry benzene to loosen the suspension. The reaction as allowed to stir at room temperature an additional 2 days. The reaction suspension was filtered through celite. Concentration and crystallization from ethyl acetate/petroleum ether afforded 580 mg of the β-isomer of the target compound as a white solid. Concentration of the filtrate and flash chromatography (silica, 5% ether in methylene chloride) afforded a mixture of the β-isomer along with the α-isomer and the corresponding ortho ester. Flash chromatography (silica, 70% ether in petroleum ether) on the mixture afforded an additional 134 mg of the β-isomer, bringing the yield to 64% (716 mg).

D. 2-(1-Phenylsulfonyl-indol-3-yl)ethyl-β-D-glucopyranoside

Sodium methoxide (221 mg, 4.09 mmol) was added to a suspension of 2-(1-phenylsulfonyl-3-yl)ethyl-2,3,4,6-tetra-O-acetyl-β-D-glucopyranoside (3.22 g, 5.12 mmol) in 26 ml of methanol at room temperature. After 20 minutes, the resulting solution was diluted with 26 ml of methanol and neutralized by addition of amberlyst $H^+$ resin. The resin was quickly removed by filtration to avoid formation of the methyl glucoside. Concentration of the filtrate and flash chromatography (silica, 5:1:1 methylene chloride, methanol, acetone) afforded the target compound (2.09 g, 88%) as a white foam.

E. 2-(1-Phenylsulfonyl-indol-3-yl ethyl-6-O-tert-butyl-diphenylsilyl-β-D-glucopyranoside To a stirred solution of 2-(1-Phenylsulfonyl-indol-3-yl)ethyl-β-D-glucopyranoside (7.11 g, 15.4 mmol) in 51 ml of dry DMF was added at room temperature, imidazole (2.93 g, 43.1 mmol) followed by tert-butyldiphenylsilyl chloride (5.58 g, 21.6 mmol). The solution was maintained at 50° C. for 24 hours. After removal of the DMF under reduced pressure, the reaction mixture was diluted with 250 ml of ethyl acetate and washed with $H_2O$ (1×100 ml), saturated aqueous NaCl (1×100 ml), and dried over magnesium sulfate. Concentration and flash chromatography (silica, 5% methanol in dichloromethane) provided pure target compound (9.15 g, 85%) as a white foam.

F. 2-(1-Phenylsulfonyl-indol-3-yl)ethyl-2,3,4-tri-O-benzyl-6-O-tert-butyldiphenylsilyl-β-D-glucopyranoside To a stirred suspension of sodium hydride (323 mg, 60% oil dispersion, 808 mmol) in 5 ml of dry THF at 0° C. was added a solution of 2-(1-phenylsulfonyl-indol-3-yl ethyl-6-O-tert-butyldiphenylsilyl-β-D-glucopyranoside (1.62 g, 2.31 mmol) in 7 ml dry THF. After stirring 1 hour at room temperature, benzyl bromide (1.09 ml, 9.24 mmol) was added dropwise to the reaction mixture at 0° C. followed by tetrabutylammonium iodide (85 mg, 0.23 mmol). After stirring 3 days at room temperature, the suspension was treated with 3 ml of saturated aqueous ammonium chloride at 0° C. The resulting solution was diluted with 80 ml of ether and washed with saturated aqueous $NH_4Cl$ (1×30 ml), saturated aqueous NaCl (1×30 ml) and dried over magnesium sulfate. Concentration and flash chromatography (silica, 20% ether in petroleum ether) afforded the target compound (1.66 g, 74%) as a white foam.

G. 2-(1-Phenylsulfonyl-indol-3-yl)ethyl-2,3,4 tri-O-benzyl-β-D-glucopyranoside

To a stirred solution of 2-(1-phenylsulfonyl-indol-3 -yl)ethyl-2,3,4-tri-O-benzyl-6-O-tert-butyldiphenyl-silyl-β-D-glucopyranoside (1.55 g, 1.60 mmol) in 8 ml of dry THF at room temperature was added tetrabutylammonium fluoride (1M in THF, 2.4 ml, 2.4 mmol). After stirring 7 hours, the solution was diluted with 70 ml of ethyl acetate and washed with $H_2O$ (1×30 ml) and saturated aqueous NaCl (1×30 ml) and dried over magnesium sulfate. Concentration and flash chromatography (silica, 30% ethyl acetate in petroleum ether) afforded the target compound (1.10 g, 94%) as a clear oil: $R_F$ 0.50 (40% ethyl acetate in petroleum ether); $^1H$ NMR (500 MHz, $CDCl_3$) δ7.84 (d, J=8.3 Hz, 1H), 7.82 (d, J=7.9 Hz, 2H), 7.53 (s, 1H), 7.48–7.17 (m, 21H), 4.92 (d, J=11.0 Hz, 1H), 4.86 (d, J=10.9 Hz, 1H), 4.81 (d, J=11.0 Hz, 1H), 4.74 (d, J=11.0 Hz, 1H), 4.62 (d, J=11.0 Hz, 1H), 4.48 (d, J=7.8 Hz, 1H), 4.20 (ddd, J=9.4, 7.0, 7.0 Hz, 1H), 3.91–3.86 (m, 2H), 3.73 (dd, J=3.5, 11.9 Hz, 1H), 3.63 (ddd, J=9.0, 9.0, 18.0 Hz, 2H), 3.40 (ap. t, J=8.0 Hz, 1H), 3.35 (ddd, J=9.4, 4.2, 2.6 Hz, 1H), 3.04–2.93 (m, 2H), 2.06 (s, 1H); $^{13}$C NMR (500 MHz, CDCl$_3$) δ138.48, 138.21, 138.13, 137.95, 135.09, 133.60, 130.92, 129.10, 128.40, 128.30, 128.25, 128.22, 127.98, 127.90, 127.82, 127.76, 127.55, 126.58, 124.72, 123.57, 123.12, 119.61, 119.31, 113.66, 103.59, 84.39, 82.25, 77.37, 75.56, 75.16, 74.99, 74.75, 68.60, 61.77, 25.57; IR (thin film) 3480 (w), 3065 (w), 3035 (w), 2920 (m), 2878 (m), 1498 (w), 1450 (s), 1365 (s), 1280 (w), 1220 (m), 1176 (s), 1123 (s), 1090 (s), 1073 (s), 1030 (s), 750 (s), 700 (s) cm$^{-1}$; UV-Vis (c=9.21×10$^{-5}$, acetonitrile) $\lambda_{max}$ 254.0 (ε=2.81×10$^3$), 211.6 (ε=3.19×10$^4$) nm; HRMS m/e calculated for C$_{43}$H$_{43}$NO$_8$S (M+H): 734.2774, found 734.2743; [α]D$^{20}$–13.3° (c=0. 135, acetonitrile); Analysis calculated for C$_{43}$H$_{43}$NO$_8$S: C, 70.37; H, 5.91; found: C, 70.30; H, 6.08.

H. 2-(1phenylsulfonyl-indol-3yl)ethyl-2,3,4-tri-O-benzyl-6-O-trifluoromethylsulfonyl-β-D-glucopyranoside To a stirred solution of 2-(1-phenylsulfonyl-indol-3yl)ethyl-2,3,4-tri-O-benzyl-β-D-glucopyranoside (196 mg, 0.27 mmol) in 2.7 mL of dry dichloromethane at –78° C. was added 2,6-di-tert-butyl-4-methyl pyridine (880 mg, 0.427 mmol) followed by triflic anhydride (58 μl, 0.347 mmol). After stirring 15 minutes at –78° C., the mixture was warmed to room temperature over 20 minutes, and then poured into saturated aqueous NaHCO$_3$ (20 mL) and extracted with ethyl acetate (60 mL). The organic layer was washed with saturated aqueous NaHCO$_3$ (3×20 mL), saturated aqueous NaCl (1×20 mL) and dried over magnesium sulfate. Concentration provided the crude triflate target compound, which used in the next step without purification.

I. N-trifluoroacetyl-5-amino pentanol

To a solution of 5-amino pentanol (1 g, 9.69 mmol) in methanol (25 ml, 0.4M) at 0° C. was added triethylamine (2 ml, 1.5 equiv, 10 mmol) followed by very slow dropwise addition of trifluoroacetic anhydride (1.8 ml, 1.3 equiv, 12.5 mmol). The reaction mixture was warmed to room temperature and stirred overnight. TLC (5% CH$_3$OH/CH$_2$Cl$_2$) stained with ninhydrin revealed starting material; TLC stained with PMA revealed product. The reaction mixture was cooled to 0° C. and triethylamine (1.3 ml, 1 equiv. 9.69 mmol) was added followed by trifluoroacetic anhydride (1 ml, 0.8 equiv.). The reaction mixture was warmed to room temperature and stirred an additional night. Concentration and flash chromatography (silica, 60% EtOAc/petroleum ether) afforded the target compound (1.7 g, 85%).

J. 2-(1-Phenylsulfonyl-indol-3yl)ethyl-2,3,4 tri-O-benzyl-6-O-(N-trifluoroacetyl-5-aminopentyl)-β-D-glucopyranoside To a stirred suspension of sodium hydride (123 mg, 0.307 mmol, 60% oil dispersion) in 17 mL of dry THF at 0° C. was added a solution of N-trifluoroacetyl-5-amino pentanol (265 mg, 1.3 mmol) in 10 mL of dry THF. After stirring 10 minutes at 0° C., the suspension was warmed to room temperature, stirred for 1 hours, and cooled to 0° C. A solution of the above 2-(1-phenylsulfonyl-indol-3yl)ethyl-2,3,4-tri-O-benzyl-6-O-trifluoromethylsulfonyl-β-D-glucopyranoside (theoretically 0.27 mmol) in 16 ml of dry dichloromethane was added slowly dropwise. The reaction mixture was stirred at 0° C. for 30 minutes and then warmed to room temperature. After stirring 24 hours, TLC (2% methanol in dichloromethane) revealed diprotected target compound and a minor amount of monoprotected product. The reaction mixture was cooled to 0° C. and quenched with 10 mL of saturated aqueous ammonium chloride. The resulting mixture was diluted with ethyl acetate (150 mL) and washed with H$_2$O (1×50 mL), saturated aqueous NaCl (1×50 mL) and dried over magnesium sulfate. Concentration and flash chromatography (silica, 2% methanol in dichloromethane) yielded a mixture of diprotected target compound and monoprotected product which was used as a mixture in the next step.

K. Structure (1), 2-(1-Phenylsulfonyl-indol-3yl)ethyl-6-O-(5-aminopentyl)-2,3,4-tri-O-benzyl-β-D-glucopyranoside To a stirred solution of the mixture of step J, above, (theoretically 0.27 mmol) in 6 mL of ethanol at room temperature was added a solution of 5M NaOH (2 mL, 10 mmol). The solution was heated to reflux for 2 hours. The solvents were removed under reduced pressure. The reaction mixture was diluted with ethyl acetate (40 mL) and washed with H$_2$O (1×15 mL), saturated aqueous NaCl (1×15 mL) and dried over magnesium sulfate. Concentration and flash chromatography (silica, 5% methanol in dichloromethane provided structure (1) (150 mg, 83% for 3 steps) as an oil: Rf 0.26 (7% methanol in dichloromethane); $^1$H NMR (500 MHz, CDCl$_3$) d 7.98 (s, 1H), 7.59 (d, J=7.9 Hz, 1H), 7.33–7.04 (m, 19H), 4.90 (d, J=10.9 Hz, 1H), 4.85 (d, J=11.1 Hz, 1H), 4.80 (d, J=11.0 Hz, 1H), 4.77 (d, J=10.9 Hz, 1H), 4.64 (d, J=11.0 Hz, 1H), 4.60 (d, J=11.1 Hz, 1H), 4.48 (d, J=7.8 Hz, 1H), 4.21 (ddd, J=9.4, 6.7, 6.7 Hz, 1H), 3.89 (ddd, J=9.4, 7.3, 7.3 Hz, 1H), 3.64 (dd, J=9.0, 9.0 Hz, 1H), 3.56 (t, J=6.4 Hz, 2H), 3.51–3.47 (m, 1H), 3.42 (t, J=9.2 Hz, 2H), 3.11 (t, 7.0 Hz, 2H), 2.96 (dd, J=12.3, 2.6 Hz 1H), 2.66 (dd, J=12.3, 7.8 Hz, 1H), 2.62–2.54 (m, 2H), 1.93 (s, 2H), 1.54–1.44 (m, 4H), 1.38–1.32 (m, 2H); $^{13}$C NMR (500 MHz, CDCl$_3$) d 138.57, 138.49, 138.14, 136.17, 128.43, 128.36, 128.29, 128.02, 127.88, 127.82, 127.60, 127.56, 127.50, 122.14, 121.96, 119.30, 118.68, 112.60, 111.13, 103.67, 84.61, 82.45, 79.70, 77.20, 75.68, 74.99, 74.73, 73.82, 70.25, 62.63, 50.52, 49.59, 32.36, 29.28, 25.86, 23.31; IR (thin film) 3420(w), 3300(w, 3063(w), 3033(w), 2938(m), 2860(m), 1495(w), 1455(m), 1360(m), 1210(w), 1072(s), 1026(m), 910(w), 538(s), 495(s) cm$^{-1}$; UV-Vis (c=1.14×10$^{-4}$, acetonitrile) $l_{max}$ 289.6 (e=4.17×10$^3$), 280.8 (e=4.97×10$^3$), 220.0 (e=2.4×10$^4$) nm; HRMS m/e calc'd C$_{42}$H$_{50}$N$_2$O$_6$(M+H): 679.373, found 679.370; [α]D$^{20}$+3.2° (c=0.31, acetonitrile).

EXAMPLE 2

Preparation of Analog Having Structure (7), 2-(1-Phenylsulfonyl-indol-3yl)ethyl-6-O-(5-acetamidopentyl)-2,3,4-tri-O-benzyl-β-D-glucopyranoside To a solution of 5-amino pentanol (0.75 g, 7.27 mmol) in methanol (15 ml, 0.5M) at 0° C. was added triethylamine (1.62 ml, 1.6 equiv, 11.6 mmol) followed by acetic anhydride (0.891 ml, 1.3 equiv, 9.45 mmol). The reaction mixture was warmed to room temperature and stirred overnight. TLC (8% CH$_3$OH/CH$_2$Cl$_2$) stained with ninhydrin revealed starting material. Triethylamine (1.6 ml, 1.6 equiv, 11.6 mmol) was added to room temperature followed by acetic anhydride (0.9 ml, 1.3 equiv, 9.45 mmol) and the reaction mixture was stirred an additional night. Concentration and flash chromatography (silica, 7% CH$_3$OH/EtOAc) afforded N—CH$_3$CO-5-amino-pentanol (1 g, 100%).

Sodium hydride (0.108 g, 60% suspension in oil, 0.307 mmol, 2.2 equiv. compared to N—CH$_3$CO-5-amino-pentanol) was quickly weigh into a flame dried flask under argon. THF (20 ml, 0.01M compared to moles of the triflate was added and the resulting suspension was cooled to 0° C.

A solution of N—CH₃CO-5-amino-pentanol (0.108 g, 0.22 moles, 5 equiv) in 5 ml of THF was added dropwise and then warmed to room temperature for 1 hour. The resulting suspension was cooled to 0° C. and a solution of the 2-(1-phenylsulfonyl-indol-3-yl)ethyl-2,3,4 tri-O-benzyl-β-D-glucopyranoside triflate prepared in Example 1H (assumed 0.245 mmol) in CH₂Cl₂ (15 ml, CH₂Cl₂:THF= 3:5) was added slowly dropwise and stirred for 1 hour. The reaction mixture was warmed to room temperature and stirred overnight. TLC (3% CH₃OH/CH₂Cl₂) revealed no starting material and a major and minor product very close in $R_f$. Both were collected since the minor product is deprotected indole and the mixture is transformed to the same product in the next step. The reaction mixture was cooled to 0° C. and quenched with aqueous saturated ammonium chloride. The reaction mixture was poured into EtOAc and washed 1×H₂O and 1×aqueous saturated NaCl. The organic layer was dried with MgSO₄ and filtered. Concentration and flash chromatography (silica, 3% CH₃OH/CH₂Cl₂) yielded the major and minor product which was used as a mixture in the next step.

To a solution of the above mixture (assumed 0.245 mmol) in ethanol (4 ml, 0.05M) at room temperature was added 2 ml of 5M NaOH and the cloudy reaction mixture was heated to reflux for 2 hours. The reaction solvent was concentrated, diluted with EtOAc, and washed 1×H₂O and 1×aqueous saturated NaCl. The organic layer was dried with MgSO₄ and filtered. Concentration and flash chromatography (silica, 4% CH₃₀H/CH₂Cl₂) yielded structure (7), 2-(1-Phenylsulfonyl-indol-3yl)ethyl-6-O-(5-acetamidopentyl)-2,3,4-tri-O-benzyl-β-D-glucopyranoside.

EXAMPLE 3

Preparation of Analog Having Structure (2), 2-(1H-indol-3-yl)ethyl-6-O-(5-aminopentyl)-2,4-di-O-deoxy-β-D-glucopyranoside;

A. Methyl 2-0-benzoyl-4,6-0-isopropylidene-α-D-glucopyranoside

To a stirred solution of methyl 2-4,6-0-isopropylidene-α-D-glucopyranoside (28.8 g, 123 mmol) in 410 mL of dichloromethane at 0° C. was added triethylamine (25.7 mL, 185 mmol) followed by benzoic anhydride (30.73 g, 135 mmol). The solution was warmed to room temperature and stirred for 24 hours. The solvent was removed under reduced pressure and the residue was extracted with ethyl acetate (500 mL) and washed with H₂O (1×200 mL), a saturated salt solution (1×200 mL), and dried over magnesium sulfate. Concentration and flash chromatography (silica, 25% ethyl acetate in petroleum ether) provided the target compound (33.4 g, 80%) as a white form.

B. Methyl 2-0-benzoyl-3-0-(methylthio)thiocarbonyl-4,6-0-isopropylidene-α-D glucopyranoside To a stirred solution of methyl 2-0-benzoyl-4,6-0-isopropylidene-α-D-glucopyranoside (1 g, 2.95 mmol) in 10 mL of dry THF at −78° was added sodium bis(trimethyl silyl)amide (1M solution in THF, 3.54 mL, 3.4 mmol) followed immediately by carbon disulfide (248 µl, 4.13 mmol). After stirring the solution for 15 minutes at −78° C., methyl iodide (550 µl, 11.8 mmol) was added. The solution was stirred at −78° C. an additional 10 minutes and then brought to room temperature. After stirring 30 minutes, the reaction was quenched with 2 mL of H₂O, diluted with 60 mL of ether, washed with H₂O (1×30 mL), a saturated solution of NaCl (1×30 mL) and dried over magnesium sulfate. Removal of the solvent yielded a crude xanthate (1.52 g crude). A 1.28 g aliquot of the crude xanthate was used in the next step without further purification. The remaining 0.24 g of target compound was purified by flash chromatography (silica, 20% either in petroleum ether) to yield a white solid.

C. Methyl 2-0-benzoyl-3-deoxy-4,6-0-isopropylidene-α-D-glucopyranoside

To a solution of crude methyl 2-0-benzoyl-3-0-(methylthio)thiocarbonyl- 4,6-0-isopropylidene-α-D glucopyranoside (1.28 g, 2.48 mmol theoretically) in 10 mL of dry toluene at room temperature was added 2,2'-azobisisobutyronitrile (AIBN, 40 mg) followed by tributyl tin hydride (2 mL, 7.48 mmol). The reaction was heated to reflux for 2 hours. The toluene was removed under reduced pressure. The resulting oil was dissolved in 60 mL of acetonitrile and washed with petroleum ether (3×20 mL). Concentration of the acetonitrile and flash chromatography (silica, 10% ethyl acetate in petroleum ether) yielded pure target compound (585 mg, 73% from 3b) as a clear oil.

D. Methyl 3-deoxy-α-D-glucopyranoside

To a stirred suspension of methyl 2-0-benzoyl-3-deoxy-4,6-0-isopropylidene-α-D-glucopyranoside (520 mg, 1.61 mmol) in 8 mL of methanol at room temperature was added sodium methoxide (70 mg, 1.29 mmol). After stirring 2 h, the benzoyl group had been completely removed as evidenced by TLC. Amberlyst H⁺ resin was added and the mixture stirred for 1 hours until the generation of the free triol was completed as evidenced by TLC. After filtration, the solvents were removed under reduced pressure. Flash chromatography (silica, 10% methanol in methylene chloride) yielded pure target compound (286 mg. 100%) as an oil.

E. Methyl 2,4,6-tri-0-acetyl-3-deoxy-α-D-glucopyranoside

To a stirred solution of methyl 3-deoxy-α-D-glucopyranoside (535 mg, 3.0 mmol) in 10 mL of methylene chloride at 0° C. was added triethylamine (2.92 mL, 21.0 mmol), acetic anhydride (1.41 mL, 15.0 mmol) and dimethyl amino pyridine, one at a time (37 mg, 0.30 mmol). The solution was warmed to room temperature. After stirring 7 hours, the solution was diluted with mL of ethyl acetate and washed with H₂O (1×30 mL), a saturated solution of NaCl (1×30 mL), and dried over magnesium sulfate. Concentration and flash chromatography (silica, 40% ether in petroleum ether) provided pure target compound (820 mg. 90%) as a clear oil.

F. 1,2,4,6-tetra-0-acetyl-3-deoxy-α-D-glucopyranoside

To a stirred solution of methyl 2,4,6-tri-0-acetyl-3-deoxy-α-D-glucopyranoside (127 mg, 0.41 mmol) in 3 mL of acetic anhydride at 0° C. was added boron trifluoride etherate (15 µl, 0.12 mmol). The solution was warmed to room temperature, stirred for 1.25 hours, and poured into 30 mL of an ice cold saturated solution of NaHCO₃ and extracted with ethyl acetate (2×50 mL). The combined organic layers were washed with saturated aqueous NaHCO₃ and extracted with ethyl acetate (2×50 mL). The combined organic layers were washed with saturated aqueous NaHCO₃ (2×40 mL), saturated aqueous NaCl (1×40 mL), and dried over magnesium sulfate. Concentration and flash chromatography (silica, 30% ethyl acetate in petroleum ether) provided the target compound (133 mg, 96%) as an oil.

G. Bromo 2,4,6-tri-0-acetyl-3-deoxy-α-D-glucopyranoside

Hydrobromic acid (30% in acetic acid solution, 3 mL, 14.0 mmol) was added to 1,2,4,6-tetra-0-acetyl-3-deoxy-α-D-glucopyranoside (750 mg, 2.26 mmol) at 0° C. After 10 minutes, the resulting solution was warmed to room temperature for 30 minutes The solution was then diluted with ether (20 mL) and poured into a mixture of ice and a saturated solution of NaHCO₃ (25 mL). An additional 30 ML of ether was added and the layers were separated. The organic layer was washed with saturated aqueous NaHCO$_3$ (3×25 mL), H$_2$O (1×25 mL), saturated aqueous NaCl (1×25 mL), and dried over magnesium sulfate. Removal of the solvent provided crude target compound, which was used in the next step without further purification.

H. 2-(1-phenylsulfonyl-indol-3-yl)ethyl-2,4,6-tri-O-acetyl-3-deoxy-β-D-glucopyranoside To a stirred suspension of flame dried 4A sieves (1.33 g) in 11 mL of dry hexane at room temperature was added a solution of N-benzenesulfonyltryptophol (1.20 g, 4.0 mmol) in 4 mL of dry benzene. Next, a solution of the above bromo 2,4,6-tri-O-acetyl-3-deoxy-α-D-glucopyranoside (theoretically 2.26 mmol) in 4 mL of dry benzene was added, followed by silver (I) oxide (523 mg, 2.26 mmol). The reaction vessel was covered with aluminum foil and the suspension stirred for 3 days. After filtration through celite, concentration of the filtrate under reduced pressure and flash chromatography (silica, 10:1 methylene chloride:ether) provided pure target compound (781 mg, 60%) as a white foam.

I. 2-(1-phenylsulfonyl-indol-3-yl)ethyl-3-deoxy-β-D-glucopyranoside

To a stirred suspension of 2-(1-phenylsulfonyl-indol-3-yl)ethyl-2,4,6-tri-O-acetyl-3-deoxy-β-D-glucopyranoside (735 mg, 1.28 mmol) in 6.4 mL of methanol was added sodium methoxide (55.2 mg, 1.02 mmol) at room temperature. After 90 minutes, the resulting solution was diluted with 6.4 mL of methanol (6.4 mL) and neutralized by addition of amberlyst H$^+$ resin. The resin was quickly removed by filtration to avoid formation of the methyl glucoside. Concentration of the filtrate and flash chromatography (silica, 12:1:1 methylene chloride, acetone, methanol) afforded pure target compound (498 mg, 87%) as a white solid.

J. 2-(1-phenylsulfonyl-indol-3yl)ethyl-3-deoxy-6-0-tert-butyldiphenylsilyl-β-D-glucopyranoside To a stirred solution of 2-(1-phenylsulfonyl-indol-3-yl)-ethyl-3-deoxy-β-D-glucopyranoside (779 mg, 1.74 mmol) in 17 mL of dry DMF was added imidazole (260 mg, 3.83 mmol) followed by tert-butyldiphenylsilyl chloride (541 µl, 2.09 mmol) at room temperature. The solution was stirred at 50° C. for 24 hours. The reaction mixture was diluted with 250 mL of ethyl acetate and washed with H$_2$O (2×100 mL), saturated aqueous NaCl (1×100 mL), and dried over magnesium sulfate. Concentration and flash chromatography (silica, 3% methanol in methylene chloride) provided pure target compound (1.04 g, 87%) as a white foam.

K. 2-(1-phenylsulfonyl-indol-3yl)ethyl-3-deoxy-2,4-di-0-benzyl-6-0-tert-butyldiphenylsilyl-β-D-glucopyranoside To a stirred suspension of sodium hydride (4.63 mmol, 185 mg, 60% oil dispersion) in 5 mL of dry THF at 0° C. was added a solution of 2-(1-phenylsulfonyl-indol-3yl)ethyl-3-deoxy-6-0-tert-butyldiphenylsilyl-β-D-glucopyranoside (1.27 g, 1.85 mmol) in 10 mL of dry THF. After 10 minutes, the mixture was warmed to room temperature. After stirring 1 hours, the suspension was cooled to 0° C. and benzyl bromide (5.55 mmol. 660 µl) was added followed by tetrabutylammonium iodide (68 mg, 0.185 mmol). The mixture was warmed to room temperature and stirred for 3 days. The reaction was then quenched with 3 mL of aqueous saturated ammonium chloride at 0° C. The resulting solution was diluted with 80 mL of ether and washed with H$_2$O (2×30 mL), saturated aqueous NaCl (1×30 mL), and dried over magnesium sulfate. Concentration under reduced pressure and flash chromatography (silica, 25% ether in petroleum ether) provided pure target compound (760 mg, 47%) as a white foam.

L. 2-(1-phenylsulfonyl-indol-3yl)ethyl-3-deoxy-2,4-di-o-benzyl-β-D-glucopyranoside To a stirred solution of 2-(1-phenylsulfonyl-indol-3yl)-ethyl-3-deoxy-2,4-di-0-benzyl-6-0-tert-butyldiphenylsilyl-β-D-glucopyranoside (675 mg, 0.780 mmol) in 10 mL of dry THF was added tetrabutylammonium fluoride (1M solution in THF, 1.17 mmol, 1.17 mL) at room temperature. After stirring 2 hours, the solution was diluted with 80 mL of ethyl acetate and washed with H$_2$O (1×30 mL), saturated aqueous NaCl (1×30 mL), and dried over magnesium sulfate. Concentration and flash chromatography (silica, 60% ether in petroleum ether) afforded pure target compound (445 mg, 91%) as an oil.

M. 2-(1-Phenylsulfonyl-indol-3yl)ethyl-3-deoxy-2,4-di-O-benzyl-6-O-trifluoromethylsulfonyl-β-D-glucopyranoside To a stirred solution of 2-(1-phenylsulfonyl-indol-3yl)-ethyl-3-deoxy-2,4-di-o-benzyl-β-D-glucopyranoside (360 mg, 0.575 mmol) in 3 mL of dichloromethane at −78° C. was added, 2.6 di-tert-butyl-4-methylpyridine (189 mg, 0.92 mmol) followed by triflic anhydride (126 µl, 0.748 mmol). After stirring 20 minutes at −78° C., the mixture was allowed to warm to room temperature for 20 minutes. The suspension was poured into aqueous saturated NaHCO$_3$ (15 mL) and extracted with ethyl acetate (1×35 mL). The organic layer was washed with saturated aqueous NaHCO$_3$ (3×15 mL), saturated aqueous NaCl (1×15 mL) and dried over magnesium sulfate. Concentration afforded crude target compound as an oil which was used in the next step without further purification.

N. 2-(1-Phenylsulfonyl-3-yl)ethyl-2,4-di-0-benzyl-3-deoxy-6-0-(N-trifluoroacetyl-5-aminopentyl)-β-D-glucopyranoside To a stirred suspension of sodium hydride (8.63 mmol, 345 mg, 60% dispersion in oil) in 20 mL of dry THF at 0° C. was added a solution of N-trifluoro acetyl 5-amino pentanol (687 mg, 3.45 mmol) in 16 mL of dry THF. After stirring 10 minutes at 0° C., the suspension was allowed to warm to room temperature and stir for 90 minutes. The reaction mixture was then cooled to 0° C. and a solution of crude triflate of step M (theoretically 0.575 mmol) in 22 mL of dry dichloromethane was added. The suspension was stirred for 30 minutes at 0° C. and then warmed to room temperature. After stirring for an additional 24 hours, the reaction was quenched at 0° C. with 10 mL of saturated aqueous ammonium chloride. The resulting mixture was diluted with ethyl acetate (200 mL) and washed with H$_2$O (1×75 mL), saturated aqueous NaCl (1×75 mL) and dried over magnesium sulfate. Concentration and flash chromatography (silica, eluted column 5 times with 1% methanol in methylene chloride to 2% methanol in methylene chloride) afforded the target compound (392 mg) as a white foam which was used without further purification in the next step.

O. Structure (2), 2-(1H-indol-3-yl)ethyl-6-0-(5-aminopentyl)-2,4-di-0-deoxy-β-D-glucopyranoside.

To a stirred solution of 2-(1-phenylsulfonyl-indol-3yl)-ethyl-3-deoxy-2,4-di-O-benzyl-6-O-trifluoromethylsulfonyl-β-D-glucopyranoside (392 mg, theoretically 0.575 mmol) in 6 mL of ethanol at room temperature was added a solution of 5M NaOH (1 mL, 5 mmol). The solution was allowed to reflux for 2 hours. The solvents were removed under reduced pressure, and the reaction mixture was diluted with dichloromethane (75 mL) and washed with aqueous HCl (25 mL, 5 mmol). The water layer was re-extracted with dichloromethane (2×75 mL). The combined organic layers were washed with saturated aqueous NaCl (2×25 ML) and dried over magnesium sulfate. Concentration and flash chromatography (silica, 8% methanol in dichloromethane)

afforded the pure product, structure (7) (172 mg, 52% for 3 steps) as an oil. $R_f$ 0.22 (8% methanol in dichloromethane); $^1$H NMR (500 MHz, CDCl$_3$) δ8.44 (s, 1H), 7.57 (d, J=7.7 Hz, 1H), 7.31–7.23 (m, 10H), 7.17–7.14 (m, 1H), 7.11–7.07(m, 1H), 7.04(d, J=2.0 Hz, 1H), 4.71 (d, J=11.8 Hz, 1 h), 4.57 (d, J=11.7 Hz, 1H), 4.56 (d, J=11.9 Hz, 1H), 4.46(d, J=7.5 Hz, 1H), d, J=11.5 Hz, 1H, 4.20 (ddd, J=13.8, 9.4, 6.8 Hz, 1H), 3.87 (ddd, J=14.9, 9.3., 7.4 Hz, 1H), 3.55–3.50 (m, 3H), 3.32–3.26 (M, 2H0, 3.11 (t, J=7.2 Hz 2H), 3.02 (dd, J=12.4, 2.9 Hz, 1H), 2.68 (dd, J=12.4, 8.1 Hz, 1H), 2.67–2.57 (m, 2H), 2.50 (ddd, J=12.3, 4.8, 4.8 Hz, 1H), 2.20 (s, 3 h), 1.57–2.44(m, 5H), 1.36–1.30(m,2H); $^{13}$C NMR (500 MHz, CDCl$_3$) δ138.61, 137.92, 136.14, 128.41, 128.27, 127.79, 127.70, 127.53, 127.49, 122.18, 121.84, 119.18, 118.67, 112.56, 111.12, 105.22, 105.18, 76.53, 75.14, 74.28, 72.69, 70.99, 69.91, 62.45, 50.69, 49.49, 34.86, 32.28, 29.16, 25.80, 23.27; IR (thin film) 3325(m), 3065(w), 3035(w), 3015(w), 2940(s), 2870(s), 1500(w), 1458(m), 1354(w), 1220(w), 1076(s), 1030(m), 745(s), 700(s), cm$^{-1}$, UV-Vis (c=6.5×1$^{-5}$. acetonitrile) $\lambda_{max}$ 281.2(ξ=6.2×10$^3$), 218.8 (ξ=3.62×10$^4$) nm; HRMS m/e calc'd for C$_{35}$H$_{44}$N$_2$O$_5$ (M+H): 573.3315, found 573.3314; [α]D$^{20}$+16.7° (c=0.15, acetonitrile).

EXAMPLE 4

Preparation of Analog Having Structure (13), Methyl 2,3,4-tri-o-benzyl-6-O-(N-trifluoroacetyl-5-aminopentyl)-β-D-glucopyranoside A. Methyl 6-O-tert-butyldiphenylsilyl-β-D-glucopyranoside To a stirred solution of methyl β-D-glucopyranoside (5 g, 25.7 mmol) in 51 mL of dry DMF was added at room temperature imidazole (5.46 g, 80.2 mmol) followed by tert-butyldiphenylsilyl chloride (11.3 mL, 43.4 mmol). The solution was heated to 50° C. for 24 hours and the DMF was removed under reduced pressure. The reaction mixture was diluted with 200 mL of ethyl acetate and washed with H$_2$O (1×100 mL), saturated aqueous NaCl (1×100 mL), and dried over magnesium sulfate. Concentration and flash chromatography (silica, 4% methanol in dichloromethane) provided pure target compound (9.82 g, 88%) as a white foam.

B. Methyl 6-O-tert-butyldiphenylsilyl-2,3,4-tri-O-benzyl-β-D-glucopyranoside

To a stirred suspension of sodium hydride (1.67 g, 41.6 mmol) in 100 mL of dry THF was added at 0° C. a solution of methyl 6-O-tert-butyldiphenylsilyl-β-D-glucopyranoside (4.0 g, 9.25 mmol) in 50 mL of dry THF. After 5 minutes, the suspension was warmed to room temperature and stirred for 1 hour. Benzyl bromide (5.50 mL, 46.2 mmol) was added at room temperature followed by tetrabutylammonium iodide (341 mg, 0.93 mmol). The suspension was warmed to 50° C. and stirred for 4 days. After quenching with 40 mL of saturated aqueous ammonium chloride, the resulting mixture was diluted with ether (600 mL) and washed with H$_2$O (2×200 mL), saturated aqueous NaCl (1×200 mL), and dried over magnesium sulfate. Concentration and flash chromatography (silica, 10% ether in petroleum ether) provided pure target compound (4.48 g, 69%) as a clear oil.

C. Methyl 2,3,4-tri-O-benzyl-β-D-glucopyranoside

To a stirred solution of methyl 6-O-tert-butyldiphenylsilyl-2,3,4-tri-O-benzyl-β-D-glucopyranoside(2.81 g, 3.98 mmol) in dry THF (40 ml, 0.1M) at room temperature was added tetrabutyl ammonium fluoride (4.37 ml, 4.37 mmol, 1M solution in THF). After stirring for 3 hours, the reaction solution was diluted with ethyl acetate (300 ml) and washed with water (1×100 ml) and saturated aqueous NaCl (1×100 ml), and dried with magnesium sulfate. Concentration and flash chromatography (silica, 50% ether in petroleum ether) provided pure target compound (1.62 g, 88%) as a white solid.

D. Methyl 2,3,4-tri-O-benzyl-6-O-trifluoromethylsulfonyl-β-D-glucopyranoside

To a stirred solution of methyl 6-O-tert-butyldiphenylsilyl- 2,3,4-tri-O-benzyl-β-D-glucopyranoside (800 mg, 1.71 mmol) in 8.55 mL of dry dichloromethane at −78° C. was added 2,6-di-tert-butyl-4-methyl pyridine (632 mg, 3.08 mmol) followed by triflic anhydride (345 µl, 2.05 mmol). After stirring 15 minutes at −78° C., the mixture was warmed to room temperature over 20 minutes, and then poured into a solution of saturated aqueous NaHCO$_3$ (20 mL) and extracted with ethyl acetate (50 mL). The organic layer was washed with saturated NaHCO$_3$ (3×20 mL), saturated aqueous NaCl (1×20 mL), and dried over magnesium sulfate. Concentration provided crude target compound, which was used in the next step without further purification.

D. Structure (13), Methyl 2,3,4-tri-O-benzyl-6-O-(N-trifluoroacetyl- 5-aminopentyl)-β-D-glucopyranoside To a stirred suspension of sodium hydride (855 mg, 21.4 mmol, 60% oil dispersion) in 60 mL of dry THF at 0° C. was added a solution of N-trifluoroacetyl-5-aminopentanol (1.7 g, 8.6 mmol) in 35 mL of dry THF. After stirring 10 minutes at 0° C., the suspension was warmed to room temperature, stirred for 1 hour, and cooled to 0° C. A solution of the above crude methyl 2,3,4-tri-O-benzyl-6-O-trifluoromethylsulfonyl-β-D-glucopyranoside (theoretically 1.71 mmol) in 57 mL of dry dichloromethane was added. The reaction mixture was stirred at 0° C. for 30 minutes and then warmed to room temperature. After stirring 24 hours, the reaction was cooled to 0° C. and quenched with 40 mL of saturated aqueous ammonium chloride. The resulting solution was diluted with ethyl acetate (400 mL) and washed with H$_2$O (1×150 mL), saturated aqueous NaCl (1×150 mL) and dried over magnesium sulfate. Concentration and flash chromatography (silica, 30% ethyl acetate in petroleum ether) provided the analog having structure (13), methyl 2,3,4-tri-O-benzyl-6-O-(N-trifluoroacetyl-5-aminopentyl)-β-D-glucopyranoside, (799 mg) as a white solid which was used without further purification.

EXAMPLE 5

Preparation of Analog Having Structure (8), Methyl 6-O-(5-aminopentyl)-2,3,4-tri-O-benzyl-β-D-glucopyranoside, To a stirred solution of methyl 2,3,4-tri-O-benzyl-6-O-(N-trifluoroacetyl-5-aminopentyl)-β-D-glucopyranoside (799 mg, theoretically 1.71 mmol, structure (13) from Example 4) in 10 mL of ethanol at room temperature was added a solution of 5M (3 mL, 15 mmol). The solution was heated to reflux for 2 hours. The solvents were removed under reduced pressure. The reaction mixture was diluted with dichloromethane (70 mL) and washed with aqueous HCl (25 mL, 15 mmol). The water layer was re-extracted with dichloromethane (3×50 mL), and the combined organic layers were washed with saturated aqueous NaCl (1×75 mL) and dried over magnesium sulfate. Concentration and crystallization from ethyl acetate/petroleum ether provided pure analog having structure (8), methyl 6-O-(5-aminopentyl)-2, 3,4-tri-O-benzyl-β-D-glucopyranoside, (675 mg, 72% from methyl 2,3,4-tri-O-benzyl-6-O-trifluoromethylsulfonyl-β-D-glucopyranoside) as a white solid: m.p. 95°–95.5° C.; $R_F$ 0.19 (6% methanol in dichloromethane); $^1$H NMR (500 MH$_z$, CDCl$_3$) δ7.35–7.24 (m, 15H), 4.92 (d, J=7.5 Hz 1H), 4.90 (d, J=7.6 Hz, 1H), 4.85 (d, J=11.0 Hz, 1H), 4.78 (d, J=11.0 Hz, 1H), 4.70 (d, J=11.0 Hz, 1H), 4.60 (d, J=11.0 Hz, 1H), 4.32 (7.8, 1H), 3.66–3.59 (m, 3H), 3.56 (s, 3H), 3.48–3.36 (m, 3H), 2.94 (dd, J=12.5, 2.1 Hz, 1H), 2.68 (dd, J=12.0, 6.8 Hz, 1H), 2.64–2.53 (m, 2H), 1.71 (s, 2H), 1.59–1.53 (m. 2H), 1.51–1.45 (m, 2H), 1.42–1.36 (m, 2H), $^{13}$C NMR (500 MHz, CDCl$_3$) δ138.55, 138.47, 138.17, 128.39, 128.33, 128.03, 127.95, 127.85, 127.77, 127.60, 127.57, 104.72, 84.56, 82.45, 79.74, 75.66, 75.02, 74.74, 74.16, 62.62, 57.20, 50.69, 49.72, 32.49, 29.65, 23.37; IR (thin film) 3280(m), 3095(w), 3065(w), 3035(w), 2935(s), 2915(s), 2860(s), 1496(w), 1454(m), 1404(w), 1393(w), 1358(m), 1214(m), 1115(s), 1072(s), 1037(m), 1027(m), 1009(m), 911(w), 826(s), 747(s), 696(s) cm$^{-1}$; HRMS m/e calc'd for C$_{33}$H$_{43}$O$_6$N (M+H): 550.3168, found 550.3179; $[α]D^{20}$+9.3° (c=0.15, acetonitrile).

EXAMPLE 6

Preparation of Analog Having Structure (12), 2-(1H-Indol-3yl)ethyl-2,3,4-tri-O-benzyl-β-D-glucopyranoside To a stirred solution of 2-(1-phenylsulfonyl-indol-3-yl-)ethyl- 2,3,4-tri-O-benzyl-β-D-glucopyranoside (100 mg, 0.136 mmol, prepared in Example 1, step G) in 3 ml of ethanol at room temperature was added a solution of 5M NaOH (1 mL, 5 mmol). The reaction mixture was refluxed for 2 h and the solvents were removed under reduced pressure. The resulting residue was diluted with dichloromethane (70 mL) and washed with aqueous HCl (24 mL, 5 mmol). The water layer was reextracted with dichloromethane (2×70 mL). The organic layers were combined and washed with saturated aqueous NaCl (1×50 mL) and dried over magnesium sulfate. Concentration and flash chromatography (silica, 25% ethyl acetate in petroleum ether) provided structure (12) (68 mg, 85%) as an oil: $R_F$ 0.42 (40% ethyl acetate in petroleum ether); $^1$H NMR (500 MHz, CDCl$_3$) d 7.83 (s, 1H), 7.59 (d, J=7.8 Hz, 1H), 7.33–7.24 (m, 15H), 7.20–7.17 (m, 2H), 7.11 (t, J=7.8 Hz, 1H), 7.01 (d, J=1.8 Hz, 1H), 4.91 (d, J=10.9 Hz, 1H), 4.85 (d, J=10.9, 1H), 4.80 (d, J=10.9 Hz, 1H), 4.79 (d, J=11.0 Hz, 1H), 4.64 (d, J=11.0 Hz, 1H), 4.63 (d, J=11.0 Hz, 1H), 4.49 (d, J=7.8 Hz, 1H), 4.22 (ddd, J=9.4, 6.7, 6.7 Hz, 1H), 3.90–3.82 (m, 2H), 3.72–3.67 (m, 1H), 3.65 9 ap. t, J=9.1 Hz, 1H), 3.56 (ap. t, J=9.3 Hz, 1H), 3.42 (ap. t, J=8.1 Hz, 1H), 3.35 (ddd, J=9.5, 4.3, 2.8 Hz, 1H), 3.11 (t, J=7.0 Hz, 2H), 1.87 (dd, J=7.6, 5.9 Hz, 1H); $^{13}$C NMR (500 MHz, CDCl$_3$) d 138.52, 138.44, 137.98, 136.17, 128.46, 128.36, 128.29, 128.05, 128.00, 127.89, 127.86, 127.60, 127.57, 127.45, 122.09, 122.01, 119.34, 118.68, 112.60, 111.13, 103.69, 84.49, 77.57, 75.64, 75.04, 75.01, 74.75, 70.25, 62.04, 25.86; IR (thin film) 3575(sh), 3435(m), 3085(sh), 3065(w), 3035(w), 2925(m), 2880(m), 1500(w), 1455(m), 1360(w), 1310(w), 1150(sh), 1085(s), 1030(s), 920(w), 810(w), 740(s), 700(s) xm$^{-1}$; UV-Vis (c=2.89×10$^{-4}$, acetonitrile) I$_{max}$ 289.6 (e=3.56× 10$^3$), 281.2 (e=4.24×10$^3$), 222.4 (e=1.01×10$^4$) nm; HR MS m/e calc'd for C$_{37}$H$_{39}$O$_6$N(M+NH$_4$): 611.3121, found 611.3043; $[α]D^{20}$–2.5° (c=1.37, acetonitrile).

EXAMPLE 7

Preparation of Analog Having Structure (10), 2-(1H-Indol-3-yl)ethyl-6-O-aminopentyl)-2,3-di-O-benzyl-4-deoxy-β-D-glucopyranoside A. Methyl 2,3,6-tri-O-benzoyl-4-(methylthio)thiocarbonyl-α-D-glucopyranoside To a solution of the methyl 2,3,6-tri-O-benzoyl-4-O-α-D-glucopyranoside (5.00 g, 9.87 mmol) in 100 mL of dry THF at –78° C. was added carbon disulfide (0.45 mL, 7.48 mmol) followed by sodium bis(trimethylsilyl)amide (10.5 mL, 51.8 mmol). The solution was stirred at –78° C. for 20 minutes. Methyl iodide (2.10 mL, 33.7 mmol) was added, the solution was stirred for 5 minutes at –78° C. and then at room temperature for 45 minutes. The reaction was quenched by the addition of water (5 mL) and the mixture was by extracted with ethyl acetate (2×100 mL). The organic layer was washed with a saturated solution of sodium chloride, and dried over anhydrous sodium sulfate. The solvent was removed under reduced pressure to yield a pale yellow oil (5.70 g, 97%). The crude xanthate was used without purification in the next step. An analytical sample was purified by flash column chromatography using 20% ethyl acetate in petroleum ether to yield the target compound as white crystals.

B. Methyl 2,3,6-tri-O-benzoyl-4-deoxy-α-D-glucopyranoside

To a solution of the crude methyl 2,3,6-tri-O-benzoyl-4-(methylthio)thiocarbonyl-α-D-glucopyranoside (5.70 g, 9.55 mmol) in 120 mL of dry toluene was added AIBN (50 mg). Tributyl tin hydride (6.68 mL, 24.8 mmol) was added and the reaction was heated to reflux for 4 hours. The toluene was removed under reduced pressure. Acetonitrile (200 mL) was added and the mixture extracted with petroleum ether (5×100 mL) to remove all tin salts. After drying over anhydrous sodium sulfate, the solvent was removed under reduced pressure to yield a clear colorless oil which solidified on standing. Purification by flash column chromatography using 20% ethyl acetate in petroleum ether as the eluant gave the target compound as a white solid.

C. 1-O-Acetyl-2,3,6-tri-O-benzoyl-4-deoxy-α-D-glucopyranose

To a solution of methyl glycoside methyl 2,3,6-tri-O-benzoyl- 4-deoxy-α-D-glucopyranoside (0.50 g, 1.1 mmol) in acetic anhydride (3.0 mL, 32 mmol) at 0° C. was added boron trifluoride etherate (0.1 mL). The solution was stirred at room temperature for 4 hours, diluted with ethyl acetate and poured in an ice-cold solution of saturated sodium bicarbonate. Extraction with ethyl acetate (2×100 mL) was followed by washing with a saturated solution of sodium chloride. The organic layer was dried over anhydrous sodium sulfate and evaporated under reduced pressure to yield the product as a colorless oil which crystallized upon standing to give the target compound as white needles (0.45 g, 85%).

D. 1-Bromo-2,3,6,-tri-O-benzoyl-4-deoxy-α-D-glucopyranose

To a stirred solution of 1-O-acetyl-2,3,6-tri-O-benzoyl-4-deoxy-α-D-glucopyranose (0.137 g, 0.29 mmol) in 3.0 mL of dry dichloromethane at 0° C. was added 30% hydrogen bromide in acetic acid (0.07 mL, 0.33 mmol). The solution was stirred under argon at room temperature for 4 hours, diluted with ethyl acetate (100 mL) and extracted with a saturated solution of sodium bicarbonate. The organic layer was washed with a saturated solution of sodium chloride, dried over anhydrous sodium sulfate and evaporated under reduced pressure to yield the target compound as a colorless oil which solidified upon standing. Crystallization from ether and petroleum ether gave the target compound as white crystals (0.15 g, 100%).

E. 2-(1-Phenylsulfonyl)-indol-3-yl-ethyl-2,3,6-tri-O-benzoyl- 4-deoxy-β-D-glucopyranoside To a mixture of activated powdered 4 Å molecular sieves (0.83 g), the protected tryptophol prepared in Example 1, step B (0.37 g, 1.23 mmol) and silver (I) oxide (0.83 g, 3.58 mmol) in a flask wrapped with aluminum foil was added a solution of 1-bromo- 2,3,6,-tri-O-benzoyl-4-deoxy-α-D-glucopyranose (0.40 g, 0.814 mmol) in 16.7 mL of 40% hexane in benzene. The mixture was stirred under argon for two days, filtered through celite, washed with ethyl acetate and the solvent was removed to yield a colorless oil. Purification by flash column chromatography using 50% ether in petroleum ether gave the target compound as a colorless solid (0.50 g, 81%).

F. 2-(1-Phenylsulfonyl)-indol-3-yl-ethyl-4-deoxy-β-D-glucopyranoside

To a solution of 2-(1-phenylsulfonyl)-indol-3-yl-ethyl-2,3,6-tri-O-benzoyl-4-deoxy-β-D-glucopyranoside (120 mg, 0.158 mmol) in 20 mL of methanol was added sodium methoxide (0.027 g, 0.507 mmol). The solution was stirred under argon overnight. Amberlyst H+ resin was added and the reaction stirred until neutral to wet pH paper. The resin was removed by filtration and washed with methanol. The filtrate was concentrated under reduced pressure to yield a tan solid. Purification by flash column chromatography using 10% methanol in dichloromethane gave the target compound as a white solid (65 mg, 91%).

G. 2-(1-Phenylsulfonyl)-indol-3-yl-ethyl-6-O-tert-butyldiphenylsilyl- 4-deoxy-β-D-glucopyranoside To a solution of diol 2-(1-phenylsulfonyl)-indol-3-yl-ethyl- 4-deoxy-β-D-glucopyranoside (0.24 g, 05.536 mmol) in 6 mL of dry DMF was added imidazole (73 mg, 1.07 mmol) followed by tert-butyldiphenylsilyl chloride (0.17 mL, 0.643 mmol). The solution was heated under argon in an oil bath at 70° C. for 48 hours. The reaction was quenched by addition of methanol (5 mL). The solvents were removed under reduced pressure. The residue was extracted with ethyl acetate (2×200 mL), washed with a saturated solution of sodium chloride and dried over anhydrous sodium sulfate. Removal of the solvent under reduced pressure gave a pale yellow oil. Purification by flash column chromatography using 3% methanol in dichloromethane gave the target compound as a colorless oil (0.36 g, 97%).

H. 2-(1-Phenylsulfonyl)-indol-3-yl-ethyl-2,3,-di-O-tert-butyldiphenylsilyl- 4-deoxy-β-D-glucopyranoside To a stirred suspension of sodium hydride (73.0 mg. 3.04 mmol, 60% oil dispersion) in 2.7 mL of dry THF at 0° C. was added a solution of diol 2-(1-phenylsulfonyl)-indol-3-yl-ethyl-6-O-tert-butyldiphenylsilyl- 4-deoxy-β-D-glucopyranoside (0.50 g, 0.729 mmol) in dry THF (6.8 mL). The reaction mixture was stirred at room temperature for 30 minutes. The mixture was cooled to 0° C. and benzyl bromide (0.26 mL, 2.18 mmol) was added dropwise. After stirring at room temperature for 3 days, the reaction was quenched by addition of ammonium chloride (10 mL) followed by extraction with ether (2×100 mL). The organic layer was washed with a saturated solution of sodium chloride, dried over anhydrous sodium sulfate and evaporated under reduced pressure to yield a pale yellow oil. Purification by flash column chromatography using 33% ether in petroleum ether afforded the target compound as a colorless oil (0.73 g, 76%).

I. 2-(1-Phenylsulfonyl)-indol-3-yl-ethyl-2,3,-di-O-benzyl- 4-deoxy-β-D-glucopyranoside To a solution of the 2-(1-phenylsulfonyl)-indol-3-yl-ethyl- 2,3,-di-O-benzyl-6-0-tert-butyldiphenylsilyl-4-deoxy-β-D-glucopyranoside (0.37 g, 0.427 mmol) in 10.5 mL of dry THF was added tetrabutylammonium fluoride (1.33 mL, 1M in THF, 1.33 mmol). The solution was stirred under argon for 3 hours, diluted with ethyl acetate (100 mL) and washed with water (100 mL). The organic layer was washed with a saturated solution of sodium chloride and dried over anhydrous sodium sulfate. Removal of the solvents under reduced pressure yielded a pale yellow oil. Purification by flash column chromatography using 33% petroleum ether in ethyl acetate yielded the target compound as a colorless oil (0.43 g, 85%).

J. 2-indol-3-yl-ethyl-2,3,-di-O-benzyl-4-deoxy-β-D-glucopyranoside

To a solution of the 2-(1-phenylsulfonyl)-indol-3-yl-ethyl- 2,3,-di-O-benzyl-4-deoxy-β-D-glucopyranoside (140 mg, 0.223 mmol) in 6.0 mL of ethanol was added 5M NaOH (2 mL) and the solution heated to reflux for hours. The solvents were removed under reduced pressure and the residue taken up in water (100 mL) and extracted with ethyl acetate (3×100 mL). The organic phase was washed with a saturated solution of sodium chloride, dried with anhydrous sodium sulfate and concentrated to yield a colorless oil. Purification by flash column chromatography using 3% methanol in dichloromethane yielded the target compound as a colorless oil (100 mg, 92%).

K. 5-Phthalimido-1-pentanol

To a solution of 5-amino-1-pentanol (5.00 g, 48.5 mmol) in benzene (150 mL) was added N-carboethoxyphthalimide (11.0 g, 50.2 mmol) and the solution was stirred at room temperature for 5 h). The solvents were removed under reduced pressure to yield a yellow oil. Purification by flash column chromatography using 25% ethyl acetate in petroleum ether yielded the target compound as a clear colorless oil (9.6 mg, 84%).

L. 5-Phthalimido-1-O-trifluoromethanesulfonylpentanol

To a solution of 5-phthalimido-1-pentanol (39.1 mg, 0.168 mmol) in dry dichloromethane (1.5 mL) was added 2,6-di-tert-butyl-4-methylpyridine (34.5 mg, 0.168 mmol) followed by triflic anhydride (28.3 µg, 0.168 mmol). The solution was stirred at room temperature for 10 minutes. The reaction was poured into water (25 mL) and extracted with dichloromethane (2×50 mL). The organic layer was washed with a saturated sodium chloride solution and dried with anhydrous sodium sulfate. The solvents were removed under reduced pressure to yield a pale yellow solid which was used immediately without further purification.

M. 2-(1-Phenylsulfonyl-3-yl)ethyl-2,3-di-O-benzyl-4-deoxy- 6-O(phthalimidopentyl)-β-D-glucopyranoside To a solution of 5-phthalimido-1-O-trifluoromethanesulfonylpentanol (theoretically 0.168 mmol) in dry dichloromethane (1.5 mL) was 2,6-di-tert-butyl-4-methylpyridine (34.5 mg, 0.168 mmol). The solution was cooled to 0° C. and to it was added a solution of 2-indol-3-yl-ethyl-2,3,-di-O-benzyl-4-deoxy-β-D-glucopyranoside (18.4 mg, 0.029 mmol, from step J, above) in dry dichloromethane (1.5 mL). The solution was stirred for 30 minutes at 0° C. and then sodium hydride (7.0 mg, 0.29 mmol, 60% dispersion in oil) was added. Stirring was continued at 0° C. for 1 hour and then at room temperature for 24 hours. The reaction was poured into water (50 mL) and extracted with dichloromethane (2×100 mL). The organic layers were combined and washed with a saturated sodium chloride solution followed by drying with anhydrous sodium sulfate. The solvents were removed under reduced pressure to yield a pale yellow oil. Purification by flash column chromatography using 20% ethyl acetate in petroleum ether yielded the target compound as a clear colorless oil (19.4 mg, 80%).

N. Structure (10), 2-(1H-Indol-3-yl)ethyl-6-O-aminopentyl)- 2,3-di-O-benzyl-4-deoxy-β-D-glucopyranoside To a solution of 2-(1-phenylsulfonyl-3-yl)ethyl-2,3-di-O-benzyl- 4-deoxy-6-O(phthalimidopentyl)-β-D-glucopyranoside (150 mg, 0.178 mmol) in methanol (8 mL) was added sodium methoxide (40 mg, 0.740 mmol). The solution was heated to reflux for 24 hours. The reaction was poured into water (100 mL) and extracted with dichloromethane (2×100 mL). The organic layers were combined and washed with a saturated solution of sodium chloride and dried with anhydrous sodium sulfate. Concentration of the solvents under reduced pressure yielded a pale yellow oil. Purification by flash column chromatography using 10% methanol in dichloromethane yielded structure (10) as a colorless oil (72.0 mg, 71%) $R_f$ 0.32 (10% methanol in dichloromethane); $^1$H NMR (500 MHz, CDCl$_3$) δ7.74 (brm, 1H), 7.48 (d, J=7.8 Hz, 1H), 7.36–6.93 (m, 15H), 4.62–4.49 (m, 4H), 4.32 (d, J=7.7 Hz, 1H), 4.11 (dt, J=9.4, 6.7 Hz, 1H), 3.78 (dt, 9.2, 7.4 Hz, 1H), 3.52 (m, 4H), 3.26 (m, 2H), 3.22 (t, J=7.2 Hz, 1H), 3.13 (t, J=7.8 Hz, 1H), 3.00 (t, J=7.0 Hz, 2H), 2.00 (ddd, J=6.7, 5.2, 1.4 1H), 1.29 (m, 9H); $^{13}$C NMR (500 MHz, CDCl$_3$) δ140.11, 138.10, 130.75, 130.59, 129.31, 128.92, 128.84, 128.57, 128.44, 122.24, 119.40, 112.82, 112.31, 105.01, 84.13, 79.55, 75.76, 74.12, 73.12, 72.53, 72.18, 71.29, 41.05, 34.54, 30.38, 29.90, 27.07, 24.72, IR (CHCl$_3$) 3350, 3060, 2930, 2860, 1630, 1520, 1450, 1400, 1270, 1100, 740, 700; UV (c=1.57×10$^{-4}$M, acetonitrile) $\lambda_{max}$ 280.0 (ε=1.41×10$^3$), 224.8 (ε=1.66×10$^3$) nm; HRMS m/e calc'd for C$_{35}$H$_{45}$N$_2$O$_5$ (M+H): 573.3328, found 573.3301; [α]D$^{20}$+3.89° (c=1.8, acetonitrile).

EXAMPLE 8

Preparation of Analog Having Structure (11), 2-Indol-3-yl-ethyl-2,3,-di-O-benzyl-4-deoxy-β-D-glucopyranoside To a solution of 2-(1-phenylsulfonyl)-indol-3ylethyl-2,3,-di-O-benzyl-4-deoxy-β-D-glucopyranoside (140 mg, 0.223 mmol, from Example 7, step I, above) in 6.0 mL of ethanol was added 5M NaOH (2 mL) and the solution heated to reflux for 2 hours. The solvents were removed under reduced pressure and the residue taken up in water (100 mL) and extracted with ethyl acetate (3×100 mL). The organic phase was washed with a saturated solution of sodium chloride, dried with anhydrous sodium sulfate and concentrated to yield a colorless oil. Purification by flash column chromatography using 3% methanol in dichloromethane yielded the analog having structure (11) (2-indol-3-yl-ethyl-2,3,-di-O-benzyl-4-deoxy-β-D-glucopyranoside) as a colorless oil (100 mg, 92%). $R_f$ 0.59 (10% methanol in dichloromethane); $^1$H NMR (500 MHz, CDCl$_3$) δ7.86 (br s, 1H), 7.59 (d, J=7.8 Hz, 1H), 7.31–6.99 (m, 14H), 4.78–4.66 (m, 4H), 4.41 (d, J=7.7 Hz, 1H), 4.22 (dt, J=9.4, 7.4 Hz, 1H), 3.61–3.56 (m, 3H), 3.49–3.45 (m, 1H), 3.32 (t, J=7.9 Hz, 1H), 3.11 (t, J=6.9 Hz, 2H), 2.03 (br s, 1H), 1.95 (ddd, J=12.8, 5.3, 1.8 Hz, 1H), 1.49 (q, J=11.7 Hz, 1H); $^{13}$C NMR (500 MHz, CDCl$_3$) δ138.72, 138.48, 136.12, 128.33, 128.20, 127.97, 127.60, 127.56, 127.46, 122.15, 121.92, 119.27, 118.66, 112.57, 111.10, 103.87, 82.81, 78.10, 74.86, 72.23, 72.13, 70.18, 65.17, 32.69, 25.84; UV-Vis (c=1.85×10$^{-4}$, acetonitrile) $\lambda_{max}$281.2 (ξ=614.13), 220.0 (ξ=864.86) nm; HRMS m/e calculated for C$_{30}$H$_{34}$NO$_5$ (M+H): 488.2436, found 488.2483; [α]D$^{20}$+5.55° (c=1.8, acetonitrile).

EXAMPLE 9

Preparation of Imidazol Compounds

Figure 2:
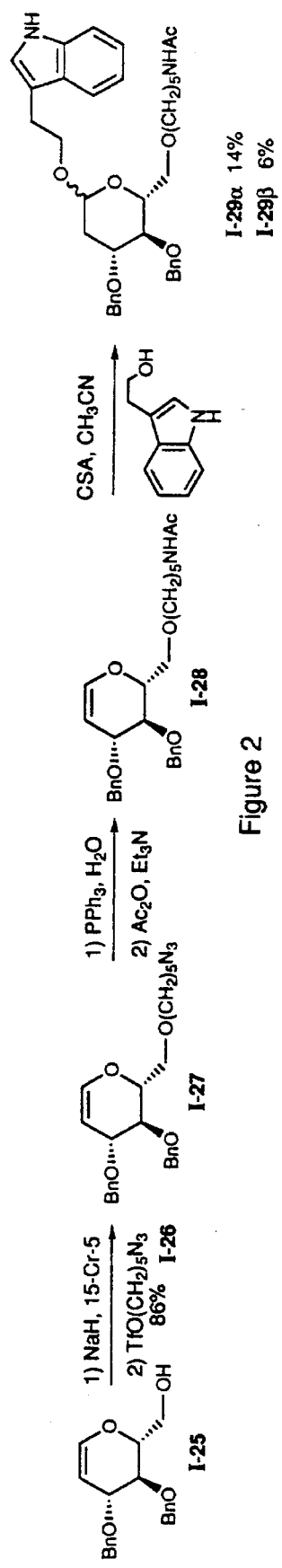
Figure 3:
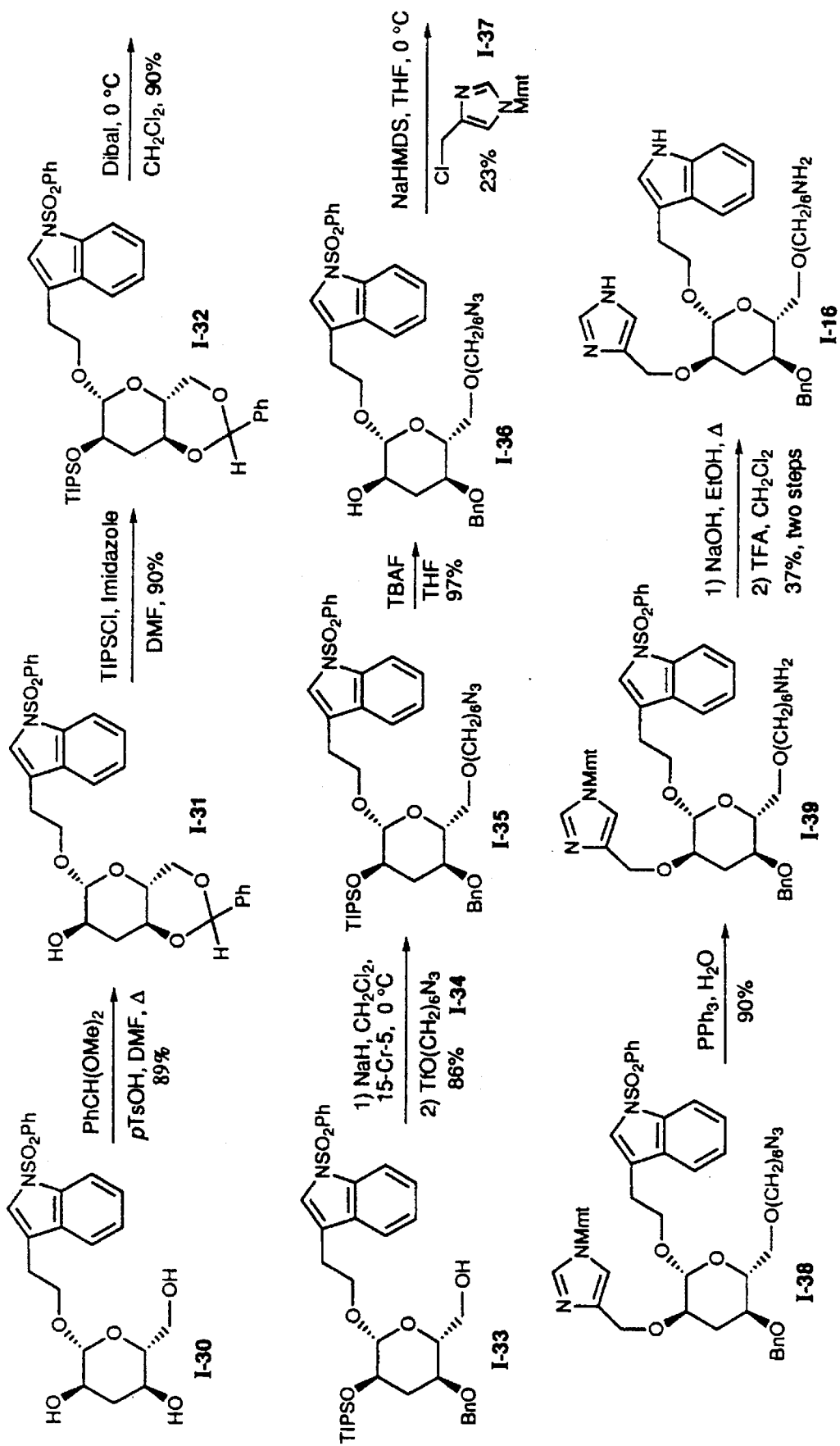
Figure 4:
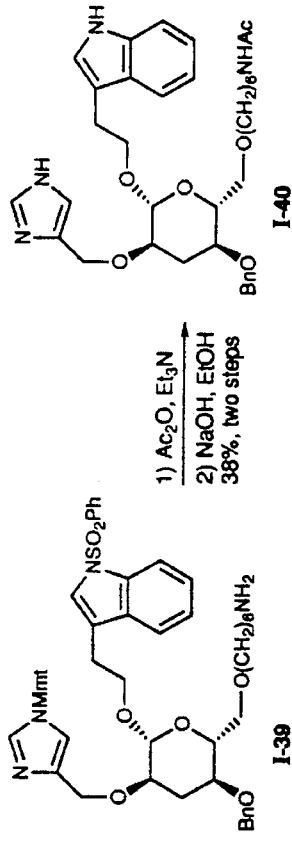
Figure 5:
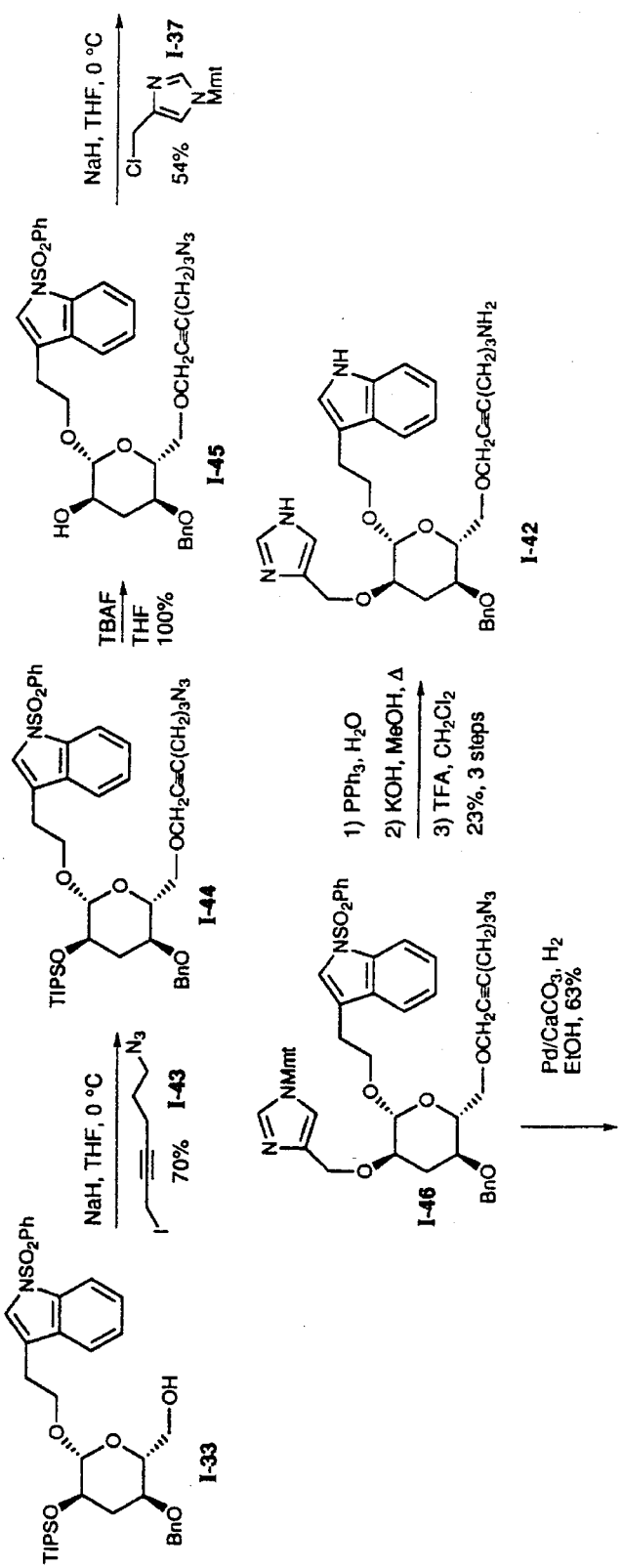
Figure 6:
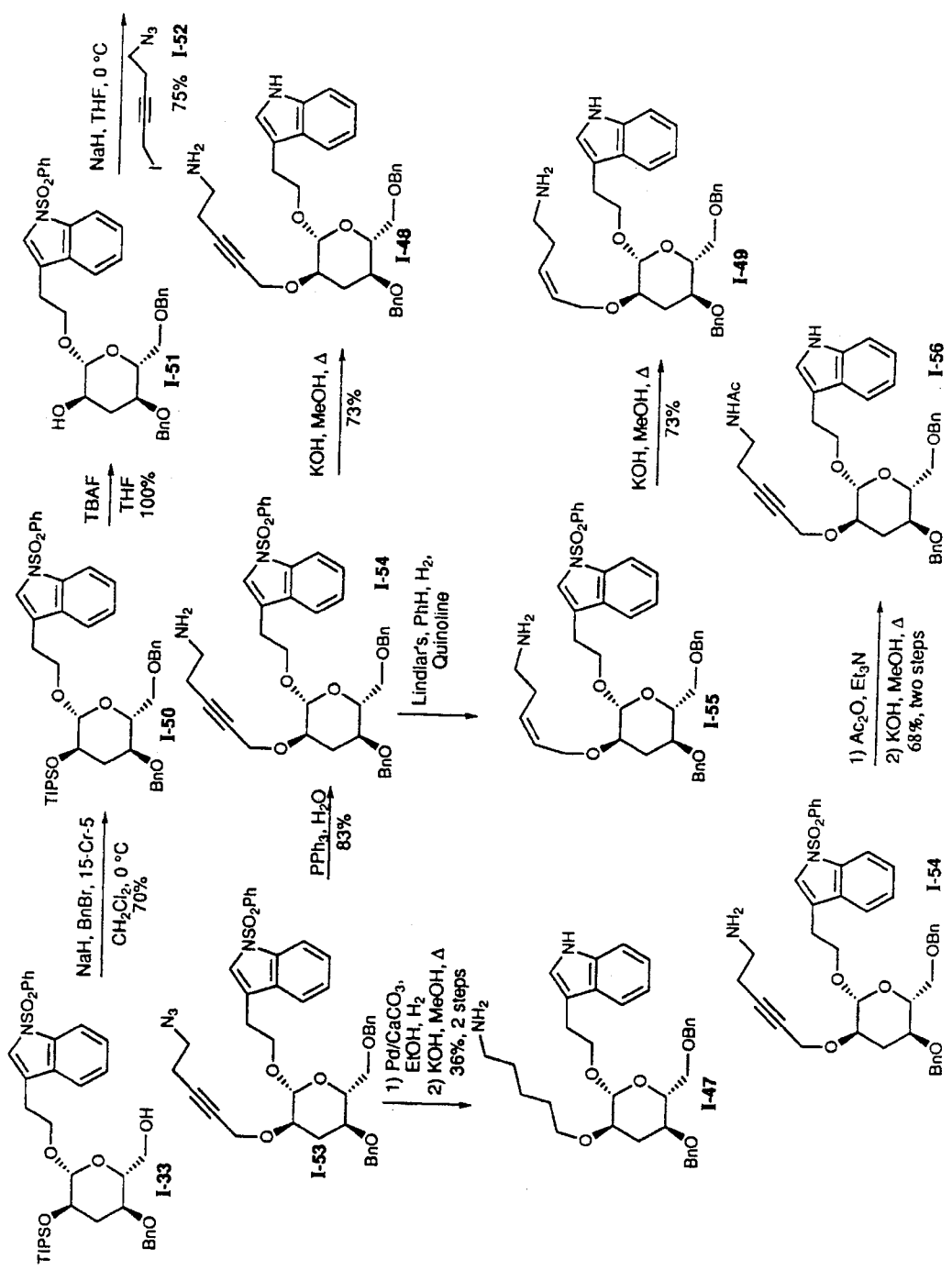
Figure 7:
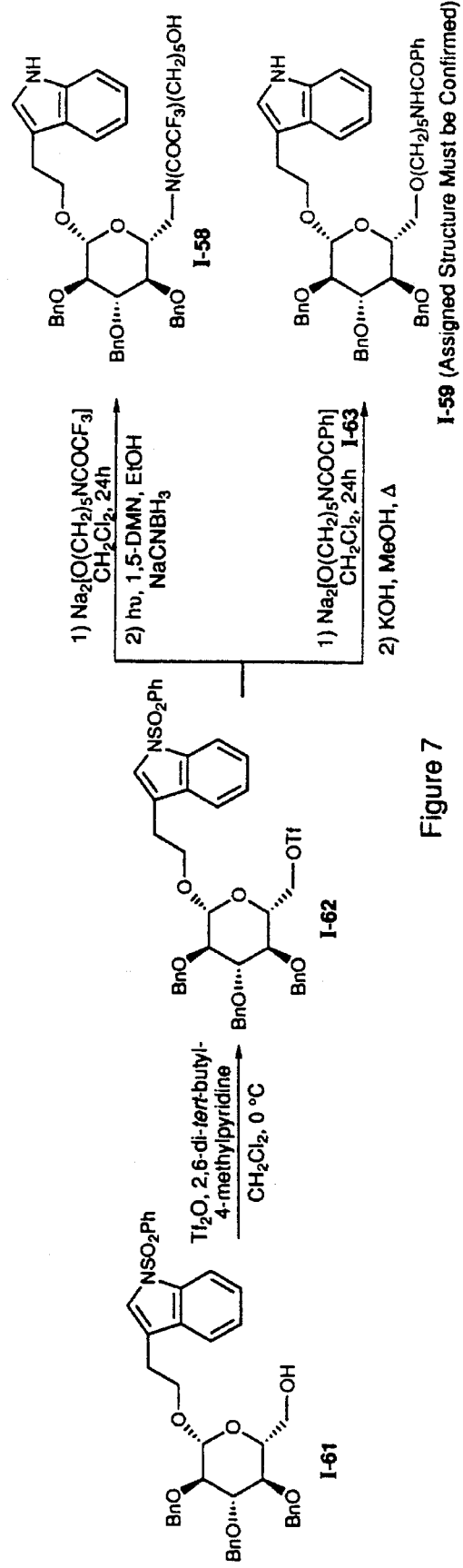

To distinguish the compounds described in this example an "I" preceeds each compound number. The chemical structures and synthetic schemes for the compounds in this example are presented in FIGS. 1–7.

A. phthalimido-protected amine (−)-I-21.

5-phthalimidopentyl triflate I-20 was prepared as follows: A stirred solution of 5-phthalimido-1-pentanol (1.32 g, 4.67 mmol) and 2,6-di-tert-butyl-4-methylpyridine (0.960 g, 4.67 mmol) in dry dichloromethane (10 ml) was treated with triflic anhydride (0.784 ml, 4.67 mmol). After 10 min at room temperature, the mixture was diluted with water (100 ml) and extracted with dichloromethane (2×200 ml). The combined extracts were washed with brine, dried over sodium sulfate, filtered, and concentrated in vacuo, affording a yellow solid which was used without purification in the next reaction. Sodium hydride (60% dispersion in oil, 0.20 g, 5.06 mmol) was added to a solution of alcohol I-19 (1.27 g, 3.89 mmol), 5-phthalimdopentyl triflate I-20 (4.67 mmol), and 15-crown-5 (20 mg, 2.3 mol %), in methylene chloride (100 ml) at 0° C. After stirring for 24 h at room temperature, the mixture was poured into water. The aqueous layer was extracted with methylene chloride (3×50 ml) and the combined extracts were washed with water, dried over magnesium sulfate and concentrated in vacuo. Flash chromatography (3% ether/methylene chloride) provided I-21 (1.82 g, 86% yield) as a colorless oil: [α]D$^{25}$−8.2° (c 0.70, CHCl$_3$); $^1$H NMR (500 MHz, CDCl$_3$) δ7.80 (m, 2H), 7.68 (m, 2H), 7.25–7.34 (m, 10H), 6.38, (dd, J=6.1, 1.2 Hz, 1H), 4.84 (m, 2H), 4.66 (d, J=11.4 Hz, 1H), 4.63 (d, J=11.7 Hz, 1H), 4.55 (d, J=11.7 Hz, 1H), 4.19 (m, 1H), 4.00 (m, 1H), 3.81 (dd, J=8.7, 6.2 Hz, 1H), 3.64–3.74 (m, 4H), 3.40–3.50 (m, 2H), 1.60–1.70 (m, 4H), 1.40 (m, 2H) ; $^{13}$C NMR (62.9 MHz, CDCl$_3$) δ168.4, 144.8, 138.4, 138.3, 133.9, 132.2, 128.4, 127.9, 127.8, 127.6, 123.2, 99.9, 76.8, 75.8, 74.5, 73.8, 71.4, 70.5, 69.2, 37.9, 29.2, 28.5, 23.5; high resolution mass spectrum (CI, NH$_3$) m/z 541.2483 (M$^+$; calcd for C$_{33}$H$_{35}$NO$_6$: 541.2464).

B. Alcohol (−)-I-23.

A solution of dimethyldioxirane in acetone (1.2 equiv, ca. 0.05M) was added dropwise to glycal I-21 (1.53 g, 2.80 mmol) in dichloromethane (26 ml) at 0° C. The mixture was stirred at 0° C. for 1 h and concentrated in vacuo.

To a solution of the crude epoxide and I-22 (1.15 g, 3.82 mmol) in THF (12 ml) at −78° C. was added ZnCl$_2$ (1.0M in ether, 5.6 ml, 5.6 mmol) and the mixture was stirred at −78° C. for 1 h. The solution was then slowly warmed to room temperature and stirred for 18 h. The mixture was poured into saturated aqueous sodium bicarbonate (50 ml) and extracted with ethyl acetate (3×50 ml) and the combined extracts were washed with water, dried over magnesium sulfate, and concentrated in vacuo. Flash chromatography (45% ethyl acetate/hexane) yielded I-23 (1.05 g, 44% yield) as a colorless oil: [α]D$^{25}$−8.1° (c 1.8 CHCl$_3$); $^1$H NMR (500 MHz, CDCl$_3$) δ7.96 (dd, J=8.1, 0.6 Hz, 1H), 7.85 (dd, J= 8.2, 0.9 Hz, 2H), 7.78 (m, 2H), 7.66 (m, 2H), 7.20–7.50 (m, 17H), 4.89 (d, J=11.3 Hz, 1H), 4.86 (d, J=11.0 Hz, 1H), 4.83 (d, J=11.4 Hz, 1H), 4.60 (d, J=10.9 Hz, 1H), 4.24 (d, J=7.6 Hz, 1H), 4.20 (dt, J=9.5, 6.4 Hz, 1H), 3.76 (dt, J=9.5, 7.2 Hz, 1H), 3.37–3.68 (m, 10H), 2.98 (m, 2H), 2.13 (br s, 1H), 1.57–1.68 (m, 4H), 1.38 (m, 2H); $^{13}$C NMR (62.9 MHz, CDCl$_3$) δ168.4, 138.6, 138.2, 135.1, 133.8, 133.7, 132.1, 131.0, 129.1, 128.4, 127.9, 127.8, 127.7, 126.7, 124.7, 123.5, 123.1, 119.7, 119.4, 113.7, 102.8, 84.4, 76.5, 75.1, 71.5, 69.6, 68.7, 37.8, 29.2, 28.4, 25.4, 23.5; high resolution mass spectrum (CI, NH$_3$) m/z 662.2774 (M$^+$; calcd for C$_{35}$H$_{42}$SO$_7$: 662.2775).

C. Dibenzyl ether (−)-I-24.

A solution of I-23 (0.455 g, 0.530 mmol) in THF (10 ml) was cooled to −78° C. and treated with carbon disulfide (27 ml, 0.583 mmol) followed by sodium bis(trimethylsilyl)amide (0.6M in toluene, 0.953 ml, 0.572 mmol). After 20 min, methyl iodide (59 ml, 0.640 mmol) was added and the solution was stirred for 5 min at −78° C. and then at room temperature for 45 min. The reaction mixture was quenched with water (50 ml) and extracted with ethyl acetate (3×50 ml). The organic layer was washed with brine, dried over sodium sulfate, filtered, and concentrated in vacuo, affording the crude xanthate as a pale yellow oil (0.462 g, 92% yield) which was used without purification in the next step.

To a solution of the crude xanthate (0.462 g, 0.487 mmol) and AIBN (10 mg) in toluene (8 ml) was added tributyltin hydride (0.214 ml, 0.795 mmol) and the reaction mixture heated at reflux for 4 h, cooled, and concentrated in vacuo. The residue was taken up in acetonitrile (30 ml) and washed with petroleum ether (5×10 ml), dried over sodium sulfate, filtered, and concentrated in vacuo to an oil. Flash chromatography (20% ethyl acetate/petroleum ether) yielded I-24 (0.296 g, 72% yield) as a colorless oil; [α]D$^{25}$−10° (c 1.1 CHCl$_3$); $^1$H NMR (500 MHz, CDCl$_3$) δ7.96 (d, J=7.5 Hz, 1H), 7.84 (m, 2H), 7.79 (m, 2H), 7.66 (m, 2H), 7.20–7.41 (m, 15H), 4.91 (d, J=11.0 Hz, 1H), 4.60 (m, 2H), 4.66 (d, J=11.7 Hz, 1H), 4.41 (dd, J=9.7, 1.8 Hz, 1H), 4.15 (dt, J=9.5, 6.6 Hz, 1H), 3.59–3.71 (m, 6H), 3.47 (m, 2H), 3.40 (m, 1H), 2.94 (t, J=6.6 Hz, 2H), 2.57 (ddd, J=14.2, 5.0, 3.2 Hz, 1H), 1.57–1.68 (m, 5H), 1.38 (m, 2 H); $^{13}$C NMR (62.9 MHz, CDCl$_3$) δ23.5, 25.5, 28.4, 29.2, 36.7, 37.9, 68.1, 70.0, 71.4, 75.0, 75.2, 78,2, 79.3, 99.9, 113.6, 119.6, 123.1, 123.5, 124.7, 126.7, 127.7, 128.0, 128.4, 129.2, 131.1, 132.1, 133.6, 133.8, 135.1, 138.3, 138.5, 168.4; high resolution mass spectrum (CI, NH$_3$) m/z 814.3287 (M$^+$; calcd for C$_{44}$H$_{50}$SO$_8$N$_2$: 814.3289).

D. Amine (−)-I-15.

A solution of hydrazine (0.2M in MeOH, 6 ml) was added to I-24 (0.034 g, 0.043 mmol). After stirring for 16 h, the reaction mixture was concentrated in vacuo, the residue was dissolved in ethanol (4 ml), and 5N NaOH (0.90 ml) added. The mixture was heated at reflux for 4 h, cooled, and extracted with methylene chloride (3×10 ml). The combined extracts were washed with brine, dried over magnesium sulfate, and concentrated in vacuo to an oil. Flash chromatography (11% methanol/methylene chloride) afforded I-15 (11 mg, 44%) as a pale yellow oil; [α]D$^{25}$−15° (c 0.62, CHCl$_3$); IR (CHCl$_3$) 3490 (m), 3345 (br, m), 3020 (m), 2945 (s), 2882 (s), 1625 (w), 1500 (w), 1459 (m), 1370 (m), 1230 (w), 1100 (s), 695 (w) cm$^{-1}$; $^1$H NMR (500 MHz, CDCl$_3$) δ8.80 (br s, 1H), 7.49 (d, J=7.9 Hz, 1H), 7.19–7.31 (m, 11H), 7.10 (t, J=7.1 Hz, 1H), 7.00 (t, J=8.0 Hz, 1H), 6.97 (s, 1H), 4.83 (d, J=11.1 Hz, 1H), 4.59 (d, J=11.7 Hz, 1H), 4.51 (d, J=11.0 Hz), 4.50 (d, J=11.7, 1H), 4.39 (d, J=9.7 Hz, 1H), 4.00 (apparent q, J=7.3 Hz, 1H), 3.67 (apparent q, J=7.3 Hz, 1H), 3.60 (d, J=9.0 Hz, 1H), 3.56 (m, 1H), 3.46 (dd, J=10.8, 5.3 Hz), 3.31 (m, 4H), 2.98 (t, J=7.2 Hz, 2H), 2.50 (t, J=7.3 Hz, 2H), 2.28 (m, 2H), 1.57 (q, J=10 Hz, 1H), 1.42 (m, 4H), 1.19 (m, 2H); $^{13}$C NMR (62.9 MHz, CDCl$_3$) δ138.3, 138.2, 136.2, 128.4, 128.0, 127.7, 127.5, 122.3, 121.8, 119.1, 118.7, 112.0, 111.4, 99.9, 79.3, 78.2, 74.9, 71.4, 71.0, 69.9, 69.8, 39.7, 36.7, 28.8, 27.6, 25.7, 23.1; high resolution mass spectrum (FAB, m-nitrobenzyl alcohol) m/z 573.3371 [(M+H)$^+$; calcd for C$_{35}$H$_{44}$N$_2$O$_5$: 573.3328].

E. Azide (−)-I-27.

5-Azidodopentyl triflate I-26 was prepared as follows: A stirred solution of 5-azido-1-pentanol (0.14 g, 1.08 mmol) and 2,6-di-tert-butyl-4-methylpyridine (0.22 g, 1.08 mmol) in dry dichloromethane (5 ml) was treated with triflic anhydride (0.19 ml, 1.08 mmol). After 10 min at room temperature, the mixture was diluted with water (100 ml) and extracted with dichloromethane (2×200 ml). The combined extracts were washed with brine, dried over sodium sulfate, filtered, and concentrated in vacuo, affording a yellow solid which was used without purification in the next reaction.

Sodium hydride (60% dispersion in oil, 0.053 g, 2.30 mmol) was added to a solution of alcohol I-25 (0.353 g, 1.08 mmol), 5-aziddopentyl triflate 26 (1.08 mmol), and 15-crown-5 (10 mg), in methylene chloride (10 ml) at 0° C. After stirring for 24 h at room temperature, the mixture was poured into water. The aqueous layer was extracted with methylene chloride (3×50 ml) and the combined extracts were washed with water, dried over magnesium sulfate and concentrated in vacuo. Flash chromatography (20% ethyl acetate/petroleum ether) provided I-27 (260 mg, 60%) as a colorless oil; [α]D$^{25}$−8.5° (c 0.89, CHCl$_3$); IR (CHCl$_3$) 3090 (w), 3062 (w), 3030 (w), 3005 (w), 2940 (m), 2865 (m), 2100 (s), 1650 (m), 1495 (w), 1455 (m), 1355 (w), 1235 (m), 1210 (m), 1100 (br, s), 1070 (s), 1028 (s), 705 (w), 691 (m), cm$^{-1}$; $^1$H NMR (500 MHz, CDCl$_3$) δ1.42 (m, 2H), 1.61 (m, 4H), 3.24 (t, J=6.9 Hz, 2H), 3.47 (m, 4H), 3.70 (dd, J=10.8, 2.7 Hz, 1H), 3.76 (dd, J=10.8, 5.1 Hz, 1H), 3.84 (dd, J=8.7, 6.2 Hz, 1H), 4.03 (m, 1H), 4.21 (ddd, J=6.2, 2.5, 1.5 Hz, 1H), 4.56 (d, J=11.6 Hz, 1H), 4.64 (d, J=11.6 Hz, 1H), 4.64 (d, J=11.6 Hz, 1H), 4.69 (d, J=11.4 Hz, 1H), 4.88 (m, 2H), 6.42 (m, 2H), 7.27–7.38 (m, 10H); $^{13}$C NMR (62.9 MHz, CDCl$_3$) δ23.4, 28.7, 29.2, 51.3, 69.2, 70.5, 71.3, 73.8, 74.5, 76.8, 99.9, 127.6, 127.8, 128.4, 138.3, 144.7; high resolution mass spectrum (FAB, m-nitrobenzyl alcohol) m/z 472.2031 [(M+Cl)$^+$; calcd for C$_{25}$H$_{31}$O$_4$N$_3$Cl: 8471.2003].

F. Amide (−)-I-28.

To a solution of sugar I-27 (0.117 g, 0.268 mmol) in THF (5 ml) was added H$_2$O (0,217 ml, 12.1 mmol) and PPh$_3$ (0.176 g, 0.671 mmol) and the reaction mixture was heated to 55° for 10 h, cooled, and concentrated in vacuo. Flash chromatography (15% methanol/methylene chloride) provided the amine as a colorless oil (82 mg, 77%); [α]D$^{25}$−7.2° (c 0.25, CHCl$_3$); IR (CHCl$_3$) 3500–2600 (br, w), 3090 (w), 3060 (w), 3003 (m), 2933 (s), 2864 (s), 1650 (m), 1495 (w), 1452 (m), 1355 (w), 1235 (m), 1220 (m), 1100 (br, s), 1025 (m), 850 (br, w), 690 (m) cm$^{-1}$; $^1$H NMR (500 MHz, CDCl$_3$) δ1.36 (m, 2H), 1.43 (quin., J=7.4 Hz, 1H), 1.59 (quin., J=6.7 Hz, 1H), 2.65 (t, J=6.9 Hz, 2H), 3.46 (m, 2H), 3.69 (dd, J=10.8, 2.7 Hz, 1H), 3.73 (dd, J=10.8, 5.1 Hz, 1H), 3.82 (dd, J=8.7, 6.3 Hz, 1H), 4.01 (m, 1H), 4.22 (m, 1H), 4.55 (d, J=11.7 Hz, 1H), 4.63 (d, J=11.7 Hz, 1H), 4.67 (d, J=11.4 Hz, 1H), 4.85 (m, 2H), 6.40 (d, J=6.2 Hz, 1H), 7.26–7.36 (m, 10H); $^{13}$C NMR (125.8 MHz, CDCl$_3$) δ22.4, 28.4, 32.5, 41.0, 68.1, 69.4, 70.5, 72.7, 73.5, 74.8, 75.7, 98.9, 126.6, 126.7, 127.3, 127.3, 137.2, 127.3, 143,7.

To a solution of the amine (0.077 g, 0.19 mmol) in CH$_2$Cl$_2$ (2.5 ml) at 0° C. was added Et$_3$N (0.040 ml, 0.29 mmol) and Ac$_2$O (0.020 ml, 0.21 mmol). After stirring for one minute, the mixture was poured into water. The aqueous layer was extracted with methylene chloride (3×20 ml) and the combined extracts were washed with water, dried over magnesium sulfate and concentrated in vacuo. Flash chromatography (8% methanol/methylene chloride) provided I-28 (80 mg, 94%) as a colorless oil; [α]D$^{25}$−8.2° (c 0.38, CHCl₃) 3450 (w), 3090 (w), 3062 (w), 3004 (m), 2940 (m), 2865 (m), 1665 (s), 1520 (br, m), 1455 (m), 1367 (br, m), 1237 (m), 1208 (m), 1102 (br, s), 1025 (m), 690 (m) cm⁻¹; ¹H NMR (500 MHz, CDCl₃) δ1.37 (m, 2H), 1.48 (quin., J=7.5 Hz, 2H), 1.59 (m, 2H), 1.92 (s, 3H), 3.20 (m, 2H), 3.45 (m, 2H), 3.68 (dd, J=10.9, 2.6 Hz, 1H), 3.73 (dd, J=10.9, 5.1 Hz, 1H), 3.81 (dd, J=8.7, 6.3 Hz, 1H), 4.00 (m, 1H), 4.20 (m, 1H), 4.55 (d, J=11.6 Hz, 1H), 4.63 (d, J=11.6 Hz, 1H), 4.67 (d, J=11.3 Hz, 1H), 4.87 (m, 2H), 5.45 (br s, 1H), 6.39 (dd, J=6.2, 1.3 Hz, 1H), 7.27–7.35 (m, 10H); ¹³C NMR (125.8 MHz, CDCl₃) δ23.3, 23.6, 29.3, 29.3, 39.5, 69.2, 70.6, 71.4, 73.8, 74.6, 75.9, 77.6, 100.0, 127.7, 127.8, 127.8, 128.5, 138.3, 144.7, 170.0; high resolution mass spectrum (FAB, m-nitrobenzyl alcohol) m/z 488.2537 [(M+Cl)⁺; calcd for C₂₇H₃₅O₅NCl: 488.2515].

G. α-Amide (+)-I-29.

To a solution of amide I-28 (0.022 g, 0.051 mmol) and tryptophol (0.041 g. 0.26 mmol) in acetonitrile (1 ml) was added CSA (1 mg). After stirring for 24 h at room temperature the mixture was added to saturated sodium bicarbonate and extracted with methylene chloride (3×20 ml). The combined extracts were washed with water, dried over magnesium sulfate and concentrated in vacuo. Flash chromatography (ethyl acetate) provided I-29α (4.2 mg, 14%) as a colorless oil; [α]D²⁵+55.0° (c 0.40, CHCl₃); IR (CHCl₃) 3485 (m), 3460 (m), 3300 (br, w), 3015 (w), 2950 (m), 2875 (m), 1670 (s), 1525 (w), 1460 (m), 1370 (w), 1130 (w), 1105 (br, s), 1030 (m), 980 (w), 695 (w) cm⁻¹; ¹H NMR (500 MHz, CDCl₃) δ1.31 (m, 2H), 1.43 (quin., J=7.4 Hz, 2H), 1.54 (m, 2H), 1.67 (dt, J=12.4, 3.3 Hz, 1H), 1.91 (s, 3H), 2.29 (dd, J=12.7, 5.0 Hz, 1H), 3.02 (m, 2H), 3.14 (m, 2H), 3.35 (m, 1H), 3.40–3.59 (m, 4H), 3.65 (m, 2H), 3.89 (q, J=7.5 Hz, 1H), 4.21 (m, 1H), 4.58 (d, J=11.1 Hz, 1H), 4.63 (d, J=11.5 Hz, 1H), 4.67 (d, J=11.5 Hz, 1H), 4.90 (d, J=11.1 Hz, 1H), 4.97 (d, J=11.7 Hz, 1H), 5.37 (br s, 1H), 6.98 (s, 1H), 7.09 (t, J=7.1 Hz, 1H), 7.17 (t, J=7.1 Hz, 1H), 7.27–7.37 (m, 11H), 7.59 (d, J=7.9 Hz, 1H), 8.30 (br s, 1H); ¹³C NMR (62.9 MHz, CDCl₃) δ23.2, 23.6, 25.6, 29.3, 35.5, 39.6, 67.4, 69.8, 70.5, 71.3, 71.7, 74.8, 97.2, 111.1, 112.8, 118.8, 119.1, 121.8, 121.9, 127.5, 127.6, 127.8, 128.4, 136.2, 138.7, 170.1; high resolution mass spectrum (FAB, m-nitrobenzyl alcohol) m/z 615.3407 [(M+H)⁺; calcd for C37H47O6N2: 615.3434].

H. β-Amide (−)-I-29.

(1.7 mg, 6%) as a colorless oil; [α]D²⁵−13.0° (c 0.16, CHCl₃); IR (CHCl₃) 3480 (w), 3010 (m), 2940 (m), 2877 (m), 1670 (s), 1532 (w), 1458 (m), 1369 (m), 1270 (w), 1100 (br s), 1011 (w), 695 (w) cm⁻¹; ¹H NMR (500 MHz, CDCl₃) δ1.22 (m, 2H), 1.45 (m, 2 H), 1.53–1.69 (m, 3H), 1.92 (s, 3H), 2.34 (m, 1H), 3.08 (t, J=7.5 Hz, 2H), 3.14 (m, 2H), 3.38 (m 1H), 3.40–3.51 (m, 3H), 3.57–3.67 (m, 2H), 3.69 (dd, J=10.8, 1.8 Hz, 1H), 3.75 (m, 1H), 4.13 (dt, J=9.6, 2.0 Hz, 1H), 4.46 (dd, J=9.7, 1.8 Hz, 1H), 4.58 (d, J=11.7 Hz, 1H), 4.61 (d, J=11.1 Hz, 1H), 4.66 (d, J=11.6 Hz, 1H), 4.92 (d, J=11.0 Hz, 1H), 5.39 (br s, 1H), 7.05 (s, 1H), 7.09 (m, 1H), 7.17 (m, 1H), 7.26–7.36 (m, 11H), 7.59 (d, J=7.8 Hz, 1H), 8.37 (br s, 1H); ¹³C NMR (125.8 MHz, CDCl₃) δ23.6, 23.7, 25.7, 29.3, 36.8, 39.7, 69.6, 70.1, 71.4, 74.9, 75.2, 76.8, 78.4, 79.4, 99.9, 111.2, 112.5, 118.7, 119.1, 121.9, 122.1, 127.7, 127.7, 127.9, 128.4, 138.3, 170.2; high resolution mass spectrum (FAB, m-nitrobenzyl alcohol) m/z 615.3410 [(M+H)⁺; calcd for C₃₇H₄₇O₆N₂: 615.3434].

I. Acetal (−)-I-31.

To a solution of the triol I-30 (9.43 g, 21.1 mmol) dissolved in DMF (35 ml) was added α,α-dimethoxytoluene (3.42 ml, 22.8 mmol) and pTsOH (100 mg) and the mixture was heated to 45° C. under aspirator pressure for 5 h. After cooling, the mixture was added to H₂O (300 ml ) and saturated sodium bicarbonate (10 ml) and extracted with ethyl acetate (3×150 ml). The combined extracts were washed with water, dried over magnesium sulfate and concentrated in vacuo. Flash chromatography (40% ethyl acetate/ptroleum ether) provided I-31 (10.0 g, 89% yield) as a colorless oil: [α]D²⁵−8.2° (c 0.70, CHCl₃); 3590 (br w), 3080 (w), 3010 (w), 2920 (w), 2880 (w), 1450 (m), 1375 (m), 1330 (w), 1280 (w), 1182 (m), 1175 (s), 1130 (m), 1120 (m), 1100 (s), 1085 (s), 1070 (s), 1018 (m), 1000 (m), 905 (w), 680 (w), 595 (m), 565 (m) cm⁻¹; ¹H NMR (500 MHz, CDCl₃) δ1.70 (q, J=11.7 Hz, 1H), 2.05 (br s, 1H), 2.43 (dt, J=9.2, 4.6 Hz, 1H), 3.00 (m, 2H), 3.44 (m, 1H), 3.59 (m, 2H), 3.79 (m, 2H), 4.24 (dt, J=9.5, 6.4 Hz, 1H), 4.31 (m, 2H), 5.52 (s, 1H), 7.25 (m, 2H), 7.36 (m, 4H), 7.40–7.54 (m, 6H), 7.87 (m, 2H), 7.99 (d, J=8.1 Hz, 1H); ¹³C NMR (125.8 MHz, CDCl₃) δ25.5, 34.9, 68.7, 68.8, 68.9, 70.5, 76.0, 101.7, 105.2, 113.6, 119.2, 119.5, 123.0, 123.3, 124.6, 126.5, 128.3, 128.8, 129.0, 131.0, 133.6, 135.0, 137.1; high resolution mass spectrum (Cl, CH₄) m/z 536.1722 [(M+H)⁺; calcd for C₂₉H₃₀SO₇N: 536.1743].

J. Acetal (−)-I-32.

To a solution of the acetal I-31 (1.84 g, 3.44 mmol) dissolved in DMF (4 ml) was added imidazole (0.52 g, 7.57 mmol) followed by TIPSCl (0.81 ml, 3.78 mmol). After stirring for 24 h, the mixture was added to H₂O (200 ml) and extracted with ether (3×100 ml). The combined extracts were washed with water, dried over magnesium sulfate and concentrated in vacuo. Flash chromatography (15% ethyl acetate/ptroleum ether) provided I-32 (2.12 g, 90% yield) as a colorless oil: [α]D²⁵−27.8° (c 0.95, CHCl₃); IR (CHCl₃) 3080 (w), 3040 (w), 3020 (w), 2960 (s), 2905 (s), 2880 (s), 1467 (m), 1453 (m), 1335 (w), 1285 (w), 1190 (m), 1179 (s), 1135 (s), 1130 (s), 1095 (s), 1000 (br m), 885 (m), 810 (m), 720 (w), 670 (br, m), 600 (m), 572 (m) cm⁻¹; ¹H NMR (500 MHz, CDCl₃) δ1.05 (m, 21H), 1.77 (q, J=11.2 Hz, 1H), 2.44 (m, 1H), 3.00 (t, J=7.7 Hz, 2H), 3.42 (m, 1H), 3.56 (m, 1H), 3.73–3.85 (m, 3H), 4.12 (m, 1H), 4.29 (dd, J=10.5, 4.9 Hz, 1H), 4.38 (d, J=7.3 Hz, 1H), 5.50 (s, 1H), 7.23 (m, 1H), 7.25 (s, 1H), 7.28–7.38 (m, 3H), 7.43 (m, 3H), 7.46–7.54 (m, 4H), 7.86 (m, 2H), 7.97 (dt, J=8.3, 0.8 Hz); ¹³C NMR (62.9 MHz, CDCl₃) δ12.4, 17.7, 18.0, 25.6, 38.0, 68.9, 69.2, 70.0, 70.2, 75.9, 101.7, 106.0, 113.7, 119.4, 123.1, 123.5, 124.8, 126.2, 126.7, 128.4, 129.1, 129.2, 131.0, 133.7, 135.2, 137.4, 138.4; high resolution mass spectrum (Cl, CH4) m/z 691.3041(M⁺; calcd for C₃₈H₄₉SiSO₇N: 691.2998).

K. Alcohol (−)-I-33.

To a solution of the acetal I-32 (1.45 g, 2.10 mmol) dissolved in CH₂Cl₂ (30 ml) was added DIBAL (1.0M toluene; 21.0 ml, 21.0 mmol) at 0° C. After stirring for 4 h the mixture was quenched with Rochelle's salt (100 ml) and water (100 ml) and extracted with ethyl acetate (3×100 ml). The combined extracts were washed with water, dried over magnesium sulfate and concentrated in vacuo. Flash chromatography (20% ethyl acetate/ptroleum ether) provided I-33 (1.31 g, 90% yield) as a colorless oil: [α]D²⁵−11.6° (c 1.12, CHCl₃); IR (CHCl₃) 3080 (w), 3040 (w), 3018 (w), 2960 (s), 2880 (s), 1455 (s), 1375 (s), 1285 (w), 1185 (m), 1179 (s), 1138 (s), 1135 (s), 1090 (s), 1040 (m), 1030 (m), 1020 (m), 885 (m), 810 (w), 680 (m), 600 (m), 57o (m) cm⁻¹; ¹H NMR (500 MHz, CDCl₃) δ1.07 (m, 21H), 1.58 (q, J=11.4 Hz, 1H), 2.10 (br s, 1H), 2.45 (dt, J=12.3, 4.8 Hz, 1H), 2.98 (m, 2H), 3.42 (m, 1H), 3.52 (m, 1H), 3.59 (m, 1H), 3.86 (m, 2H), 4.13 (dt, J=9.2, 7.7 Hz, 1 H), 4.32 (d, J=7.3 Hz, 1H), 4.54 (d, J=1.5 Hz, 1H), 4.64 (d, J=11.5 Hz, 1H), 7.24 (m, 1H), 7.28 (s, 1H), 7.24–7.39 (m, 5H), 7.43 (m, 2H), 7.48

(d, J=7.8 Hz, 1H), 7.51 (m, 2H), 7.87 (m, 2H), 8.00 (d, J=8.3 Hz, 1H); $^{13}$C NMR (62.9 MHz, CDCl$_3$) δ12.6, 18.2, 25.8, 38.2, 62.6, 68.5, 69.5, 71.8, 72.2, 78.2, 104.8, 113.9, 19.3, 119.6, 123.5, 123.9, 124.8, 127.0, 128.0, 128.5, 129.8, 131.2,133.9, 135.4,138.1, 138.5; high resolution mass spectrum (CI, NH$_3$) m/z 693.3167(M$^+$; calcd for C$_{38}$H$_{51}$SiSO$_7$ N: 693.3155).

L. Azide (−)-I-35.

6-Azidohexyl triflate I-34 was prepared as follows: A stirred solution of 6-azido-1-hexanol (0.17 g, 1.17 mmol) and 2,6-di-tert-butyl-4-methylpyridine (0.24 g, 1.17 mmol) in dry dichloromethane (10 ml) was treated with triflic anhydride (0.19 ml, 1.17 mmol). After 10 min at room temperature, the mixture was diluted with water (50 ml) and extracted with dichloromethane (3×25 ml). The combined extracts were washed with brine, dried over sodium sulfate, filtered, and concentrated in vacuo, affording a yellow solid which was used without purification in the next reaction. To a solution of alcohol I-33 (0.54 g, 0.78 mmol) in dry CH$_2$Cl$_2$ (30 ml) at 0° C. was added NaH (60%, 0.050 g, 1.17 mmol) and 15-crown-5 (5 mg). After stirring for 20 minutes, triflate 34 (0.32 g, 1.17 mmol) as a solution in CH$_2$Cl$_2$ (2 ml) was added via cannula. The mixture was stirred for an additional 24 h, quenched with water (30 ml) and the layers were separated. The aqueous layer was further extracted with CH$_2$Cl$_2$ (3×20 ml) and the combined extracts were washed with water, dried over magnesium sulfate and concentrated in vacuo. Flash chromatography (12 % ethyl acetate/ptroleum ether) provided I-35 (0.57 g, 89% yield) as a colorless oil; [α]D$^{25}$−14.6° (c 1.22, CHCl$_3$); IR (CHCl$_3$) 3075 (w), 3017 (w), 2955 (s), 2880 (s), 2105 (s), 1450 (m), 1375 (m), 1275 (br, w), 1180 (s), 1125 (s), 1097 (s), 1070 (s), 975 (w), 885 (w), 810 (w), 670 (br, w), 600 (m), 570 (m) cm$^{-1}$; $^1$H NMR (500 MHz, CDCl$_3$) δ1.03 (s, 21H), 1.31 (m, 4H), 1.51 (m, 5H), 2.40 (dt, J=12.3, 4.7 Hz, 1H), 2.98 (t, J=7.2 Hz, 2H), 3.15 (t, J=6.9 Hz, 2H), 3.40 (m, 4H), 3.56 (m, 2H), 3.77 (m, 2H), 4.09 (m, 1H), 4.24 (d, J=7.3 Hz, 1H), 4.48 (d, J=11.6 Hz, 1H), 4.59 (d, J=11.6 Hz, 1H), 7.22 (t, J=7.6 Hz, 1H), 7.25 (s, 1H), 7.30 (m, 5H), 7.40 (m, 3H), 7.47 (m, 2H), 7.84 (d, J=7.9 Hz, 2H), 7.96 (d, J=8.4 Hz, 1H); $^{13}$C NMR (62.9 MHz, CDCl$_3$) δ12.4, 18.0, 25.6, 25.7, 26.6, 28.8, 29.5, 38.3, 51.4, 68.5, 69.4, 70.1, 71.4, 71.5, 72.3, 78.1, 105.6, 113.7, 119.4, 119.7, 123.1, 123.4, 124.7, 126.8, 127.8, 128.4, 129.3, 131.1, 133.6, 135.2, 138.2, 138.3; high resolution mass spectrum (FAB, m-nitrobenzyl alcohol) m/z 853.3835 [(M+Cl)$^+$; calcd for C$_{44}$H$_{62}$SiSO$_7$ N$_4$Cl: 853.3797).

M. Alcohol (−)-I-36.

A solution of azide I-35 (0.18 g 0.22 mmol) in THF (3 ml) was cooled to 0° C. and TBAF (0.26 ml, 1.00M, 0.26 mmol) was added dropwise. The mixture was stirred for 2 h, added to water and extracted with EtOAc (3×20 ml). The combined extracts were washed with water, dried over magnesium sulfate and concentrated in vacuo. Flash chromatography (12% ethyl acetate/petroleum ether) yielded the alcohol as a colorless oil (0.14 g, 99%); [α]D$^{25}$−8.8° (c 1.1, CHCl$_3$); IR (CHCl$_3$) 3002 (w), 2940 (m), 2870 (m), 2100 (s), 1450 (s), 1370 (s), 1280 (w), 1172 (s), 1130 (s), 1120 (s), 1100 (s), 1088 (s), 1070 (s), 970 (w), 600 (m), 570 (m) cm$^{-1}$; $^1$H NMR (500 MHz, CDCl$_3$) δ1.38 (m, 4H), 1.59 (m, 5H), 2.10 (br s, 1H), 2.47 (dt, J=12.5, 4.5 Hz, 1H), 3.01 (m, 2H), 3.23 (t, J=6.9 Hz, 2H), 3.45 (m, 3H), 3.59 (m, 5H), 3.70 (dd, J=12.3, 4.3 Hz, 1H), 3.77 (dt, J=9.5, 7.0 Hz, 1H), 4.21 (dt, J=9.6, 6.5 Hz, 1H), 4.29 (d, J=6.9 Hz, 1H), 4.51, (d, J=11.5 Hz, 1H), 4.63 (d, J=11.6 hz, 1H), 7.26 (t, J=7.7 Hz, 1H), 7.28 (s, 1H), 7.35 (m, 5H), 7.45 (m, 3H), 7.53 (m, 2H), 7.89 (m, 2H), 8.00 (d, J=7.9 Hz, 1H); $^{13}$C NMR (62.9 MHz, CDCl$_3$) δ25.5, 25.7, 26.5, 28.7, 29.4, 33.8, 51.3, 68.3, 68.6, 70.0, 71.3, 71.4, 72.1, 77.7, 04.5, 113.8, 119.4, 119.9, 123.1, 123.5, 124.8, 126.7, 127.7, 127.8, 128.4, 129.2, 131.0, 133.7, 135.2, 137.9, 138.3; high resolution mass spectrum (FAB, m-nitrobenzyl alcohol) m/z 62.2811(M$^+$; calcd for C$_{35}$H$_{42}$SO$_7$ N$_4$: 662.2774).

N. Mmt-Chloromethylimidazole (I-37).

To a solution of the chloromethylimidazole (0.20 g, 1.30 mmol) and MmtCl (0.82 g, 2.65 mmol) in dichloromethane at 0° C. was rapidly added Hunig's base (0.51 ml, 2.91 mmol). After stirring for 0.5 h the mixture was added to water and the layers were separated. The aqueous layer was further extracted with dichloromethane (2×20 ml). The combined extracts were washed with water, dried over magnesium sulfate and concentrated in vacuo. Flash chromatography (30% ethyl acetate/petroleum ether) yielded I-37 as a colorless oil (0.24 g, 47%) which was used immediately in the next reaction; IR (CHCl$_3$) 3095 (w), 3060 (w), 3005 (m), 2960 (m), 2840 (m), 1586 (w), 1510 (s), 1487 (m), 1463 (m), 1445 (m), 1300 (w), 1255 (s), 1180 (m), 1155 (m), 1120 (m), 1085 (w), 1031 (m), 990 (w), 905 (w), 825 (m), 695 (m); $^1$H NMR (500 MHz, CDCl$_3$) δ3.79 (s, 3H), 4.56 (s, 2H), 6.84 (m, 3H), 7.05 (d, J=8.8 Hz, 2H), 7.10 (m, 4H), 7.32 (m, 6H), 7.39 (br s, 1H); $^{13}$C NMR (62.9 MHz, CDCl$_3$) δ39.9, 55.2, 75.1, 113.3, 120.2, 128.0, 129.6, 131.1, 134.1, 137.4, 139.2, 147.4, 159.1.

O. Imidazole-Azide (+)-I-38.

To a solution of alcohol I-36 (0.20 g, 0.31 mmol) in dry THF (4 ml) at 0° C. was added NaHMDS (0.6M toluene, 0.56 ml, 0.34 mmol). After 10 minutes, chloro-imidazole I-37 (0.24 g, 0.62 mmol) as a solution in THF (5 ml) was added via cannula. After stirring for 48 h at room temperature, the mixture was added to water and extracted with CH$_2$Cl$_2$ (3×20 ml). The combined extracts were washed with water, dried over magnesium sulfate and concentrated in vacuo. Flash chromatography (toluene/ethyl acetate/methanol, 7.7:2.0:0.3) provided I-38 (0.071 g, 23% yield) as a colorless oil; [α]D$^{25}$+1.4° (c 0.86, CHCl$_3$); IR (CHCl$_3$) 3009, (m), 2965 (m), 2880 (m), 2110 (s), 1610 (w), 1510 (m), 1455 (m), 1375 (m), 1260 (m), 1180 (s), 1135 (s), 1125 (s), 1090 (s), 1075 (s) 1040 (m), 830 (w), 700 (w), 600 (m), 570 (m) cm$^{-1}$; $^1$H NMR (500 MHz, CDCl$_3$) δ1.32 (m, 4H), 1.55 (m, 5H), 2.58 (m, 1H), 2.92 (t, J=7.2 Hz, 2H), 3.17 (t, J=6.9 Hz, 2H), 3.35 (m, 1H), 3.42 (m, 3H), 3.46 (dt, J=9.5, 6.5 Hz, 1H), 3.55 (dd, J=10.7, 5.1 Hz, 1H), 3.75 (m, 2H), 3.76 (s superimposed on a m, 3H), 4.11 (dt, J=9.6, 7.1 Hz, 1H), 4.37 (d, J=7.6 Hz, 1H), 4.40 (d, J=11.4 Hz, 1H), 4.46 (d, J=12.1 Hz, 1H), 4.58 (d, J=11.4 Hz, 1H), 4.65 (d, J=12.2 Hz, 1H), 6.76 (s, 1H), 6.80 (m, 2H), 7.04 (m, 2H), 7.11 (m, 4H), 7.15 (m, 1H), 7.21–7.37 (m, 15H), 7.45 (m, 3H), 7.81 (m, 2H), 7.93 (d, J=8.3 Hz, 1H); $^{13}$C NMR (125.8 MHz, CDCl$_3$) δ25.6, 25.7, 26.5, 28.7, 29.5, 34.9, 51.3, 55.2, 66.9, 68.3, 70.0, 71.1, 71.5, 72.4, 74.9, 75.2, 78.0, 105.1, 113.2, 113.6, 119.5, 120.0, 123.0, 123.6, 126.7, 127.7, 127.9, 128.0, 128.3, 129.0, 129.6, 131.0, 131.1, 133.6, 134.5, 135.1, 138.1, 138.5, 139.0, 142.3, 159.0; high resolution mass spectrum (FAB, m-nitrobenzyl alcohol) m/z 1015.4496[(M+H)$^+$; calcd for C$_{59}$H$_{63}$SO$_8$ N$_6$: 1015.4496].

P. Amine (+)-I-39.

To a solution of azide I-38 (0.071 g, 0.070 mmol) in THF (5 ml) was added H$_2$O (0.059 ml, 3.30 mmol) and PPh$_3$ (0.046 g, 0.17 mmol) and the reaction mixture heated to 55° C. for 10 h, cooled, and concentrated in vacuo. Flash chromatography (15% methanol/methylene chloride) provided I-39 as a colorless oil (62 mg, 90%); [α]D$^{25}$+1.8° (c 1.24, CHCl$_3$); IR (CHCl$_3$) 3300 (br, w), 3080 (w), 3005 (w), 2940 (m), 2880 (m), 1605 (w), 1510 (w), 1450 (m), 1375

(m), 1290 (w), 1255 (w), 1175 (s), 1130 (s), 1120 (s), 1095 (s), 1085 (s), 830 (w), 595 (m), 565 (m) cm$^{-1}$; $^1$H NMR (500 MHz, CDCl$_3$) δ1.29 (m, 4H), 1.42 (m, 2H), 1.54 (m, 3H), 2.56 (m, 1H), 2.67 (t, J=7.1 Hz, 2H), 2.92 (t, J=7.1 Hz, 2H), 3.23 (br s, 2H), 3.33 (m, 1H), 3.42 (m, 4H), 3.56 (dd, J=10.7, 4.5 Hz, 1H), 3.70 (d, J=10.6 Hz, 1H), 3.76 (m, 1H), 3.76 (s superimposed on a m, 3H), 4.13 (dt, J=9.5, 7.1 Hz, 1H), 4.37 (d, J=7.5 Hz, 1H), 4.40 (d, J=11.1 Hz, 1H), 4.46 (d, J=12.1 Hz, 1H), 4.57 (d, J=11.4 Hz, 1H), 4.64 (d, J=12.1 Hz, 1H), 6.76 (s, 1H), 6.80 (m, 2H), 7.04 (m, 2H), 7.15 (t, J=7.8 Hz, 1H), 7.20–7.46 (m, 18H), 7.81 (dd, J=8.2, 0.9 Hz, 2H), 7.91 (d, J=8.3 Hz, 1H); $^{13}$C NMR (125.8 MHz, CDCl$_3$) δ25.5, 25.9, 26.5, 29.5, 29.7, 34.9, 55.2, 66.8, 58.3, 70.0, 71.1, 71.6, 72.3, 74.9, 75.2, 78.0, 105.1, 113.2, 113.6, 119.5, 119.9, 120.1, 123.1, 124.6, 126.7, 127.7, 127.7, 127.9, 128.0, 128.4, 129.1, 129.7, 131.1, 131.1, 133.6, 134.4, 135.0, 138.1, 138.3, 138.4, 139.0, 142.7, 159.1; high resolution mass spectrum (FAB, m-nitrobenzyl alcohol) m/z 989.4483 [(M+H)$^+$; calcd for C$_{59}$H$_{65}$SO$_8$N$_4$: 989.4522].

Q. Free imidazole (+)-I-16.

To a solution of amine I-39 (0.020 g, 0.020 mmol) in EtOH (3 ml) was added 5M NaOH (0.50 ml) and the mixture was heated at reflux for 4 h. After cooling, the mixture was diluted with water and extracted with methylene chloride (3×10 ml). The combined extracts were washed with brine, dried over magnesium sulfate, and concentrated in vacuo to an oil. Flash chromatography (15% methanol/methylene chloride) afforded the amine (11 mg, 63%) as a pale yellow oil; [α]D$^{25}$+10.1° (c 0.54, CHCl$_3$); IR (CHCl$_3$) 3480 (w), 3500–2700 (br, w), 3060 (w), 3005 (m), 2955 (s), 2860 (m), 1605 (w), 1505 (m), 1450 (m), 1290 (w), 1255 (m), 1180 (w), 1155 (w), 1128 (s), 1075 (br, s), 1030 (s), 820 (w), 690 (w) cm$^{-1}$; $^1$H NMR (500 MHz, CDCl$_3$) δ1.25–1.45 (m, 6H), 1.55 (m, 3H), 2.33 (br s, 2H), 2.59 (m, 1H), 2.65 (t, J=7.1 Hz, 2H), 3.08 (m, 2H), 3.38 (m, 1H), 3.40–3.56 (m, 6H), 3.58 (dd, J=10.8, 5.2 Hz, 1H), 3.75 (d, J=9.6 Hz, 1H), 3.81 (s superimposed on a m, 3H), 3.81 (m, 1H), 4.24 (m, 2H), 4.45 (m, 2H), 4.49 (d, J=11.9 Hz, 1H), 4.60 (d, J=11.4 Hz, 1H), 4.66 (d, J=12.0 Hz, 1H), 6.75 (s, 1H), 6.85 (m, 2H), 7.05–7.18 (m, 8H), 7.25 (d, J=8.2 Hz, 1H), 7.27–7.38 (m, 12H), 7.42 (s, 1H), 7.57 (d, J=7.9 Hz, 1H), 8.41 (br s, 1H); $^{13}$C NMR (125.8 MHz, CDCl$_3$) δ24.6, 24.9, 25.6, 28.6, 31.8, 33.9, 40.6, 54.2, 65.8, 68.5, 69.0, 70.5, 71.4, 74.1, 76.9, 104.0, 110.0, 111.6, 112.2, 117.6, 119.0, 120.6, 121.3, 126.6, 126.9, 126.9, 127.3, 128.6, 130.1, 133.4, 135.0, 137.0, 137.5, 137.9, 141.7, 158.0; high resolution mass spectrum (FAB, m-nitrobenzyl alcohol) m/z 849.4672[(M+H)$^+$; calcd for C$_{53}$H$_{61}$O$_6$N$_4$: 849.4591].

To a solution of the amine (0.023 g, 0.027 mmol) in dry CH$_2$Cl$_2$ (2 ml) was added TFA (3.5 ml, 0.045 mmol). After stirring for 5 minutes, the mixture was added to brine (20 ml) that had been adjusted to pH 8.0 with aqueous sodium bicarbonate and extracted with methylene chloride (3×15 ml). The combined extracts were washed with brine, dried over magnesium sulfate, and concentrated in vacuo to an oil. Purification by RP HPLC (water/acetonitrile) afforded I-16 (9.7 mg, 63%) as a pale yellow oil; [α]D$^{25}$+11.2° (c 0.42, CH$_3$OH); $^1$H NMR (500 MHz, CD$_3$OD) δ1.26–1.42 (m, 5H), 1.52 (m, 4H), 2.44 (m, 1H), 2.78 (t, J=6.6 Hz, 2H), 3.16 (m, 1H), 3.36–3.48 (m, 4H), 3.52 (dd, J=10.9, 4.8 Hz, 1H), 3.64 (dd, J=11.1, 1.5 Hz, 1H), 3.79 (dt, J=9.4, 7.3 Hz, 1H), 4.15 (dt, J=9.4, 6.1 Hz, 1H), 4.35 (m, 2H), 4.39 (d, J=11.7 Hz, 1H), 4.42 (d, J=13.0 Hz, 1H), 4.53 (d, J=11.6 Hz, 1H), 6.92 (m, 2H), 6.99 (m, 1H), 7.02 (s, 1H), 7.25 (m, 6H), 7.49 (d, J=7.9 Hz, 1H), 8.64 (s, 1H); $^{13}$C NMR (62.9 MHz, CD$_3$OD) δ26.8, 26.9, 27.2, 28.5, 30.5, 35.8, 40.6, 62.8, 71.0, 72.3, 72.5, 73.2, 76.8, 79.1, 106.2, 112.2, 113.0, 117.9, 119.5, 119.6, 122.3, 123.8, 128.8, 128.9, 129.4, 132.5, 135.3, 138.0, 139.6; high resolution mass spectrum (FAB, m-nitrobenzyl alcohol) m/z 577.3421[(M+H)$^+$; calcd for C$_{33}$H$_{45}$O$_5$N$_4$: 577.3390].

R. Amide (+)-I-40.

To a solution of amine I-39 (0.043 g, 0.043 mmol) in methylene chloride (1 ml) and methanol (2 ml) was added acetic anhydride (4.4 ml, 0.043 mmol). After 2 h, two additional equivalents of acetic anhydride (8.8 ml) were added and stirring was continued for a total of 24 h. The mixture was diluted with methylene chloride (15 ml) and washed sequentially with saturated sodium bicarbonate and water. The organic layer was dried over magnesium sulfate, and concentrated in vacuo to an oil. Flash chromatography (15% methanol/methylene chloride) afforded two inseperable components which were used uncharacterized in the following reaction.

To a solution of the above sugars in ethanol (4 ml) was added 5N NaOH (0.200 ml) and mixture was heated at reflux for 2 h. After cooling, the mixture was diluted with water, adjusted to pH 8.0 with HCl, and extracted with methylene chloride (3×10 ml). The combined extracts were washed with brine, dried over magnesium sulfate, and concentrated in vacuo to an oil. Purification by RP HPLC (water/acetonitrile) afforded I-40 (10 mg, 38%) as a colorless oil; [α]D$^{25}$+13.4°(c 0.62, C$_2$H$_5$OH); $^1$H NMR (500 MHz, CD$_3$OD) δ1.21–1.35 (m, 4H), 1.36 (m, 3H), 1.48 (m, 2H), 1.83 (s, 3H), 2.40 (dt, J=12.2, 4.7 Hz, 1H), 2.99 (t, J=6.7 Hz, 2H), 3.03 (t, J=7.1 Hz, 2H), 3.15 (m, 1H), 3.35–3.46 (m, 4H), 3.51 (dd, J=10.9, 4.9 Hz, 1H), 3.63 (dd, J=11.0, 1.7 Hz, 1H), 3.79 (dt, J=9.4, 7.3 Hz, 1H), 4.13 (dt, J=9.3, 6.1 Hz, 1H), 4.33 (d, J=7.5 Hz, 1H), 4.37 (d, J=13.0 Hz, 1H), 4.39 (d, J=11.7 Hz, 1H), 4.42 (d, J=13.0 Hz, 1H), 4.52 (d, J=11.6 Hz, 1H), 6.92 (m, 2H), 6.99 (dt, J=7.1, 1.0 Hz, 1H), 7.02 (s, 1H), 7.22 (m, 6H), 7.48 (d, J=7.9 Hz, 1H), 8.63 (s, 1H); $^{13}$C NMR (125.8 MHz, CD$_3$OD) δ22.5, 26.9, 27.0, 30.3, 30.6, 35.8, 40.5, 62.7, 70.8, 70.9, 72.4, 72.6, 73.3, 76.8, 79.2, 106.2, 112.2, 113.1, 118.0, 119.5, 119.6, 122.3, 123.8, 128.8, 128.9, 129.4, 132.5, 135.3, 138.0, 139.7, 173.2; high resolution mass spectrum (FAB, m-nitrobenzyl alcohol) m/z 619.3521[(M+H)$_+$; calcd for C$_{35}$H$_{47}$O$_6$N$_4$: 619.3495].

S. Azide (−)-44.

1-Iodo-6-azido-2-hexyne I-43 was prepared as follows: To a stirred solution of 6-azido-2-hexyn-1-ol (0.10 g, 0.72 mmol), imidazole (0.059 g, 0.86 mmol), and triphenylphosphine (0.23 g, 0.86 mmol) in Et$_2$O/CH$_3$CN (2 ml; 5:3) at 0° C., was added iodine (0.23 g, 0.86 mmol). After 5 min at room temperature, the mixture was diluted with ether (10 ml) and washed successively with saturated Na$_2$S$_2$O$_3$ and CuSO$_4$. The ether layer was dried over magnesium sulfate, filtered, and concentrated in vacuo, affording a yellow solid which was used without purification in the next reaction.

To a solution of alcohol I-33 (0.13 g, 0.19 mmol) and iodide I-43 (0.13 g, 0.52 mmol) in dry THF (2 ml) at 0° C. was added NaH (60%, 0.012 g, 0.30 mmol). After stirring for 6 h the mixture was poured into water (30 ml) and extracted with Et$_2$O (3×15 ml). The combined extracts were washed with water, dried over magnesium sulfate and concentrated in vacuo. Flash chromatography (15% ethyl acetate/petroleum ether) provided I-44 (107 mg, 70% yield) as a colorless oil: [α]D$^{25}$−15.1° (c 0.72, CHCl$_3$); IR (CHCl$_3$) 3075 (w), 3039 (w), 3018 (w), 2958 (s), 2876 (s), 2108 (s), 1452 (m), 1371 (br, m), 1175 (s), 1135 (s), 1122 (s), 1100 (s), 1060 (m), 1020 (w), 882 (w), 810 (w), 670 (br, w), 595 (m) cm$^{-1}$; $^1$H NMR (500 MHz, CDCl$_3$) δ1.03 (s, 21H), 1.53 (m, 1H), 1,69 (m, 2H), 2.24 (tt, J=7.0, 1.9 Hz, 2H), 2.40 (m, 1H), 2.98 (t, J=7.0 Hz, 2H), 3.30 (t, J=6.6 Hz, 2H), 3.46 (m, 2H), 3.58 (m, 1H), 3.72–3.80 (m, 3H), 4.11 (m, 1H), 4.14–4.22 (m, 2H), 4.24 (d, J=7.3 Hz, 1H), 4.53 (d, J=11.5 Hz, 1H), 4.60 (d, J=11.6 Hz, 1H), 7.21 (t, J=7.4 Hz, 1H), 7.25 (s, 1H), 7.26–7.33 (m, 5H), 7.39 (m, 3H), 7.48 (m, 2H), 7.85 (d, J=7.5 Hz, 2H), 7.96 (d, J=7.9 Hz, 1H); $^{13}$C NMR (62.9 MHz, CDCl$_3$) δ12.4, 16.1, 18.0, 25.6, 27.7, 38.3, 50.2, 59.1, 68.5, 68.7, 69.4, 71.5, 71.9, 77.9, 85.1, 105.6, 113.7, 119.4, 119.7, 123.1, 123.4, 124.7, 126.8, 127.8, 128.4, 129.2, 131.1, 133.6, 135.2, 138.2, 138.4.

T. Alcohol (−)-I-45.

A solution of azide I-44 (0.20 g 0.24 mmol) in THF (5 ml) was cooled to 0° C. and TBAF (0.29 ml, 1.0M, 0.29 mmol) was added dropwise. The mixture was stirred for 2 h, added to water and extracted with Et$_2$O (3×20 ml). The combined extracts were washed with water, dried over magnesium sulfate and concentrated in vacuo. Flash chromatography (40% ethyl acetate/petroleum ether) yielded the alcohol as a colorless oil (0.16 g, 100%); $[α]D^{25}$−12.8° (c 0.39, CHCl$_3$); IR (CHCl$_3$) 3050 (w), 3039 (w), 3020 (w), 2945 (m), 2888 (m), 2117 (s), 1455 (s), 1375 (s), 1280 (br, m), 1185 (s), 1140 (s), 1130 (s), 1105 (s), 1093 (s), 1075 (s), 1056 (s), 600 (m), 575 (m) cm$^{-1}$; $^1$H NMR (500 MHz, CDCl$_3$) δ1.52 (m, 1H), 1.60 (quin., J=6.8 Hz, 2H), 2.19 (d, J=3.1 Hz, 1H), 2.26 (tt, J=7.0, 2.0 Hz, 2H), 2.45 (m, 1H), 2.98 (m, 2H), 3.22 (t, J=6.6 Hz, 2H), 3.43 (m, 1H), 3.75 (m, 3H), 4.11–4.23 (m, 3H), 4.25 (d, J=7.1 Hz, 1H), 4.52 (d, J=11.5 Hz, 1H), 4.61 (d, J=11.5 Hz, 1H), 7.23 (m, 1H), 7.27–7.36 (m, 2H), 7.43 (m, 3H), 7.50 (m, 2H), 7.86 (m, 2H), 7.98 (m, 1H); $^{13}$C NMR (125.8 MHz, CDCl$_3$) δ16.1, 25.5, 27.7, 34.2, 50.1, 59.1, 68.3, 68.6, 68.6, 71.4, 71.8, 77.7, 85.2, 104.7, 113.8, 119.4, 123.2, 123.5, 124.8, 126.7, 127.7, 127.8, 128.4, 129.2, 131.1, 133.7, 135.2, 138.0, 139.0, 139.2; high resolution mass spectrum (FAB, m-nitrobenzyl alcohol) m/z 658.2482 (M$^+$; calcd for C$_{35}$H$_{38}$SO$_7$ N$_4$: 658.2461].

U. imidazole-Azide (−)-I-46.

To a solution of alcohol I-45 (0.16 g, 0.24 mmol) and chloro-imidazole I-37 (0.27 g, 0.69 mmol) at 0° C. in dry THF (4 ml) was added NaH (60%, 0.015 g, 0.36 mmol). After stirring for 12 h at room temperature, the mixture was added to water and extracted with Et$_2$O (3×20 ml). The combined extracts were washed with water, dried over magnesium sulfate and concentrated in vacuo. Flash chromatography (60% ethyl acetate/petroleum ether) yielded I-46 as a colorless oil (0.13 g, 54%); $[α]D^{25}$−0.4° (c 1.14, CHCl$_3$); IR (CHCl$_3$) 3025 (w), 3017 (w), 3010 (m), 2980 (m), 2959 (m), 2880 (m), 2108 (s), 1613 (w), 1590 (w), 1516 (m), 1452 (s), 1385 (s), 1360 (s), 1290 (s), 1280 (s), 1238 (s), 1225 (s), 1100 (s), 1075 (s), 1050 (s), 830 (m), 700 (m), 600 (m), 572 (m) cm$^{-1}$; $^1$H NMR (500 MHz, CDCl$_3$) δ1.51 (m, 1H), 1.70 (quin., J=6.8 Hz, 2H), 2.25 (tt, J=7.0, 2.1 Hz, 2H), 2.59 (m, 1H), 2.92 (t, J=7.0 Hz, 2H), 3.29–3.39 (m, 3H), 3.45 (m, 2H), 3.69–3.80 (m, 3H), 3.28 (s superimposed to a m, 3H), 4.10–4.20 (m, 3H), 4.37 (d, J=7.6 Hz, 1H), 4.44 (d, J=11.4 Hz, 1H), 4.46 (d, J=12.2 Hz, 1H), 4.59 (d, J=11.5 Hz, 1H), 4.64 (d, J=12.2 Hz, 1H), 6.79 (m, 3H), 7.04 (m, 2H), 7.10 (m, 4H), 7.15 (m, 1H), 7.20–7.49 (m, 18H), 7.82 (m, 2H), 7.91 (d, J=8.2 Hz, 1H); $^{13}$C NMR (125.8 MHz, CDCl$_3$) δ13.1, 15.0, 24.5, 26.7, 33.9, 49.1, 54.2, 58.1, 65.9, 67.3, 67.6, 70.1, 71.0, 73.8, 74.0, 76.2, 76.7, 84.0, 104.1, 112.2, 112.6, 118.4, 118.8, 122.0, 122.5, 125.5, 125.6, 126.6, 126.8, 126.9, 127.3, 128.1, 128.6, 130.0, 130.1, 132.5, 133.4, 134.1, 137.0, 137.2, 137.4, 137.9, 141.7, 158.0; high resolution mass spectrum (FAB, m-nitrobenzyl alcohol) m/z 1011.4100 [(M+H)$^+$; calcd for C$_{59}$H$_{59}$SO$_8$ N$_6$: 1011.4115].

V. Free imidazole (+)-42.

To a solution of azide I-45 (0.11 g, 0.11 mmol) in THF (5 ml) was added H$_2$O (0.095 ml, 5.27 mmol) and PPh$_3$ (0.073 g, 0.28 mmol) and the reaction mixture heated to 55° C. for 6 h, cooled, and concentrated in vacuo. Flash chromatography (10% methanol/methylene chloride) provided the amine as a colorless oil (103 mg, 93%); $[α]D^{25}$+2.2° (c 0.87, CHCl$_3$); IR (CHCl$_3$) 3070 (w), 3010 (m), 2960 (m), 2942 (m), 2878 (m), 1612 (m), 1590 (w), 1515 (m), 1452 (m), 1374 (m), 1259 (m), 1179 (s), 1145 (s), 1120 (s), 1090 (s), 1070 (m), 1050 (m), 827 (w), 700 (w), 597 (w), 569 (w) cm$^{-1}$; $^1$H NMR (500 MHz, CDCl$_3$) δ1.52 (m, 1H), 1.76 (m, 2H), 2.23 (m, 2H), 2.55 (m, 1H), 2.91 (m, 4H), 3.38 (m, 1H), 3.47 (m, 2H), 3.69 (dd, J=10.5, 4.8 Hz, 1H), 3.77 (m, 5H), 4.11 (m, 3H), 4.40 (d, J=7.7 Hz, 1H), 4.43 (d, J=11.4 Hz, 1H), 4.44 (d, J=12.2 Hz, 1H), 4.59 (d, J=11.2 Hz, 1H), 4.60 (d, J=12.2 Hz,1H), 5.60 (br s, 1H), 6.71 (s, 1H), 6.78 (m, 2H), 7.00 (m, 2H), 7.08 (m, 4H), 7.12 (m, 1H), 7.20 (m, 1H), 7.22–7.38 (m, 14H), 7.45 (m, 3H), 7.81 (dd, J=8.4, 1.0 Hz, 2H), 7.91 (d, J=7.6 Hz, 1H); $^{13}$C NMR (62.9 MHz, CDCl$_3$) δ16.2, 25.6, 28.0, 34.8, 39.7, 55.3, 59.1, 66.7, 68.4, 68.7, 71.2, 72.2, 75.0, 75.2, 77.4, 77.5, 77.7, 85.1, 105.0, 113.3, 113.6, 119.6, 119.9, 120.1, 123.1, 123.7, 124.6, 126.7, 127.8, 128.0, 128.4, 129.2, 129.7, 131.2, 133.6, 134.4, 135.1, 138.1, 138.3, 138.3, 139.0, 142.6, 159.1; high resolution mass spectrum (FAB, m-nitrobenzyl alcohol) m/z 985.4254 [(M+H)$^+$; calcd for C$_{59}$H$_{61}$SO$_8$ N$_4$: 985.4210].

To a solution of the amine (0.085 g, 0.087 mmol) in EtOH (3 ml) was added 5M NaOH (0.50 ml) and mixture was heated at reflux for 4 h. After cooling, the mixture was diluted with water and extracted with methylene chloride (3×10 ml). The combined extracts were washed with brine, dried over magnesium sulfate, and concentrated in vacuo to an oil. Flash chromatography (15% methanol/methylene chloride) afforded the amine (39 mg, 56%) as a colorless oil; $[α]D^{25}$+3.1° (c 1.95, CHCl$_3$); IR (CHCl$_3$) 3480 (w), 3520–2500 (br, w), 3020 (s), 2960 (s), 2940 (s), 2880 (s), 1609 (m), 1590 (w), 1513 (s), 1493 (m), 1459 (m), 1447 (m), 1355 (m), 1340 (m), 1302 (m), 1257 (s), 1185 (m), 1156 (m), 1130 (s), 1090 (s), 1037 (s), 1010 (m), 910 (w), 825 (m0, 695 (m), 660 (w), 582 (w) cm$^{-1}$; $^1$H NMR (500 MHz, CDCl$_3$) δ1.50 (q, J=11.4 Hz, 1H), 1.61 (m, 1H), 1.69 (m, 1H), 2.11 (m, 2H), 2.52 (m, 1H), 2.79 (m, 2H), 3.01 (m, 2H), 3.36–3.49 (m, 3H), 3.65 (dd, J=10.8, 5.0 Hz, 1H), 3.77 (m, 5H), 4.05–4.17 (m, 3H), 4.40 (m, 2H), 4.47 (d, J=11.9 Hz, 1H), 4.54 (d, J=11.4 Hz, 1H), 4.60 (d, J=12.0 Hz, 1H), 6.72 (br s, 1H), 6.80 (apparent d, J=9.0 Hz, 2H), 6.98–7.13 (m, 9H), 7.23–7.33 (m, 12H), 7.40 (br s, 1H), 7.50 (d, J=7.1 Hz, 1H), 8.75 (br s, 1H); $^{13}$C NMR (62.9 MHz, CDCl$_3$) δ16.1, 25.8, 26.0, 34.8, 38.9, 55.3, 59.1, 66.3, 68.7, 70.0, 71.2, 72.2, 75.1, 77.7, 84.7, 105.1, 111.5, 112.2, 113.3, 118.6, 119.0, 120.2, 121.7, 122.8, 128.1, 128.4, 129.7, 131.2, 134.2, 136.2, 138.0, 138.8, 142.5, 159.2; high resolution mass spectrum (FAB, m-nitrobenzyl alcohol) m/z 845.4261 [(M+H)$^+$; calcd for C$_{53}$H$_{57}$SO$_6$ N$_4$: 845.4278].

To a solution of the amine (0.040 g, 0.047 mmol) in dry CH$_2$Cl$_2$ (2 ml) was added TFA (24 ml, 0.31 mmol). After stirring for 5 minutes, the mixture was added to brine (20 ml) that had been adjusted to pH 8.0 with aqueous sodium bicarbonate and extracted with methylene chloride (3×15 ml). The combined extracts were washed with brine, dried over magnesium sulfate, and concentrated in vacuo to an oil. Purification by RP HPLC (water/acetonitrile) afforded I-42 (12.3 mg, 45%) as a pale yellow oil; $[α]D^{25}$+0.9° (c 0.56, CH$_3$OH); $^1$H NMR (500 MHz, CD$_3$OD) δ1.42 (m, 1H), 1.78 (apparent quin., J=7.0 Hz, 2H), 2.30 (tt, J=7.0, 2.1 Hz, 2H), 2.47 (m, 1H), 2.95 (t, J=7.6 Hz, 2H), 3.06 (t, J=6.7 Hz, 2H), 3.20 (m, 2H), 3.47 (m, 2H), 3.69 (dd, J=10.7, 4.4 Hz, 1H), 3.76 (dd, J=11.0, 1.4 Hz, 1H), 3.86 (dt, J=9.4, 7.3 Hz, 1H), 4.18 (m, 3H), 4.40 (m, 2H), 4.49 (m, 2H), 4.60 (d, J=11.6 Hz, 1H), 6.98 (m, 2H), 7.06 (m, 1H), 7.09 (s, 1H), 7.26–7.34 (m, 7H), 7.55 (d, 7.8 Hz, 1H), 8.70 (br s, 1H); $^{13}$C NMR (62.9 MHz, CD$_3$OD) δ16.6, 26.9, 27.5, 35.8, 39.8, 59.7, 62.7, 69.6, 71.0, 72.3, 73.1, 76.8, 78.4, 79.0, 85.6, 106.2, 112.2, 113.1, 117.9, 119.5, 119.6, 122.3, 124.0, 128.8, 128.9, 129.4, 132.5, 135.4, 139.7, 142.2; high resolution mass spectrum (FAB, m-nitrobenzyl alcohol) m/z 573.3062 [(M+H)$^+$; calcd for C$_{33}$H$_{41}$SO$_5$ N$_4$: 845.4278].

W. Saturated amine I-16 from Pd/CaCO3 reduction of acetylene-azide I-46.

To a solution of azide I-46 (8 mg) in ethanol (1.7 ml) was added Pd/CaCO$_3$ (1 mg). The system was evacuated and back flushed with H$_2$ gas four times and then allowed to stir under an atmosphere of H$_2$ gas for 2.5 h. The mixture was filtered through celite, the celite was washed with Et$_2$O (20 ml), and the filtrate was concentrated in vacuo. Flash chromatography (20% methanol/methylene chloride) afforded I-16 (5.1 mg, 64%) as a pale yellow oil which was identical in all respects with material obtained by other methods.

X. Benzyl ether (−)-I-50.

To a solution of the alcohol I-33 (0.044 g, 0.063 mmol) and benzyl bromide (8.3 ml, 0.070) in dichloromethane (2 ml) at 0° C. was added NaH (60%, 3.0 mg, 0.070 mmol) and 15-crown-5 (1 ml). After stirring for 5 h, the mixture was added to H$_2$O (200 ml) and extracted with dichloromethane (3×10 ml). The combined extracts were washed with water, dried over magnesium sulfate and concentrated in vacuo. Flash chromatography (10% ethyl acetate/petroleum ether) provided I-50 (0.035 g, 70% yield) as a colorless oil: [α]D$^{25}$−10.2° (c 3.0, CHCl$_3$); IR (CHCl$_3$) 3065 (w), 3010 (m), 2950 (s), 2877 (s), 1610 (w), 1496 (w), 1465 (m), 1452 (s), 1370 (s), 1270 (w), 1205 (m), 1175 (s), 1125 (s), 1098 (s), 1070 (s), 880 (m), 725 (br, s), 665 (s), 595 (m), 569 (m) cm$^{-1}$; $^1$H NMR (500 MHz, CDCl$_3$) δ1.04 (s, 21H), 1.51 (apparent q. J=11.1 Hz, 1H), 2.41 (dt, J=12.3, 4,8 Hz, 1H), 3.00 (t, J=7.9 Hz, 3H), 3.43–3.52 (m, 2 H), 3.60 (m, 1H), 3.66 (dd, 10.7, 5.1 Hz, 1H), 3.78 (m, 2H), 4.12 (m, 1H), 4.26 (d, J=7.3 Hz, 1H), 4.43 (d, J=11.5 Hz, 1H), 4.53 (d, J=7.0 Hz, 1H), 4.57 (d, J=6.2 Hz, 1H), 4.59 (d, J=12.3 Hz, 1H), 7.18–7.32 (m, 12H), 7.36–7.41 (m, 3H), 7.47 (m, 2H), 7.83 (m, 2H), 7.97 (apparent d, J=8.4 Hz, 1H); $^{13}$C NMR (62.9 MHz, CDCl$_3$) δ12.4, 18.0, 25.7, 38.3, 68.5, 69.4, 71.4, 72.2, 73.5, 78.1, 105.6, 113.7, 119.4, 119.7, 123.1, 123.4, 124.7, 126.7, 127.5, 127.7, 128.3, 128.4, 129.2, 131.1, 133.6, 135.2, 138.1, 138.4; high resolution mass spectrum (FAB, m-nitrobenzyl alcohol) m/z 783.3662(M$^+$; calcd for C$_{45}$H$_{57}$SiSO$_7$ N: 83.3625).

Y. Alcohol (−)-I-51.

A solution of benzyl ether I-50 (0.080 g 0.10 mmol) in THF (2 ml) was cooled to 0° C. and TBAF (0.11 ml, 1.0M, 0.11 mmol) was added dropwise. The mixture was stirred for 2 h, added to water and extracted with EtOAc (3×20 ml). The combined extracts were washed with water, dried over magnesium sulfate and concentrated in vacuo. Flash chromatography (40% ethyl acetate/petroleum ether) yielded alcohol I-51 as a colorless oil (0.070 g, 100%); [α]D$^{25}$−7.7° (c 0.27, CHCl$_3$); IR (CHCl$_3$) 3080 (w), 3040 (w), 3010 (m), 2955 (m), 2880 (m), 1450 (m), 1370 (m), 1280 (w), 1173 (s), 1120 (s), 1100 (s), 1060 (s), 690 (w), 680 (w) cm$^{-1}$; $^1$H NMR (500 MHz, CDCl$_3$) δ1.53 (apparent q, J=10.2 Hz, 1H), 2.30 (br s, 1H), 2.45 (dt, J=12.4, 4.6 Hz, 1H), 2.99 (m, 2H), 3.46 (m, 1H), 3.55 (m, 1H), 3.59 (m, 2H), 3.65 (dd, J=10.5, 5.0 Hz, 1H), 3.74 (m, 2H), 4.20 (dt, J=9.5, 6.5 Hz, 1H), 4.27 (d, J=6.9 Hz, 1H), 4.43 (d, J=11.5 Hz, 1H), 4.49–4.58 (m, 3H), 7.21–7.33 (m, 12H), 7.39 (m, 2H), 7.43 (s, 1H), 7.49 (d, 2H), 7.85 (m, 2H), 7.99 (d, J=8.4 Hz, 1H); $^{13}$C NMR (62.9 MHz, CDCl$_3$) δ24.5, 32.8, 67.2, 67.5, 68.3, 70.2, 71.0, 72.3, 76.7, 103.5, 112.7, 118.4, 118.8, 122.1, 122.4, 123.7, 125.6, 126.5, 126.6, 126.7, 126.7, 127.3, 127.4, 128.1, 130.0, 132.6, 134.1, 136.8, 137.2; high resolution mass spectrum (FAB, m-nitrobenzyl alcohol) m/z 628.2335 [(M+H)$^+$; calcd for C$_{36}$H$_{38}$SO$_7$ N: 628.2368].

Z. Azide (−)-I-53.

1-Iodo-5-azido-2-Pentyne I-52 was prepared as follows: To a stirred solution of 5-azido-2-pentyn-1-ol (0.13 g, 1.00 mmol), imidazole (0.085 g, 1.25 mmol), and triphenylphosphine (0.32 g, 1.25 mmol) in Et$_2$O/CH$_3$CN (2 ml; 5:3) at 0° C., was added iodine (0.32 g, 1.25 mmol). After 5 min at room temperature, the mixture was diluted with ether (10 ml) and washed successively with saturated Na$_2$S$_2$O$_3$ and CuSO$_4$. The ether layer was dried over magnesium sulfate, filtered, and concentrated in vacuo, affording a yellow solid which was used without purification in the next reaction.

To a solution of alcohol I-51 (0.073 g, 0.12 mmol) and iodide I-52 (0.24 g, 1.00 mmol) in dry dichloromethane (2 ml) at 0° C. was added NaH (60 %, 6.0 mg, 0.15 mmol). After stirring for 6 h the mixture was poured into water (30 ml) and extracted with CH$_2$Cl$_2$ (3×15 ml). The combined extracts were washed with water, dried over magnesium sulfate and concentrated in vacuo. Flash chromatography (30% ethyl acetate/petroleum ether) provided I-53 (64 mg, 75% yield) as a colorless oil: [α]D$^{25}$−8.9° (c 0.63, CHCl$_3$); IR (CHCl$_3$) 3070 (w), 3028 (w), 3010 (m), 2940 (m), 2870 (m), 2110 (s), 1450 (s), 1378 (s), 1270 (m), 1250 (s), 1178 (s), 1133 (s), 1120 (s), 1090 (s), 1072 (s), 1045 (s), 690 (w), 595 (m) cm$^{-1}$; $^1$H NMR (500 MHz, CDCl$_3$) δ1.48 (q, J=12.0 Hz, 1H), 2.50 (tt, J=6.9, 2.1 Hz, 2H), 2.55 (dt, J=12.2, 4.7 Hz, 1H), 3.00 (t, J=6.9 Hz, 2H), 3.39 (m, 3H), 3.50 (m, 2H), 3.66 (dd, J=10.7, 5.0 Hz, 1H), 3.78 (m, 2H), 4.19 (m, 1H), 4.24 (tq, J=15.2, 2.2 Hz, 2H), 4.34 (d, J=7.6 Hz, 1H), 4.40 (d, J=11.4 Hz, 1H), 4.58 (m, 3H), 7.19–7.31 (m, 12H), 7.39 (m, 2H), 7.48 (m, 4H), 7.85 (m, 2H), 7.98 (d, J=8.3 Hz, 1H); $^{13}$C NMR (62.9 MHz, CDCl$_3$) δ19.9, 25.6, 34.8, 49.7, 58.3, 68.3, 69.2, 71.3, 72.1, 73.4, 74.3, 78.0, 78.5, 82.4, 104.9, 113.7, 123.1, 123.6, 124.7, 126.7, 127.5, 127.7, 128.3, 128.4, 129.2, 131.0, 133.6, 135.1, 137.9, 138.3; high resolution mass spectrum (FAB, m-nitrobenzyl alcohol) m/z 735.2827 [(M+H)$^+$; calcd for C$_{41}$H$_{43}$SO$_7$ N$_4$: 735.2852].

AA. Amine (−)-I-54.

To a solution of azide I-53 (0.021 g, 0.027 mmol) in THF (1.5 ml) was added H$_2$O (0.012 ml, 0.69 mmol) and PPh$_3$ (0.014 g, 0.055 mmol) and the reaction mixture was heated to 55° C. for 4 h, cooled, and concentrated in vacuo. Flash chromatography (6% methanol/methylene chloride) provided I-54 as a colorless oil (16.2 mg, 83%); [α]D$^{25}$−9.0° (c 0.81, CHCl$_3$); IR (CHCl$_3$) 3070 (w), 3038 (w), 3017 (w), 2940 (m), 2878 (w), 1451 (m), 1370 (br, m), 1210 (s), 1187 (m), 1179 (m), 1122 (m), 1090 (m), 1072 (m), 930 (w), 750 (br, s), 665 (s), 595 (m), 569 (m) cm$^{-1}$; $^1$H NMR (500 MHz, CDCl$_3$) δ1.48 (q, J=12.0 Hz, 1H), 2.00 (br s, 2H), 2.36 (br s, 2H), 2.55 (dt, J=12.3, 4.7 Hz, 1H), 2.83 (br s, 2H), 3.00 (t, J=6.7 Hz, 2H), 3.39 (m, 1H), 3.50 (m, 2H), 3.66 (dd, J=10.8, 5.0 Hz, 1H), 4.19 (m, 1H), 4.25 (tq, J=15.3, 2.1 Hz, 2H), 4.35 (d, J=7.6 Hz, 1H), 4.40 (d, J=11.4 Hz, 1H), 4.56 (m, 3H), 7.20–7.33 (m, 12H), 7.38 (m, 3H), 7.48 (m, 4H), 7.85 (m, 2H), 7.97 (d, J=8.4 Hz, 1H); $^{13}$C NMR (125.8 MHz, CDCl$_3$) δ25.6, 34.8, 58.4, 68.3, 69.2, 71.3, 72.1, 73.4, 74.3, 77.9, 80.0, 84.2, 104.9, 113.7, 119.4,119.8,123.7, 124.7, 126.7, 127.5, 127.7, 127.7, 127.8, 128.3, 128.4, 129.1, 131.0, 133.6, 135.1, 137.9, 138.3, 138.3; high resolution mass spectrum (FAB, m-nitrobenzyl alcohol) m/z 709.2980 [(M+H)$^+$; calcd for C$_{41}$H$_{45}$SO$_7$ N$_2$: 709.2947].

AB. Amine (+)-I-48.

To a solution of amine I-54 (0.012 g, 0.017 mmol) in MeOH (1.5 ml) was added 5M KOH (0.30 ml) and the mixture was heated at reflux for 8 h. After cooling, the mixture was diluted with water and extracted with methylene chloride (3×10 ml). The combined extracts were washed with brine, dried over magnesium sulfate, and concentrated in vacuo to an oil. Flash chromatography (8% methanol/methylene chloride) afforded I-48 (7.1 mg, 73%) as a pale yellow oil; [α]D$^{25}$+13.5° (c 0.31, CHCl$_3$); IR (CHCl$_3$) 3480 (m), 3010 (s), 2930 (s), 2879 (s), 2861 (s), 1460 (m), 1270 (w), 1140 (w), 1105 (m), 1079 (s), 861 (w), 690 (m) cm$^{-1}$; $^1$H NMR (500 MHz, CDCl$_3$) δ1.49 (q, J=11.9 Hz, 1H), 2.38 (br s, 2H), 2.51 (dt, J=12.3, 4.6 Hz, 2H), 2.66 (br s, 2H), 2.84 (br s, 2H), 3.09 (t, J=6.7 Hz, 2H), 3.33 (m, 1H), 3.45–3.55 (m, 2H), 3.66 (dd, J=10.7, 4.9 Hz, 1H), 3.76 (dd, J=10.9, 1.8 Hz, 1H), 3.83 (dt, J=9.4, 7.2 Hz, 1H), 4.17 (dt, J=15.0, 2.0 Hz, 1H), 4.24 (dt, J=9.5, 6.3 Hz, 1H), 4.29 (dt, J=15.0, 2.1 Hz, 1H), 4.39 (m, 2H), 4.56 (m, 3H), 7.08 (t, J=7.9 Hz, 1H), 7.12 (s, 1H), 7.16 (t, J=7.3Hz, 1H), 7.20–7.35 (m, 11H), 7.58 (d, J=7.8 Hz, 1H), 8.63 (br s, 1H); $^{13}$C NMR (62.9 MHz, CDCl$_3$) δ22.7, 29.7, 34.9, 58.6, 69.1, 69.5, 71.3, 72.2, 73.5, 74.4, 77.9, 78.4, 83.6, 104.9, 111.1, 112.7, 118.7, 119.1, 121.7, 122.5, 127.6, 127.8, 128.3, 128.4, 136.2, 138.0, 138.3; high resolution mass spectrum (FAB, m-nitrobenzyl alcohol) m/z 569.3029 [(M+H)$^+$; calcd for C$_{35}$H$_{41}$O$_5$ N$_2$: 569.3015].

AC. Amide (+)-I-56.

To a solution of amine I-54 (8.4 mg, 0.012 mmol) in CH$_2$Cl$_2$ (1 ml) at 0° C. was added Et$_3$N (1.8 ml, 0.013 mmol) and Ac$_2$O (1.2 ml, 0.013 mmol). After stirring for one minute, the mixture was poured into water. The aqueous layer was extracted with methylene chloride (3×20 ml) and the combined extracts were washed with water, dried over magnesium sulfate and concentrated in vacuo. $^1$H NMR (500 MHz, CDCl$_3$, Crude) δ1.47 (q, J=11.9 Hz, 1H), 1.95 (s, 3H), 2.40 (m, 2H), 2.53 (dt, J=12.2, 4.8 Hz, 1H), 2.99 (m, 2H), 3.28 (m, 1H), 3.39 (m, 2H), 3.49 (m, 2H), 3.65 (dd, J=10.7, 5.0 Hz, 1H), 3.78 (m, 2H), 4.22 (m, 3H), 4.34 (d, J=7.6 Hz, 1H), 4.40 (d, J=11.4 Hz, 1H), 4.56 (m, 3H), 6.05 (br s, 1H), 7.20–7.33 (m, 12H), 7.39 (apparent t, J=8.2 Hz, 2H), 7.48 (m, 3H), 7.85 (m, 2H), 7.95 (d, J=8.2 Hz, 1H).

To a solution of the crude amide in MeOH (1 ml) was added 5M KOH (0.20 ml) and mixture was heated at reflux for 6 h. After cooling, the mixture was diluted with water and extracted with methylene chloride (3×10 ml). The combined extracts were washed with brine, dried over magnesium sulfate, and concentrated in vacuo to an oil. Flash chromatography (2% methanol/methylene chloride) afforded I-56 (4.9 mg, 68% from I-54) as a pale yellow oil; [α]D$^{25}$+18.4° (c 0.25, CHCl$_3$); IR (CHCl$_3$) 3480 (w), 3010 (m), 2940 (m), 2870 (m), 1675 (s), 1520 (w), 1456 (m), 1367 (w), 1250 (br, w), 1285 (br, s0, 695 cm$^{-1}$; $^1$H NMR (500 MHz, CDCl$_3$) δ1.50 (q, J=11.9 Hz, 1H), 1.95 (s, 3H), 2.41 (m, 2H), 2.51 (dt, J=12.2, 4.7 Hz, 1H), 3.10 (t, J=7.0 Hz, 2H), 3.27 (m, 1H), 3.40 (m, 2H), 3.45–3.55 (m, 2H), 3.66 (dd, J=10.8, 4.9 Hz, 1H), 3.76 (dd, J=10.8, 1.8 Hz, 1H), 3.85 (dt, J=9.5, 7.3 Hz, 1H), 4.19–4.29 (m, 3H), 4.37 (d, J=7.6 Hz, 1H), 4.41 (d, J=11.4 Hz, 1H), 4.53–4.61 (m, 3H), 7.09 (m, 2H), 7.16 (m, 1H), 7.20–7.36 (m, 11H), 7.59 (d, J=8.2 Hz, 1H), 8.15 (br s, 1H); $^{13}$C NMR (125.8 MHz, CDCl$_3$) δ19.9, 23.9, 25.8, 34.8, 38.2, 58.3, 69.1, 69.6, 71.3, 72.2, 73.4, 74.1, 78.0, 78.1, 83.7, 104.8, 11.1, 112.7, 118.7, 119.2, 121.9, 122.2, 127.5, 127.7, 128.3, 128.4, 136.2, 138.0, 170.3; high resolution mass spectrum (FAB, m-nitrobenzyl alcohol) m/z 633.2923 [(M+Na)$^+$; calcd for C$_{37}$H$_{42}$O$_6$ N$_2$Na: 633.2940].

AD. Alkane (+)-I-47.

To a solution of azide I-53 (0.020 g, 0.027 mmol) in EtOH (1 ml) was added 5% Pd/CaCO$_3$ (6 mg, 33 wgt. %). The system was evacuated and back flushed with H$_2$ gas four times and then allowed to stir under an atmosphere of H$_2$ gas for 4 h. The mixture was filtered through celite, the celite was washed with Et$_2$O (20 ml), and the filtrate was concentrated in vacuo. Flash chromatography (20% methanol/methylene chloride) afforded the amine (12 mg, 62%) as a pale yellow oil; [Cα]D$^{25}$+6.0° (c 0.57, CHCl$_3$); IR (CHCl$_3$) 3059 (w), 3020 (w), 3017 (m), 2845 (m), 2878 (m), 1455 (m), 1372 (br, m), 1209 (w), 1179 (s), 1122 (s), 1095 (s), 720 (br, m), 600 (m), 570 (m) cm$^{-1}$; $^1$H NMR (500 MHz, CD$_3$OD) δ1.35 (m, 2H), 1.42–1.54 (m, 4H), 2.45 (m, 1H), 2.59 (t, J=7.4 Hz, 1H), 2.90 (t, J=5.9 Hz, 2H), 3.04 (m, 1H), 3.32 (dt, J=9.4, 6.4 Hz, 1H), 3.38–3.46 (m, 3H), 3.58 (dd, J=10.8, 4.9 Hz, 1H), 3.69 (dd, J=11.0, 1.5 Hz, 1H), 3.76 (dt, J=9.7, 6.5 Hz, 1H), 4.11 (dt, J=9.7, 5.9 Hz, 1H), 4.25 (d, J=7.5 Hz, 1H), 4.36 (d, J=11.6 Hz, 1H), 4.44 (d, J=12.0 Hz, 1H), 4.48 (d, J=12.0 Hz, 1H), 4.52 (d, J=11.5 Hz, 1H), 7.11–7.26 (m, 12H), 7.37 (m, 3H), 7.47 (m, 3H), 7.80 (m, 2H), 7.88 (d, J=8.3 Hz, 1H); $^{13}$C NMR (62.9 MHz, CD$_3$OD) δ24.3, 26.4, 30.8, 32.0, 35.9, 41.9, 69.3, 70.4, 71.7, 72.3, 73.4, 74.4, 77.0, 79.1, 106.2, 114.7, 120.8, 122.0, 124.4, 125.3, 125.7, 127.9, 128.7, 128.8, 129.0, 129.4, 130.4, 132.6, 135.1, 136.6, 139.4, 139.6; high resolution mass spectrum (FAB, m-nitrobenzyl alcohol) m/z 713.3251 [(M+H)$^+$; calcd for C$_{41}$H$_{49}$SO$_7$ N$_2$: 713.3260].

To a solution of the amine (0.011 g, 0.016 mmol) in MeOH (1.5 ml) was added 5M KOH (0.30 ml) and mixture was heated at reflux for 6 h. After cooling, the mixture was diluted with water and extracted with methylene chloride (3×10 ml). The combined extracts were washed with brine, dried over magnesium sulfate, and concentrated in vacuo. Flash chromatography (20% methanol/methylene chloride) afforded I-47 (5.2 mg, 58%) as a pale yellow oil; [α]D$^{25}$+3.8° (c 0.16, CHCl$_3$); IR (CHCl$_3$) 3492 (m), 3018 (m), 2960 (m), 2872 (m), 1455 (m), 1370 (w), 1208 (s), 1090 (br, s), 720 (br, s) cm$^{-1}$; $^1$H NMR (500 MHz, CDCl$_3$) δ1.35 (m, 2H), 1.48 (m, 2H), 1.80 (br s, 2H), 2.54 (m, 1H), 2.73 (t, J=4.0 Hz, 2H), 3.12 (t, J=6.7 Hz, 2H), 3.21 (m, 1H), 3.50 (m, 3H), 3.67 (m, 2H), 3.81 (d, J=10.1 Hz, 1H), 3.85 (dt, 9.5, 7.3 Hz, 1H), 4.28 (dt, J=9.3, 6.2 Hz, 1H), 4.38 (d, J=5.6 Hz, 1H), 4.42 (d, J=11.3 Hz, 1H), 4.61 (m, 3H), 7.11 (t, J=7.1 Hz, 1H), 7.15 (br s, 1H), 7.19 (t, J=7.1 Hz, 1H), 7.25–7.37 (m, 11H), 7.62 (d, J=7.8 Hz, 1H), 8.87 (br s, 1H); $^{13}$C NMR (125.8 MHz, CDCl$_3$) δ23.3, 25.6, 30.0, 32.8, 34.9, 41.7, 69.3, 69.5, 70.8, 71.2, 72.4, 73.4, 75.8, 78.0, 105.0, 111.0, 112.9, 118.7, 119.0, 121.6, 122.4, 127.5, 127.6, 127.7, 128.1, 128.3, 128.4, 136.2, 138.1, 138.4; high resolution mass spectrum (Cl, NH$_3$) m/z 573.3301 [(M+H)$^+$; calcd for C$_{35}$H$_{45}$O$_5$N$_2$: 573.3328].

AE. Alkene (I-49).

To a solution of amine I-54 (0.018 g, 0.026 mmol) and quinoline (6 ml) in benzene (1.5 ml) was added Linlar's catalyst (6 mg, 30 wgt. %). The system was evacuated and back flushed with H$_2$ gas four times and then allowed to stir under an atmosphere of H$_2$ gas for 4 h. The mixture was filtered through celite, the celite was washed with Et$_2$O (20 ml), and the filtrate was concentrated in vacuo. The residue was used without purification in the next reaction.

To a solution of the crude amine in MeOH (1.5 ml) was added 5M KOH (0.30 ml) and mixture was heated at reflux for 6 h. After cooling, the mixture was diluted with water and extracted with methylene chloride (3×10 ml). The combined extracts were washed with brine, dried over magnesium sulfate, and concentrated in vacuo to an oil. Flash chromatography (methylene chloride/toluene/methanol; 9: 8:3) afforded I-49 (1.5 mg, 10% from I-54) as a pale yellow oil; $^1$H NMR (500 MHz, CDCl$_3$) δ1.49 (m, 1H), 2.06 (m, 2H), 2.49 (m, 2H), 2.57 (m, 1H), 3.09 (t, J=5.8 Hz, 2H), 3.28 (m, 1H), 3.51 (m, 2H), 3.67 (m, 1H), 3.75 (d, J=10.8 Hz, 1H), 3.87 (dt, 9.3, 7.4 Hz, 1H), 3.94–4.08 (m, 2H), 4.25 (dt, J=9.3, 7.0 Hz, 1H), 4.40 (m, 2H), 4.56 (m, 3H), 5.35 (m, 1H), 5.60 (m, 1H), 7.08 (t, J=7.0 Hz, 1H), 7.08 (s, 1H), 7.14 (t, J=7.1 Hz, 1H), 7.21–7.35 (m, 11H), 7.59 (d, 7.7 Hz, 1H), 8.90 (br s, 1H); high resolution mass spectrum (Cl, NH$_3$) m/z 571.3182 [(M+H)$^+$; calcd for C$_{35}$H$_{43}$O$_5$N$_2$: 571.3171].

AF. Benzoylamide (+)-I-59.

Triflate I-62 was generated in the following way: A stirred solution of alcohol I-61 (0.20 g, 0.27 mmol) and 2,6-di-tert-butyl-4-methylpyridine (0.089 g, 0.44 mmol) in dry dichloromethane (3 ml) at −11° C. was treated with triflic anhydride (0.060 ml, 0.35 mmol). After 10 min, the mixture was diluted with water (100 ml), saturated sodium bicarbonate (2 ml) and extracted with dichloromethane (2×200 ml). The combined extracts were washed with brine, dried over magnesium sulfate, filtered, and concentrated in vacuo, affording a yellow oil which was used without purification in the next reaction.

To a stirred solution of N-benzoyl-5-amino-1-pentanol (0.28 g, 1.36 mmol) in THF (6 ml) was added sodium hydride (60% dispersion in oil, 0.11 g, 2.80 mmol). The mixture was allowed to stir for 1.5 h, then cooled to 0° C. before triflate I-62 was added via cannula (4 ml THF). After stirring an additional 18 h, the mixture was added to water (100 ml) and extracted with ether (3×20 ml). The combined extracts were washed with water, dried over magnesium sulfate, and concentrated in vacuo. Flash chromatography (40% ethyl acetate/hexanes) afforded the amide (90 mg, 36%) as a pale yellow oil which was used immediately in the next reaction.

To a solution of the amine (0.055 g, 0.060 mmol) in MeOH (3 ml) was added 5M KOH (0.30 ml) and the mixture was heated at reflux for 3 h. After cooling, the mixture was diluted with water and extracted with methylene chloride (4×10 ml). The combined extracts were washed with brine, dried over magnesium sulfate, and concentrated in vacuo to an oil. Flash chromatography (40% ethyl acetate/hexanes) afforded I-59 (42 mg, 90%) as a clear yellow oil; [α]D$^{25}$+12.3° (c 0.31, CHCl$_3$); IR (CHCl$_3$) 3480 (m), 3097 (w), 3069 (w), 3035 (w), 3010 (m), 2960 (m), 2875 (m), 1660 (br, m), 1582 (w), 1520 (br, m), 1489 (m), 1455 (m), 1360 (br, m), 1305 (br, w), 1285 (br, w), 1070 (br, s), 695 (m) cm$^{-1}$; $^1$H NMR (500 MHz, CDCl$_3$) δ1.43 (m, 2H), 1.59 (m, 4H), 3.11 (t, J=7.0 Hz, 2H), 3.36 (m, 2H), 3.44 (m, 4H), 3.49–3.56 (m, 2H), 3.60 (dd, J=10.8, 5.5 Hz, 1H), 3.64 (t, J=9.0 Hz, 1H), 3.69 (dd, J=10.8, 1.6 Hz, 1H), 3.85 (dt, J=9.3, 7.4 Hz, 1H), 4.22 (dt, J=9.4, 6.8 Hz, 1H), 4.45 (d, J=7.8 Hz, 1H), 4.60 (d, J=11.0 Hz, 1H), 4.65 (d, J=11.0 Hz, 1H), 4.76 (d, J=10.9 Hz, 1H), 4.85 (m, 2H), 4.91 (d, J=10.9 Hz, 1H), 6.09 (br s, 1H), 7.03 (m, 1H), 7.09 (m, 1H), 7.16 (m, 1H), 7.21 (m, 2H), 7.25–7.33 (m, 14H), 7.40 (m, 2H), 7.47 (m, 1H), 7.59 (d, J=7.8 Hz, 1H), 7.73 (m, 2H), 8.22 (br s, 1H); $^{13}$C NMR (125.8 MHz, CDCl$_3$) δ23.7, 25.7, 29.3, 29.4, 40.0, 69.7, 70.1, 71.5, 74.7, 74.8, 74.9, 75.7, 78.1, 82.3, 84.7, 103.7, 11.2, 112.5, 118.6, 119.2, 122.2, 126.8, 127.5, 127.5, 127.6, 127.8, 127.9, 128.0, 128.3, 128.3, 128.4, 128.5, 131.3, 134.7, 136.2, 138.2, 138.5, 138.6, 167.6; high resolution mass spectrum (FAB, m-nitrobenzyl alcohol) m/z 782. 3900 (M$^+$; calcd for C$_{49}$H$_{54}$O$_7$N$_2$: 782.3931).

AG. Trifluoroacetamide (+)-I-58.

To a stirred solution of N-trifluoracetyl-5-amino-1-pentanol (0.27 g, 1.36 mmol) in THF (4 ml) was added sodium hydride (60% dispersion in oil, 0.12 g, 3.00 mmol). The mixture was allowed to stir for 1.5 h, then cooled to 0° C. before triflate I-62 was added via cannula (8 ml dichloromethane). After stirring an additional 18 h, the mixture was added to water (100 ml) and extracted with dichloromethane (2×50 ml). The combined extracts were washed with water, dried over magnesium sulfate, and concentrated in vacuo. Flash chromatography (40% ethyl acetate/hexanes) afforded the amide (178 mg, 84%) as a pale yellow oil which was used immediately in the next reaction.

A solution of the amide (0.010 g, 0.011 mmol), 1,5-dimethoxynaphthalene (0.0062 g, 0.033 mmol) and NaCNBH$_3$ (0.0021 g, 0.011 mmol) in EtOH (4.8 ml) and water (0.16 ml) was purged with argon then irradiated with a Hanovia apparatus through pyrex for 4 h. The solvent was removed in vacuo and the remaining oil was diluted with water and extracted with dichloromethane (3×10 ml). The combined extracts were washed with water, dried over magnesium sulfate, and concentrated in vacuo. Preparative TLC (0.5 mm, 3% MeOH/CH$_2$Cl$_2$, 2×) afforded the amide (5 mg, 59%) as a pale yellow oil; [α]D$^{25}$+17.6° (c 0.46, CH$_2$Cl$_2$); IR (CHCl$_3$) 3490 (m), 3100 (w), 3075 (w), 3034 (w), 3014 (w), 2945 (m), 2880 (m), 1692 (s), 1610 (w), 1460 (m), 1362 (w), 1230 (w), 1200 (m), 1152 (s), 1090 (s), 1070 (s), 1040 (m), 910 (m), 697 (w) cm$^{-1}$; $^1$H NMR (500 MHz, d6-DMSO, 380 K) δ1.26 (m, 2H), 1.42 (m, 2H), 1.56 (m, 2H), 3.00 (t superimposed on a br s, J=7.2 Hz, 2H), 3.00 (br s, 2H), 3.35–3.42 (m, 3H), 3.45 (m, 2H), 3.68 (t, J=8.8 Hz, 2H), 3.81 (dr superimposed on a br s, J=9.6, 7.2 Hz, 1H), 3.81 (br s, 1H), 4.10 (dt, J=9.7, 6.9 Hz, 1H), 4.56 (br d, J=7.2 Hz, 1H), 4.61 (d, J=11.6 Hz, 1H), 4.63 (d, J=11.3 Hz, 1H), 4.71 (d, J=11.5 Hz, 1H), 4.77 (d, J=11.5 Hz, 1H), 4.79 (d, J=11.4 Hz, 1H), 4.83 (d, J=11.5 Hz, 1H), 6.96 (m, 1H), 7.05 (m, 1H), 7.08 (br s, 1H), 7.20–7.34 (m, 16H), 7.49 (d, J=7.7 Hz, 1H); $^{13}$C NMR (125.8 MHz, CDCl$_3$) δ22.7, 22.9, 25.8, 26.2, 28.2, 32.1, 32.2, 47.9, 48.4, 48.5, 48.7, 62.5, 62.6, 70.0, 70.2, 72.5, 74.5, 74.7, 74.7, 74.8, 75.0, 75.7, 75.8, 78.9, 79.5, 82.1, 82.2, 84.3, 84.5, 103.5, 103.5, 111.1, 111.2, 115.2, 115.4, 117.5, 117.7, 118.6, 119.3, 119.3, 122.0, 122.0, 122.0, 122.1, 127.6, 27.6, 27.7, 127.7, 127.9, 127.9, 127.9, 128.0, 128.1, 128.1, 128.2, 128.3, 128.3, 128.4, 128.4, 128.4, 128.5, 136.2, 136.2, 137.5, 137.9, 138.2, 138.3, 138.3, 138.4, 156.4, 156.7, 157.0, 157.3; high resolution mass spectrum (FAB, m-nitrobenzyl alcohol ) m/z 775.3543 [(M+H)$^+$; calcd for C$_{44}$H$_{50}$O$_7$N$_2$F$_3$: 782.3931).

EXAMPLE 10

Preparation of Ester Compounds

Figure 8:
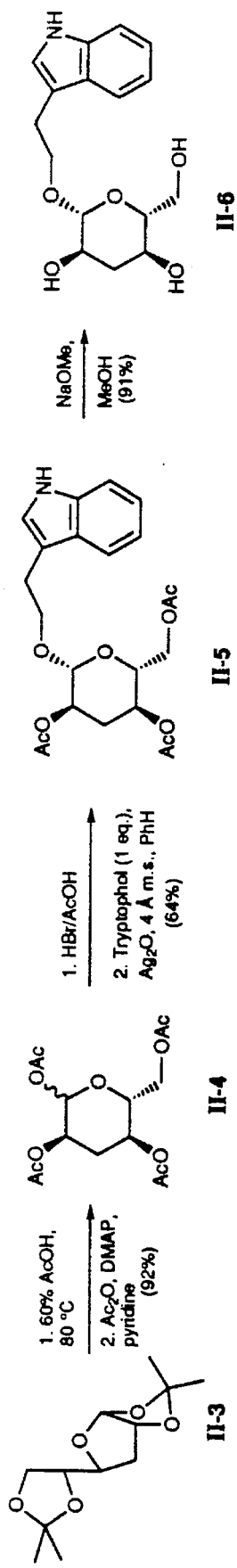
FIGS. 8–16 depict synthetic schemes for the Ester compounds of Example 10.
Figure 9:
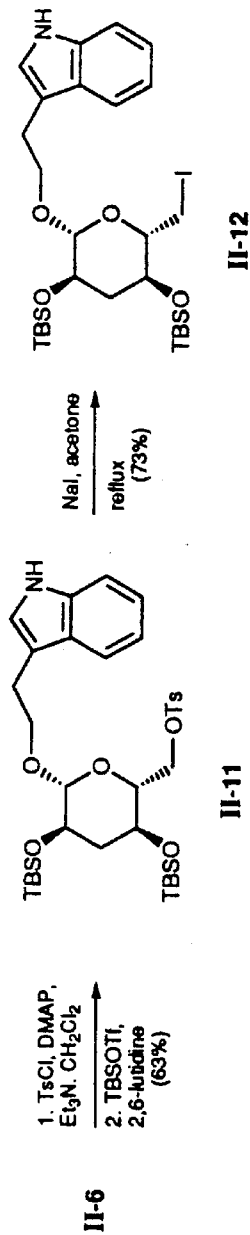
Figure 10:
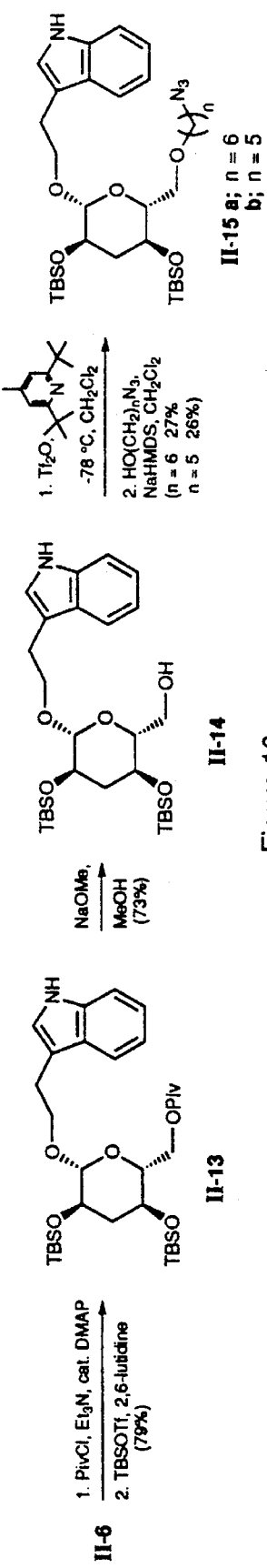
Figure 11:
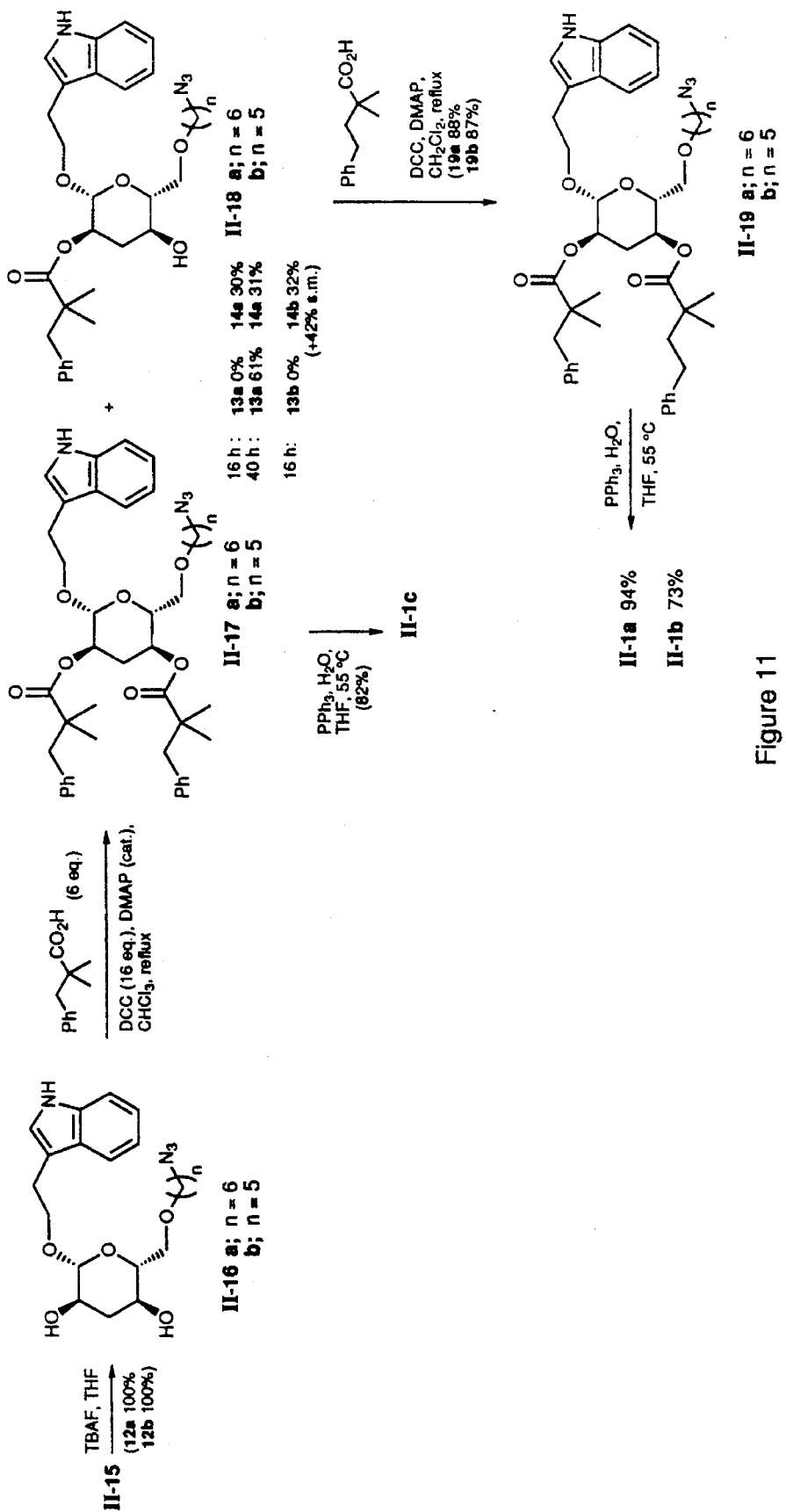
Figure 12:
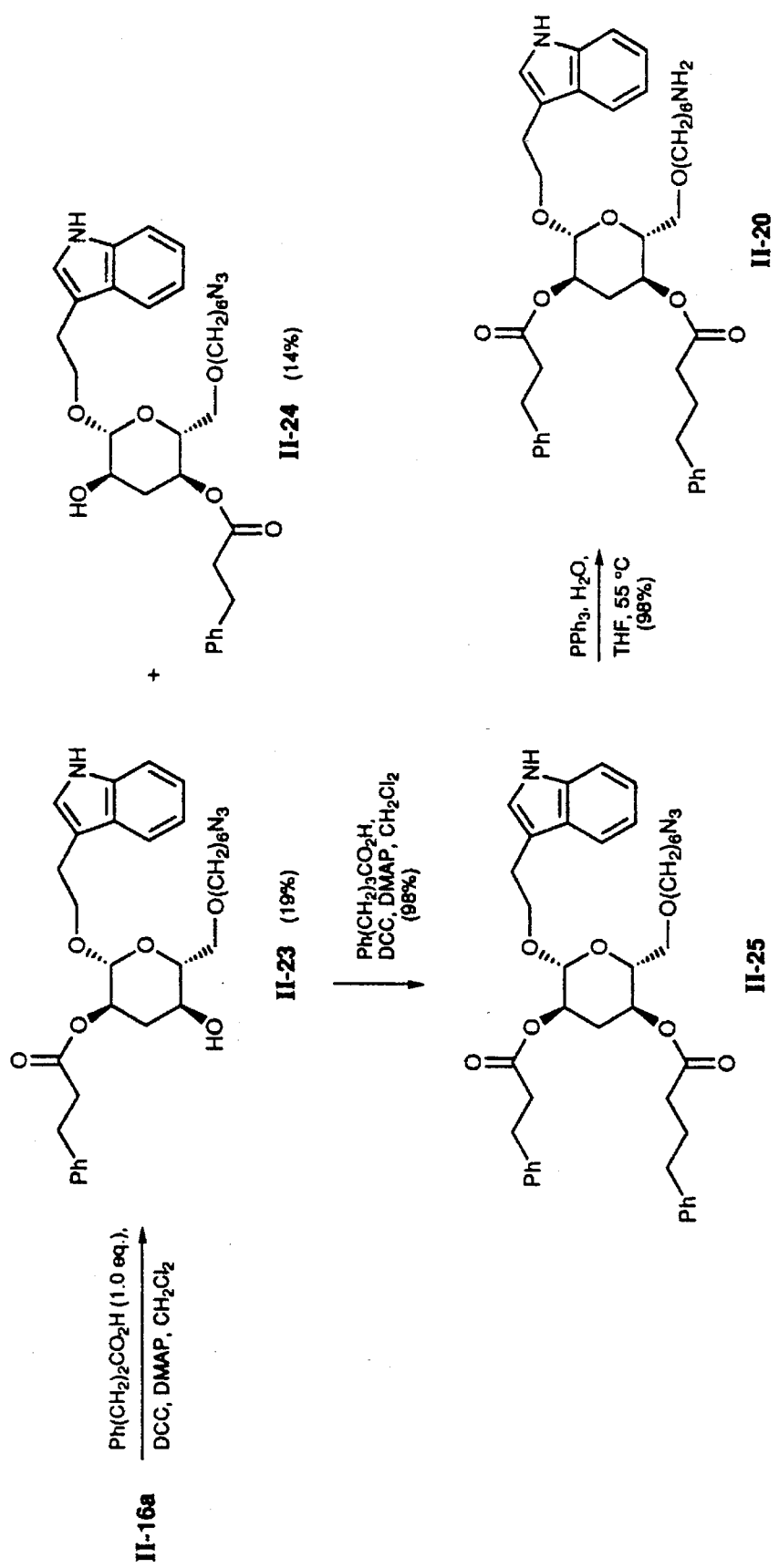
Figure 13:
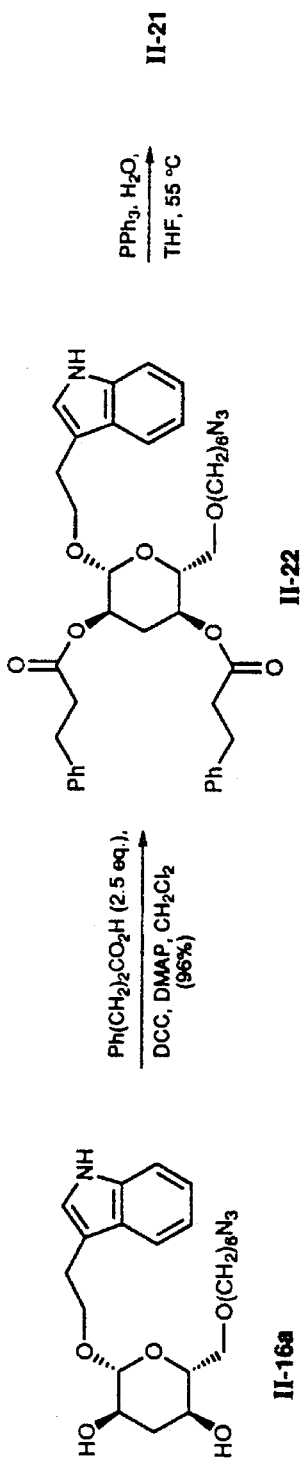
Figure 14:
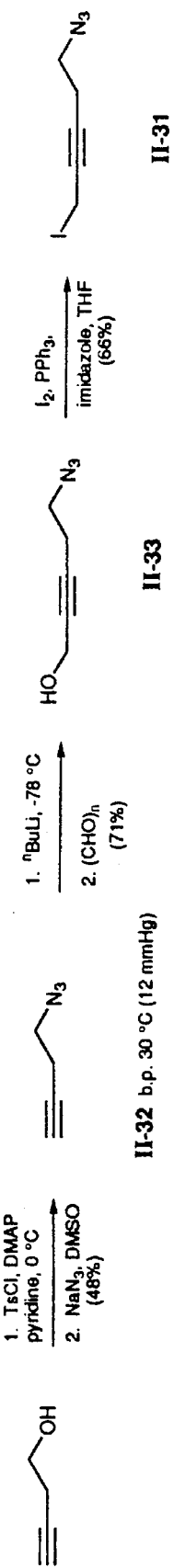
Figure 15:
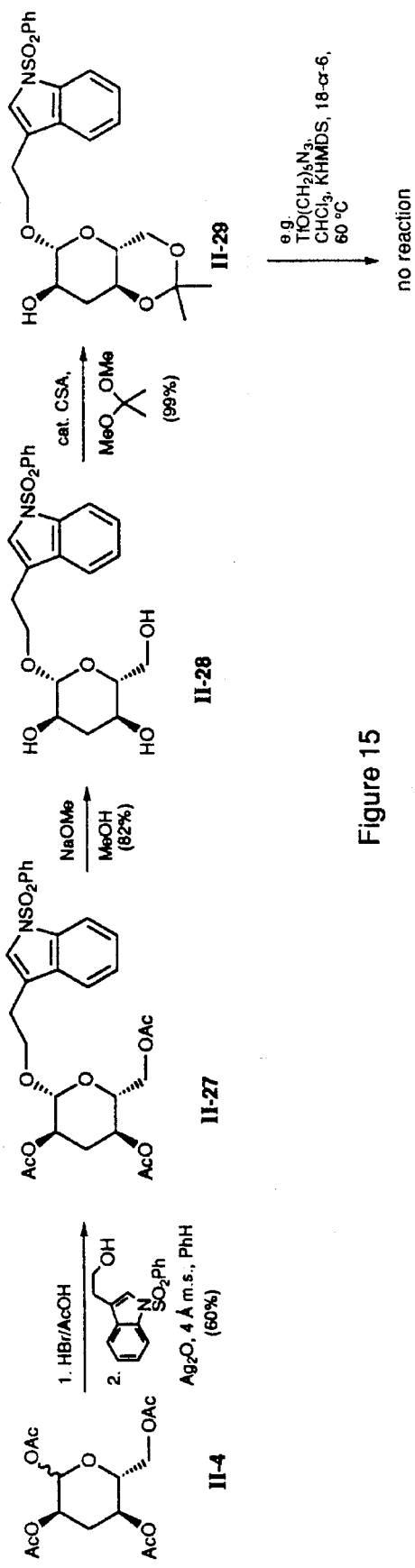
Figure 16:
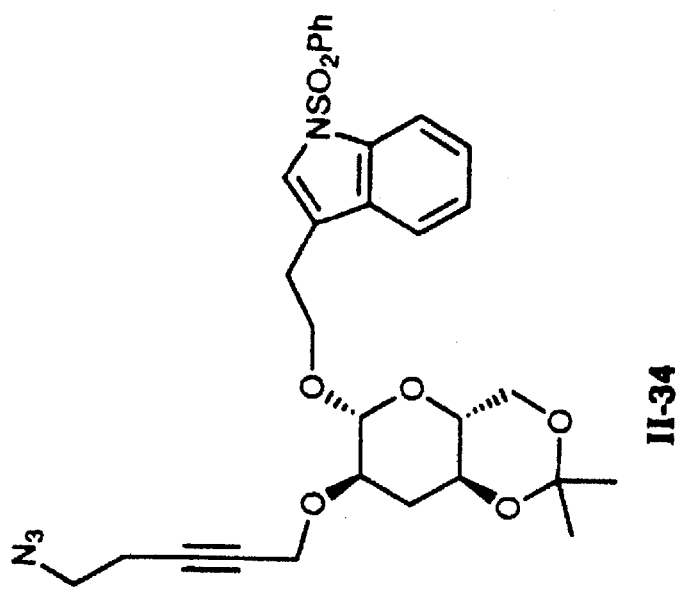
Figure 16:
Figure 16:
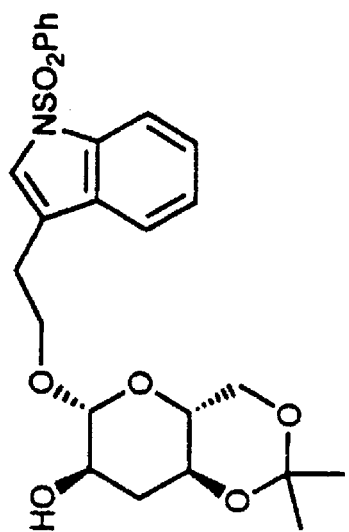

In order to distinguish these compounds from those previously described, each compound number is preceeded by "-II". The chemical structures and the synthesis schemes for the compounds of Example 10 are presented in FIGS. 8–16.

A. 1,2,4,6-Tetra-O-acetyl-β-D-glucopyranoside (II-4).

A solution of 3-deoxy-diacetone-D-glucose II-3 in 60% aqueous acetic acid (200 ml) was heated at 90° C. for 1 h, evaporated and azeotroped with dry benzene (4×20 ml). The residue was taken up in dry pyridine (250 ml), acetic anhydride (107 ml, 1.13 mol), DMAP (2 mol%, 275 mg) was added, and the solution was stirred at room temperature for 30 minutes. The mixture was evaporated, diluted with water (40 ml) and extracted with methylene chloride (3×40 ml). The combined extracts were washed with brine (40 ml), dried over sodium sulphate and evaporated. The residue was recrystallised from ether to afford the pure β-anomer as a fine white powder (11.3 g). The supernatent was evaporated and purified by flash chromatography eluting with 45% ethyl acetate in hexane to give a mixture of α-and β-anomers II-4 as a colorless gum (23.0 g, total yield 91.7%). β-Anomer II-4 : m.p. 127°–128° (ether) (lit. 129°–130° )13]; $[\alpha]D^{25}$–17.14° (c 1.05, $CH_3OH$); IR ($CHCl_3$) 3010 (m) 2940 (w), 2870 (w), 1745 (s), 1510 (w), 1365 (m), 1230 (s), 1210 (s), 1030 (s) $cm^{-1}$; $^1H$ NMR (500 MHz, $CDCl_3$) δ5.67 (d, J=7.9 Hz, 1H), 4.89–4.81 (m, 2H), 4.21 (dd, J=5.1, 12.3 Hz, 1H), 4.12 (dd, J=2.5, 12.2 Hz, 1H), 3.81–3.79 (m, 1H), 2.60 (ddd, J=5.0, 5.0, 12.3 Hz, 1H), 2.10 (s, 3H), 2.06 (s, 3H), 2.03 (s, 3H), 2.02 (s, 3H), 1.64 (dd, J=11.0, 23.2 Hz, 1H); $^{13}C$ NMR (62.9M Hz, $CDCl_3$) δ170.69, 169.43, 169.31, 169.19, 93.06, 75.68, 67.33, 65.00, 62.07, 32.69, 20.92, 20.77; high resolution mass spectrum (Cl) m/z 367.0773 [(M+Cl$^+$); calcd for $C_{14}H_{20}O_9Cl$: 367.0796].

Anal. calcd for $C_{14}H_{20}O_9$: C, 50.60; H, 6.07; found: C, 50.65; H, 6.16.

B. 2-(1H-Indol-3-yl)ethyl 2,4,6-Tri-O-acetyl-3-deoxy-β-D-glucopyranoside (II-5).

Hydrogen bromide (30% in acetic acid) was added dropwise to a solution of the tetraacetate II-4 (9.97 g, 30.0 mmol) in methylene chloride at 0° C. Stirring was continued at room temperature for 3 h, the mixture was poured into saturated aqueous sodium bicarbonate (500 ml) and extracted with ether (3×100 ml). The combined extracts were washed with saturated aqueous sodium bicarbonate (200 ml) and brine (200 ml), dried over sodium sulphate and evaporated. The pale yellow oil was azeotroped with benzene (4×20 ml) and dried under vacuum. A solution of the crude bromide in benzene (200 ml) was introduced into a flask containing activated powdered 4 Angstrom molecular sieves (10 g) and tryptophol (4.84 g, 30.0 mmol). Hexane (50 ml) and silver oxide (21 g, 90 mmol) were added, and the mixture was stirred vigorously in the dark for 18h. The solution was filtered through celite, evaporated, and purified by flash chromatography eluting with 10% ether in methylene chloride to afford the triacetate II-5 as a pale pinkish oil. (8.37 g, 64.4%): $[\alpha]D^{25}$+22.04° (c 1.08, $CHCl_3$); IR ($CHCl_3$) $cm^{-1}$ 3020 (w), 2965 (w), 1745 (s), 1370 (m), 1230 (s), 1220 (s), 1205 (s), 1050 (s), 1035 (m), 740 (m) $cm^{-1}$; $^1H$ NMR (500 MHz, $CDCl_3$) δ8.06 (br s, 1H), 7.57 (d, J=16.9 Hz, 1H), 7.32 (d, J=17.8 Hz, 1H), 7.16 (ddd, J=1.0, 8.8 Hz, 1H ), 7.09 (ddm, J=8, 8 Hz, 1H), 7.02 (d, J=2.2, 1H), 4.84–4.77 (m, 1H), 4.49 (d, J=7.5 Hz, 1H), 3.84–3.77 (m, 3H), 3.77 (dd, J=7.3, 16.9 Hz, 1H), 3.69–3.65 (m, 1H), 3.04 (t, J=7.1 Hz, 2H), 2.52 (ddd, J=5.1, 5.1, 12.3 Hz, 1H), 2.04 (s, 1H), 2.02 (s, 1H), 1.89 (s, 1H), 1.57 (dd, J=9.0, 22 Hz, 1H); $^{13}C$ NMR (62.9 MHz, $CDCl_3$) δ170.83,169.52, 136.06, 127.43,122.26, 121.82, 119.19, 118.64, 112.41, 111.05, 102.08, 74.82, 69.80, 68.39, 65.83, 62.66, 32.71, 25.53, 20.83, 20.75 ; high resolution mass spectrum (Cl) m/z 434. 1782 [(M+H$^+$); calcd for $C_{22}H_{28}O_8$: 434.1815].

C. 2-(1H-Indol-3-yl)ethyl 3-Deoxy-β-D-glucopyranoside (II-6).

Sodium methoxide (9.42 mmol) was added in aliquots to a stirred solution of the triacetate II-5 (1.17 g, 2.69 mmol) in methanol (50 ml) at 0° C., and the solution stirred at room temperature for 15 h. Amberlyst® 15 ion-exchange resin was added to pH 7, and the mixture was filtered, evaporated and purified by flash chromatography eluting with 15% methanol in methylene chloride to afford the title compound II-6 as a colorless oil (752 mg, 90.9%): $[\alpha]D^{25}$+76.19° (c1.05, $CH_{30}H$); IR ($CHCl_3$) 3600–3200 (br), 2900 (s) $cm^{-1}$; $^1H$ NMR (500 MHz, $CDCl_3$) δ7.55 (d, J=8.8 Hz, 1H), 7.30 (d, J=9 Hz, 1H), 7.10–6.96 (m, 3H), .4.27 (d, J=7.6 Hz, 1H), 4.18–4.13 (m, 1H), 3.85–3.80 (m, 2H), 3.64 (dd, J=5.9, 11.8 Hz, 1H), 3.53–3.48 (m, 1H), 3.42–3.37 (m, 1H), 3.34–3.29 (m, 1H), 3.25–3.21 (m, 1H), 3.09–3.03 (m, 2H), 2.28 (ddd, J=4.9, 4.9, 21.1 Hz, 1H), 1.47 (dd, J=11.5, 23.4 Hz, 1H); $^{13}C$ NMR (62.9 MHz, $CDCl_3$) δ137.98, 128.87, 123.63, 122.21, 119.5, 119.28, 112.55, 112.16, 106.49, 81.68, 71.11, 69.38, 66.14, 62.79, 40.56, 26.78; high resolution mass spectrum (Cl) m/z [(M+H$^+$]; calcd for $C_{16}H_{21}O_5N$: ].

D. 2-(1H-Indol-3-yl)ethyl 6-(p-Toluenesulphonyl)-2,4-di-O-(tert-butyldimethyl)silyl-3-de oxy-β-D-glucopyranoside (II-11).

p-Toluenesulphonyl chloride (0.559 mmol, 106 mg) and DMAP (10 mg) were added to a stirred solution of triol II-6 (56 mg, 0.508 mmol) and triethylamine (4.06 mmol, 0.76 ml) in methylene chloride (10 ml) at 0° C. and the solution was stirred at room temperature for 30 min. More p-toluenesulphonyl chloride (5 mg) was added and the solution was stirred for a further 1 h, poured into saturated aqueous sodium bicarbonate (40 ml), extracted with methylene chloride (2×20 ml) and the combined extracts were washed with brine (20 ml), dried over sodium suphate and evaporated. The resulting yellow oil was dissolved in methylene chloride (12 ml) and 2,6-lutidine (0.36 ml, 3.05 mmol) was added, followed by dropwise addition of tributyldimethylsilyl triflate (2.03 mmol, 0.47 ml) at 0° C. The solution was stirred at room temperature for 16 h, diluted with saturated aqueous sodium bicarbonate (25 ml), extracted with methylene chloride (3×20 ml) and the combined organic extracts were washed with brine (50 ml), dried over sodium sulphate and evaporated. The residue was purified by flash chromatography eluting with 30% ethyl acetate in hexane to give the title compound II-11 as a colorless oil (201 mg, 57.4%): $[\alpha]D^{25}$+ 2.25° (c 0.71, $CHCl_3$); IR ($CHCl_3$) 2960 (s), 2950 (s), 2900 (s), 2860 (s), 1800 (w), 1605 (w), 1460 (s), 1365 (s), 1260 (s), 1100 (s), 980 (s) 920–890 (br), 840 (s), 695 (s), 550 (s) $cm^{-1}$; $^1H$ NMR (500 MHz, $CDCl_3$) δ8.01 (br s, 1H), 7.72 (d, J=8.3 Hz, 2H), 7.56 (d, J=7.8 Hz, 1H), 7.34 (d, J=8.1 Hz, 1H), 7.19–7.09 (m, 5H), 4.21 (dd, J=2.0, 10.3 Hz, 1H), 4.18 (d, J=7.6 Hz, 1H), 4.07–3.99 (m, 2H), 3.79–3.74 (m, 1H), 3.51–3.34 (m, 3H), 3.06–3.03 (m, 2H), 2.29 (s, 3H), 2.14–2.10 (m, 1H), 1.52 (app. q, J=11.4 Hz, 1H), 0.86 (s, 9H), 0.81 (s, 9H), 0.03 (s, 6 H), 0.00 (s, 6H); $^{13}C$ NMR (62.9 MHz, $CDCl_3$) δ144.61, 136.10, 132.75, 129.67, 127.87, 127.52, 122.14, 121.79, 119.16, 118.56, 112.40, 111.08, 105.09, 77.26, 69.88, 69.29, 69.00, 65.7, 41.50, 25.71, 25.58, 21.42, 18.11, 17.72.

E. 2-(1H-Indol-3-yl)ethyl 6-Iodo-2,4-di-O-(tert-butyldimethyl)silyl-3-deoxy-β-D-glucopyr anoside (II-12).

A solution of tosylate II-11 (147 mg, 0.213 mmol) and sodium iodide (4.26 mmol, 639 mg) in dry acetone (8.0 ml) was thiosulphate (15 ml) and extracted with methylene chloride (3×15 ml). The combined extracts were washed with brine (10 ml), dried over sodium sulphate and evaporated. The residue was purified by flash chromatography eluting with 10% ethyl acetate in hexane to give the title compound II-12 ($r_f$ 0.40) (91.3 mg, 66.3%) and starting material II-11 ($r_f$ 0.20) (37.1 mg, 25.2%).

2-(1H -Indol-3-yl)ethyl 6-(p-Toluenesulphonyl)-2,4-di-O-(tert-butyldimethyl) silyl-3-de oxy-β-D-glucopyranoside II-12: $[\alpha]D^{25}$–4.63° (c 0.67, $CHCl_3$); IR ($CHCl_3$) 3490 (w), 3010 (w), 2960 (m), 2930 (m), 2895 (w), 2860 (m), 1350 (w), 1090 (s), 835 (s) $cm^{-1}$; $^1H$ NMR (500 MHz, $CDCl_3$) δ7.93 (br s, 1H), 7.61 (d, J=6.8 Hz, 1H), 7.33 (d, J=8.1 Hz, 1H), 7.18–7.15 (m, 1H), 7.11–7.08 (m, 2H), 4.28 (d, J=7.4 Hz, 1H), 4.19 (dt, J=6.4, 9.3 Hz), 3.84 (dt, J=6.4, 9.3 Hz, 1H), 3.53–3.39 (m, 3H), 3.18–3.07 (m, 3H), 2.15–2.10 (m, 1H), 1.57 (app. q, J=11.3 Hz, 1H), 0.87 (s, 9H), 0.86 (s, 9H), 0.07 (s, 6H), 0.06 (s, 6 H); $^{13}$C NMR (62.9 MHz, CDCl$_3$) δ136.11, 127.56, 122.06, 121.87, 119.23, 118.82, 112.58, 111.03, 105.35, 78.82, 70.00, 69.92, 69.50, 41.50, 25.82, 25.76, 25.70, 18.18, 17.83, 6.78, −4.08, −4.43, −4.63, −4.90.

F. 2-(1H-Indol-3-yl)ethyl 6-(Trimethyl)acetyl-2,4-di-O-(tert-butyldimethyl)silyl-3-deoxy-β-D-glucopyranoside (II-13).

Pivaloyl chloride (18.6 mmol, 2.31 ml) was added dropwise at 0° C. to a solution of the triol II-6 (5.18 g, 16.9 mmol) and DMAP (20 mg) in methylene chloride (150 ml) and triethylamine (135 mmol, 25.6 ml). The solution was stirred for 20 minutes at room temperature, an extra 0.32 ml (0.15 mmol) of pivaloyl chloride was added, and stirring was continued for 15 minutes. The solution was poured into ice-cold 1N HCl (200 ml), extracted with methylene chloride (3×50 ml) and the extracts were washed with saturated aqueous sodium bicarbonate (150 ml) and back-extracted with methylene choride (50 ml). The combined organic extracts were washed with brine (100 ml), dried (sodium sulphate) and evaporated. The resulting yellow oil was dissolved in methylene chloride and 2,6-lutidine (12.0 ml, 135 mmol) was added, followed by tributyldimethylsilyl triflate (50.7 mmol, 11.6 ml) added dropwise at 0° C. The solution was stirred at room temperature for 15 h, diluted with saturated aqueous sodium bicarbonate (100 ml), extracted with methylene chloride (3×50 ml) and the combined organic extracts were washed with brine (100 ml), dried over sodium sulphate and evaporated. The residue was purified by flash chromatography eluting with 15% ethyl acetate in hexane to give the title compound II-13 as a colorless oil (8.23 g, 78.7%): [α]D$^{25}$−1.31° (c 3.29, CHCl$_3$); IR (CHCl$_3$) 3480 (m), 3020 (m), 2960 (s), 2920 (s), 2890 (m), 2860 (s), 1730 (s), 1470 (m), 1420 (m), 1390 (m), 1250 (s), 1230 (s), 1155 (s), 1080 (s), 1045 (s), 920 (m), 835 (s), 780–725 (s), 660 (s) cm$^{-1}$; $^1$H NMR (500 MHz, CDCl$_3$) δ7.97 (br s, 1H), 7.56 (d, J=7.8, 1H), 7.33 (d, J=8.1 Hz, 1H), 7.16 (dd, J=7, 9 Hz, 1H), 7.09 (dd, J=7, 8 Hz, 1H), 7.04 (dd, J=1.1, 1.1 Hz, 1H), 4.38 (d, J=11.6, 1H), 4.23 (d, J=7.4 Hz, 1H), 4.13–4.03 (m, 2H), 3.79 (m, 1H), 3.57–3.41 (m, 3H), 3.09 (dd, J=7.2, 7.3 Hz, 1H), 2.14 (dt, J=4.9, 12.4 Hz, 1H), 1.56 (dd, J=11.4, 23.8 Hz, 1H), 1.22 (s, 9H), 0.89 (s, 9H), 0.86 (s , 9H), 0.08 (s, 3H), 0.08 (s, 3H), 0.06 (s, 3H), 0.05 (s, 3H); $^{13}$C NMR (62.9 MHz, CDCl$_3$) δ178.33, 136.12, 127.52, 121.98, 118.64, 112.49, 111.02, 105.23, 77.73, 69.83, 69.22, 66.58, 63.65, 41.78, 38.76, 27.16, 27.01, 25.74, 25.65, 18.16, 17.83, −3.60, −4.16, −4.45, −4.95; high resolution mass spectrum (+ve FAB) m/z 619. 3705 (M$^+$; calcd for C$_{33}$H$_{37}$O$_6$NSi$_2$: 619.3724).

G. 2-(1H-Indol-3-yl)ethyl 2,4-Di-O-(tert-butyldimethyl)silyl-3-deoxy-β-D-glucopyranoside (II-14).

Sodium methoxide (6.0 mmol, 1.32 ml) was added in aliquots with stirring to pivaloate II-13 (740 mg, 1.20 mmol) in methanol (50 ml) and stirring was continued for 15 h. The solution was neutralised with Amberlyst® 15 ion-exchange resin, filtered and evaporated. The residue was purified by flash chromatography eluting with 30% ethyl acetate in hexane to afford the title compound II-14 as a colorless oil (468 mg, 73.2%): [α]D$^{25}$+15.67° (c 5.68, CHCl$_3$); IR (CHCl$_3$) 3480 (m), 3000 (s), 2960 (s), 2925 (s),m 2880 (s), 2845 (s), 1710 (m), 1415 (m), 1360 (m), 1250 (s), 1220 (s), 1085 (s), 1030 (s), 1000 (m), 905 (m), 875 (s), 830 (s), 520 (m) cm$^{-1}$; $^1$H NMR (500 MHz, CDCl$_3$) δ7.97 (br s, 1H), 7.57 (d, J=7.8 Hz, 1H), 7.33 (d, J=7.8 Hz, 1H), 7.17 (ddd, J=1.1, 7.7, 7.5), 7.10 (ddd, J=0.9, 8, 8 Hz), 7.03 (s, 1H), 4.28 (d, J=7.4 Hz, 1H), 4.10 (dd, J=8.5, 16.3 Hz, 1H), 3.83–3.77 (m, 2H), 3.63–3.56 (m, 2H), 3.50–3.45 (m, 1H), 3.28–3.24 (m, 1H), 3.09 (t, J=7 Hz, 2H), 2.26–2.22 (m, 1H), 1.58 (dd, J=11.3, 22.1 Hz, 1H), 0.88 (s, 9H), 0.84 (s, 9H), 0.09 (s, 6H), 0.08 (s, 6 H); $^{13}$C NMR (62.9 MHz, CDCl$_3$) δ136.14, 127.45, 121.96, 119.27, 118.64, 112.35, 111.09, 105.35, 79.65, 70.16, 69.39, 66.09, 62.42, 41.62, 25.75, 25.67, 18.17, 17.84, −4.28, −4.46, −4.87, −5.01; high resolution mass spectrum (CI) m/z 535.3172 [(M+H$^+$); calcd for C$_{28}$H$_{49}$O$_5$NSi$_2$: 535.3149].

H. 2-(1H-Indol-3-yl)ethyl 2,4-Di-O-(tert-butyldimethyl)silyl-3-deoxy-O-(6-azidohexyl)-β-D-glucopyranoside (II-15a).

Triflic anhydride (2.15 mmol, 0.36 ml) was added dropwise at −78° C. to a solution of the alcohol II-14 (764 mg, 1.43 mmol) and 2,2-di-tert-butyl-4-methylpyridine (2.57 mmol, 528 mg) in methylene chloride (45 ml). The solution was stirred for 20 minutes, warmed to room temperature for 20 minutes, poured into saturated aqueous sodium bicarbonate (80 ml) and extracted with methylene chloride (2×40 ml). The extracts were combined, washed with brine (40 ml), dried over sodium sulphate, evaporated and dried under vacuum. Sodium hexamethyldisilylazide (0.6M in toluene, 1.86 mmol, 3.10 ml) was added dropwise to a solution of 6-azidohexanol (494 mg, 3.45 mmol) in methylene chloride (40 ml) at 0° C. The colorless triflate (purified by thin layer chromatography) was dissolved in methylene chloride and then added to the above solution at 0° C. via cannula. Stirring was continued at room temperature for 38 h, the solution diluted with saturated aqueous sodium bicarbonate (50 ml) and extracted with methylene chloride (3×25 ml). The combined organic extracts were washed with brine (40 ml ), dried over sodium sulphate and evaporated. Purification by flash chromatography (eluting with methylene chloride) furnished the title compound II-15a as a colorless viscous oil (257 mg, 27.3%): [α]D$^{25}$+10.05° (c 2.13, CHCl$_3$); IR (CHCl$_3$) 3480 (w), 3000 (w), 2950 (m), 2930 (m), 2855 (m), 2090 (m), 1360 (m), 1250 (w), 1080 (s), 830 (s) cm$^{-1}$; $^1$H NMR (500 MHz, CDCl$_3$) δ8.00 (br s, 1H), 7.58 (d, J=7.7 Hz, 1H), 7.33 (d, J=8.2 Hz, 1H), 7.16 (dd, J=7.1, 7.1, 1H), 7.09 (dd, J=7.0, 7.0 Hz, 1H), 7.02 (s, 1H), 4.23 (d, J=6.4 Hz, 1H), 4.15–4.09 (m, 1H), 3.80–3.75 (m, 1H), 3.66 (dd, J=1.9, 10.8 Hz, 1H), 3.58–3.41(m, 4H), 3.35–3.31 (m, 1H), 3.14 (t, J=7.0 Hz, 2H), 3.09 (t, J=7.5 Hz, 2H), 2.17–2.12 (m, 1H), 1.60–1.45 (m, 5H), 1.35–1.24 (m, 4 H)), 0.87 (s, 9H), 0.86 (s, 9H), 0.08 (s, 3H), 0.07 (s, 3H), 0.06 (s, 3H), 0.04 (s, 3H); $^{13}$C NMR (62.9 MHz, CDCl$_3$) δ136.11, 127.54, 121.96, 121.84, 119.17, 117.70, 112.52, 111.03, 105.35, 79.65, 51.31, 41.83, 29.50, 28.67, 26.51, 25.77, 25.69, 18.19, 17.86, −4.19, −4.43, −4.90, −4.96; high resolution mass spectrum (+ve FAB) m/z 661. 4213 [(M+H$^+$); calcd for C$_{34}$H$_{61}$N$_4$O$_5$Si$_2$: 661.4180].

I. 2-(1H-Indol-3-yl)ethyl 2,4-Di-O-(tert-butyldimethyl)silyl-3-deoxy-O-(5-azidopentyl)-β-D-glucopyranoside (II-15b).

The same procedure as detailed above, using 5-azido-1-pentanol (2.4 eq. , 4.08 mmol, 461 mg) furnished the title compound II-15b as a colorless oil (284 mg, 25.9%): [α]D$^{25}$+7.31° (c 1.67, CHCl$_3$); IR (CHCl$_3$) 3460 (m), 3000 (m), 2940 (s), 2920 (S), 2850 (S), 2080 (S), 1450 (w), 1250 (m), 1110 (s), 1080 (s), 830 (s) cm$^{-1}$; $^1$H NMR (500 MHz, CDCl$_3$) δ8.00 (br s, 1H), 7.57 (d, J=7.7 Hz, 1H), 7.33 (d, J=8.2 Hz, 1H), 7.17 (dt, J=8.1, 1, 1H), 7.09 (t, J=7.0 Hz, 1H), 7.03 (d, J=2.2, 1H), 4.23 (d, J=7.4 Hz, 1H), 4.11 (app. dd, J=8.5, 16.6 Hz, 1H), 3.77 (app. dd, J=8.6, 16.8 Hz, 1H), 3.58–3.43 (m, 5H), 3.34–3.31 (m, 1H), 3.12–3.07 (m, 4H), 2.17–2.12 (m, 2H), 1.58–1.48 (m, 5H), 1.38–1.33 (m, 2H)), 0.88 (s, 9H), 0.86 (s, 9H), 0.08 (s, 3H), 0.07 (s, 3H), 0.05 (s, 3H), 0.04 (s, 3H); $^{13}$C NMR (62.9 MHz, CDCl$_3$) δ136.12, 127.50, 121.99, 119.11, 118.64, 112.39, 111.055, 105.35, 79.62, 71.33, 70.13, 69.99, 69.30, 66.10, 51.21, 41.80, 29.15, 28.53, 25.74, 25.67, 23.32, 18.16, 17.83, −4.20, −4.45, −4.92, −4.98; high resolution mass spectrum (+ve CI) m/z 646.3887 (M$^+$; calcd for C$_{33}$H$_{58}$N$_4$O$_5$Si : 646.3946).

J. 2-(1H-Indol-3-yl)ethyl 3-Deoxy-O-(6-azidohexyl)-β-D-glucopyranoside (II-16a).

Tetrabutylammoniumflouride (1.0M in THF (1.74 mmol, 1.74 ml) was added to a solution of the azide II-15a (230 mg, 0.348 mmol) in THF (10 ml) and stirred for 1 h. The solution was evaporated and the residue was purified by flash chromatography eluting with 10% methanol in methylene chloride to afford the title compound II-16a as a colorless oil (150 mg, 100%): [α]D$^{25}$+38.24° (c 1.53, CHCl$_3$); IR (CHCl$_3$) 3600 (w), 3470 (m), 3000 (w), 2930 (m), 2860 (m), 2090 (s), 1200 (m), 1080 (s), 1060 (s), 710 (s), 655 (s) cm−1; $^1$H NMR (500 MHz, CDCl$_3$) δ8.08 (br s, 1H), 7.60 (d, J=7.8 Hz, 1H), 7.34 (d, J=8.1 Hz, 1H), 7.17 (dd, J=7,7 Hz, 1H), 7.10 (dd, J=7,7 Hz, 1H), 7.03 (s, 1H), 4.22–4.16 (m, 2H), 3.85–3.38 (m, 10H), 3.25–2.99 (m, 4H), 2.35–2.27 (m, 1H), 2.14 (br s, 1H), 1.72–1.24 (m, 9H); $^{13}$C NMR (62.9 MHz, CDCl$_3$) δ136.2, 122.12, 121.90, 119.43, 118.70, 111.25, 105.14, 76.06, 72.78, 71.85, 70.42, 69.17, 68.29, 51.32, 37.28, 29.33, 28.72, 26.46, 25.74, 25.61; high resolution mass spectrum (+ve FAB) m/z 432.2411 (M$^+$; calcd for C$_{22}$H$_{32}$N$_4$O$_5$: 432.2373).

K. 2-(1H-Indol-3-yl)ethyl 3-Deoxy-O-(5-azidopentyl)-β-D-glucopyranoside (II-16b).

The same procedure as detailed above afforded the title compound II-16b as a colorless oil (173 mg, 100%): [α]D$^{25}$+31.01° (c 0.79, CHCl$_3$); IR (CHCl$_3$) 3480 (m), 3005 (w), 2950 (m), 2880 (m), 2100 (s), 1455 (w), 1280 (w), 1090 (w), 1070 (s), 1060 (s), 1020 (w), 1010 (w) cm$^{−1}$; $^1$H NMR (500 MHz, CDCl$_3$) δ8.02 (br s, 1H), 7.61 (d, J=7 Hz, 1H), 7.33 (dd, J=0.7, 8.0 Hz, 1H), 7.18 (app. t, J=8 Hz, 1H), 7.11 (app. t, J=8 Hz, 1H), 7.03 (d, J=2.3, 1H), 4.22–4.18 (m, 2H), 3.75–3.65 (m, 3H), 3.61 (dd, J=7.2, 9.6 Hz, 1H), 3.52–3.38 (m, 4H), 3.23 (t, J=6.9 Hz, 2H); 3.13–3.00 (m, 4H), 2.35–2.31 (m, 1H), 2.11 (br s, 1H), 1.75–1.68 (m, 1H), 1.61–1.35 (m, 7 H); $^{13}$C NMR (62.9 MHz, CDCl$_3$) δ1136.10, 127.45, 122.03, 121.84, 119.16, 118.52, 112.43, 111.23, 104.95, 76.53, 72.15, 71.54, 70.16, 68.27, 68.15, 52.83, 51.15, 37.37, 28.89, 28.45, 25.60, 25.19, 23.15, 19.74, 13.39; high resolution mass spectrum (+re CI) m/z 436.2537 [(M+NH4$^+$); calcd for C$_{21}$H$_{34}$N$_5$O$_5$ : 436.2560].

L. 2-(1H-Indol-3-yl)ethyl 2,4-Di-O-(2,2-dimethyl-3-phenylpropanoyl)-3-deoxy-O-(6-azidohe xyl)-β-D-glucopyranoside (II-17a) and 2-(1H-Indol-3-yl)ethyl 2-O-(2,2-Dimethyl-3-phenylpropanoyl)-3-deoxy-O-(6-azidohexyl)-β-D-glucopyranoside (II-18a).

2,2-Dimethyl-4-aminopyridine (40 mol%, 11 mg) was added to a vigorously stirrred solution of diol II-16a (91.4 mg, 0.212 mmol), 2,2-dimethyl-3-phenylpropanoic acid (242 mg, 1.27 mmol) and dicyclohexylcarbodiimide (703 mg, 3.39 mmol) in chloroform (5 ml) and the mixture was refluxed for 40 h. The cooled solution was evaporated, taken up in ether, filtered and evaporated again. The residue was purified by flash chromatography eluting with 25 % ethyl acetate in hexane to afford an impure component (RF 0.28). The gradient was increased to 40% ethyl acetate in hexane affording an impure component (RF 0.23). The higher-running compound was recolumned in 50% methylene chloride in hexane increasing to 10% ether in methylene chloride to afford the pure bis-ester II-17a as a colorless oil (97.2 mg, 61.1%). The lower-running compound was recolumned in 10% ether in methylene chloride to give the pure mono-ester II-18a as a colorless oil (39.5 mg, 31.3%).

2-(1H-Indol-3-yl)ethyl 2,4 -Di -O-(2,2 -dimethyl-3-phenylpropanoyl)-3 -deoxy-O-(6-azidohe xyl)-β-D-glucopyranoside (II-17a) (bis-ester): [α]D$^{25}$+36.18° (c 0.34, CHCl$_3$); IR (CHCl$_3$) 3480 (w), 3020 (w), 2935 (m), 2860 (m), 1730 (s), 1725 (s), 1455 (w), 1120 (s), 1005 (w), 690 (m) cm$^{−1}$; $^1$H NMR (500 MHz, CDCl$_3$) d7.84 (br s, 1H), 7.53 (d, J=7.8 Hz, 1H), 7.32 (d, J=8.0 Hz, 1H), 7.26–7.03 (m, 12H), 6.99 (s, 1H), 4.83–4.75 (m, 2H), 4.54 (d, J=7.8 Hz, 1H), 4.09 (ddm, J=8, 17 Hz, 1H), 3.79 (ddm, J=8,16 Hz, 1H), 3.67=3.64 (m, 1H), 3.54 (d, J=11.2 Hz, 1H), 3.48–3.35 (m, 3H), 3.18 (br s, 2H), 3.05–3.02 (m, 2H), 2.88 (d, J=13.4 Hz, 1H), 2.74 (d, J=13.4 Hz, 1H), 2.53–2.47 (m, 2H), 1.80 (t, J=8.4 Hz, 2H), 1.52–1.14(m, 9H), 1.21 (s, 6H), 1.14 (s, 3H), 1.08 (s, 3 H); $^{13}$C NMR (62.9 MHz, CDCl$_3$) δ176.13, 175.99, 141.93, 137.67, 136.25, 130.23, 128.43, 128.22, 127.95, 127.46, 126.43, 125.93, 122.29, 121.70, 119.02, 118.57, 111.78, 111.21, 102.34, 77.20, 71.75, 70.00, 69.89. 68.73, 66.33, 45.94, 43.48, 42.43, 42.36, 33.88, 33.35, 31.42, 29.68, 29.59, 29.33, 26.52, 25.70, 25.36, 25.18, 24.92, 24.31; high resolution mass spectrum (+ve FAB) m/z 753.4263 [(M+H$^+$); calcd for C$_{44}$H$_{57}$N$_4$O$_7$: 753.4227].

2-(1H-Indol-3-yl)ethyl 2-O-(2,2-Dimethyl-3-phenylpropanoyl)-3-deoxy-O-(6-azidohexyl)-β-D-glucopyranoside (II-18a) (mono-ester): [α]D$^{25}$+31.15° (c 1.11, CHCl$_3$); IR (CHCl$_3$) 3680 (w), 3620 (w), 3480 (s), 3020 (s), 2975 (m), 2935 (m), 2875 (m), 2090 (m), 1725 (m), 1520 (m), 1470 (m), 1420 (m), 1220 (s), 1070 (m), 925 (m), 760 (s), 660 (s), 615 (m) cm$^{−1}$; $^1$H NMR (500 MHz, CDCl$_3$) d7.87 (br s, 1H), 7.53 (d, J=8.0 Hz, 1H), 7.31 (d, J=8.1 Hz, 1H), 7.23–7.06 (m, 7H), 6.98 (s, 1H), 4.77–4.72 (m, 1H), 4.50 (d, J=7.7 Hz, 1H), 4.07 (dd, J=8.2, 16.0 Hz, 1H), 3.78–3.70 (m, 2H), 3.61 (app. t, J=7.6 Hz, 1H), 3.51–3.43 (m, 2H), 3.23 (t, J=6.9 Hz, 1H), 3.01 (dt, J=3, 7 Hz, 2H), 2.84 (d, J=13.3 Hz, 1H), 2.76 (d, J=13.3 Hz, 1H), 2.42 (app. dt, J=12.2, 5.0 Hz, 1H), 1.58–1.47 (m, 5H), 1.36–1.34 (m, 4H), 1.12 (s, 3 H); $^{13}$C NMR (62.9 MHz, CDCl$_3$) δ176.15, 137.73, 136.07, 130.22, 127.96, 127.41, 126.43, 122.11, 121.88, 119.22, 118.60, 112.29, 111.06, 102.26, 76.02, 72.70, 69.71, 69.18, 68.71, 51.30, 45.87, 43.47, 35.80, 29.31, 28.69, 26.44, 25.68, 25.59, 25.13, 24.49; high resolution mass spectrum (+ve FAB) m/z 592.3228 [(M+H$^+$); calcd for C$_{33}$H$_{44}$N$_4$O$_6$: 592.3261].

M. 2-(1H-Indol-3-yl)ethyl 2-O-(2,2-Dimethyl-3-phenylpropanoyl)-4-O-(2,2-dimethyl-3 -phenylbutanoyl)-3-deoxy-O-(6-azidohexyl)-β-D-glucopyranoside (II-19a).

2,2-Dimethyl-4-aminopyridine (2 mg) was added to a vigorously stirrred solution of mono-ester II-18a (25.6 mg, 0.0430 mmol), 2,2-dimethyl-4-phenylbutanoic acid (49.5 mg, 0. 258 mmol) and dicyclohexylcarbodiimide (88.7 mg, 0.430 mmol) in methylene chloride (2 ml) and the mixture refluxed for 18 h. The cooled solution was evaporated, taken up in ether, filtered and evaporated. The residue was purified by flash chromatography eluting with 20% ethyl acetate in hexane to furnish the title compound II-19a as a colorless oil (29.0 mg, 87.7%): [α]D$^{25}$+8.33° (c 0.60, CHCl$_3$); IR (CHCl$_3$) 3480 (w), 3020 (w), 2940 (m), 2860 (m), 2100 (m), 1735 (s), 1455 (m), 1120 (s), 895 (w) cm$^{−1}$; $^1$H NMR (500 MHz, CDCl$_3$) d7.94 (br s, 1H), 7.54 (d, J=7.9 Hz, 1H), 7.31 (d, J=8.1 Hz, 1H), 7.28–7.07 (m, 12H), 6.99 (d, J=1.2 Hz, 1H), 4.86–4.78 (m, 2H), 4.55 (d, J= 7.8 Hz, 1H), 4.13 (ddm, J=8.5, 15.9 Hz, 1H), 3.80 (ddm, J=8.5, 16.4 Hz, 1H), 3.69–3.65 (m, 1H), 3.56 (dd, J=2.1, 11.0 Hz, 1H), 3.51–3.36 (m, 3H), 3.15 (t, J=7.0 Hz, 2H), 3.08–3.01 (m, 1H), 2.87 (d, J=13.3 Hz, 1H), 2.74 (d, J=13.3 Hz, 1H), 2.56–2.47 (m, 3H), 1.82 (t, J=8.8 Hz, 2H), 1.54–1.45 (m, 4H), 1.36–1.25 (m, 6H), 1.23 (s, 6H), 1.13 (s, 3H), 1.07 (s, 3H); $^{13}$C NMR (62.9 MHz, CDCl$_3$) δ176.07, 175.90, 141.93, 137.69, 136.07, 130.23, 128.41, 128.20, 127.93, 127.43, 126.41, 125.92, 122.17, 121.87, 119.20, 118.61, 112.29, 111.06, 102.34, 77.17, 71.75, 70.03, 69.73, 68.77, 66.28, 51.30, 45.90, 43.44, 42.44, 42.33, 33.22, 31.41, 29.44, 28.68, 26.47, 25.63, 25.27, 25.16, 24.95, 24.28; high resolution mass spectrum (+ve FAB) m/z 767. 4361 [(M+H$^+$); calcd for C$_{45}$H$_{59}$N$_4$O$_7$: 767.4384].

N. 2-(1H-Indol-3-yl)ethyl 2-O-(2,2-Dimethyl-3-phenylpropanoyl)-4-O-(2,2-dimethyl-3-phenylbutanoyl)-3-deoxy-O-(6-aminohexyl)-β-D-glucopyranoside (II-1a).

A solution of bis-ester II-19a (11.7 mg, 0.0152 mmol) and triphenylphosphine (9.97 mg, 0. 0380 mmol) in THF (0.8 ml) and water (12 ml) was heated at 55° C. for 15 h. The cooled solution was evaporated and purified by flash chromatography eluting with methanol/methylene chloride/acetic acid (10:90:1) increasing the gradient to (30:70:1). Fractions containing the title compound were treated with solid sodium bicarbonate, filtered, evaporated, redissolved in methylene chloride, filtered and evaporated, to afford the title cmpound Ii-1a as a colorless oil (10.6 mg, 93.8%): [α]D$^{25}$+36.18° (c 0.34, CHCl$_3$); IR (CHCl$_3$) 3480 (w), 3020 (w), 2935 (m), 2860 (m), 1730 (s), 1725 (s), 1455 (w), 1120 (s), 1005 (w), 690 (m) cm$^{-1}$; $^1$H NMR (500 MHz, CDCl$_3$) d8.84(br s, 1H), 7.53 (d, J=7.8 Hz, 1H), 7.32 (d, J=8.0 Hz, 1H), 7.26–7.03 (m, 12H), 6.99 (s, 1H), 4.83–4.75 (m, 2H), 4.54 (d, J=7.8 Hz, 1H), 4.09 (ddm, J=8, 17 Hz, 1H), 3.79 (ddm, J=8,16 Hz, 1H), 3.67–3.64 (m, 1H), 3.54 (d, J=11.2 Hz, 1H), 3.48–3.35 (m, 3H), 3.18 (br s, 2H), 3.05–3.02 (m, 2H), 2.88 (d, J=13.4 Hz, 1H), 2.74 (d, J=13.4 Hz, 1H), 2.53–2.47 (m, 2H), 1.80 (t, J=8.4 Hz, 2H), 1.52–1.14 (m, 9H), 1.21 (s, 6H), 1.14 (s, 3H), 1.08 (s, 3 H); $^{13}$C NMR (62.9 MHz, CDCl$_3$) δ176.13, 175.99, 141.93, 127.67, 136.25, 130.23, 128.43, 128.22, 127.95, 127.46, 126.43, 125.93, 122.29, 121.70, 119.02, 118.57, 111.78, 111.21, 102.34, 77.20, 71.75, 70.00, 69.89, 68.73, 66.33, 45.94, 43.48, 42.43, 42.36, 33.88, 33.35, 31.42, 29.68, 29.59, 29.33, 26.52, 25.70, 25.36, 25.18, 24.92, 24.31; high resolution mass spectrum (+ve FAB) m/z 741.4430 [(M+H$^+$); calcd for C$_{45}$H$_{61}$N$_2$O$_7$: 741.4478].

O. 2-(1H-Indol-3-yl)ethyl 2,4-Di-O-(2,2-dimethyl-3-phenylpropanoyl)-3-deoxy-O-(6-aminohe xyl)-β-D-glucopyranoside (II-1c).

The same procedure as detailed above afforded the title compound II-1c as a colorless oil (27.5 mg, 81.6%): [α]D$^{25}$+ 2.86° (c 0.28, CHCl$_3$); IR (CHCl$_3$) 3680 (w), 3480 (w), 3025 (w), 3005 (w), 2965 (w), 2930 (m), 2860 (w)m 1730 (s), 1600 (w), 1450 (w), 1115 (s), 895 (w) cm$^{-1}$; $^1$H NMR (500 MHz, CDCl$_3$) δ8.55 (br s, 1 H), 7.51 (d, J=7.9 Hz, 1H), 7.32 (d, J=9.4 Hz, 1H), 4.74–4.69 (m, 1H), 4.51 (d, J=7.8 Hz, 1H), 4.09 (ddm, J=8, 14 Hz, 1H), 3.78 (ddm, J2=8, 17 Hz, 1H), 3.62–3.58 (m, 1H), 3.38–3.33 (m, 3H), 3.06–3.0 (m, 2H), 2.88 (d, J=13.3 Hz, 1 H), 2.81 (s, 2H), 2.75 (d, J=13.3 Hz, 1H), 2.47–2.42 (m, 1H), 2.3 (br s, 2H), 1.49–1.16 (m, 9H), 1.14 (s, 6H), 1.14 (s, 3H), 1.08 (s, 3H); $^{13}$C NMR (62.9 MHz, CDCl$_3$) δ176.04, 175.92, 137.69, 137.43, 136.14, 130.22, 127.98, 127.43, 126.53, 126.41, 122.23, 121.73, 119.07, 118.55, 112.01, 111.14, 102.24, 77.12, 71.74, 69.91, 69.73, 68.74, 66.56, 45.98, 45.88, 43.45, 33.18, 29.56, 26.55, 25.85, 25.60, 25.28, 24.83, 24.31; high resolution mass spectrum (+ve FAB) m/z 727.4341 (M+H$^+$); calcd for C$_{44}$2H$_{59}$N$_2$O$_7$: 727.4322).

P. 2-(1H-Indol-3-yl)ethyl 2-O-(2,2-dimethyl-3-phenylpropanoyl)-3-deoxy-O-(5-azidopentyl) -β-D-glucopyranoside (II-14b).

2,2-Dimethyl-4-aminopyridine (40 mol%, 18 mg) was added to a vigorously stirrred solution of diol II-16b (146 mg, 0.349 mmol), 2,2-dimethyl-3-phenylpropanoic acid (333 mg, 1.75 mmol) and dicyclohexylcarbodiimide (1.09 g, 5.24 mmol) in chloroform (10 ml) and the mixture refluxed for 18 h. The cooled solution was evaporated, taken up in ether, filtered and evaporated. The residue was purified by flash chromatography eluting with 40% ethyl acetate in hexane to afford the somewhat impure mono-ester (RF 0.20). The eluant was changed to 10% methanol/dichloromethane to afford recovered starting material (61.2 mg, 41.9%). The mono-ester was further purified by flash chromatography eluting with 10% ether/dichloromethane to give the title compound II-18b as a colorless oil (65.3 mg, 32.1%): [α]D$^{25}$+36.61° (c 1.21, CHCl$_3$); IR (CHCl$_3$) 3500 (m), 3010 (w), 2940 (m), 2880 (m), 2100 (s), 1460 (m), 1120 (s), 1070 (s) cm$^{-1}$; $^1$H NMR (500 MHz, CDCl$_3$) d7.92 (br s, 1H), 7.54 (d, J=7.9 Hz, 1H), 7.32 (d, J=8.1 Hz, 1H), 7.26-7.07 (m, 7H), 7.08 (d, J=7, 1H), 4.79–4.74 (m, 1H), 4.52 (d, J=7.6 Hz, 1H), 4.10 (m, 1H), 3.80–3.71 (m, 3H), 3.62 (dd, J=7.3, 9.6 Hz, 1H), 3.54–3.45 (m, 3H), 3.24 (t, J=6.9 Hz, 2H), 3.12 (br s, 1H), 3.06–3.00 (m, 2H), 2.86 (d, J=13.4 Hz, 1H), 2.77 (d, J=13.4 Hz, 1H), 2.46–2.41 (m, 1H), 1.63–1.38 (m, 7H), 1.14 (s, 3H), 1.09 (s, 3H); $^{13}$C NMR (62.9 MHz, CDCl$_3$) δ176.16, 137.67, 136.05, 130.17, 127.93, 127.37, 126.40, 122.12, 121.80, 119.13, 118.53, 112.12, 111.06, 102.20, 76.27, 72.43, 71.64, 69.70, 69.18, 68.30, 51.18, 45.83, 43.44, 35.82, 28.95, 28.51, 25.65, 25.10, 24.45, 23.20; high resolution mass spectrum (+ve CI) m/z 578. 3107 (M+; calcd for C$_{23}$H$_{42}$N$_4$O$_6$: 578.3104).

Q. 2-(1H-Indol-3-yl)ethyl 2-O-(2,2-Dimethyl-3-phenylpropanoyl)-4-O-(2,2-dimethyl-3-pheny lbutanoyl)-3-deoxy-O-(5-azidopentyl)-β-D-glucopyranoside (II-19b).

2,2-Dimethyl-4-aminopyridine (2 mg) was added to a vigorously stirrred solution of mono-ester II-18b (34.8 mg, 0.0598 mmol), 2,2-dimethyl-4-phenylbutanoic acid (68.9 mg, 0.359 mmol) and dicyclohexylcarbodiimide (123 mg, 0.598 mmol) in methylene chloride (2.5 ml) and the mixture was refluxed for 20 h. The cooled solution was evaporated, taken up in ether, filtered and evaporated. The residue was purified by flash chromatography eluting with 20% ethyl acetate in hexane to furnish the title compound II-19b as a colorless oil (39.4 mg, 87.2%): [Cα]D$^{25}$+6.03° (c 0.58, CHCl$_3$); IR (CHCl$_3$) 33490 (w), 2940 (m), 2930 (m), 2100 (m), 1735 (s), 1730 (s), 1140 (s) cm$^{-1}$; $^1$H NMR (500 MHz, CDCl$_3$) d7.89 (br s, 1H), 7.53 (d, J=7.9 Hz, 1H), 7.31 (dd, J=0.5, 8.1 Hz, 1H), 7.27–7.06 (m, 12H), 7.00 (d, J=2.0 Hz, 1H), 4.84–4.78 (m, 2H), 4.53 (d, J=7.8 Hz, 1H), 4.12 (dt, J=6.7, 8.6 Hz, 1H), 3.80–3.76 (m, 1H), 3.54 (dd, J=2.0, 11.0 Hz), 3.49–3.35 (m, 3H), 3.12 (t, J=6.9 Hz, 2H), 3.07–3.00 (m, 1H), 2.85 (d, J=13.3 Hz, 1H), 2.73 (d, J=13.3 Hz, 1H), 2.55–2.48 (m, 2H), 1.81 (t, J=8.8 Hz, 2H), 1.54–1.44 (m, 7H), 1.36–1.29 (m, 2H), 1.22 (s, 6H), 1.12 (s, 3H), 1.06 (s, 3H); $^{13}$C NMR (62.9 MHz, CDCl$_3$) δ176.06, 175.89, 141.90, 137.66, 136.06, 130.21, 128.40, 128.17, 127.90, 127.41, 126.39, 125.90, 122.16, 121.85, 119.17, 118.57, 112.25, 111.06, 102.32, 77.12, 71.56, 70.03, 69.71, 68.74, 66.24, 51.21, 45.89, 43.42, 42.39, 42.33, 33.29, 31.37, 29.07, 28.54, 25.63, 25.25, 25.12, 24.92, 24.27, 23.27; high resolution mass spectrum (+ve CI) m/z 753.4261 [(M+H$^+$); calcd for C$_{44}$H$_{57}$N$_4$O$_7$: 753.4228].

R. 2-(1H-Indol-3-yl)ethyl 2-O-(2,2-Dimethyl-3-phenyl-propahoyl)-4-O-(2,2-dimethyl-3-pheny lbutanoyl)-3-deoxy-O-(5-aminopentyl)-β-D-glucopyranoside (II1b)

A solution of bis-ester II-19b (26.7 mg, 0.0353 mmol) and triphenylphosphine (23.2 mg, 0.0833 mmol) in THF (1.5 ml) and water (20 ml) was heated at 55° C. for 15 h. The cooled solution was evaporated and purified by flash chromatography eluting with methanol/methylene chloride/acetic acid (10:90:1) increasing the gradient to (30:70:1). Fractions containing the title compound were treated with solid sodium bicarbonate, filtered, evaporated, redissolved in methylene chloride, refiltered and evaporated to afford the title compound II-1b as a colorless oil (18.7 mg, 72.58): $[\alpha]D^{25}+25.00°$ (c 0.32, $CHCl_3$); IR ($CHCl_3$) 3480 (w), 3010 (s), 2920 (m), 2860 (w), 2390 (m), 1730 (m), 1520 (m), 1470 (m), 1420 (m), 1210 (s), 1120 (m), 920 (m), 840 (m), 750 (s), 660 (s), 615 (m) $cm^{-1}$; $^1H$ NMR (500 MHz, $CDCl_3$) δ9.13 (br s, 1H), 7.52 (d, J=7.9 Hz, 1H), 7.32–7.11 (m, 12H), 7.05 (t, J=5.7 Hz, 1H), 6.98 9s, 1H), 4.83–4.75 (m, 2H), 4.68 (br s, 2H), 4.53 (d, J=7.8 Hz, 1H), 4.10–4.05 (m, 1H), 3.81–3.76 (m, 1H), 3.66–3.63 (m, 1H), 3.51 (dd, J=1.8, 11.1 Hz, 1H), 3.45–3.31 (m, 3H), 3.06–3.00 (m, 2H), 2.89 (d, J=13.3 Hz, 1H), 2.74 (d, J=13.3 Hz, 1H), 2.55–2.45 (m, 4H), 1.80 (t, J=8.8 Hz, 2H), 1.52–1.34 (m, 5H), 1.30–1.21 (m, 3H), 1.21 (s, 6H), 1.15 (s, 3H), 1.09 (s, 3H); $^{13}C$ NMR (62.9 MHz, $CDCl_3$) δ176.17, 175.99, 141.90, 137.67, 136.24, 130.23, 128.43, 128.21, 127.96, 126.45, 125.95, 122.31, 121.70, 119.01, 118.55, 11.82, 111.26, 102.28, 71.48, 69.83, 68.72, 66.27, 45.95, 43.51, 42.36, 33.32, 31.42, 29.70, 29.22, 25.61, 25.39, 25.17, 24.95, 24.32, 23.28; high resolution mass spectrum (−ve CI) m/z 761. 3902 [(M+Cl$^+$); calcd for $C_{44}H_{58}N_2O_7Cl$: 761.3932].

S. 2-(1H-Indol-3-yl)ethyl 2-O-(3-phenylpropanoyl)-3-deoxy-O-(6-azidohexyl)-β-D-glucopyra noside (II-23).

A solution of diol II-16a (143 mg, 0.331 mmol) in methylene chloride (10 ml) was added dropwise to a stirred solution of hydrocinnamic acid (0.331 mmol, 49.7 mg), dicyclohexylcarbodiimide (0.331 mmol, 68.2 mg) and 2,2'-dimethyl-4-aminopyridine (1 mg) in methylene chloride at 0° C. The solution was warmed to room temperature and stirred for 16 h, evaporated, taken up in ether, filtered and evaporated. The residue was purified by flash chromatography eluting with 45% ethyl acetate/hexane to give a higher component (C-4 monoester II-24) (Rf 0.25), mixed fractions and a lower component (C-2 monoester II-23) (Rf 0.23). The mixed fractions were combined and the process was repeated twice. This produced a pure sample of the lower, C-2 monoester II-23 as a colorless oil (35.0 mg, 18.7%): $[\alpha]D^{25}+25.00°$ (c 0.32, $CHCl_3$); IR ($CHCl_3$) 3480 (w), 3010 (s), 2920 (m), 2860 (w), 2390 (m), 1730 (m), 1520 (m), 1470 (m), 1420 (m), 1210 (s), 1120 (m), 920 (m), 840 (m), 750 (s), 660 (s), 615 (m) $cm^{-1}$; $^1H$ NMR (500 MHz, $CDCl_3$) δ9.13 (br s, 1H), 7.52 (d, J=7.9 Hz, 1H), 7.32–7.11 (m, 12H), 7.05 (t, J=5.7 Hz, 1H), 6.98 (s, 1H), 4.83–4.75 (m, 2H), 4.68 (br s, 2H), 4.53 (d, J=7.8 Hz, 1H), 4.10–4.05 (m, 1H), 3.81–3.76 (m, 1H), 3.66–3.63 (m, 1H), 3.51 (dd, J=1.8, 11.1 Hz, 1H), 3.45–3.31 (m, 3H), 3.06–3.00 (m, 2H), 2.89 (d, J=13.3 Hz, 1H), 2.74 (d, J=13.3 Hz, 1H), 2.55–2.45 (m, 4H), 1.80 (t, J=8.8 Hz, 2H), 1.52–1.34 (m, 5H), 1.30–1.21 (m, 3H), 1.21 (s, 6H), 1.15 (s, 3H), 1.09 (s, 3H); $^{13}C$ NMR (62.9 MHz, $CDCl_3$) δ176.17, 175.99, 141.90, 137.67, 136.24, 130.23, 128.43, 128.21, 127.96, 126.45, 125.95, 122.31, 121.70, 119.01, 118.55, 11.82, 111.26, 102.28, 71.48, 69.83, 68.72, 66.27, 45.95, 43.51, 42.36, 33.32, 31.42, 29.70, 29.22, 25.61, 25.39, 25.17, 24.95, 24.32, 23.28; high resolution mass spectrum (−ve CI) m/z 761.3902 [(M+Cl$^+$); calcd for $C_{44}H_{58}N_2O_7Cl$: 761.3932].

T. 2-(1H-Indol-3-yl)ethyl 2-O-(3-phenylpropanoyl)-4-O-(4-phenylbutanoyl) -3-deoxy-O-(6-az idohexyl)-β-D-glucopyranoside (II-25).

2,2-Dimethyl-4-aminopyridine (1 mg) was added to a vigorously stirrred solution of mono-ester II-23 (13.8 mg, 0.0245 mmol), 4-phenylbutyriic acid (8.0 mg, 0.0490 mmol) and dicyclohexylcarbodiimide (20.2 mg, 0.0980 mmol) in methylene chloride (1.5 ml) and the mixture was stirred at room temperature for 20 h, evaporated, taken up in ether, refiltered and evaporated. The residue was purified by flash chromatography eluting with 25% ethyl acetate/hexane to furnish the title compound II-25 as a colorless oil (17.0 mg, 97.9%): $[C\alpha]D^{25}+9.15°$ (c 0.59, $CHCl_3$); IR ($CHCl_3$) 3490 (m), 3020 (w), 2950 (m), 2870 (m), 2100 (s), 1745 (s), 1460 (m), 1160 (m), 1135 (m), 1080 (m) $cm^{-1}$; $^1H$ NMR (500 MHz, $CDCl_3$) δ7.86 (br s, 1H), 7.56 (d, J=7.3 Hz, 1H), 7.33–7.07 (m, 13H), 6.99 (d, J=2.3 Hz, 1H), 4.82–4.77 (m, 2H), 4.46 (d, J=7.5 Hz, 1H), 4.14–4.10 (m, 1H), 3.76–3.72 (m, 1H), 3.62–3.58 (m, 1H), 3.54–3.50 (m, 1H), 3.47–3.35 (m, 3H), 3.17 (t, J=7.0 Hz, 2H), 3.03–3.00 (m, 2H), 2.92–2.83 (m, 3H), 2.63–2.57 (m, 3H), 2.49–2.41 (m, 3H), 2.27 (t, J=7.4 Hz, 2H), 2.27–2.15 (obs m, 1H), 1.95–1.87 (m, 3H), 1.57–1.24 (m, 11H); $^{13}C$ NMR (125 MHz, $CDCl_3$) δ172.00, 171.44, 141.14, 140.44, 136.07, 128.47, 128.43, 128.29, 127.53, 126.26, 126.07, 122.17, 121.91, 119.26, 118.75, 112.71, 111.04, 101.94, 76.82, 71.69, 70.17, 69.61, 68.69, 66.44, 51.35, 35.63, 35.05, 33.59, 32.87, 30.74, 29.47, 28.73, 26.50, 26.45, 25.63, 25.58; high resolution mass spectrum (+ve FAB) m/z 710.3717 (M$^+$; calcd for $C_{41}H_{50}N_4O_7$: 710.3680).

U. 2-(1H-Indol-3-yl)ethyl 2-O-(3-phenylpropanoyl)-4-O-(4-phenylbutanoyl)-3-deoxy-O-(6-am inohexyl)-β-D-glucopyranoside (II-20).

A solution of bis-ester 25 (17.0 mg, 0.0239 mmol) and triphenylphosphine (15.6 mg, 0.0599 mmol) in THF (2.0 ml) and water (20 ml) was heated at 55° C. for 16 h. The cooled solution was evaporated and purified by flash chromatography eluting with methanol/methylene chloride/acetic acid (10:90:1) increasing the gradient to (30:70:1). Fractions containing the title compound were treated with solid sodium bicarbonate, filtered, evaporated, redissolved in methylene chloride, filtered and evaporated, to afford the title compound II-20 as a colorless oil (16.0 mg, 97.8%) $[\alpha]D^{25}+6.25°$ (c 0.24, $CHCl_3$); IR ($CHCl_3$) 3480 (w), 3020 (w), 2930 (s), 2860 (m), 1740 (s), 1450 (w), 1155 (m), 1140 (m), 690 (w) $cm^{-1}$; $^1H$ NMR (500 MHz, $CDCl_3$) δ8.87 (br s, 1H), 7.55 (d, J=8.0 Hz, 1H), 7.30–7.04 (m, 13H), 6.98 (s, 1H), 4.82–4.73 (m, 2H), 5.0–4.7 (br s, 2H), 4.47 (d, J=7.4 Hz, 1H), 4.10–4.05 (m, 1H), 3.78–3.74 (m, 1H), 3.62–3.58 (m, 1H), 3.49 (dd, J=2.6, 11.1 Hz, 1H), 3.44–3.33 (m, 3H), 3.02 (t, J=7.3 Hz, 2H), 2.87 (t, J=7.8 Hz, 2H), 2.63–2.56 (m, 3H), 2.50 (t, J=8 Hz, 2H), 1.96–1.88 (m, 4H), 1.53–1.22 (m, 11 H); $^{13}C$ NMR (125 MHz, $CDCl_3$) δ172.03, 171.50, 141.11, 140.38, 136.20, 128.46, 128.43, 128.28, 127.53, 126.26, 126.07, 122.26, 121.72, 119.05, 118.68, 112.19, 111.13, 101.88, 71.71, 70.09, 69.69, 68.69, 66.41, 40.46, 35.69, 35.03, 33.56, 32.86, 30.77, 29.69, 29.59, 26.51, 26.43, 25.76, 25.61.

V. 2-(1H-Indol-3-yl)ethyl 2,4-Di-O-(3-phenylpropanoyl)-3-deoxy-O-(6-azidohexyl)-β-D-gluc opyranoside (II-22).

2,2'-dimethyl-4-aminopyridine (1 mg) was added to a stirred solution of diol II-16a (18.0 mg, 0. 0417 mmol), hydrocinnamic acid (0.104 mmol, 15.7 mg) and dicyclohexylcarbodiimide (0.209 mmol, 42.9 mg) in methylene chloride (2.0 ml). The solution was stirred for 1 h, evaporated, taken up in ether, filtered and evaporated. The residue was purified by flash chromatography eluting with 30% ethyl acetate/hexane to give the title compound II-22 as a colorless oil (27.8 mg, 95.9%): $[\alpha]_D^{25}$+5.96° (c 0.94, CHCl$_3$); IR (CHCl$_3$) 3480 (m), 3010 (w), 2950 (m), 2860 (m), 2100 (s), 1745 (m), 1300 (w), 1290 (m), 1260 (w), 1160 (m), 1140 (m), 1080 (m), 690 (w) cm$^{-1}$; $^1$H NMR (500 MHz, CDCl$_3$) δ7.86 (br s, 1H), 7.57 (d, J=6.9 Hz, 1H), 7.34–7.02 (m, 13H), 6.99 (d, J=2.4 Hz, 1H), 4.81–4.75 (m, 2H), 4.44 (d, J=7.4 Hz, 1H), 4.14–4.09 (m, 1H), 3.80–3.70 (m, 1H), 3.59–3.55 (m, 1H), 3.50–3.31 (m, 4H), 3.18 (t, J=6.9 Hz, 2H), 3.01 (t, J=6.3 Hz, 2H), 2.91 (t, J=7.5 Hz, 2H), 2.85 (t, J=7.9 Hz, 2H), 2.63–2.37 (m, 5H), 1.57–1.24 (m, 9H); $^{13}$C NMR (62.9 MHz, CDCl$_3$) δ171.42, 140.09, 140.08, 128.48, 128.25, 128.20, 126.33, 126.23, 122.17, 121.84, 119.18, 118.70, 112.55, 111.02, 101.88, 76.67, 71.58, 70.02, 69.59, 68.63, 66.52, 51.29, 35.72, 35.59, 32.75, 30.79, 30.69, 29.42, 28.68, 26.45, 25.56; high resolution mass spectrum (–ve CI) m/z 731.3245 [(M+Cl)$^+$; calcd for C$_{40}$H$_{48}$O$_7$Cl: 731.3211].

W. 2-(1H-Indol-3-yl)ethyl 2,4-Di-O-(3-phenylpropanoyl)-3-deoxy-O-(6-aminohexyl)-β-D-gluc opyranoside (II-21).

The same procedure as that detailed above for the preparation of compound II-20 yielded the title compound II-21 as a clear colorless oil (20.1 mg, 83.9%): $[\alpha]_D^{25}$+23.10° (c 0.58, CHCl$_3$); IR (CHCl$_3$) 3480 (w), 3020 (w), 2920 (m), 2850 (w), 1745 (s), 1455 (w), 1155 (m), 690 cm–1; $^1$H NMR (500 MHz, CDCl$_3$) δ9.08 (br s, 1H), 7.54 (d, J=7.9 Hz, 1H), 7.32–7.00 (m, 13H), 6.96 (s, 1H), 6.65 (br s, 1H), 4.80–4.70 (m, 2H), 4.46 (d, J=7.4 Hz, 1H), 4.08–4.03 (m, 1H), 3.77–3.72 (m, 1H), 3.59–3.55 (m, 1H), 3.51–3.28 (m, 4H), 3.02 (t, J=7.5 Hz, 2H), 2.97–2.86 (m, 4H), 2.64–2.50 (m, 5H), 2.42–2.37 (m, 1H); $^{13}$C NMR (125 MHz, CDCl$_3$) δ171.47, 140.06, 136.23, 128.51, 128.46, 128.26, 128.21, 127.51, 126.35, 126.25, 122.25, 121.66, 119.00, 118.66, 112.04, 111.14, 101.84, 76.90, 71.56, 69.98, 69.73, 68.67, 66.51, 35.75, 35.69, 32.77, 30.82, 30.77, 29.69, 29.57, 26.45, 25.68, 25.62.

X. 4-Azido-1-butyne (II-32).

p-Toluenesulphonyl chloride (127 mmol, 24.3 g) was added in aliquots to a solution of 3-butyn-1-ol (84.9 mmol, 5.86 g) in pyridine (20 ml) at 0° C. and DMAP was added (10 mg). The mixture was allowed to stand for 15 h, then poured into water (100 ml) and extracted with ether (100 ml). The ether extract was washed with 1N HCl (100 ml), water (100 ml) and brine (50 ml), dried over sodium suphate and evaporated to afford a yellow oil. To a stirred solution of this tosylate in DMSO (100 ml) at 35° C. was added sodium azide (170 mmol, 11.0 g). After stirring for 3 h, the mixture was poured into ether (50 ml), washed with water (3×100 ml), dried over sodium sulphate and evaporated at 0° C. (water aspirator). Cautious distillation into a flask cooled to –78° C. yielded the pure azide II-32 as a colorless, volatile liquid (b.p. 30°–32° C. at 12 mmHg) (3.90 g, 48.3%): IR (CHCl$_3$) 3300 (s), 3000 (m), 2950 (m), 2880 (w), 2120 (s), 1450 (m), 1420 (m), 1350 (m), 1320 (m), 1290–1210 (br), 1050 (w), 950 (w), 910 (w), 630 (s) cm$^{-1}$; $^1$H NMR (500 MHz, CDCl$_3$) δ3.40 (t, J=6.9 Hz, 2H), 2.48–2.44 (m, 2H), 2.04 (t, J=2.8 Hz, 1H); $^{13}$C NMR (62.9 MHz, CDCl$_3$) δ80.29, 70.44, 49.62, 19.39.

Y. 5-Azido-2-pentyn-1-ol (II-33).

n-Butyl lithium (1.6M in hexane, 18.8 mmol, 11.7 ml) was added dropwise at –78° C. to a solution of 4-azido-1-butyne II-32 (1.28 g, 17.3 mmol) in THF (35 ml). After stirring the resulting green solution for 1 h, paraformaldehyde was added in one portion, the solution was stirred for 5 min, and then warmed to room temperature for 2 h (an orange suspension gradually formed). The reaction mixture was poured into saturated aqueous ammonium chloride (100 ml) and extracted with ether (3×50 ml). The combined extracts were washed with brine (50 ml), dried over sodium sulphate and evaporated to give a yellow oil. This was purified by flash chromatography eluting with pentane/ether 1:1 to afford the title compound II-33 as a pale yelow oil (930 mg, 70.7%): IR (CHCl$_3$) 3600 (m), 3000 (m), 2940 (m), 2880 (m), 2100 (s), 1550 (w), 1380 (m), 1270 (m), 1220 (br), 1140 (m), 1000 (s) cm$^{-1}$; $^1$H NMR (500 MHz, CDCl$_3$) δ4.24–4.22 (m, 2H), 3.37 (t, J=6.8 Hz, 2H), 2.51–2.48 (m, 2H), 1.84 (t, J=6.0 Hz, 1H); $^{13}$C NMR (62.9 MHz, CDCl$_3$) δ77.42, 70.47, 49.68, 19.45.

Z. 5-Azido-1-iodo-2-pentyne (II-31).

Iodine (2.94 g, 11.6 mmol) was added to a stirred solution of triphenylphosphine (12.2 mmol, 3.20 g) and imidazole (14.5 mmol, 987 mg) in THF (25 ml) at 0° C. To the resulting brown solution was added 5-azido-2-pentyn-1-ol 33 (725 mg, 5.80 mmol) in THF (10 ml). The mixture was warmed to room temperature, stirred for 10 min and evaporated (water aspirator). Pentane was added and the solid was filtered off. Evaporation yielded the iodide II-31 (contaminated with a small amount of triphenylphosphine) (905 mg, 66.4%).

AA. 2-[(N-Benzenesulphonyl)indol-3-yl]ethyl 4,6-Di-O-isopropylidene-3-deoxy-β-D-glucopyranoside (II-29).

Triol II-28 (25.0 mg, 0. 0534 mmol) was stirred with dl-camphorsulphonic acid (1 mg) in 2,2-dimethoxypropane (2.0 ml) for 15 h, triethylamine (0.05 ml) was added and the solution was evaporated. The residue was purified by flash chromatography (50% ethyl acetate/hexane) to yield the title compound II-29 as a colorless foam (26.9 mg, 99.1%): $[\alpha]_D^{25}$+38.9° (c 0.99, CHCl$_3$); IR (CHCl$_3$) 3600 (w), 3010 (w), 2890 (w), 1730 (w), 1520 (w), 1450 (m), 1380 (m), 1220 (s), 1210 (s), 1180 (m), 1100 (m), 1055 (m), 930 (m), 780–720 (br), 660 (s) cm$^{-1}$; $^1$H NMR (500 MHz, CDCl$_3$) δ7.96 (br s, 1H), 7.84 (d, J=7.8 Hz, 2H), 7.52–7.39 (m, 4H), 7.30 (app. t, J=8.1 Hz, 1H), 7.22 (app. t, J=8.3 Hz, 2H), 4.23 (d, J=7.5 Hz, 1H), 4.18 (dt, J=6.6,9.5 Hz, 1H), 3.87 (dd, J=5.3, 10.9 Hz, 1H), 3.77–3.73 (m, 2H), 3.64–3.59 (m, 1H), 3.54–3.49 (m, 1H), 3.23–3.19 (m, 1H), 3.02–2.92 (m, 2H), 2.27–2.11 (m, 1H), 1.56 (app. q, J=18.5 Hz, 1H), 1.47 (s, 3H), 1.39 (s, 3H); $^{13}$C NMR (125 MHz, CDCl$_3$) δ138.25, 135.16, 133.73, 130.99, 129.23, 126.69, 124.87, 123.49, 123.20, 119.63, 119.34, 113.79, 105.43, 99.34, 71.68, 69.22, 69.03, 68.40, 62.44, 35.38, 29.11, 25.48, 19.01.

AB. 2-[(N-Benzenesulphonyl)indol-3-yl]ethyl 2-O-(5-azido-2-pentynyl)-4,6-di-O-isopropylidene-3-deoxy-β-D-g lucopyranoside (II-34).

Sodium hydride (60% dispersion in mineral oil, 0.276 mmol, 11.0 mg) was added to a solution of acetonide II-29 (100 mg, 0.197 mmol) and 5-azido-1-iodo-2-pentyne II-31 (93 mg, 0.39 mmol) in dry acetonitrile (3.0 ml) at 0° C. followed by the addition of 15-crown-5 ether (0.001 ml). The solution was warmed to room temperature and stirred for 36 h (a brown color gradually appeared), then poured into saturated aqueous sodium bicarbonate (10 ml) and extracted with methylene chloride (3×5 ml). The combined extracts were washed with brine (10 ml), dried over sodium sulphate and evaporated. The residue was purified by flash chromatography eluting with 30% ethyl acetate/hexane to afford the title compound II-34 as a colorless oil (30.7 mg, 25.4%). The gradient was increased to 50% ethyl acetate/ hexane to yield the starting material II-29 as a colorless oil (65 mg , 65%).

2-[(N-Benzenesulphonyl)indol-3-yl]ethyl 2-O-(5-azido-2-pentynyl)-4,6-di-O-isopropylidene-3-deoxy-β-D-glucopyranoside: $[\alpha]D^{25}$ +11.59° (c 0.63, CHC$_3$3); IR (CHCl$_3$) 3020 (m), 2950 (w), 2890 (w), 2890 (w), 2110 (s), 1450 (m), 1370 (m), 1260 (m), 1175 (s), 1090 (s), 1080 (s), 850 (w), 600 (m), 570 (m) cm$^{-1}$; $^1$H NMR (500 MHz, CDCl$_3$) δ7.95 (d, J=7.6 Hz, 1H), 7.84 (d, J=8 Hz, 2H), 7.52–7.39 (m, 5H), 7.29 (dt, J=1.2, 7.4 Hz, 1H), 7.23–7.20 (m, 1H), 4.37 (d, J=7.5 Hz, 1H), 4.24–4.20 (m, 2H), 4.17–4.12 (m, 1H), 3.86 (dd, J=10.8, 5.3 Hz, 1H), 3.81–3.72 (m, 2H), 3.62–3.57 (m, 1H), 3.49–3.42 (m, 1H), 3.35 (t, J=6.8 Hz, 2H), 3.20–3.15 (m, 1H), 2.96 (t, J=6.2 Hz, 2H), 2.50–2.46 (m, 2H), 2.32–2.28 (m, 1H), 1.52 (app. q, J=11.7 Hz, 1H), 1.47 (s, 3H), 1.39 (s, 3H); $^{13}$C NMR (62.9 MHz, CDCl$_3$) δ138.50, 135.09, 133.65, 130.95, 129.17, 126.70, 124.73, 123.11, 119.61, 119.35, 113.67, 105.00, 99.26, 82.59, 78.29, 74.96, 71.15, 68.59, 68.32, 62.46, 58.32, 49.74, 35.02, 29.11, 25.49, 19.84, 19.01.

EXAMPLE 11

Preparation of Other Compounds

Figure 17:
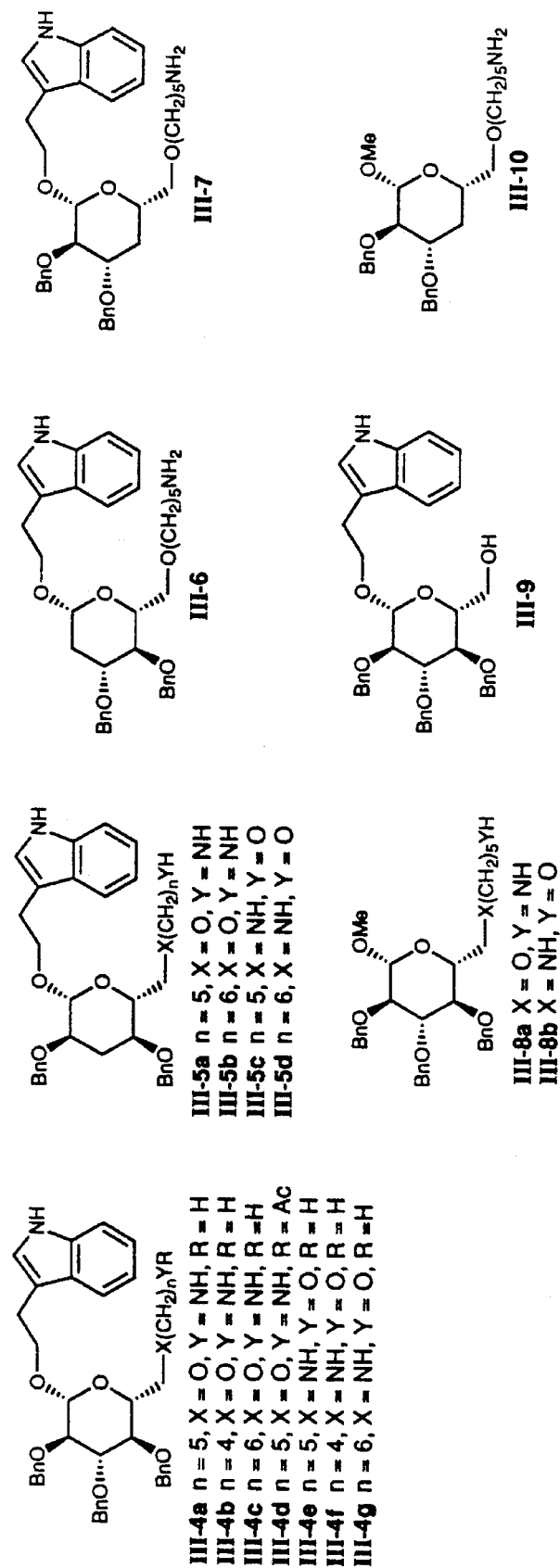
FIGS. 17–23 depict synthetic schemes for the other compounds of Example 11.
Figure 18:
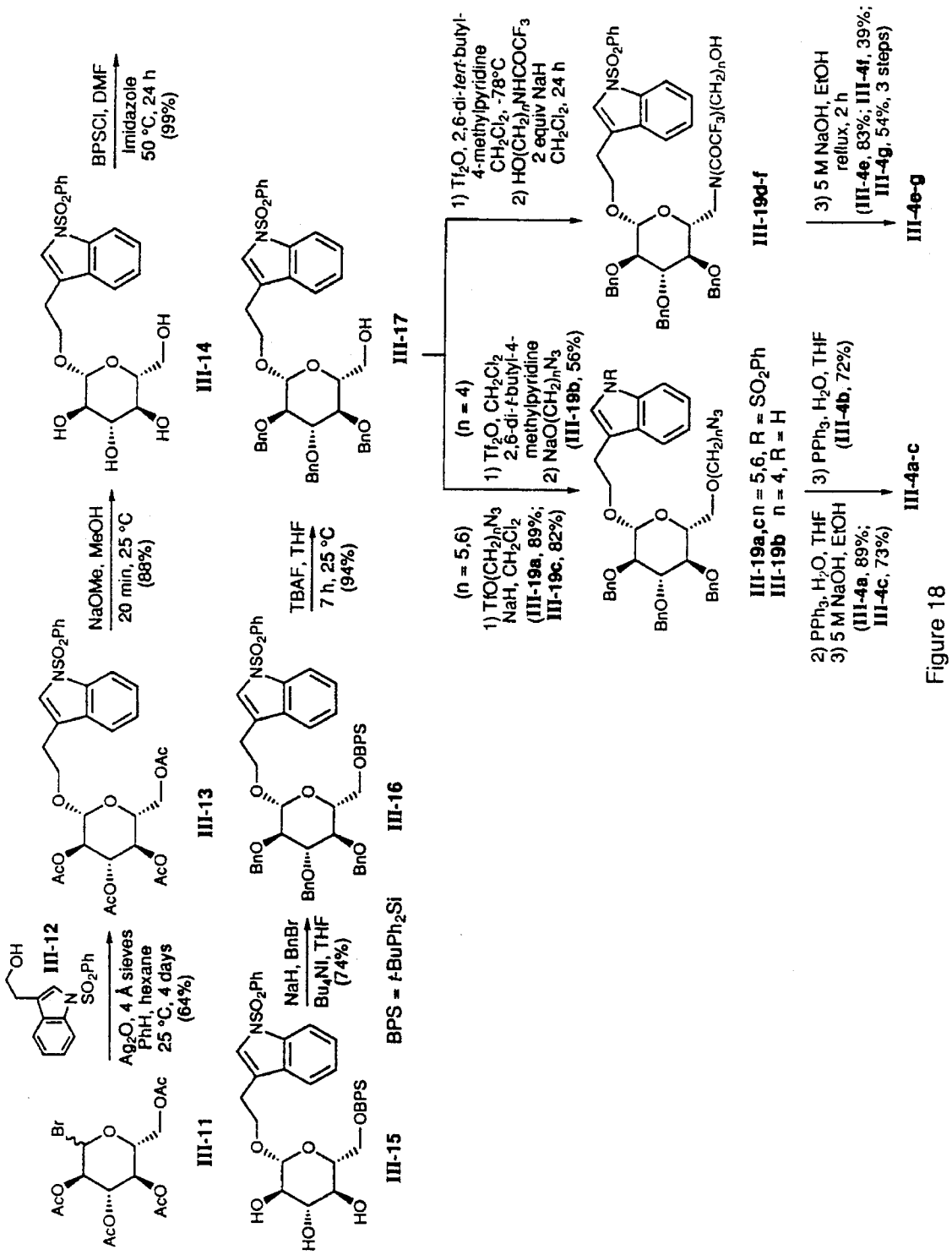
Figure 19:
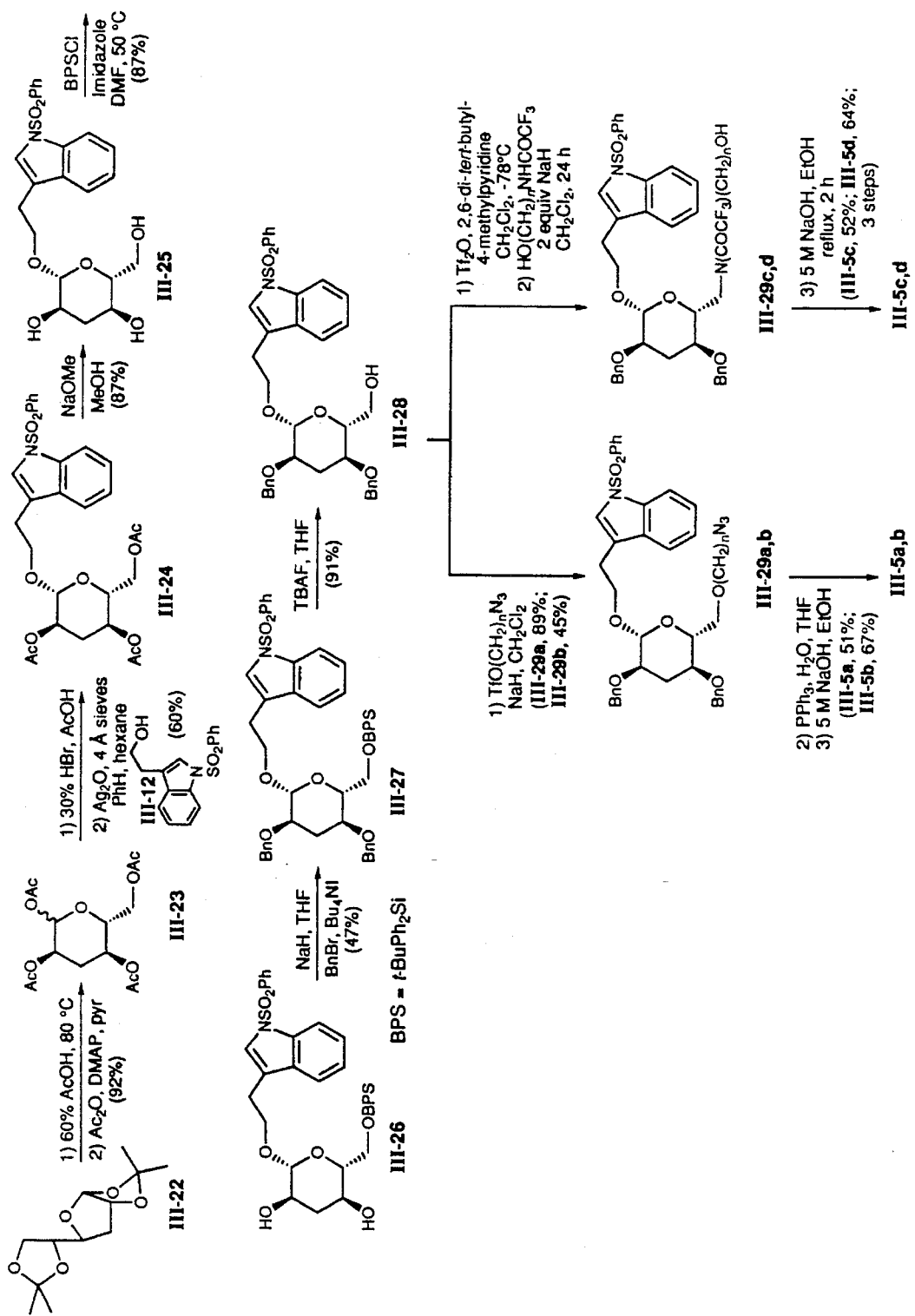
Figure 20:
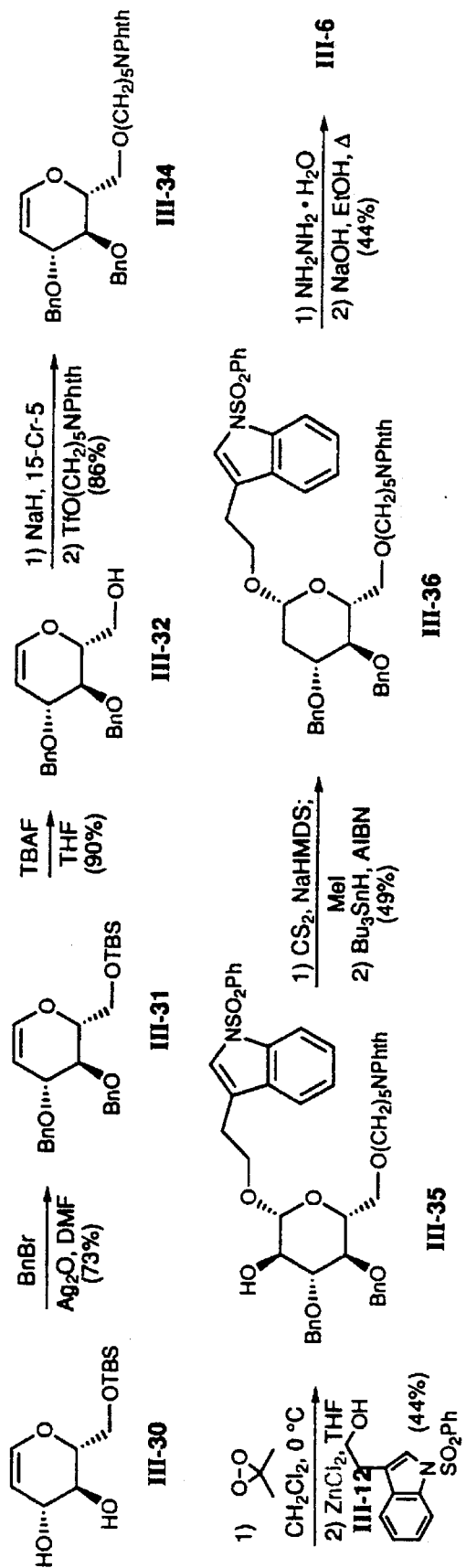
Figure 21:
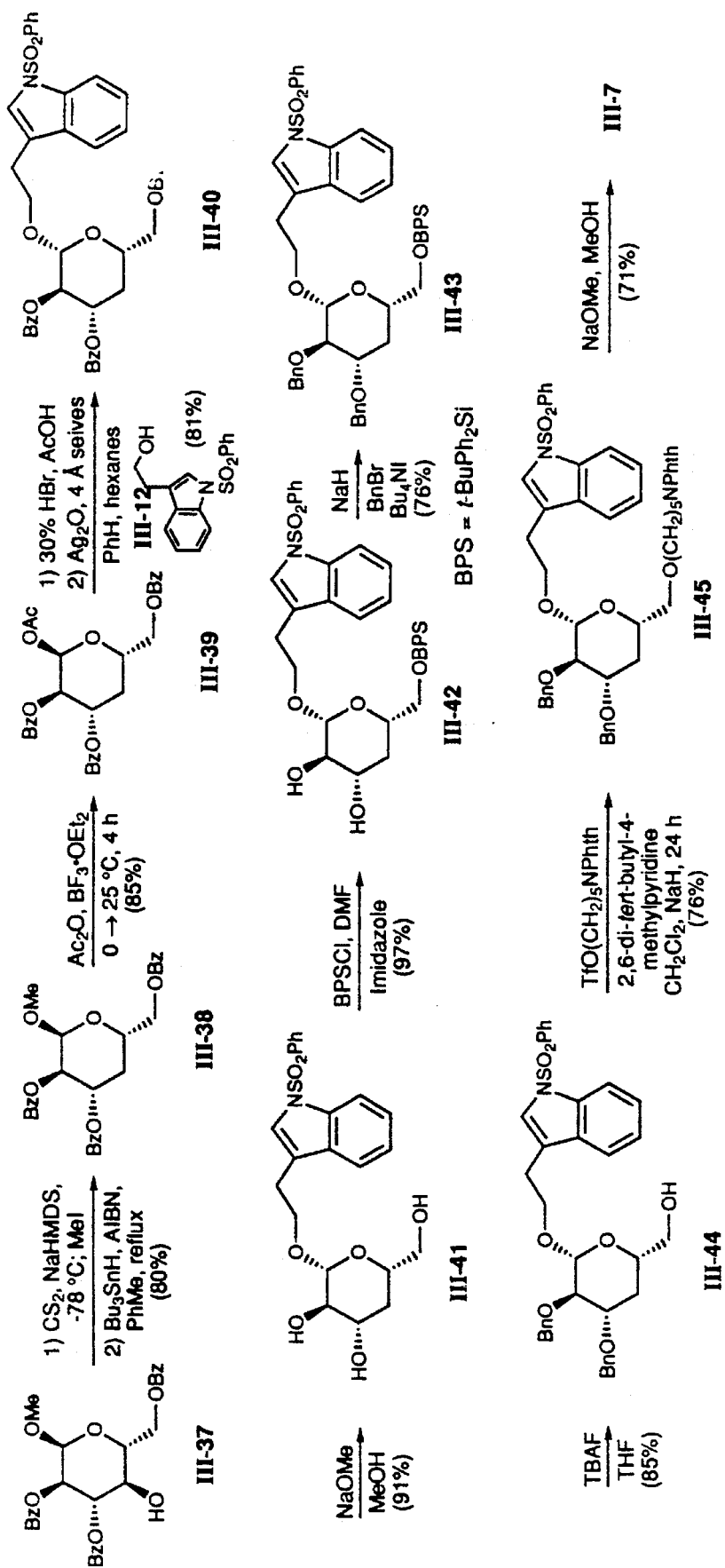
Figure 22:
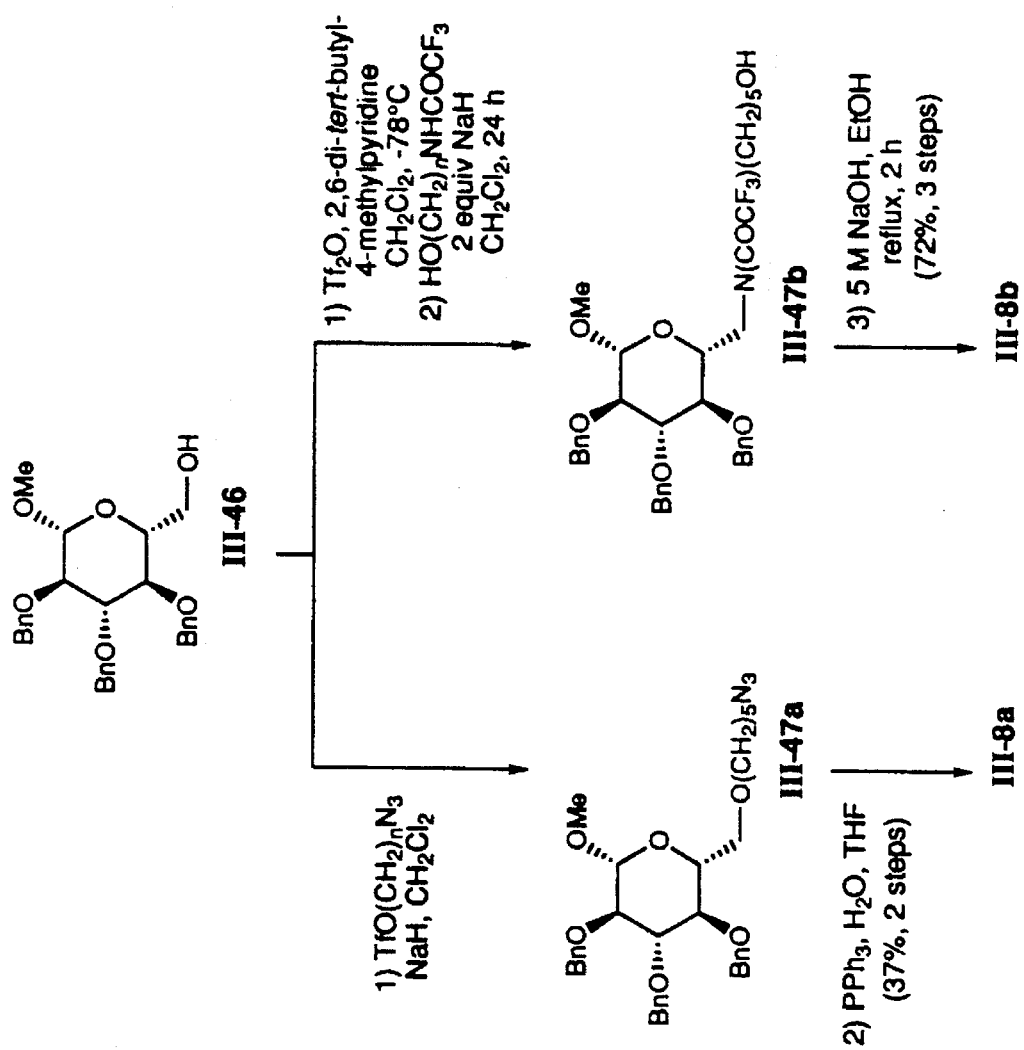
Figure 23:
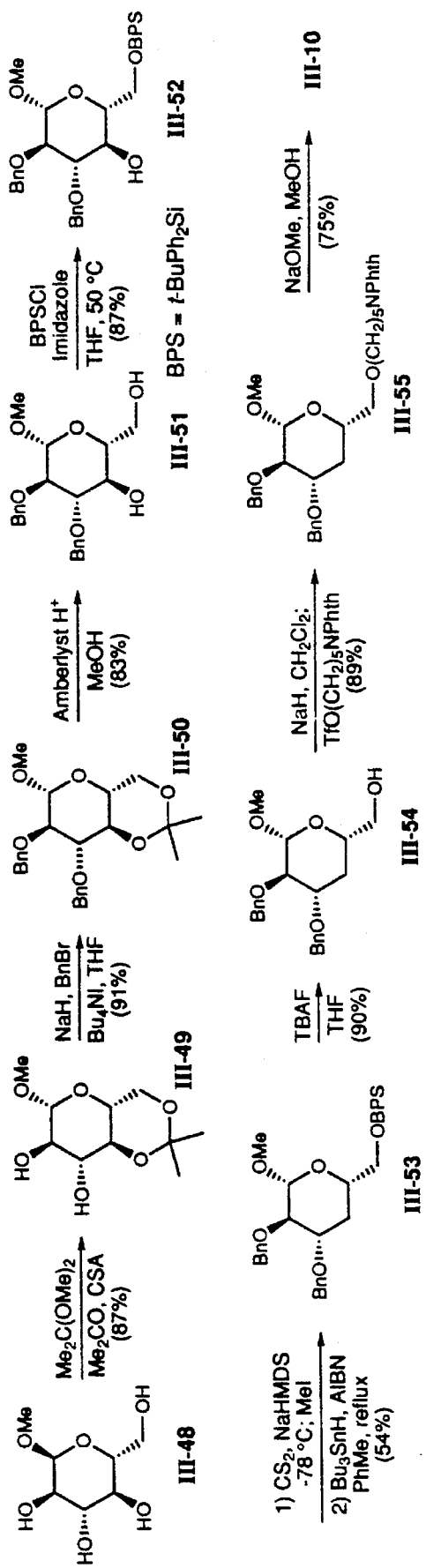

To distinguish the compounds described in this example from those described in other examples, a "III" preceeds each compound number. The chemical structures and synthetic schemes of Example 11 are presented in FIGS. 17–23.

A. N-(phenylsulfonyl)tryptophol (III-12).

(a) 1-O-tert-Butyldimethylsilyl-2-(3-indolyl)ethanol.

A solution of tryptophol (5.0 g, 31 mmol) in DMF (30 ml) was treated with imidazole (4.64 g, 68 mmol) and cooled to 0° C. tert-Butyldimethylsilyl chloride (5.14 g, 34.1 mmol) was added and the mixture was stirred at room temperature for 16 h. The mixture was then diluted with ethyl acetate (100 ml) and washed with water (2×100 ml) and the aqueous solutions were extracted with ethyl acetate (200 ml). The combined organic layers were dried over sodium sulfate, filtered, and concentrated in vacuo. Flash chromatography (30% ether/petroleum ether) yielded the title compound (8.43 g, 99% yield) as a colorless oil: IR (CCl$_4$) 3910 (s), 3060 (w), 2960 (s), 2930 (s), 2850 (s), 1450 (m), 1370 (w), 1260 (s), 1100 (s), 900 (m), 840 (s), 780 (s), 750 (s) cm$^{-1}$; $^1$H NMR (500 MHz, CDCl$_3$) δ8.26 (br s, 1H), 7.99 (d, J=7.8 Hz, 1H), 7.64–7.50 (m, 4H), 4.28 (t, J=7.3 Hz, 2H), 3.38 (t, J=7.3 Hz, 2H), 1.29 (s, 9H), −0.43 (s, 6H); $^{13}$C NMR (125 MHz, CDCl$_3$) δ136.08, 127.62, 122.08, 121.75, 119.12, 118.79, 112.84, 111.04, 63.89, 28.98, 25.98, 18.34, −5.29; high resolution mass spectrum (Cl, NH$_3$) m/z 276.1750 [(M+H)$^+$; calcd for C$_{16}$H$_{25}$NOSi: 276.1783].

(b) 1-O-tert-Butyldimethylsilyl-2-[3-(1-N-Phenyl sulfonyl)indolyl]ethanol.

A suspension of sodium hydride (1.91 g, 60% oil dispersion) in dry DMF (64 ml) was cooled to 0° C. and a solution of 1-O-tert-butyldimethytsilyl-2-(3-indolyl)ethanol (8.43 g, 30.6 mmol) in DMF (30 ml) was added. The mixture was stirred at room temperature for 30 min, recooled to 0° C., and treated dropwise with benzenesulfonyl chloride (5.30 ml, 39.7 mmol). The reaction was then stirred at room temperature for 16 h, quenched with saturated aqueous ammonium chloride (100 ml), and extracted with ether (3×200 ml). The combined extracts were washed with brine, dried over sodium sulfate, filtered, and concentrated in vacuo. Flash chromatography (30% ether/petroleum ether) afforded the title compound (7.37 g, 79% yield) as a colorless oil: $^1$H NMR (500 MHz, CDCl$_3$) δ7.77 (d, J=8.4 Hz, 1H), 7.62 (d, J=7.5 Hz, 2H), 7.26–6.98 (m, 7H), 3.64 (t, J=6.7 Hz, 2H), 2.64 (t, J=6.7 Hz, 2H), 0.64 (s, 9H), −0.24 (s, 6H); $^{13}$C NMR (125 MHz, CDCl$_3$) δ135.10, 133.55, 131.21, 129.12, 126.65, 124.56, 123.42, 122.00, 120.31, 119.57, 113.59, 62.51, 28.51, 25.87, 18.22, −5.44; high resolution mass spectrum (FAB, m-nitrobenzyl alcohol) m/z 433.1920 [(M+NH$_4$)$^+$; calcd for C$_{22}$H$_{29}$NSO$_3$Si: 433.1971].

(c) N-Phenylsulfonyltryptophol (III-12).

Tetrabutylammonium fluoride (21 ml, 1M in THF) was added to a solution of 1-O-tert-butyldimethylsilyl-2-[3-(1-N-Phenylsulfonyl)indoyl]ethanol (6.6 g, 22 mmol) in THF (100 ml) and the reaction was stirred at room temperature for 16 h. The mixture was then diluted with ethyl acetate (100 ml) and extracted with water (2×100 ml). The organic layer was washed with brine, dried over sodium sulfate, filtered, and concentrated in vacuo. Flash chromatography (40% ethyl acetate/petroleum ether) furnished III-11 (4.00 g, 84% yield) as a pale yellow oil which crystallized upon standing: mp 63°–64° C.; IR (CCl$_4$) 3580 (m), 3400 (m), 3100 (w), 3080 (w), 2950 (m), 2890 (m), 1460 (s), 1360 (s), 1280 (m), 1160 (s), 1120 (s), 1100 (m), 1080 (w), 1060 (w), 1020 (w), 980 (w), 750 (s), 720 (s), 690 (s) cm$^{-1}$; $^1$H NMR (500 MHz, CDCl$_3$) δ7.86 (d, J=7.6 Hz, 1H), 7.70 (d, J=7.6 Hz, 2H), 7.32–7.04 (m, 7H), 3.68 (t, J=6.2 Hz, 2H), 2.72 (t, J=6.2 Hz, 2H), 2.36 (br s, 1H); $^{13}$C NMR (125 MHz, CDCl$_3$) δ137.79, 134.99, 133.55, 130.78, 129.00, 126.43, 124.63, 123.39, 123.05, 119.67, 119.38, 61.40, 28.07; high resolution mass spectrum (Cl, NH$_3$) m/z 301.0748 (M$^+$; calcd for C$_{16}$H$_{15}$NO$_3$S: 301.0772).

B. 2-(N-Phenylsulfonylindol-3-yl)ethyl 2,3,4,6-Tetra-O-acetyl-b-D-glucopyranoside (III-13).

A solution of III-12 (537 mg, 1.78 mmol) in dry benzene (3 ml) was added to a suspension of powdered, activated 4 Angstrom molecular sieves (0.89 g) and silver (I) oxide (412 mg, 17.8 mmol) in dry hexane (9 ml) at room temperature. A solution of bromide III-11 (804 mg, 1.95 mmol) in dry benzene (3 ml) was then added, the flask was covered with aluminum foil and the mixture allowed to stir for 2 days at room temperature. More silver(I) oxide (206 mg, 8.9 mmol) and benzene (1 ml) were added and the reaction was stirred at room temperature for an additional 2 days. After filtration through Celite, concentration in vacuo and recrystallization (ethyl acetate/petroleum ether) afforded pure II-13 (580 mg) as a white solid. Concentration of the filtrate in vacuo and flash chromatography (5 % ether/dichloromethane) afforded III-13 admixed with the a anomer and the corresponding ortho ester. Further flash chromatography (70% ether/petroleum ether) then gave an additional 134 mg of pure III-13 (64% total yield): mp 145°–146° C.; $[\alpha]D^{25}$ −16° (c 0.14, acetonitrile); UV (1.05×10$^{-4}$M, acetonitrile) λmax 253.6 (ε1.19×10$^4$), 214.0 (2.50×104) nm; IR (thin film) 3028 (w), 2950 (w), 2880 (w), 1758 (s), 1450 (m), 1377 (s), 1225 (s), 1178 (s), 1122 (m), 1040 (s), 910 (w), 754 (s), 688 (w) cm$^{-1}$; $^1$H NMR (500 MHz, CDCl$_3$) δ7.96 (d, J=8.3 Hz, 1H), 7.87–7.21 (m, 9H), 5.18 (dd, J=9.5, 9.5 Hz, 1H), 5.09 (dd, J=9.6, 9.6 Hz, 1H), 5.00 (dd, J=9.5, 8.0 Hz, 1H), 4.53 (d, J=8.0 Hz, 1H), 4.26 (dd, J=12.3, 4.7 Hz, 1H), 4.18–4.12 (m, 2H), 3.76 (ddd, J=9.3, 6.9, 6.9 Hz, 1H), 3.69 (ddd, J=9.8, 4.6, 2.4 Hz, 1H), 2.94 J=6.6 Hz, 2H), 2.07 (s, 3H), 2.02 (s, 3H), 2.00 (s, 3H), 1.89 (s, 3H); $^{13}$C NMR (125 MHz, CDCl$_3$) δ170.66, 170.24, 169.34, 138.24, 135.08, 133.70, 130.94, 129.22, 126.73, 124.75, 123.56, 123.21, 119.57, 119.42, 113.65, 106.61, 100.70, 72.87, 71.16, 68.75, 68.39, 61.91, 25.31, 20.72, 20.57, 20.43; high resolution mass spectrum (Cl, NH$_3$) m/z 649.2021 [(M+NH$_4$)$^+$; calcd for C$_{30}$H$_{33}$NO$_{12}$S: 649.2054]. Anal. Calcd for C$_{30}$H$_{33}$NO$_{12}$S: C, 57.04; H, 5.27. Found: C, 56.75; H, 5.30.

2-(N-phenylsulfonylindol-3-yl)ethyl β-D-glucopyranoside (III-14).

Sodium methoxide (221 mg, 4.09 mmol) was added to a suspension of III-13 (3.22 g, 5.12 mmol) in methanol (26 ml) at room temperature. After 20 min, the resultant solution was diluted with methanol (26 ml) and neutralized with Amberlyst® 15 ion exchange resin. The resin was quickly removed by filtration to avoid formation of the methyl glucoside. Concentration and flash chromatography (5:1:1 dichloromethane/methanol/acetone) afforded III-13 (2.09, 88% yield) as a white foam: $[\alpha]D^{25}$–23° (c 0.09, acetonitrile); UV ($1.62\times10^{-4}$M, acetonitrile) λmax 253.6 ($\epsilon1.17\times10^4$), 214.0 ($1.93\times10^4$) nm; IR (film) 3390 (s), 3065 (w), 3015 (w), 2920 (m), 2880 (m), 1450 (s), 1363 (s), 1282 (m), 1175 (s), 1123 (s), 1085 (s), 1021 (s), 748 (s), 725 (m), 686 (m), cm$^{-1}$; $^1$H NMR (500 MHz, acetone-d$_6$) δ8.00–7.97 (m, 3H), 7.71 (s, 1H), 7.64–7.53 (m, 4H), 7.35–7.31 (m, 1H), 7.26–7.23 (m, 1H), 4.40 (d, J=7.7 Hz, 1H), 4.30 (d, J=3.7 Hz, 1H), 4.25 (d, J=3.7 Hz, 1H), 4.22 (d, J=4.0 Hz, 1H), 4.16 (ddd, J=9.7, 6.7, 6.7 Hz, 1H), 3.89–3.82 (m, 2H), 3.70 (ddd, J=1.8, 5.9, 5.9 Hz, 1H), 3.58 (t, J=6.4 Hz, 1H), 3.45 (ddd, J=8.8, 8.8, 3.8 Hz, 1H), 3.39 (ddd, J=8.5, 8.5, 4.0 Hz, 1H), 3.34 (ddd, J=9.3, 5.5, 2.7 Hz, 1H), 3.25 (ddd, J=8.6, 7.8, 3.8 Hz, 1H), 2.98 (t, J=6.6 Hz, 2H); $^{13}$C NMR (125 MHz, acetone-d$_6$) δ139.40, 136.57, 134.87, 132.21, 130.31, 127.67, 125.41, 125.30, 124.07, 121.33, 120.56, 114.35, 104.07, 78.07, 77.53, 74.93, 71.73, 68.76, 63.00, 49.72, 25.92; high resolution mass spectrum (CI, NH$_3$) m/z 481.1656 [(M+NH$_4$)$^+$; calcd for C$_{22}$H$_{25}$NO$_8$S: 481.1634].

D. 2-(N-phenylsulfonylindol-3-yl)ethyl 6-O-tert-Butyldiphenylsilyl-β-D-glucopyranoside (III-15).

At room temperature a stirred solution of III-14 (7.11 g, 15.4 mmol) in dry DMF (51 ml) was treated with imidazole (2.93 g, 43.1 mmol) followed by tert-butyldiphenylsilyl chloride (5.58 g, 21.6 mmol). The solution was heated at 50° C. for 24 h. After concentration in vacuo, the mixture was diluted with ethyl acetate (250 ml) and washed with water (100 ml). The organic phase was then washed with brine (100 ml), dried over magnesium sulfate, filtered, and concentrated in vacuo. Flash chromatography (5% methanol/dichloromethane) provided pure III-15 (9.15 g, 85% yield) as a white foam: $[\alpha]D^{25}$–26° (c 0.14, acetonitrile); UV ($5\times10^{-5}$M, acetonitrile) λmax 280.0 ($\epsilon7.1\times10^3$), 220.8 ($5.17\times10^4$) nm; IR (film) 3410 (s), 3070 (w), 3045 (w), 3010 (w), 2925 (m), 2885 (m), 2855 (m), 1474 (w), 1458 (w), 1430 (m), 1363 (w), 1220 (w), 1113 (s), 1047 (s), 1010 (s), 823 (m), 805 (w), 742 (s), 704 (s) cm$^{-1}$; $^1$H NMR (500 MHz, acetone-d$_6$) δ8.02 (d, J=8.3 Hz, 1H), 7.96–7.95 (m, 2H), 7.78–7.74 (m, 4H), 7.70 (s, 1H), 7.57 (d, J=7.8 Hz, 1H), 7.54–7.50 (m, 1H), 7.47–7.43 (m, 2H), 7.39–7.30 (m, 7H), 7.21–7.18 (m, 1H), 4.49 (m, 2H), 4.46 (d, J=7.7 Hz, 1H), 4.20 (ddd, J=9.7, 6.7, 6.7 Hz, 1H), 4.11 (dd, J=11.2, 0.9 Hz, 1H), 3.96 (dd, J=11.0, 4.9 Hz, 1H), 3.85 (ddd, J=9.7, 6.9, 6.9 Hz, 1H), 3.52 (m, 2H), 3.38–3.34 (m, 1H), 3.05 (t, J=6.6 Hz, 2H), 2.86 (s, 1H), 2.75 (s, 1H), 1.02 (s, 9H); $^{13}$C NMR (125 MHz, acetone-d$_6$) δ206.17, 138.97, 136.39, 136.30, 135.95, 134.83, 134.60, 134.47, 132.13, 130.45, 130.41, 130.26, 128.47, 127.59, 125.40, 125.01, 124.04, 121.24, 120.60, 114.31, 104.11, 78.17, 77.76, 74.94, 71.14, 68.93, 64.72, 27.12, 26.10, 19.82; high resolution mass spectrum (CI, NH$_3$) m/z 684.2532 [(M—OH)$^+$; calcd for C$_{38}$H$_{43}$NO$_8$SSi: 684.2449]. Anal. Calcd for C$_{38}$H$_{43}$NO$_8$SSi: C, 65.03; H, 6.18. Found: C, 64.96; H, 6.28.

E. 2-(N-Phenylsulfonylindol-3-yl)ethyl 2,3,4-Tri-O-benzyl-6-O-tert-butyldiphenylsilyl-β-D-glucopyranoside (III-16).

A solution of III-15 (1.62 g, 2.31 mmol) in THF (7 ml) was added to a stirred suspension of sodium hydride (323 mg, 60% oil dispersion, 8.08 mmol) in THF (5 ml) at 0° C. After the mixture was stirred for 1 h at room temperature and recooled to 0° C., benzyl bromide (1.09 ml, 9.24 mmol) was added dropwise followed by tetrabutylammonium iodide (85 mg, 0.23 mmol). The reaction was then allowed to stir for 3 days at room temperature. The resultant suspension was diluted with saturated aqueous ammonium chloride (3 ml) at 0° C. and extracted with ether (2×80 ml). The combined extracts were washed with saturated aqueous ammonium chloride (30 ml) and brine (30 ml), dried over magnesium sulfate, filtered, and concentrated in vacuo. Flash chromatography (20% ether/petroleum ether) afforded III-16 (1.66 g, 74% yield) as a white foam: $[\alpha]D^{25}$–7.0° (c 0.12, acetonitrile); UV ($5.90\times10^{-5}$M, acetonitrile) λmax 253.6 ($\epsilon2.90\times10^3$), 213.6 ($5.11\times10^4$) nm; IR (film) 3065 (m), 3030 (m), 2930 (s), 2855 (s), 1608 (w), 1590 (w), 1496 (w), 1472 (w), 1464 (w), 1449 (s), 1429 (m), 1377 (s), 1338 (w), 1312 (w), 1280 (m), 1215 (m), 1176 (s), 1113 (s), 1088 (s), 1072 (s), 1029 (s), 952 (w), 920 (w), 825 (m), 805 (w), 746 (s), 700 (s) cm$^{-1}$; $^1$H NMR (500 MHz, CDCl$_3$) δ7.99 (d, J=8.3 Hz, 1H), 7.82 (d, J=7.5 Hz, 2H), 7.73 (d, J=6.7 Hz, 2H), 7.68 (d, J=6.7 Hz, 2H), 7.50 (d, J=7.8 Hz, 1H), 7.44–7.17 (m, 27H), 4.91 (d, J=10.9 Hz, 1H), 4.88 (d, J=11.2 Hz, 1H), 4.80 (d, J=10.7 Hz, 1H), 4.77 (d, J=11.2 Hz, 1H), 4.68 (d, J=10.8 Hz, 1H), 4.63 (d, J=10.8 Hz, 1H), 4.44 (d, J=7.7 Hz, 1H), 4.19 (dd, J=14.6, 7.1 Hz, 1H), 3.92 (d, J=2.9 Hz, 2H), 3.81 (dd, J=15.4, 7.6 Hz, 1H), 3.74 (dd, J=8.8, 8.8 Hz, 1H), 3.64 (dd, J=9.1, 9.1 Hz, 1H), 3.46 (dd, J=8.1, 8.1 Hz, 1H), 3.35 (apparent d, J=7.6 Hz, 1H), 3.05 (t, J=7.0 Hz, 2H), 1.04 (s, 9H); $^{13}$C NMR (125 MHz, CDCl$_3$) δ138.58, 138.47, 138.32, 138.19, 135.83, 135.35, 135.23, 133.64, 133.58, 133.18, 130.96, 129.60, 129.13, 128.39, 128.30, 127.97, 127.90, 127.72, 127.66, 127.55, 127.51, 126.63, 124.77, 123.38, 123.16, 119.74, 119.57, 113.71, 103.62, 84.71, 82.55, 77.66, 75.81, 75.79, 75.10, 74.80, 68.53, 62.80, 26.78, 25.90, 19.29; high resolution mass spectrum (FAB, m-nitrobenzyl alcohol) m/z 972.4071 [(M+H)$^+$; calcd for C$_{59}$H$_{61}$NO$_8$SSi: 972.3970].

F. 2-(N-phenylsulfonylindol-3-yl)ethyl 2,3,4-Tri-O-benzyl-β-D-glucopyranoside (III-17).

Tetrabutylammonium fluoride (1M in THF, 2.4 ml, 2.4 mmol) was added to a stirred solution of III-16 (1.55 g, 1.60 mmol) in THF (8 ml) at room temperature. After 7 h the reaction mixture was diluted with ethyl acetate (70 ml), washed with water (30 ml) and brine (30 ml), dried over magnesium sulfate, filtered, and concentrated in vacuo. Flash chromatography (30% ethyl acetate/petroleum ether) afforded III-17 (1.10 g, 94% yield) as a clear oil: $[\alpha]D^{25}$–13° (c 0.14, acetonitrile); UV ($9.21\times10^{-5}$M, acetonitrile) λmax 254.0 ($\epsilon2.81\times10^3$), 211.6 ($3.19\times10^4$)nm; IR (film) 3480 (w), 3065 (w), 3035 (w), 2920 (m), 2878 (m), 1498 (w), 1450 (s), 1365 (s), 1280 (w), 1220 (m), 1176 (s), 1123 (s), 1090 (s), 1073 (s), 1030 (s), 750 (s), 700 (s) cm$^{-1}$; $^1$H NMR (500 MHz, CDCl$_3$) δ7.84 (d, J=8.3 Hz, 1H), 7.82 (d, J=7.9 Hz, 2H), 7.53 (s, 1H), 7.48–7.17 (m, 21H), 4.92 (d, J=11.0 Hz, 1H), 4.86 (d, J=10.9 Hz, 1H), 4.81 (d, J=11.0 Hz, 1H), 4.74 (d, J=11.0 Hz, 1H), 4.65 (d, J=10.9 Hz, 1H), 4.62 (d, J=11.0 Hz, 1H), 4.48 (d, J=7.8 Hz, 1H), 4.20 (ddd, J=9.4, 7.0, 7.0 Hz, 1H), 3.91–3.86 (m, 2H), 3.73 (dd, J=3.5, 11.9 Hz, 1H), 3.63 (ddd, J=9.0, 9.0, 18.0 Hz, 2H), 3.40 (apparent t, J=8.0 Hz, 1H), 3.35 (ddd, J=9.4, 4.2, 2.6 Hz, 1H), 3.04–2.93 (m, 2H), 2.06 (s, 1H); $^{13}$C NMR (125 MHz, CDCl$_3$) δ138.48, 138.21, 138.13, 137.95, 135.09, 133.60, 130.92, 129.10, 128.40, 128.30, 128.25, 128.22, 127.98, 127.90, 127.82, 127.76, 127.55, 126.58, 124.72, 123.57, 123.12, 119.61, 119.31, 113.66, 103.59, 84.39, 82.25, 77.37, 75.56, 75.16, 74.99, 74.75, 68.60, 61.77, 25.57; high resolution mass spectrum (CI, NH$_3$) m/z 734.2743 [(M+H)$^+$; calcd for C$_{43}$H$_{43}$NO$_8$S: 734.2774]. Anal. Calcd for C$_{43}$H$_{43}$NO$_8$S: C, 70.37; H, 5.91. Found: C, 70.30; H, 6.08.

G. 2-(N-Phenylsulfonylindol-3-yl)ethyl 2,3,4-Tri-O-benzyl-6-O-(5-azidopentyl)-β-D-glucopyranoside (III-19a).

Sodium azide (1.83 g, 28.2 mmol) was added to a stirred solution of 5-bromo-1-pentanol (0.79 g, 4.7 mmol) in DMSO (15 ml). The resultant mixture was stirred at room temperature for 2.5 h, diluted with water, and extracted with diethyl ether. The combined organic solutions were washed with saturated aqueous sodium bicarbonate and brine, dried over magnesium sulfate, filtered, and concentrated in vacuo. The azide was used without purification in the next step.

A stirred solution of crude 5-azido-1-pentanol (280 mg, equivalent to 2.17 mmol) and 2,6-di-tert-butyl-4-methylpyridine (441 mg, 2.17 mmol) in dichloromethane (9 ml) was treated dropwise with triflic anhydride (0.36 ml, 2.17 mmol). After 10 min the mixture was poured into brine (40 ml) and extracted with dichloromethane (2×40 ml). The combined organic layers were dried over magnesium sulfate, filtered, and concentrated in vacuo. The resultant triflate was used without purification in the next step. Sodium hydride (12.4 mg, 0.31 mmol, 60% dispersion in oil) was added to a solution of alcohol 17 (225 mg, 0.309 mmol) and crude azidotriflate (161 mg, equivalent to 0.62 mmol) in dichloromethane (4 ml) at room temperature. The mixture was stirred for 24 h, diluted with dichloromethane (40 ml), and poured into saturated aqueous ammonium chloride (40 ml). The aqueous phase was extracted with dichloromethane and the combined organic layers were washed with brine, dried over magnesium sulfate, filtered, and concentrated in vacuo. Flash chromatography (15% ethyl acetate/hexane) furnished III-19a (248 mg, 95% yield) as a colorless oil: [α]D$^{25}$+1.3° (c 0.48, CHCl$_3$); IR (CHCl$_3$) 3070 (w), 3015 (m), 2935 (s), 2875 (s), 2100 (s), 1450 (s), 1370 (s), 1280 (w), 1178 (m), 1122 (m), 1070 (s), 695 (m), 597 (m) cm$^{-1}$; $^1$H NMR (500 MHz, CDCl$_3$) δ7.93 (d, J=8.4 Hz, 1H), 7.78 (apparent d, J=8.4 Hz, 2H), 7.44–7.41 (m, 3H), 7.39–7.10 (m, 19H), 4.86 (d, J=10.9 Hz, 1H), 4.81 (d, J=10.9 Hz, 1H), 4.73 (d, J=11.0 Hz, 1H), 4.67 (d, J=11.0 Hz, 1H), 4.56 (d, J=10.9 Hz, 1H), 4.54 (d, J=11.0 Hz, 1H), 4.36 (dd, J=7.8, 1.0 Hz, 1H), 4.15 (dt, J=9.5, 7.1 Hz, 1H), 3.79 (dt, J=9.5, 7.3 Hz, 1H), 3.64–3.44 (m, 5H), 3.36 (m, 3H), 3.13 (t, J=7.0 Hz, 2H), 2.96 (t, J=7.0 Hz, 2H), 1.56–1.48 (m, 4H), 1.39–1.31 (m, 2H); $^{13}$C NMR (125 MHz, CDC$_{13}$) δ138.56, 138.31, 138.28, 138.22, 135.18, 133.60, 130.96, 129.13, 128.42, 128.35, 128.28, 128.00, 127.85, 127.82, 127.77, 127.57, 127.51, 126.67, 124.74, 123.47, 123.11, 119.65, 119.44, 113.72, 103.74, 84.64, 82.25, 77.93, 75.66, 74.97, 74.90, 74.75, 71.40, 69.70, 68.76, 29.67, 29.18, 28.66, 25.71, 23.41; high resolution mass spectrum (FAB, m-nitrobenzyl alcohol) m/z 867.3532 (M$^+$; calcd for C$_{48}$H$_{52}$N$_4$O$_8$S: 867.3494).

H. 2-(1H-Indol-3-yl)ethyl 2,3,4-Tri-O-benzyl-6-O-(5-aminopentyl)-β-D-glucopyranoside (III-4a).

A stirred solution of azide III-19a (31 mg, 0.037 mmol) in THF (2 ml) and water (0.032 ml) was treated with triphenylphosphine (25 mg, 0.095 mmol). The mixture was heated at reflux for 2.5 h, cooled, and concentrated in vacuo. Flash chromatography (10% methanol/dichloromethane) furnished the corresponding amine (26 mg, 86% yield) as a colorless oil: ([α]D$^{25}$) xx° (C 0.xx, CHCl$_3$); IR (CHCl$_3$) xxx cm$^{-1}$; $^1$H NMR (500 MHz, CDCl$_3$) δ8.03 (d, J=8.2 Hz, 1H), 7.89 (dd, J=8.5, 0.9 Hz, 2H), 7.39–7.21 (m, 22H), 4.96 (d, J=10.9 Hz, 1H), 4.91 (d, J=10.9 Hz, 1H), 4.84 (d, J=10.9 Hz, 1H), 4.78 (d, J=11.3 Hz, 1H), 4.67 (d, J=10.8 Hz, 1H), 4.65 (d, J=11.0 Hz, 1H), 4.47 (d, J=7.8 Hz, 1H), 4.26 (dt, J=9.5, 6.9 Hz, 1H), 3.90 (dt, J=9.5, 7.1 Hz, 1H), 3.75–3.62 (m, 4H), 3.56 (dt, J=9.4, 6.5 Hz, 1H), 3.49–3.44 (m, 3H), 3.06 (t, J=6.9 Hz, 2H), 2.68 (t, J=6.9 Hz, 2H), 1.91 (br s, 2H), 1.66–1.58 (m, 2H), 1.50–1.34 (m, 4H); $^{13}$C NMR (62.5 MHz, CDCl$_3$) δ138.49, 138.23, 138.14, 135.25, 133.56, 133.20, 132.08, 131.56, 131.90, 130.09, 129.08, 128.52, 128.32, 128.23, 127.93, 127.79, 127.52, 126.59, 124.67, 123.39, 123.06, 119.60, 119.40, 113.62, 103.65, 84.56, 82.17, 77.85, 75.60, 74.91, 74.80, 74.68, 71.56, 69.56, 68.68, 41.88, 33.18, 29.37, 25.63, 23.36; high resolution mass spectrum (FAB, m-nitrobenzyl alcohol) m/z 819.3687 (M$^+$; calcd for C$_{48}$H$_{54}$N$_2$O$_8$S: 819.3679).

The above amine (26 mg, 0.032 mmol) was dissolved in ethanol (4 ml) and treated with 5M aqueous sodium hydroxide (0.65 ml). The resultant mixture was heated at reflux for 3 h, cooled, diluted with brine, and poured into dichloromethane. The aqueous layer was extracted with dichloromethane (2×40 ml) and the combined organic solutions were dried over sodium sulfate, filtered, and concentrated in vacuo. Flash chromatography (10% methanol/dichloromethane) afforded III-4a (19.7 mg, 91% yield) as a colorless oil: [Cα]D$^{25}$+13° (c 0.03, CHCl$_3$); IR (CHCl$_3$) 3009 (s), 2930 (m), 2860 (m), 1450 (w), 1360 (w), 1200 (s), 1062 (s), 920 (w), 690 (m) cm$^{-1}$; $^1$H NMR (500 MHz, CDCl$_3$) δ8.75 (br s, 1H), 7.59 (d, J=7.9 Hz, 1H), 7.38–7.24 (m, 16H), 7.17 (t, J=7.2 Hz, 1H), 7.10 (t, J=7.2 Hz, 1H), 7.07 (s, 1H), 4.93 (d, J=10.9 Hz, 1H), 4.89 (d, J=11.0 Hz, 1H), 4.85 (d, J=11.0 Hz, 1H), 4.80 (d, J=10.9 Hz, 1H), 4.71 (d, J=11.0 Hz, 1H), 4.57 (d, J=11.0 Hz, 1H), 4.48 (d, J=7.8 Hz, 1H), 4.18 (dt, J=9.4, 7.1 Hz, 1H), 3.88 (dt, J=9.4, 7.1 Hz, 1H), 3.68–3.64 (m, 2H), 3.55–3.35 (m, 6H), 3.12 (t, J=7.1 Hz, 2H), 2.43 (br t, J=7.1 Hz, 2H), 1.59–1.54 (m, 2H), 1.52–1.54 (m, 2H), 1.37–1.28 (m, 4H); $^{13}$C NMR (62.5 MHz, CDCl$_3$) δ138.48, 138.20, 138.05, 136.14, 130.90, 128.97, 128.45, 128.37, 128.07, 127.88, 127.61, 127.40, 122.47, 121.87, 119.17, 118.64, 112.15, 111.44, 103.70, 84.62, 82.29, 77.88, 77.21, 75.68, 74.97, 74.79, 74.56, 71.03, 70.46, 69.51, 66.80, 29.69, 28.89, 28.64, 25.77, 22.95; high resolution mass spectrum (FAB, m-nitrobenzyl alcohol) calcd for C$_{42}$H$_{50}$N$_2$O$_6$).

I. 2-(1H-Indol-3-yl)ethyl 2,3,4-Tri-O-benzyl-6-O-(4-azidobutyl)-β-D-glucopyranoside (III-19b).

Alcohol 17 (0.164 g, 0.223 mmol) and 2,6-di-tert-butyl-4-methyl-pyridine (0.06 g, 0.29 mmol) were dissolved in dichloromethane (5 ml) and triflic anhydride (0.041 ml, 0.246 mmol) was added dropwise. The mixture was stirred at room temperature for 10 min, diluted with dichloromethane (40 ml), and poured into brine (40 ml). The organic phase was dried over magnesium sulfate, filtered, and concentrated. The resultant white solid was redissolved in dichloromethane (3 ml) and treated sequentially with 4-azido-1-butanol (0.13 g, 1.21 mmol), prepared in a similar manner to 5-azido-1-pentanol above, and sodium hydride (0.045 g, 1.13 mmol, 60% dispersion in oil). The mixture was then stirred for 24 h, diluted with dichloromethane (40 ml), and poured into saturated aqueous ammonium chloride (40 ml). The aqueous phase was extracted with dichloromethane (2×20 ml) and the combined organic solutions were washed with brine (40 ml), dried over magnesium sulfate, filtered, and concentrated in vacuo. Flash chromatography (15% ethyl acetate/hexane) yielded III-19b (85.2 mg, 56% yield) as a colorless oil: [α]D$^{25}$+10.2° (c 0.3, CH$_2$Cl$_2$); IR (CH$_2$Cl$_2$) 3485 (m), 3044 (w), 2910 (m), 2885 (m), 2090 (s), 1735 (m), 1610 (w), 1460 (m), 1420 (m), 1360 (m), 1250 (m), 1060 (s) cm$^{-1}$; $^1$H NMR (500 MHz, CDCl$_3$) δ7.84 (br s, 1H), 7.60 (d, J=7.8 Hz, 1H), 7.16–7.33 (m, 17H), 7.11 (apparent t, J=7.2 Hz, 1H), 7.03 (br s, 1H), 4.91 (d, J=10.9 Hz, 1H), 4.86 (d, J=11.0 Hz, 1H), 4.80 (d, J=11.0 Hz, 1H), 4.78 (d, J=10.9 Hz, 1H), 4.64 (d, J=11.0 Hz, 1H), 4.59 (d, J=7.8 Hz, 1H), 4.43 (d, J=7.8 Hz, 1H), 4.24 (dt, J=9.3, 6.8 Hz, 1H), 3.86 (dt, J=9.3, 7.4 Hz, 1H), 3.68–3.60 (m, 3H), 3.57–3.51 (m, 2H), 3.44 (t, J=5.9 Hz, 2H), 3.46–3.40 (m, 1H), 3.24 (br t, J=6.5 Hz, 2H), 3.12 (t, J=6.9 Hz, 2H), 1.65–1.62 (m, 4H); $^{13}$C NMR (125 MHz, CDCl$_3$) δ138.60, 138.56, 138.24, 136.17, 128.43, 128.28, 128.04, 127.90, 127.86, 127.78, 127.60, 127.53, 122.12, 121.96, 119.29, 118.73, 112.81, 111.10, 103.71, 84.70, 82.33, 77.99, 75.69, 74.97, 74.84, 74.69, 70.97, 70.05, 69.76, 51.29, 26.88, 25.84, 25.81.

J. 2-(1H-Indol-3-yl)ethyl 2,3,4-Tri-O-benzyl-6-O-(4-aminobutyl)-β-D-glucopyranoside (III-4b).

A solution of azide III-19b (0.037 g, 0.056 mmol) in THF (3 ml) was treated sequentially with water (0.025 ml, 1.39 mmol) and triphenylphosphine (0.29 g, 0.11 mmol). The mixture was then heated at 60° C. for 6 h, cooled, and concentrated in vacuo. Flash chromatography (10% methanol/dichloromethane) yielded III-4b (26.6 mg, 72% yield) as a colorless oil: [α]D$^{25}$ (CH$_2$Cl$_2$); IR (CH$_2$Cl$_2$) 3700 (w), 3487 (m), 3028 (m), 3020 (m), 2918 (s), 2878 (s), 1608 (w), 1498 (w), 1277 (m), 1212 (m), 1072 (s), 1465 (s), 1371 (s) cm$^{-1}$; $^1$H NMR (500 MHz, CDCl$_3$) δ8.29 (br s, 1H), 7.60 (d, J=7.8 Hz, 1H), 7.34–7.60 (m, 18H), 7.09 (br s, 1H), 4.92 (d, J=10.9 Hz, 1H), 4.86 (d, J=10.9 Hz, 1H), 4.83 (d, J=11.0 Hz, 1H), 4.79 (d, J=10.9 Hz, 1H), 4.66 (d, J=11.0 Hz, 1H), 4.61 (d, J=10.9 Hz, 1H), 4.45 (d, J=7.8 Hz, 1H), 4.24 (dt, J=9.3, 6.9 Hz, 1H), 3.89 (dt, J=9.3, 7.1 Hz, 1H), 3.12 (t, J=6.9 Hz, 2H), 2.66 (t, J=6.8 Hz, 2H), 1.62–1.47 (m, 6H); $^{13}$C NMR (125 MHz, CDCl$_3$) δ137.55, 137.49, 137.21, 135.11, 127.34, 127.27, 127.20, 126.96, 126.80, 126.67, 126.49, 126.45, 121.18, 120.75, 118.09, 117.59, 111.69, 110.04, 102.60, 83.61, 81.28, 76.09, 74.59, 73.90, 73.73, 73.63, 70.42, 68.88, 68.51, 40.90, 29.29, 26.00, 24.69.

K. 2-(N-Phenylsulfonylindol-3-yl)ethyl 2,3,4-Tri-O-benzyl-6-O-(6-azidohexyl)-β-D-glucopyranoside (III-19c).

A stirred solution of 6-azido-1-hexanol (0.087 g, 0.61 mmol), prepared in a manner similar to 5-azido-1-pentanol above, and 2,6-di-tert-butyl-4-methylpyridine (0.125 g, 0.061 mmol) in dichloromethane (5 ml) was treated with triflic anhydride (0.1 ml, 0.61 mmol) at room temperature. After 15 min the solution was diluted with dichloromethane (20 ml) and poured into saturated aqueous sodium bicarbonate (20 ml). The organic phase was washed with brine, dried over magnesium sulfate, filtered, and concentrated, to afford a white semisolid which was used without purification. A solution of the alcohol III-17 (0.3 g, 0.41 mmol) and the crude triflate in dichloromethane (3 ml) was treated with sodium hydride (0.024 g, 0.6 mmol, 66% dispersion in oil) followed by 15-crown-5 (10 mg). The mixture was then stirred at ambient temperature for 48 h, diluted with dichloromethane (25 ml), and poured into saturated aqueous ammonium chloride (20 ml). The aqueous phase was extracted with dichloromethane (2×20 ml) and the combined organic solutions were washed with brine (25 ml), dried over magnesium sulfate, filtered, and concentrated in vacuo. Flash chromatography (15% ethyl acetate/hexane) furnished III-19c (302 mg, 86% yield) as a colorless oil: [α]D$^{25}$–4.8° (c 1.06, CH$_2$Cl$_2$); IR (solvent?) 3030 (m), 2991 (w), 2920 (m), 2832 (m), 2110 (s), 1720 (w), 1609 (w), 1450 (s), 1372 (s), 1252 (s), 1212 (w), 1180 (s), 1122 (s), 1091 (s), 1071 (s), 892 (w), 692 (br), 600 (s), 573 (s) cm$^{-1}$; $^1$H NMR (500 MHz, CDCl$_3$) δ7.97 (d, J=7.8 Hz, 1H), 7.83 (dd, J=8.5, 1.1 Hz, 2H), 7.50–7.16 (m, 22H), 4.91 (d, J=10.9 Hz, 1H), 4.85 (d, J=10.9 Hz, 1H), 4.78 (d, J=10.9 Hz, 1H), 4.73 (d, J=11.0 Hz, 1H), 4.61 (d, J=10.9 Hz, 1H), 4.41 (d, J=7.7 Hz, 1H), 4.20 (dt, J=9.4, 7.1 Hz, 1H), 3.83 (dt, J=9.4, 7.5 Hz, 1H), 3.69–3.56 (m, 4H), 3.53–3.48 (m, 1H), 3.43–3.40 (m, 3H), 3.19 (t, J=6.9 Hz, 2H), 3.01 (t, J=7.0 Hz, 2H), 1.63–1.20 (m, 8H); $^{13}$C NMR (125 MHz, CDCl$_3$) δ138.56, 138.37, 138.27, 138.23, 135.17, 133.59, 130.96, 129.12, 128.41, 128.33, 128.27, 127.99, 127.84, 127.75, 127.57, 127.56, 126.66, 124.72, 123.46, 123.11, 119.64, 119.44, 113.70, 103.74, 84.64, 82.24, 77.93, 75.66, 74.96, 74.89, 74.73, 71.52, 69.65, 68.75, 51.33, 29.48, 28.72, 26.52, 25.73, 25.71; high resolution mass spectrum (FAB, m-nitrobenzyl alcohol) m/z 881.3538 [(M+Na)$^+$; calcd for C$_{49}$H$_{34}$N$_4$O$_8$S: 881.3560].

L. 2-(1H-Indol-3-yl)ethyl 2,3,4-Tri-O-benzyl-6-O-(6-aminohexyl)-β-D-glucopyranoside (III-4c).

A solution of azide III-19c (0.234 g, 0.272 mmol) in THF (15 ml) was treated sequentially with water (0.12 ml, 6.67 mmol) and triphenylphosphine (0.142 g) and then heated to 60° C. for 4 h. The mixture was then cooled and concentrated to a gum. Flash chromatography (10% methanol/dichloromethane) yielded the requisite amine (190 mg, 84% yield) as a colorless oil: [α]D$^{25}$–1.7° (c 0.52, CHCl$_3$); IR (CH$_2$Cl$_2$) 3730 (w), 3045 (m), 2940 (m), 610 (w), 1450 (m), 1426 (s), 1372 (m), 1271 (s), 1183 (s), 1180 (s), 1115 (s), 1091 (s), 1076 (s), 900 (s), 730 (br s) cm$^{-1}$; $^1$H NMR (500 MHz, CDCl$_3$) δ7.97 (d, J=8.3 Hz, 1H), 7.83 (apparent d, J=7.4 Hz, 2H), 7.49–7.44 (m, 3H), 7.37–7.14 (m, 17H), 4.90 (d, J=10.9 Hz, 1H), 4.85 (d, J=10.9 Hz, 1H), 4.78 (d, J=10.9 Hz, 1H), 4.72 (d, J=11.0 Hz, 1H), 4.61 (d, J=10.9 Hz, 1H), 4.59 (d, J=11.0 Hz, 1H), 4.41 (d, J=7.8 Hz, 1H), 4.20 (dt, J=9.6, 6.9 Hz, 1H), 3.83 (dt, J=9.6, 7.2 Hz, 1H), 3.67 (apparent t, J=9.0 Hz, 2H), 3.63–3.60 (m, 1H), 3.58 (apparent t, J=9.0 Hz, 2H), 3.49 (dt, J=9.4, 6.5 Hz, 1H), 3.41 (t, J=6.7 Hz, 2H), 3.39–3.37 (m, 1H), 3.00 (t, J=6.9 Hz, 2H), 2.99–2.97 (br, 2H), 1.57–1.25 (m, 8H); $^{13}$C NMR (125 MHz, CDCl$_3$) δ138.24, 133.60, 129.13, 128.41, 128.34, 128.27, 128.00, 127.85, 127.84, 127.56, 126.67, 124.74, 123.47, 123.12, 119.68, 113.71, 103.73, 84.65, 82.25, 77.95, 75.65, 74.97, 74.90, 74.74, 71.64, 69.65, 68.76, 29.55, 26.60, 25.88, 25.71.

A solution of the above amine (0.248 g, 0.30 mmol) in ethanol (22.5 ml) was treated with 5M aqueous potassium hydroxide (4.5 ml) and heated to reflux. After 5 h the mixture was cooled, diluted with saturated aqueous ammonium chloride (30 ml), and poured into dichloromethane (30 ml). The aqueous phase was extracted with dichloromethane and the combined organic solutions were washed with brine, dried over anhydrous sodium sulfate, and concentrated in vacuo. Flash chromatography (10% methanol/dichloromethane) furnished III-4c (179 mg, 87% yield) as a colorless oil: [α]D$^{25}$+9.4° (c 0.25, CHCl$_3$); IR (CH$_2$Cl$_2$) 3700 (br), 3026 (s), 2980 (s), 2925 (m), 2860 (m), 2085 (m), 1610 (w), 1440 (s), 1421 (s), 1365 (s), 1255 (s), 1175 (s), 1120 (s), 1085 (s), 1075 (s), 980 (w), 890 (s), 700 (br) cm$^{-1}$; $^1$H NMR (500 MHz, CDCl$_3$) δ8.49 (br s, 1H), 7.49 (d, J=7.8 Hz, 1H), 7.26–7.15 (m, 16H) 7.07 (t, J=8.0 Hz, 1H), 7.00 (t, J=7.1 Hz, 1H), 6.92 (s, 1H), 4.84 (d, J=11.0 Hz, 1H), 4.77 (d, J=10.9 Hz, 1H), 4.76 (d, J=10.9 Hz, 1H), 4.70 (d, J=10.9 Hz, 1H), 4.59 (d, J=11.0 Hz, 1H), 4.49 (d, J=11.0 Hz, 1H), 4.38 (d, J=7.8 Hz, 1H), 4.08 (dt, J=9.3, 6.9 Hz, 1H), 3.77 (dt, J=9.3, 7.1 Hz, 1H), 3.62–3.28 (m, 8H), 3.03 (t, J=7.3 Hz, 2H), 2.67 (t, J=7.5 Hz, 2H), 1.48–1.37 (m, 4H), 1.17–1.13 (m, 4H); $^{13}$C NMR (125 MHz, CDCl$_3$) δ138.54, 138.48, 136.15, 136.11, 128.39, 128.32, 128.27, 128.03, 127.84, 127.75, 127.54, 127.47, 122.20, 121.79, 119.12, 118.64, 112.16, 111.23, 103.68, 84.65, 82.29, 78.09, 75.62, 74.91, 74.83, 74.68, 71.37, 70.26, 69.77, 39.74, 29.35, 27.37, 26.13, 25.83, 25.42.

M. 5-Trifluoroacetamido-1-pentanol (III-18a).

A solution of 5-amino-1-pentanol (1.00 g, 9.69 mmol) in methanol (8 ml) was cooled to 0° C. and treated with triethylamine (3.28 ml, 23.5 mmol), followed by dropwise addition of trifluoroacetic anhydride (1.88 ml, 13.4 mmol). The reaction mixture was stirred at room temperature for 16 h. Concentration and flash chromatography (60% ethyl acetate/petroleum ether) then furnished III-18a (1.7 g, 89% yield) as an oil: IR (film) 3300 (s), 3100 (m), 2950 (s), 2875 (m), 1705 (s), 1563 (m), 1450 (w), 1375 (w), 1345 (w), 1210 (s), 1185 (s), 1160 (s), 1075 (w), 1055 (m), 1028 (w), 1003 (w), 970 (w), 875 (w), 720 (m) cm$^{-1}$; $^1$H NMR (500 MHz, CDCl$_3$) δ6.72 (s, 1H), 3.66 (m, 2H), 3.37 (dd, J=13.3, 6.8 Hz, 2H), 1.77 (s, 1H), 1.66–1.58 (m, 4H), 1.47–1.41 (m, 2H); high resolution mass spectrum (Cl, CH$_4$) m/z 200.0901 [(M+H)$^+$; calcd for C$_7$H$_{13}$F$_3$NO$_2$: 200.0696].

N. 2-(1H-Indol-3-yl)ethyl 2,3,4-Tri-O-benzyl-6-amino-6-deoxy-6-N-(5-hydroxypentyl)-β-D-glucopyranoside (III-4e).

A stirred solution of III-17 (196 mg, 0.27 mmol) in dry dichloromethane (2.7 ml) was cooled to −78° C. and treated with 2,6-di-tert-butyl-4-methylpyridine (880 mg, 0.427 mmol) followed by triflic anhydride (58 ml, 0.347 mmol). The mixture was stirred for 15 min at −78° C., warmed to room temperature over 20 min, and then poured into saturated aqueous sodium bicarbonate (20 ml) and extracted with ethyl acetate (60 ml). The organic layer was washed with saturated aqueous sodium bicarbonate (3×20 ml) and brine (20 ml) and dried over magnesium sulfate. Filtration and concentration in vacuo provided crude triflate which was used without purification.

A solution of 5-trifluoroacetamido-1-pentanol (III-18a) (265 mg, 1.3 mmol) in THF (10 ml) was added to a stirred suspension of sodium hydride (123 mg, 3.07 mmol, 60% oil dispersion) in THF (17 ml) at 0° C. After 10 min the suspension was warmed to room temperature, stirred for 1 h, and recooled to 0° C. and a solution of the above triflate (0.574 mmol) in dichloromethane (25 ml) was added dropwise. The reaction was stirred at 0° C. for 30 min and then at room temperature for 24 h, cooled to 0° C., quenched with saturated aqueous ammonium chloride (10 ml), and extracted with ethyl acetate (2×150 ml). The combined extracts were washed with water (50 ml) and brine (50 ml), dried over magnesium sulfate, filtered, and concentrated in vacuo. Flash chromatography (2% methanol/dichloromethane) afforded an inseperable mixture of compounds, presumably III-19d and its benzenesulfonamide deprotected counterpart, which was used directly in the next step.

A stirred solution of the above mixture in ethanol (6 ml) was treated with 5M aqueous NaOH (2 ml, 10 mmol) and the reaction mixture was heated to reflux for 2 h, cooled, and concentrated in vacuo. The residue was dissolved in ethyl acetate (40 ml) and the solution was washed with water (15 ml) and brine (15 ml), dried over magnesium sulfate, filtered, and concentrated in vacuo. Flash chromatography (5% methanol/dichloromethane) afforded III-4e (150 mg, 83% yield for 3 steps) as a pale yellow oil: [α]D$^{25}$+3.2° (c 0.31, acetonitrile); UV (1.14×10$^{-4}$M, acetonitrile) λmax 289.6 (ε4.17×10$^3$), 280.8 (4.97×10$^3$), 220.0 (2.4×10$^4$) nm; IR (film) 3420 (w), 3300 (w), 3063 (w), 3033 (w), 2938 (m), 2860 (m), 1495 (w), 1455 (m), 1360 (m), 1210 (w), 1072 (s), 1026 (m), 910 (w), 538 (s), 495 (s) cm$^{-1}$; $^1$H NMR (500 MHz, CDCl$_3$) δ7.98 (s, 1H), 7.59 (d, J=7.9 Hz, 1H), 7.33–7.04 (m, 19H), 4.90 (d, J=10.9 Hz, 1H), 4.85 (d, J=11.1 Hz, 1H), 4.80 (d, J=11.0 Hz, 1H), 4.77 (d, J=10.9 Hz, 1H), 4.64 (d, J=11.0 Hz, 1H), 4.60 (d, J=11.1 Hz, 1H), 4.48 (d, J=7.8 Hz, 1H), 4.21 (ddd, J=9.4, 6.7, 6.7 Hz, 1H), 3.89 (ddd, J=9.4, 7.3, 7.3 Hz, 1H), 3.64 (dd, J=9.0, 9.0 Hz, 1H), 3.56 (t, J=6.4 Hz, 2H), 3.51–3.47 (m, 1H), 3.42 (t, J=9.2 Hz, 1H), 3.11 (t, J=7.0 Hz, 2H), 2.96 (dd, J=12.3, 2.6 Hz, 1H), 2.66 (dd, J=12.3, 7.8 Hz, 1H), 2.62–2.54 (m, 2H), 1.93 (s, 2H), 1.54–1.44 (m, 4H), 1.38–1.32 (m, 2H); $^{13}$C NMR (125 MHz, CDCl$_3$) δ138.57, 138.49, 138.14, 136.17, 128.43, 128.36, 128.29, 128.02, 127.88, 127.82, 127.60, 127.56, 127.50, 122.14, 121.96, 119.30, 118.68, 112.60, 111.13, 103.67, 84.61, 82.45, 79.70, 77.20, 75.68, 74.99, 74.73, 73.82, 70.25, 62.63, 50.52, 49.59, 32.36, 29.28, 25.86, 23.31; high resolution mass spectrum (FAB, m-nitrobenzyl alcohol) m/z 679.3700 [(M+H)$^+$; calcd for C$_{42}$H$_{50}$N$_2$O$_6$: 679.3747].

O. 4-Trifluoroacetamido-1-butanol (III-18b).

Trifluoroacetylation of 4-amino-1-butanol (0.700 g, 7.86 mmol) as described for III-18a followed by flash chromatography (55% ethyl acetate/hexane) afforded III-18b (1.32 g, 85% yield) as an oil: IR (film) 3310 (s), 3100 (m), 2950 (m), 2890 (m), 1710 (s), 1568 (m), 1450 (w), 1380 (w), 1348 (w), 1215 (s), 1186 (s), 1160 (s), 1073 (m), 1053 (m), 1028 (w), 900 (w), 880 (w), 857 (w), 723 (m) cm$^{-1}$; $^1$H NMR (500 MHz, CDCl$_3$) δ7.28 (s, 1H), 3.72 (dd, J=10.2, 5.8 Hz, 2H), 3.40 (dd, J=12.6, 6.3 Hz, 2H), 1.99 (t, J=4.2 Hz, 1H), 1.78–1.70 (m, 2H), 1.68–1.62 (m, 2H); high resolution mass spectrum (Cl, CH$_4$) m/z 186.0732 [(M+H)$^+$; calcd for C$_6$H$_{11}$F$_3$NO$_2$: 186.0742].

P. 2-(1H-Indol-3-yl)ethyl 2,3,4-Tri-O-benzyl-6-amino-6-deoxy-6-N-(4-hydroxybutyl)-β-D-glucopyranoside (III-4f).

A solution of 4-trifluoroacetamido-1-butanol (III-18b) (425 mg, 2.29 mmol) in THF (10 ml) was added to a stirred suspension of sodium hydride (60% dispersion in oil, 210 mg, 5.27 mmol) in THF (28 ml) at 0° C. After 10 min the suspension was warmed to room temperature, stirred for 1 h, and recooled to 0° C. Crude triflate (0.27 mmol), prepared as described for III-4e, was dissolved in dichloromethane (16 ml) and added dropwise. The reaction was stirred at 0° C. for 1 h and then at room temperature for 24 h, cooled to 0° C., quenched with saturated aqueous ammonium chloride (10 ml), and extracted with ethyl acetate (2×150 ml). The combined extracts were washed with water (50 ml) and brine (50 ml), dried over magnesium sulfate, filtered, and concentrated in vacuo. Flash chromatography (3% methanol/dichloromethane) afforded an inseperable mixture of compounds, presumably III-19e and its benzenesulfonamide deprotected counterpart, which was used directly in the next step.

A stirred solution of the above mixture in ethanol (11 ml) was treated with 2.5M aqueous NaOH (7.0 ml, 17.5 mmol) and the reaction mixture was heated to reflux for 2 h, cooled to room temperature, and concentrated in vacuo. The residue was taken up in dichloromethane (60 ml) and the solution was washed with brine (20 ml), dried over magnesium sulfate, filtered, and concentrated in vacuo. Flash chromatography (5% methanol/dichloromethane) provided III-4f (148 mg, 39%) as a pale yellow oil: IR (film) 3435 (w), 3310 (w), 2930 (m), 2870 (m), 1502 (w), 1460 (m), 1364 (m), 1215 (w), 1075 (s), 1032 (sh), 1012 (sh), 913 (m), 815 (w), 740 (s), 700 (s) cm$^{-1}$; $^1$H NMR (500 MHz, CDCl$_3$) δ7.98 (s, 1H), 7.59 (d, J=7.9 Hz, 1H), 7.33–7.21 (m, 1 5H), 7.19–7.16 (m, 2H), 7.12–7.09 (m, 1H), 7.04 (d, J=2.1 Hz, 1H), 4.90 (d, J=10.9 Hz, 1H), 4.86 (d, J=11.1 Hz, 1H), 4.78 (d, J=11.1 Hz, 1H), 4.76 (d, J=10.9 Hz, 1H), 4.63 (d, J=11.0 Hz, 1H), 4.58 (d, J=11.1 Hz, 1H), 4.46 (d, J=7.8 Hz, 1H), 4.20 (ddd, J=9.5, 6.7, 6.7 Hz, 1H), 3.89 (ddd, J=9.5, 7.3, 7.3 Hz, 1H), 3.62 (apparent t, J=9.0 Hz, 1H), 3.53 (t, J=5.3 Hz, 2H), 3.46 (ddd, J=9.5, 4.4, 2.9 Hz, 1H), 3.41 (dd, J=9.1, 7.9 Hz, 1H), 3.36 (apparent t, J=9.2 Hz, 1H), 3.11 (t, J=6.9 Hz, 2H), 2.93 (dd, J=12.3, 2.9 Hz, 1H), 2.63 (dd, J=12.3, 7.9 Hz, 1H), 2.59 (t, J=5.7 Hz, 2H), 1.61 (m, 2H), 1.55 (m, 2H); $^{13}$C NMR (125 MHz, CDCl$_3$) δ138.50, 138.46, 138.07, 136.15, 128.43, 128.35, 128.28, 127.98, 127.87, 127.82, 127.59, 127.53, 127.46, 122.15, 121.95, 119.29, 118.67, 112.60, 111.14, 103.61, 84.58, 82.38, 79.73, 75.66, 74.97, 74.69, 73.36, 70.20, 62.54, 50.32, 49.49, 32.11, 28.10, 25.85; high resolution mass spectrum (Cl, $NH_3$) m/z 665.3640 [$(M+H)^+$; calcd for $C_{41}H_{49}N_2O_6$: 665.3590].

Q. 2-(1H-Indol-3-yl)ethyl 2,3,4-Tri-O-benzyl-6-amino-6-deoxy-6-N-(6-hydroxyhexyl)-β-D-gl ucopyranoside (III-4g).

A solution of 6-trifluoroacetamido-1-hexanol (III-18c) (145.0 mg, 0.680 mmol) in THF (2 ml) was added to a suspension of sodium hydride (60.0 mg, 1.50 mmol, 60% dispersion in oil) in THF (2 ml) at 0° C. The mixture was stirred at room temperature for 1.5 h, cooled to 0° C., and treated with a solution of the triflate derived from III-17 (0.136 mmol), prepared as described for the synthesis of III-4e, in dichloromethane (4 ml). The reaction mixture was then stirred at room temperature for 48 h, cooled to 0° C., quenched with saturated aqueous ammonium chloride (10 ml), and extracted with ethyl acetate (3×10 ml). The combined organic layers were dried over sodium sulfate, filtered, and concentrated in vacuo. Flash chromatography (5% methanol/dichloromethane) afforded an inseperable mixture of compounds, presumably III-19f and its benzenesulfonamide deprotected counterpart, which was used directly in the next step.

A stirred solution of the above mixture in ethanol (6 ml) was treated with 5N aqueous sodium hydroxide (2 ml) and heated to reflux for 2 h. Cooling followed by concentration in vacuo gave an oily residue which was taken up in water (5 ml) and extracted with dichloromethane (3×5 ml). The organic layer was dried over anhydrous sodium sulfate, filtered, and concentrated in vacuo. Flash chromatography (6% methanol/dichloromethane) furnished III-4g as a colorless oil (36.4 mg, 54% yield): $[\alpha]D^{25} -18°$ (c 0.18, acetonitrile); UV (1.72×10$^{-4}$M, acetonitrile) λmax 290.0 (ε1.02× 10$^3$), 281.2 (1.13×10$^3$), 228.4 (1.39×10$^3$) nm; IR (film) 3440 (m), 3310 (m), 3060 (m), 3030 (m), 2930 (s), 2860 (s), 2240 (w), 1497 (w), 1455 (s), 1360 (m), 1210 (w), 1070 (s), 910 (s), 740 (s), 700 (s) cm$^{-1}$; $^1$H NMR (500 MHz, CDCl$_3$) δ8.17 (br s, 1H), 7.59 (d, J=7.9 Hz, 1H), 7.33–7.00 (m, 1 9H), 4.91 (d, J=10.9 Hz, 1H), 4.86 (d, J=11.1 Hz, 1H), 4.80 (d, J=11.3 Hz, 1H), 4.78 (d, J=11.1 Hz, 1H), 4.65 (d, J=11.0 Hz, 1H), 4.60 (d, J=11.1 Hz, 1H), 4.47 (d, J=7.8 Hz, 1H), 4.21 (dt, J=9.4, 6.8 Hz, 1H), 3.86 (dt, J=9.4, 7.6 Hz, 1H), 3.64 (t, J=9.0 Hz, 1H), 3.55 (t, J=6.6 Hz, 2H), 3.51–3.40 (m, 3H), 3.12 (t, J=7.2 Hz, 2H), 2.96–2.13 (dd, J=12.2, 2.6 Hz, 1H), 2.68–2.51 (m, 3H), 1.87 (br s, 2H), 1.51–1.41 (m, 4H), 1.33–1.25 (m, 4H); $^{13}$C NMR (125 MHz, CDCl$_3$) δ138.47, 138.39, 138.05, 136.11, 128.39, 128.34, 128.27, 128.02, 127.96, 127.88, 127.80, 127.59, 127.55, 127.40, 122.10, 121.87, 119.21, 118.62, 112.32, 111.13, 103.61, 84.55, 82.38, 79.77, 75.69, 75.00, 74.72, 73.91, 70.25, 62.67, 50.64, 49.61, 32.55, 29.78, 26.97, 25.81, 25.55; high resolution mass spectrum (Cl, CH$_4$) m/z 693.3946 (M$^+$; calcd for $C_{43\ H50}N_2O_6$: 693.3903).

R. 5-Acetamido-1-pentanol (III-20).

A solution of 5-amino-1-pentanol (0.650 g, 6.31 mmol) in methanol (15 ml) was cooled to 0° C. and treated with triethylamine (1.62 ml, 11.6 mmol) followed by acetic anhydride (0.891 ml, 9.45 mmol). The reaction mixture was stirred at room temperature overnight. TLC analysis (8% methanol/dichloromethane) then revealed some unreacted material, so additional triethylamine (1.6 ml, 11.6 mmol) and acetic anhydride (0.9 ml, 9.5 mmol) were added at room temperature and the solution was stirred 16 h further. Concentration in vacuo and flash chromatography (7% methanol/dichloromethane) afforded III-20 (1 g, 94% yield) as a pale yellow oil: IR (film) 3300 (s), 3100 (m), 2940 (s), 2870 (m), 1650 (s), 1560 (s), 1439 (m), 1372 (m), 1295 (m), 1220 (w), 1180 (w), 1050 (m), 1010 (w) cm$^{-1}$; $^1$H NMR (500 MHz, CDCl$_3$) δ6.21 (s, 1H), 3.62 (t, J=6.4 Hz, 2H), 3.23 (dd, J=12.9, 7.0 Hz, 2H), 2.87 (s, 1H), 1.97 (s, 3H), 1.60–1.50 (m, 4H), 1.43–1.37 (m, 2H); high resolution mass spectrum (Cl, CH$_4$) m/z 146.1164 [$(M+H)^+$; calcd for $C_7H_{16}NO_2$: 146.1181].

S. 2-(N-Phenylsulfonylindol-3-yl)ethyl 2,3,4-Tri-O-benzyl-6-O-(5-acetamidopentyl)-β-D-glucopyranoside (III-4d).

A solution of 5-acetamido-1-pentanol (177 mg, 1.22 mmol) in THF (8 ml) was added to a stirred suspension of sodium hydride (60% dispersion in oil, 108 mg, 2.70 mmol) in THF (20 ml) at 0° C. After 10 min the mixture was stirred at room temperature for 1.5 h and cooled to 0° C. The triflate derived from III-17 (0.245 mmol), prepared as described for the synthesis of III-4a, was dissolved in dichloromethane (20 ml) and slowly added dropwise. The reaction was stirred at 0° C. for 1 h and at room temperature for 24 h, and then was cooled to 0° C., quenched with saturated aqueous ammonium chloride (10 ml) and diluted with ethyl acetate (150 ml). The organic layer was washed with water and brine, dried over magnesium sulfate, filtered, and concentrated in vacuo. Flash chromatography (3% methanol/dichloromethane) afforded an inseperable mixture of compounds, presumably III-21 and its benzenesulfonamide deprotected counterpart, which was used directly in the next step.

A stirred solution of the above mixture in ethanol (4 ml) was treated with 5N aqueous NaOH (2 ml, 10 mmol) and then heated to reflux for 2 h, cooled, and concentrated in vacuo. The residue was dissolved in ethyl acetate (40 ml) and the resultant solution was washed with water and brine, dried over magnesium sulfate, filtered, and concentrated in vacuo. Flash chromatography (4% methanol/dichloromethane) provided III-4d (88 mg, 50% yield) as a colorless oil: $[\alpha]D^{25}+14.5°$ (c 0.53, CHCl$_3$); IR (film) 3300 (s), 3090 (w), 3065 (m), 3035 (m), 2940 (s), 2870 (s), 1960 (w), 1885 (w), 1815 (w), 1662 (s), 1550 (m), 1500 (m), 1458 (s), 1369 (s), 1285 (m), 1213 (m), 1070 (s), 914 (w), 810 (w), 742 (s), 700 (s) cm$^{-1}$; $^1$H NMR (500 MHz, CDCl$_3$) a 8.26 (s, 1H), 7.59 (d, J=8.1 Hz, 1H), 7.34–7.21 (m, 1 6H), 7.19–7.16 (m, 1H), 7.12–7.08 (m, 1H), 7.03 (d, J=2.2 Hz, 1H), 5.41 (s, 1H), 4.92 (d, J=10.9 Hz, 1H), 4.85 (d, J=11.0 Hz, 1H), 4.83 (d, J=11.0 Hz, 1H), 4.78 (d, J=11.0 Hz, 1H), 4.66 (d, J=11.0 Hz, 1H), 4.59 (d, J=11.0 Hz, 1H), 4.45 (d, J=7.8 Hz, 1H), 4.22 (ddd, J=9.4, 6.9, 6.9 Hz, 1H), 3.86 (ddd, J=9.4, 7.5, 7.5 Hz, 1H), 3.68 (dd, J=10.9, 1.8 Hz, 1H), 3.64 (apparent t, J=9.0 Hz, 1H), 3.59 (dd, J=10.9, 5.1 Hz, 1H), 3.55 (apparent t, J=9.0 Hz, 1H), 3.51–3.39 (m, 4H), 3.17–3.13 (m, 2H), 3.12 (t, J=7.2 Hz, 2H), 1.91 (s, 3H), 1.58–1.53 (m, 2H), 1.48–1.42 (m, 2H), 1.38–1.32 (m, 2H); $^{13}$C NMR (125 MHz, CDCl$_3$) δ170.06, 138.57, 138.22, 136.21, 128.41, 128.35, 128.27, 128.03, 127.87, 127.84, 127.76, 127.59, 127.55, 127.49, 122.18, 121.81, 119.14, 118.61, 112.46, 111.19, 103.68, 84.68, 82.33, 78.04, 77.20, 75.67, 74.93, 74.83, 74.67, 71.42, 70.06, 69.71, 39.56, 29.29, 25.76, 23.61, 23.27; high resolution mass spectrum (Cl. NH$_3$) m/z 721.3790 [$(M+H)^+$; calcd for $C_{44}H_{53}N_2O_7$: 721.3852].

T. 1,2,4,6-Tetra-O-acetyl-3-deoxy-β-D-glucopyranoside (III-23).

A solution of 3-deoxydiacetone-D-glucose (III-22) (27.5 g, 113 mmol) in 60% aqueous acetic acid (200 ml) was heated at 90° C. for 1 h, cooled, and concentrated in vacuo, and the residue was azeotroped with dry benzene (4×20 ml).

A solution of the concentrate in dry pyridine (250 ml) was treated with acetic anhydride (107 ml, 1.13 mol) and DMAP (2 mol%, 275 mg) and stirred at room temperature for 30 min. After concentration in vacuo the residue was diluted with water (40 ml) and extracted with dichloromethane (3×40 ml), and the combined extracts were then washed with brine (40 ml), dried over sodium sulfate, filtered, and concentrated in vacuo. Recrystallization from ether afforded the pure β-anomer (11.3 g) as a fine white powder. Concentration of the filtrate and flash chromatography (45% ethyl acetate/hexane) gave a mixture of α- and β-anomers as a colorless gum (23.0 g, total yield 91.7%). β-Anomer III-23: $[\alpha]D^{25}17.1°$ (c 1.05, $CH_3OH$); IR ($CHCl_3$) 3010 (m), 2940 (w), 2870 (w), 1745 (s), 1510 (w), 1365 (m), 1230 (s), 1210 (s), 1030 (s) $cm^{-1}$; $^1H$ NMR (500 MHz, $CDCl_3$) δ5.67 (d, J=7.9 Hz, 1H), 4.89–4.81 (m, 2H), 4.21 (dd, J=5.1, 12.3 Hz, 1H), 4.12 (dd, J=2.5, 12.2 Hz, 1H), 3.81–3.79 (m, 1H), 2.60 (ddd, J=5.0, 5.0, 12.3 Hz, 1H), 2.10 (s, 3H), 2.06 (s, 3H), 2.03 (s, 3H), 2.02 (s, 3H), 1.64 (apparent q, J=11.0, 1H); $^{13}C$ NMR (62.9 MHz, $CDCl_3$) δ170.69, 169.43, 169.31, 169.19, 93.06, 75.68, 67.33, 65.00, 62.07, 32.69, 20.92, 20.77; high resolution mass spectrum (CI, $NH_3$) m/z 350.1412 [(M+$NH_4$)+; calcd for $C_{14}H_{20}O_9Cl$: 350.1450]. Anal. Calcd for $C_{14}H_{20}O_9$: C, 50.60; H, 6.07. Found: C, 50.65; H, 6.16.

U. 2-(N-Phenylsulfonylindol-3-yl)ethyl 2,4,6-Tri-O-acetyl-3-deoxy-β-D-glucopyranoside (III-24).

Hydrobromic acid (30% in acetic acid, 3 ml, 14.0 mmol) was added to III-23 (750 mg, 2.26 mmol) at 0° C. After 10 min, the solution was warmed to room temperature, stirred for 30 min, diluted with ether (20 ml), and poured into a mixture of ice and saturated aqueous sodium bicarbonate (25 ml). An additional 30 ml of ether was added and the layers were separated. The organic layer was washed with saturated aqueous sodium bicarbonate (3×25 ml), water, and brine, dried over magnesium sulfate, filtered, and concentrated in vacuo. The crude bromide was used without purification in the next step: high resolution mass spectrum (FAB, m-nitrobenzyl alcohol) m/z 370.0470 [(M+$NH_4$)+; calcd for $C_{12}H_{17}BrO_7$: 370.0494].

A solution of N-(benzenesulfonyl)tryptophol (III-12) (1.20 g, 4.0 mmol) in dry benzene (4 ml) was added to a stirred suspension of activated, powdered 4 Angstrom molecular sieves (1.33 g) in dry hexane (11 ml) at room temperature. A solution of the bromide (2.26 mmol) in dry benzene (4 ml) was introduced, followed by silver(I) oxide (523 mg, 2.26 mmol). The reaction vessel was covered with aluminum foil, and the mixture was stirred for 3 days and then filtered through Celite. Concentration and flash chromatography (10:1 dichloromethane/ether) provided pure III-24 (781 mg, 60% yield) as a white foam: mp 49°–51° C.; $[\alpha]D^{25}-12°$ (c 0.21, acetonitrile); UV (8.3×$10^{-5}$M, acetonitrile) λmax 253.6 (ε1.12×$10^4$), 214.0 (2.43×$10^4$) nm; IR (film) 3045 (w), 2970 (w), 2895 (w), 1745 (s), 1449 (m), 1370 (s), 1230 (s), 1167 (m), 1120 (w), 1083 (m), 1035 (m), 908 (w), 853 (w), 748 (s), 720 (w), 682 (w) $cm^{-1}$; $^1H$ NMR (500 MHz, $CDCl_3$) δ7.97 (d, J=8.3 Hz, 1H), 7.86–7.84 (m, 2H), 7.53–7.41 (m, 5H), 7.32-7.29 (m, 1H), 7.25–7.22 (t, J=7.6 Hz, 1H), 4.84 (ddd, J=10.7, 9.6, 4.9 Hz, 1H), 4.77 (ddd, J=12.8, 7.6, 5.2 Hz, 1H), 4.49 (d, J=7.6 Hz, 1H), 4.24–4.14 (m, 3H), 3.76 (ddd, J=9.4, 6.9, 6.9 Hz, 1H), 3.68 (ddd, J=9.2, 5.0, 3.0 Hz, 1H), 2.96 (t, J=7.1 Hz, 2H), 2.55 (ddd, J=12.2, 5.0, 3.0 Hz, 1H), 2.06 (s, 3H), 2.04 (s, 3H), 1.93 (s, 3H), 1.56 (apparent q, J=11.5 Hz, 1H); $^{13}C$ NMR (125 MHz, $CDCl_3$) δ170.80, 169.47, 133.68, 131.06, 129.20, 126.72, 124.73, 123.56, 123.16, 119.84, 119.50, 113.66, 106.62, 102.09, 75.03, 68.46, 68.38, 65.83, 62.65, 32.92, 25.37, 20.87, 20.79; high resolution mass spectrum (FAB, m-nitrobenzyl alcohol) m/z 573.1623 ($M^+$; calcd for $C_{28}H_{31}NO_{10}S$: 573.1669).

V. 2-(N-Phenylsulfonylindol-3-yl)ethyl 3-Deoxy-β-D-glucopyranoside (III-25).

Sodium methoxide (55.2 mg, 1.02 mmol) was added to a suspension of III-24 (735 mg, 1.28 mmol) in methanol (6.4 ml). The mixture was stirred at room temperature for 90 min, diluted with methanol (6 ml), and neutralized with Amberlyst® 15 ion exchange resin. The resin was quickly filtered. Concentration in vacuo and flash chromatography (12:1:1 dichloromethane/acetone/methanol) afforded pure III-25 (498 mg, 87% yield) as a white solid: mp 55°–57° C.; $[\alpha]D^{25}-26°$ (c 0.25, methanol); UV (1.39×$10^{-4}$M, acetonitrile) λmax 254.0 (ε1.24×$10^4$), 216.0 (2.02×$10^4$) nm; IR (film) 3415 (s), 3070 (w), 3025 (w), 2945 (m), 2890 (m), 1605 (w), 1449 (s), 1366 (s), 1279 (w), 1215 (w), 1173 (s), 1125 (m), 1078 (s), 1028 (s), 975 (w), 741 (s), 720 (m), 681 (m) $cm^{-1}$; $^1H$ NMR (500 MHz, $CD_3OD$) δ7.96–7.94 (m, 1H), 7.91–7.89 (m, 1H), 7.61 (s, 1H), 7.59–7.54 (m, 2H), 7.49–7.45 (m, 2H), 7.31–7.28 (m, 1H), 7.24–7.21 (m, 1H), 4.30 (d, J=7.6 Hz, 1H), 4.18 (ddd, J=9.6, 7.0, 7.0 Hz, 1H), 3.88–3.82 (m, 2H), 3.66 (dd, J=11.8, 6.2 Hz, 1H), 3.50 (ddd, J=11.2, 9.4, 4.8 Hz, 1H), 3.40 (ddd, J=12.4, 7.6, 5.0 Hz, 1H), 3.31 (s, 2H), 3.27 (ddd, J=9.2, 6.1, 2.5 Hz, 1H), 3.00 (t, J=6.8 Hz, 2H), 2.31 (ddd, J=12.2, 4.9, 4.9 Hz, 1H), 1.50 (apparent q, J=11.8 Hz, 1H); $^{13}C$ NMR (500 MHz, $CD_3OD$) δ139.40, 136.57, 135.02, 132.62, 130.38, 127.89, 125.65, 125.30, 124.36, 121.74, 120.63, 114.70, 106.49, 81.82, 69.41, 69.37, 66.27, 62.95, 40.72, 26.32; high resolution mass spectrum (CI, $NH_3$) m/z 465.1627 [(M+$NH_4$)+; calcd for $C_{22}H_{25}NO_7S$: 465.1685].

W. 2-(N-Phenylsulfonylindol-3-yl)ethyl 3-Deoxy-6-O-tert-butyldiphenylsilyl-β-D-glucopyranoside (III-26).

A stirred solution of III-25 (779 mg, 1.74 mmol) in dry DMF (17 ml, 0.1M) was treated with imidazole (260 mg, 3.83 mmol) followed by tert-butyldiphenylsilyl chloride (0.541 ml, 2.09 mmol). The solution was heated at 50° C. for 24 h, cooled, diluted with ethyl acetate (250 ml), and washed with water and brine. The organic phase was dried over magnesium sulfate, filtered, and concentrated in vacuo. Flash chromatography (3% methanol/dichloromethane) provided pure III-26 (1.04 g, 87% yield) as a white foam: $[C\alpha]D^{25}-24°$ (c 0.46, acetonitrile); UV (1.68×$10^{-4}$M, acetonitrile) λmax 254.0 (ε1.11×$10^4$), 220.4 (1.90×$10^4$) nm; IR (film) 3430 (s), 3080 (w), 3060 (w), 3020 (w), 2940 (s), 2865 (s), 1668 (m), 1449 (s), 1428 (m), 1370 (s), 1275 (w), 1213 (w), 1112 (s), 1070 (s), 855 (w), 820 (w), 740 (s), 720 (w), 700 (m), 680 (w) $cm^{-1}$; $^1H$ NMR (500 MHz, acetone-$d_6$) δ7.98–7.96 (m, 1H), 7.84–7.82 (m, 2H), 7.68–7.65 (m, 4H), 7.51–7.36 (m, 11H), 7.31–7.28 (m, 1H), 7.21–7.18 (m, 1H), 4.19 (d, J=7.4 Hz, 1H), 4.09 (ddd, J=9.5, 6.2, 6.2 Hz, 1H), 3.92 (dd, J=10.3, 5.0 Hz, 1H), 3.84 (dd, J=10.4, 7.3 Hz, 1H), 3.82–3.77 (m, 1H), 3.68 (ddd, J=9.5, 7.1, 7.1 Hz, 1H), 3.48–3.40 (m, 2H), 3.29 (d, J=2.3 Hz, 1H), 2.97–2.89 (m, 2H), 2.37 (ddd, J=12.4, 4.8, 4.8 Hz, 1H), 2.10 (d, J=2.5 Hz, 1H), 1.53 (apparent q, J=11.5 Hz, 1H), 1.06 (s, 9H); $^{13}C$ NMR (125 MHz, acetone-$d_6$) δ138.24, 135.54, 135.51, 135.14, 133.65, 132.46, 132.38, 130.97, 130.00, 129.17, 128.30, 127.86, 126.65, 124.79, 123.42, 123.13, 119.67, 119.34, 113.73, 104.73, 77.34, 68.83, 68.58, 68.28, 66.11, 37.34, 26.77, 25.45, 19.09; high resolution mass spectrum (FAB, m-nitrobenzyl alcohol) m/z 686.2651 [(M+H)+; calcd for $C_{38}H_{43}NO_7SSi$: 686.2607]. Anal. Calcd for $C_{38}H_{43}O_7NSSi$: C, 66.54; H, 6.32. Found: C, 66.18; H, 6.14.

X. 2-(N-Phenylsulfonylindol-3-yl)ethyl 3-Deoxy-2,4-di-O-benzyl-6-O-tert-butyldiphenylsilyl-β-D-glucopyranoside (III-27).

A stirred suspension of sodium hydride (4.63 mmol, 185 mg, 60% oil dispersion) in THF (5 ml) was cooled to 0° C. and a solution of III-26 (1.27 g, 1.85 mmol) in THF (10 ml) was added. After 10 min the reaction mixture was warmed to room temperature, stirred for 1 h, recooled to 0° C. and treated with benzyl bromide (5.55 mmol, 0. 660 ml) followed by tetrabutylammonium iodide (68 mg, 0.185 mmol). The reaction was then warmed to room temperature, stirred for 3 days, and quenched with saturated aqueous ammonium chloride (3 ml ) at 0° C. The mixture was diluted with ether (80 ml), washed with water (2×30 ml) and brine (30 ml), dried over magnesium sulfate, filtered, and concentrated in vacuo. Flash chromatography (25% ether/petroleum ether) furnished pure III-27 (760 mg, 47% yield) as a white foam: $[\alpha]_D^{25}$ −2.7° (c 0.66, acetonitrile); UV (1.9×10$^{-4}$M, acetonitrile) $\lambda$max 254.0 ($\epsilon$1.19×10$^4$), 220.8 (1.71×10$^4$)nm; IR (film) 3080 (m), 3040 (m), 2945 (s), 2870 (s), 1585 (w), 1494 (w), 1445 (s), 1425 (m), 1369 (s), 1330 (w), 1307 (w), 1275 (m), 1205 (m), 1171 (s), 1109 (s), 1100 (s), 1025 (s), 972 (m), 935 (w), 905 (w), 849 (w), 817 (m), 739 (s), 695 (s) cm$^{-1}$; $^1$H NMR (500 MHz, CDCl$_3$) $\delta$7.99–7.97 (m, 1H), 7.83–7.80 (m, 2H), 7.71–7.67 (m, 4H), 7.51–7.18 (m, 2 3H), 4.70 (d, J=12.0 Hz, 1H), 4.59 (d, J=11.4 Hz, 1H), 4.56 (d, J=12.0 Hz, 1H), 4.44 (d, J=11.5 Hz, 1H), 4.42 (d, J=7.5 Hz, 1H), 4.19 (ddd, J=9.6, 6.7, 6.7 Hz, 1H), 3.95 (dd, J=11.2, 1.9 Hz, 1H), 3.88 (dd, J=11.2, 5.0 Hz, 1H), 3.80 (ddd, J=9.6, 7.3, 7.3 Hz, 1H), 3.55 (ddd, J=11.0, 9.4, 4.6 Hz, 1H), 3.41 (ddd, J=9.2, 4.9, 1.8 Hz, 1H), 3.32 (m, 1H), 3.04 (t, J=7.2 Hz, 2H), 2.52 (ddd, J=12.3, 4.9, 4.9 Hz, 1H), 1.55 (apparent q, J=11.6 Hz, 1H), 1.03 (s, 9H); $^{13}$C NMR (125 MHz, CDCl$_3$) $\delta$138.68, 138.32, 138.08, 135.72, 135.56, 135.18, 133.74, 133.54, 133.49, 131.06, 129.52, 129.10, 128.36, 128.30, 127.66, 127.63, 127.59, 127.51, 127.45, 126.63, 124.69, 123.47, 123.12, 119.94, 119.57, 113.67, 105.11, 79.10, 75.27, 72.68, 72.06, 71.37, 68.18, 63.23, 34.99, 26.77, 25.80, 19.29; high resolution mass spectrum (FAB, m-nitrobenzyl alcohol) m/z 865.3419 (M$^+$; calcd for C$_{52}$H$_5$NO$_7$SSi: 865.3468).

Y. 2-(N-Phenylsulfonylindol-3-yl)ethyl 3-Deoxy-2,4-di-O-benzyl-b-D-glucopyranoside (III-28).

Tetrabutylammonium fluoride (1.0M in THF, 1.17 mmol, 1.17 ml) was added to a stirred solution of III-27 (675 mg, 0.780 mmol) in THF (10 ml). The solution was stirred for 2 h, diluted with ethyl acetate, washed with water and brine, and dried over magnesium sulfate, filtered, and concentrated in vacuo. Flash chromatography (60% ether/petroleum ether) afforded pure III-28 (445 mg, 91% yield) as a pale yellow oil: $[\alpha]_D^{25}$ +2.5° (c 0.44, acetonitrile); UV (9.97× 10$^{-5}$M, acetonitrile) $\lambda$max 254.0 ($\epsilon$1.06×10$^4$), 210.0 (2.88× 10$^4$) nm; IR (film) 3485 (m), 3080 (w), 3045 (w), 2945 (m), 2890 (m), 1603 (w), 1484 (w), 1447 (s), 1369 (s), 1277 (w), 1206 (w), 1173 (s), 1118 (m), 1082 (s), 1039 (m), 1025 (m), 948 (w), 900 (w), 745 (s), 717 (m), 693 (m), 678 (m) cm$^{-1}$; $^1$H NMR (500 MHz, CDCl$_3$) $\delta$7.97 (d, J=8.3 Hz, 1H), 7.84–7.82 (m, 2H), 7.53 (s, 1H), 7.49–7.44 (m, 2H), 7.37–7.21 (m, 14H), 4.67 (d, J=12.0 Hz, 1H), 4.60 (d, J=11.4 Hz, 1H), 4.54 (d, J=12.0 Hz, 1H), 4.47 (d, J=11.6 Hz, 1H), 4.45 (d, J=7.5 Hz, 1H), 4.19 (ddd, J=9.5, 6.8, 6.8 Hz, 1H), 3.89–3.84 (m, 2H), 3.73 (dd, J=11.9, 4.6 Hz, 1H), 3.47 (ddd, J=11.0, 9.3, 4.6 Hz, 1H), 3.39 (ddd, J=9.1, 4.5, 3.1 Hz, 1H), 3.26 (ddd, J=11.7, 9.2, 5.1 Hz, 1H), 2.99 (m, 2H), 2.51 (ddd, J=12.3, 4.8, 4.8 Hz, 1H), 1.89 (s, 1H), 1.55 (dd, J=23.4, 11.7 Hz, 1H); $^{13}$C NMR (125 MHz, CDCl$_3$) $\delta$138.44, 138.30, 137.82, 135.15, 133.63, 131.03, 129.15, 128.49, 128.35, 127.89, 127.79, 127.63, 127.58, 126.68, 124.75, 123.65, 123.15, 119.80, 119.38, 113.73, 105.19, 78.18, 75.02, 72.71, 72.23, 71.29, 68.38, 62.38, 34.83, 25.61; high resolution mass spectrum (FAB, m-nitrobenzyl alcohol) m/z 627.2370 (M$^+$; calcd for C$_{36}$H$_{37}$NO$_7$S: 627.2291).

Z. 2-(N-Phenylsulfonylindol-3-yl)ethyl 2,4-Di-O-benzyl-3-deoxy-6-O-(5-azidopentyl)-$\beta$-D-glucopyranoside (III-29a).

A stirred solution of 5-bromo-1-pentanol (0.79 g, 4.7 mmol) in DMSO (15 ml) was treated with sodium azide (1.83 g, 28.2 mmol). The resultant mixture was stirred at room temperature for 2.5 h, diluted with water, and extracted with diethyl ether. The combined organic layers were washed with saturated aqueous sodium bicarbonate and brine, dried over magnesium sulfate, filtered, and concentrated in vacuo. The azide was used without purification in the next step.

Crude 5-azido-1-pentanol (280 mg, equivalent to 2.17 mmol) and 2,6-di-tert-butyl-4-methylpyridine (441 mg, 2.17 mmol) were dissolved in dichloromethane (9 ml) and triflic anhydride (0.36 ml, 2.17 mmol) was added dropwise. After 10 min the mixture was poured into brine (40 ml) and extracted with dichloromethane (2×40 ml). The combined organic layers were dried over magnesium sulfate, filtered, and concentrated in vacuo. The triflate was used without purification in the next step.

Sodium hydride (16 mg, 0.40 mmol, 60% dispersion in oil) was added to a solution of alcohol III-28 (120 mg, 0.198 mmol) and azido triflate (105 mg, equivalent to 0.40 mmol) in dichloromethane (3 ml) at room temperature. The mixture was stirred for 24 h, diluted with dichloromethane (40 ml) and poured into saturated ammonium chloride (40 ml). The aqueous phase was extracted with dichloromethane and the combined organic solutions were washed with brine, dried over magnesium sulfate, filtered, and concentrated in vacuo. Flash chromatography (15% ethyl acetate/hexane) afforded III-29a (121 mg, 83% yield) as a colorless oil: $[\alpha]_D^{25}$+4.0° (c 0.24, CHCl$_3$); IR (CHCl$_3$) 3022 (s), 2940 (s), 2880 (m), 2105 (s), 1455 (s), 1375 (s), 1270 (s), 1210 (m), 1180 (m), 1125 (m), 1090 (m), 725 (s), 599 (m) cm$^{-1}$; $^1$H NMR (500 MHz, CDCl$_3$) $\delta$7.96 (d, J=8.1 Hz, 1H), 7.82 (dd, J=8.2, 0.9 Hz, 2H), 7.50–7.43 (m, 3H), 7.29–7.19 (m, 14H), 4.65 (d, J=12.0 Hz, 1H), 4.58 (d, J=11.4 Hz, 1H), 4.52 (d, J=12.0 Hz, 1H). 4.42 (d, J=11.5 Hz, 1H), 4.18 (dt, J=9.5, 6.7 Hz, 1H), 3.81 (dt, J=9.5, 7.1 Hz, 1H), 3.71 (d, J=10.6 Hz, 1H), 3.57 (dd, J=10.8, 4.7 Hz, 1H), 3.51–3.38 (m, 4H), 3.31–3.21 (m, 1H), 3.16 (t, J=6.9 Hz, 2H), 3.00 (t, J=6.9 Hz, 2H), 2.50–2.46 (dt, J=12.1, 4.5 Hz, 1H),1.63–1.50 (m, 5H), 1.48–1.32 (m, 3H); $^{13}$C NMR (62.5 MHz, CDCl$_3$) $\delta$138.52, 138.23, 137.00, 135.07, 133.59, 131.09, 129.14, 128.43, 128.31, 127.78, 127.68, 127.50, 126.70, 126.69, 124.70, 123.54, 123.09, 119.71, 119.48, 113.70, 105.26, 78.01, 74.92, 72.67, 72.25, 71.38, 71.24, 69.96, 68.41, 34.97, 29.62, 29.15, 28.66, 25.65, 23.39; high resolution mass spectrum (FAB, m-nitrobenzyl alcohol) m/z 761.2973 (M$^+$; calcd for C$_{41}$H$_{46}$N$_4$O$_7$S: 761.2985).

AA. 2-(1H-Indol-3-yl)ethyl 2,4-Di-O-benzyl-3-deoxy-6-O-(5-aminopentyl)-$\beta$-D-glucopyranoside (III-5a).

A stirred solution of azide III-29a (80 mg, 0.109 mmol) in THF (5.2 ml) and water (0.083 ml was treated with triphenylphosphine (65 mg, 0.248 mmol), heated at reflux for 2.5 h, cooled, and concentrated in vacuo. Flash chromatography (10% methanol/dichloromethane) furnished the corresponding amine (70 mg, 90% yield) as a colorless oil: IR (CHCl$_3$) 3028 (m), 2940 (s), 2875 (m), 1450 (s), 1370 (s), 1280 (w), 1178 (s), 1122 (m), 1070 (m), 695 (w), 597 (w) cm$^{-1}$; $^1$H NMR (500 MHz, CDCl3) $\delta$ xxx; $^{13}$C NMR (125 MHz, CDCl$_3$) $\delta$138.51, 138.25, 138.00, 135.13, 133.58, 131.05, 129.11, 128.40, 128.27, 127.76, 127.69, 127.62, 127.46, 126.65, 124.68, 123.54, 123.09, 119.91, 119.48, 133.66, 105.21, 77.97, 74.96, 72.64, 72.18, 71.34, 71.21, 69.94, 68.39, 39.70, 34.94, 28.89, 25.59, 23.44, 23.26; high resolution mass spectrum (FAB, m-nitrobenzyl alcohol) m/z 713.3241 (M$^+$; calcd for $C_{41}H_{48}N_2O_7S$: 713.3260).

The above amine (14 mg, 0.020 mmol) was dissolved in ethanol (2.2 ml) and treated with 5M aqueous sodium hydroxide (0.36 ml). The resultant mixture was heated at reflux for 3 h, cooled, diluted with brine, and poured into dichloromethane. The aqueous layer was extracted with dichloromethane (2×40 ml) and the combined organic solutions were dried over sodium sulfate, filtered, and concentrated in vacuo. Flash chromatography (10% methanol/dichloromethane) afforded III-5a (7 mg, 61% yield) as a colorless oil: $[\alpha]D^{25}$ −12° (c 0.11, $CHCl_3$); $^1$H NMR (500 MHz, $CDCl_3$) δ9.05 (br s, 1H), 7.58 (d, J=7.8 Hz, 1H), 7.34–7.25 (m, 11H), 7.14 (t, J=7.5 Hz, 1H), 7.07 (t, J=7.5 Hz, 1H), 7.04 (s, 1H), 4.77 (d, J=11.8 Hz, 1H), 4.60 (d, J=12.0 Hz, 1H), 4.57 (d, J=11.6 Hz, 1H), 4.44 (d, J=7.5 Hz, 1H), 4.39 (d, J=11.5 Hz, 1H), 4.16 (dt, J=9.3, 7.3 Hz, 1H), 3.85 (dt, J=9.3, 7.2 Hz, 1H), 3.70 (d, J=10.4 Hz, 1H), 3.51 (dd, J=10.6, 5.8 Hz, 1H), 3.46–3.36 (m, 4H), 3.35–3.29 (m, 1H), 3.11 (t, J=7.2 Hz, 2H), 2.68 (br t, J=7.1 Hz, 2H), 2.53–2.49 (dt, J=12.3, 4.7 Hz, 1H), 1.56–1.42 (m, 5H), 1.36–1.25 (m, 4H); $^{13}$C NMR (125 MHz, $CDCl_3$) δ138.53, 137.86, 136.12, 128.45, 128.38, 127.86, 127.82, 127.72, 127.62, 127.12, 123.06, 122.02, 119.32, 118.62, 112.26, 111.63, 105.43, 77.49, 75.28, 72.79, 71.34, 71.19, 71.05, 70.39, 68.85, 39.21, 34.65, 27.54, 26.16, 25.72, 22.51; high resolution mass spectrum (FAB, m-nitrobenzyl alcohol) m/z 573.3313 (M$^+$; calcd for $C_{35}H_{44}N_2O_5$: 573.3328).

AB. 2-(N-phenylsulfonylindol-3-yl)ethyl 2,4-Di-O-benzyl-3-deoxy-6-O-(6-azidohexyl)-β-D-glucopyranoside (III-29b).

A solution of alcohol III-28 (0.21 g, 0.317 mmol) and benzyl bromide (0.307 g, 1.79 mmol) in THF (4 ml) was sequentially treated with sodium hydride (0.016 g, 0.4 mmol, 60% dispersion in oil) and tetra-n-butylammonium iodide (0.01 g. The mixture was then stirred for 36 h, diluted with saturated aqueous ammonium chloride (10 ml), and poured into ethyl acetate (30 ml). The aqueous phase was extracted with ethyl acetate (3×20 ml) and the combined organic solutions were, washed with brine (20 ml), dried over magnesium sulfate, filtered, and concentrated in vacuo. Flash chromatography (15% ethyl acetate/hexane) furnished III-29b (192 mg, 81% yield) as a colorless oil: $[\alpha]D^{25}$+6.2° (c 0.45, $CH_2Cl_2$); IR ($CH_2Cl_2$) 3041 (s), 2980 (m), 2940 (m), 2865 (m), 2100 (s), 1610 (m), 1450 (s), 1375 (s), 1262 (s), 1190 (s), 1178 (s), 680 (br) cm$^{-1}$; $^1$H NMR (500 MHz, $CDCl_3$) δ7.97 (dd, J=6.4, 0.5 Hz, 1H), 7.83 (apparent t, J=7.5 Hz, 2H), 7.51–7.45 (m, 3H), 7.38–7.20 (m, 14H), 4.66 (d, J=12.0 Hz, 1H), 4.59 (d, J=11.4 Hz, 1H), 4.53 (d, J=12.0 Hz, 1H), 4.43 (d, J=11.4 Hz, 1H), 4.41 (d, J=7.6 Hz, 1H), 4.19 (dt, J=9.5, 6.8 Hz, 1H), 3.82 (dt, J=9.5, 7.1 Hz, 1H), 3.72 (d, J=10.9 Hz, 1H), 3.59 (dd, J=10.9, 4.9 Hz, 1H), 3.51–3.39 (m, 4H), 3.30–3.25 (m, 1H), 3.18 (t, J=6.9 Hz, 2H), 3.01 (t, J=6.9 Hz, 2H), 2.49 (dt, J=12.2, 4.4 Hz, 1H), 1.56–1.49 (m, 5), 1.36–1.31 (m, 4H); $^{13}$C NMR (125 MHz, $CDCl_3$) δ138.54, 138.32, 138.04, 135.16, 133.58, 131.06, 129.13, 128.41, 128.30, 127.78, 127.69, 127.66, 127.49, 126.69, 124.69, 123.54, 123.09, 119.87, 119.48, 113.69, 105.26, 78.03, 74.96, 72.67, 72.29, 71.52, 71.27, 69.94, 68.41, 51.35, 34.99, 29.48, 28.75, 26.53, 25.72, 25.66; high resolution mass spectrum (FAB, m-nitrobenzyl alcohol) m/z 775.3132 [(M+Na)$^+$; calcd for $C_{42}H_{48}N_4O_7S$: 775.3142].

AC. 2-(1H-Indol-3-yl)ethyl 2,4-Di-O-benzyl-3-deoxy-6-O-(6-aminohexyl)-β-D-glucopyranoside (III-5b).

A solution of azide III-29b (0.16 g, 0.21 mmol) in THF (13.3 ml) was treated sequentially with water (0.093 ml, 5.16 mmol) and triphenylphosphine (0.112 g, 0.43 mmol). The mixture was then heated at 60° C. for 5 h, cooled to room temperature, and concentrated in vacuo. Flash chromatography (10% methanol/dichloromethane) yielded the corresponding amine (142.3 mg, 92% yield) as a colorless oil: $[\alpha]D^{25}$+7.0° (c 1.7, $CHCl_3$); IR ($CH_2Cl_2$) 3680 (w), 3045 (m), 2938 (s), 2880 (s), 1606 (m), 1582 (m), 1450 (s), 1370 (s), 1260 (s), 1208 (m), 1180 is), 1090 (s), 1075 (s), 590 (m), 570 (m) cm$^{-1}$; 1NMR (500 MHz, $CDCl_3$) δ7.90 (d, J=8.4 Hz, 1H), 7.76 (d, J=7.9 Hz, 1H), 7.76 (d, J=8.4 Hz, 1H), 7.43–7.13 (m, 17H), 4.58 (d, J=12.0 Hz, 1H), 4.52 (d, J=11.5 Hz, 1H), 4.45 (d, J=12.0 Hz, 1H), 4.36 (d, J=11.5 Hz, 1H), 4.33 (d, J=7.5 Hz, 1H), 4.13 (dt, J=9.5, 6.8 Hz, 1H), 3.75 (dt, J=9.51, 7.2 Hz, 1H), 3.65 (d, J=10.4 Hz, 1H), 3.51 (dd, J=10.7, 4.7 Hz, 1H), 3.44–3.32 (m, 4H), 3.20 (m, 1H), 2.93 (t, J=6.9 Hz, 2H), 2.55 (t, J=7.0 Hz, 2H), 2.41 (dt, J=12.3, 4.2 Hz, 1H), 1.53–1.42 (m, 7H), 1.34–1.18 (m, 6H); $^{13}$C NMR (125 MHz, $CDCl_3$) δ138.30, 138.06, 137.81, 134.93, 133.32, 130.82, 128.87, 128.15, 128.04, 127.51, 127.45, 127.40, 127.23, 126.43, 124.43, 123.29, 122.84, 119.63, 119.24, 113.43, 105.01, 76.49, 72.41, 72.05, 71.42, 71.03, 69.66, 68.14, 44.72, 41.80, 34.77, 33.26, 29.34, 26.45, 25.75, 25.37.

A solution of the above amine (0.119 g, 0.16 mmol) in ethanol (15 ml) was treated with 5M aqueous potassium hydroxide (3 ml) and then heated to reflux. After 5 h the mixture was cooled, diluted with saturated aqueous ammonium chloride (25 ml), and poured into dichloromethane (30 ml). The aqueous phase was extracted with dichloromethane (4×10 ml) and the combined organic solutions were dried over sodium sulfate, filtered, and concentrated in vacuo. Flash chromatography (15% methanol/dichloromethane) furnished III-5b (80.9 mg, 73% yield) as a colorless oil: $[\alpha]D^{25}$+11.8° (c 0.43, $CH_2Cl_2$); IR, 3681 (w), 3436 (m), 3025 (m), 2918 (s), 2862 (s), 1729 (m), 1609 (m), 1458 (s), 1251 (m), 1098 (s), 1076 (s) cm$^{-1}$; $^1$H NMR (500 MHz, $CDCl_3$) δ8.64 (br s, 1H), 7.49 (d, J=8.6 Hz, 1H), 7.2–7.16 (m, 11H), 7.05 (apparent t, J=7.1 Hz, 1H), 6.98 (apparent t, J=5.9 Hz, 1H), 6.93 (s, 1H), 4.67 (d, J=11.8 Hz, 1H), 4.51 (d, J=11.8 Hz, 1H), 4.49 (d, J=11.4 Hz, 1H), 4.36 (d, J=7.6 Hz, 1H), 4.31 (d, J=11.4 Hz, 1H), 4.07 (dt, J=9.5, 7.3 Hz, 1H), 3.75 (dt, J=9.5, 7.5 Hz, 1H), 3.44–3.21 (m, 6H), 3.02 (t, J=7.4 Hz, 2H), 2.63 (br t, J=6.9 Hz, 2H), 2.42 (dt, J=12.3, 4.7 Hz, 1H), 1.49–1.35 (m, 6H), 1.18–1.1 (m, 5H); $^{13}$C NMR (125 MHz, $CDCl_3$) δ138.70, 138.04, 136.20, 128.42, 128.31, 127.75, 127.71, 127.58, 127.50, 122.27, 121.78, 119.11, 118.71, 112.42, 111.22, 105.30, 77.92, 75.09, 72.70, 72.40, 71.31, 71.09, 70.00, 69.93, 39.76, 34.91, 29.29, 27.37, 26.09, 25.82, 25.42; high resolution mass spectrum (FAB m-nitrobenzyl alcohol) m/z 609.3332 [(M+Na)$^+$; calcd for $C_{36}H_{46}N_2O_5$: 609.3305].

AD. 2-(1H-Indol-3-yl)ethyl 2,4-Di-O-benzyl-3,6-dideoxy-6-amino-6-N-(5-hydroxypentyl)-β-D-glucopyranoside (III-5c).

Triflic anhydride (126 ml, 0.748 mmol) was added to a stirred solution of III-28 (360 mg, 0.575 mmol) and 2,6-di-tert-butyl-4-methylpyridine (189 mg, 0.92 mmol) in dichloromethane (3 ml) at −78° C. After 20 min at −78° C., the mixture was allowed to warm to room temperature over 20 min. The resultant suspension was poured into saturated aqueous sodium bicarbonate and extracted with ethyl acetate. The organic layer was washed with saturated aqueous sodium bicarbonate and brine, dried over magnesium sulfate, filtered, and concentrated in vacuo. The oily crude triflate was used without purification in the next step.

A solution of 5-trifluoroacetamido-1-pentanol (III-18a) (687 mg, 3.45 mmol) in THF (16 ml) was added to a stirred suspension of sodium hydride (8.63 mmol, 345 mg, 60% dispersion in oil) in THF (20 ml) at 0° C. After 10 min the mixture was allowed to warm to room temperature, stirred for 90 min, recooled to 0° C., and treated with a solution of crude triflate (0.575 mmol) in dichloromethane (22 ml). The suspension was stirred for 30 min at 0° C. and then at room temperature for an additional 24 h. The reaction was quenched at 0° C. with saturated aqueous ammonium chloride (10 ml) and extracted with ethyl acetate, and the extracts were washed with water and brine, dried over magnesium sulfate, filtered, and concentrated in vacuo. Flash chromatography (gradient elution, 1% to 2% methanol/dichloromethane) afforded an inseperable mixture of compounds, presumably III-29c and its benzenesulfonamide deprotected counterpart, which was used directly in the next step.

A stirred solution of the above mixture in ethanol (6 ml) was treated with 5N NaOH (1 ml, 5 mmol), heated at reflux for 2 h, cooled, and concentrated in vacuo. The residue was taken up in dichloromethane and the resultant solution washed with 2N HCl. The aqueous layer was extracted with dichloromethane and the combined organic layers were washed with brine, dried over magnesium sulfate, filtered, and concentrated in vacuo. Flash chromatography (8% methanol/dichloromethane) yielded pure III-5c (172 mg, 52% yield for 3 steps) as a colorless oil: $[\alpha]D^{25}+17°$ (c 0.15, acetonitrile); UV ($6.5 \times 10^{-5}$M, acetonitrile) $\lambda$max 281.2 ($\epsilon 6.2 \times 103$), 218.8 ($3.62 \times 10^4$) nm; IR (film) 3325 (m), 3065 (w), 3035 (w), 3015 (w), 2940 (s), 2870 (s), 1500 (w), 1458 (m), 1354 (w), 1220 (w), 1076 (s), 1030 (m), 745 (s), 700 (s) cm$^{-1}$; $^1$H NMR (500 MHz, CDCl$_3$) $\delta$8.44 (s, 1H), 7.57 (d, J=7.7 Hz, 1H), 7.31–7.23 (m, 10H), 7.17–7.14 (m, 1H), 7.11–7.07 (m, 1H), 7.04 (d, J=2.0 Hz, 1H), 4.71 (d, J=11.8 Hz, 1H), 4.57 (d, J=11.7 Hz, 1H), 4.56 (d, J=11.9 Hz, 1H), 4.46 (d, J=7.5 Hz, 1H), 4.40 (d, J=11.5 Hz, 1H), 4.20 (ddd, J=13.8, 9.4, 6.8 Hz, 1H), 3.87 (ddd, J=14.9, 9.3, 7.4 Hz, 1H), 3.55–3.50 (m, 3H), 3.32–3.26 (m, 2H), 3.11 (t, J=7.2 Hz, 2H), 3.02 (dd, J=12.4, 2.9 Hz, 1H), 2.68 (dd, J=12.4, 8.1 Hz, 1H), 2.67–2.57 (m, 2H), 2.50 (ddd, J=12.3, 4.8, 4.8 Hz, 1H), 2.20 (s, 3H), 1.57–1.44 (m, 5H), 1.36–1.30 (m, 2H); $^{13}$C NMR (125 MHz, CDCl$_3$) $\delta$138.61, 137.92, 136.14, 128.41, 128.27, 127.79, 127.70, 127.53, 127.49, 122.18, 121.84, 119.18, 118.67, 112.56, 111.12, 105.22, 105.18, 76.53, 75.14, 74.28, 72.69, 70.99, 69.91, 62.45, 50.69, 49.49, 34.86, 32.28, 29.16, 25.80, 23.27; high resolution mass spectrum (FAB, m-nitrobenzyl alcohol) m/z 573.3314 [(M+H)$^+$; calcd for $C_{35}H_{44}N_2O_5$: 573.3328].

AE. 2-(1H-Indol-3-yl)ethyl 2,4-Di-O-benzyl-3,6-dideoxy-6-amino-6-N-(6-hydroxyhexyl)-β-D-g lucopyranoside (III-5d).

A solution of 6-trifluoroacetamido-1-hexanol (III-18c) (147 mg, 0.690 mmol) in THF (1 ml) was added to a suspension of sodium hydride (60% oil dispersion, 69.0 mg, 1.73 mmol) in THF (3 ml) at 0° C. The mixture was stirred at room temperature for 1 h, recooled to 0° C., and treated with a solution of the crude triflate derived from 28 (0.115 mmol), prepared as described for the synthesis of III-5c, in dry dichloromethane (5 ml). The reaction mixture was then warmed to room temperature, stirred for 48 h, and quenched at 0° C. with saturated ammonium chloride solution. The mixture was extracted with ethyl acetate and the combined organic layers were dried over sodium sulfate, filtered, and concentrated in vacuo, affording an inseperable mixture of compounds, presumably III-29d and its benzenesulfonamide deprotected counterpart, which was used directly in the next step.

A stirred solution of the above mixture in ethanol (6 ml) was treated with 5N sodium hydroxide (2 ml), heated to reflux for 2 h, cooled, and concentrated in vacuo. The oily residue was taken up in water and extracted with dichloromethane, and the organic layer was dried over sodium sulfate, filtered, and concentrated in vacuo. Flash chromatography (5% methanol/dichloromethane) yielded III-5d (56 mg, 64% yield for 2 steps) as a colorless oil: $[\alpha]D^{25}+13°$ (c 0.12, acetonitrile); UV ($1.23 \times 10^{-4}$M, acetonitrile) $\lambda$max 289.6 ($\epsilon 1.78 \times 10^3$), 280.8 ($1.37 \times 10^3$), 228.0 ($2.63 \times 10^3$) nm; IR (film) 3300 (br), 3060 (w), 3030 (w), 2930 (s), 2860 (m), 1450 (m), 1350 (w), 1070 (s), 740 (s), 700 (s) cm$^{-1}$; $^1$H NMR (500 MHz, CDCl$_3$) $\delta$8.16 (br s, 1H), 7.60 (d, J=7.8 Hz, 1H), 7.35–7.04 (m, 1 4H), 4.71 (d, J=11.8 Hz, 1H), 4.60 (d, J=11.6 Hz, 1H), 4.57 (d, J=11.9, 1H), 4.47 (d, J=7.6 Hz, 1H), 4.41 (d, J=11.5 Hz, 1H), 4.20 (dt, J=9.4, 6.8 Hz, 1H), 3.87 (dt, J=9.3, 7.6 Hz, 1H), 3.56 (t, J=10.0 Hz, 1H), 3.52 (m, 1H), 3.12 (t, J=6.9 Hz, 2H), 3.04 (d, J=2.8 Hz, 1H), 3.02 (d, J=2.8 Hz, 1H), 2.70–2.48 (m, 4H), 2.05 (br s, 2H), 1.54 (q, J=11.6 Hz, 1H), 1.48–1.26 (m, 8H); $^{13}$C NMR (125 MHz, CDCl$_3$) $\delta$138.61, 137.95, 136.14, 128.40, 128.27, 127.77, 127.69, 127.53, 127.49, 122.12, 121.85, 119.19, 118.68, 112.54, 111.10, 105.24, 76.87, 76.74, 75.17, 74.37, 72.70, 71.00, 69.92, 62.71, 50.81, 49.58, 34.90, 32.53, 29.67, 26.94, 25.81, 25.53; high resolution mass spectrum (Cl, CH$_4$) m/z 587.3557 [(M+H)$^+$; calcd for $C_{36}H_{47}N_2O_5$: 587.3485].

AF. 5-phthalimido-1-pentanol (III-33).

A solution of 5-amino-1-pentanol (5.00 g, 48.5 mmol) in benzene (150 ml) was treated with N-carboethoxyphthalimide (11.0 g, 50.2 mmol) and stirred at room temperature for 5 h. Concentration in vacuo and flash chromatography (25% ethyl acetate/petroleum ether) yielded III-33 (9.6 mg, 84% yield) as a clear, colorless oil: UV ($9.65 \times 10^{-4}$M, acetonitrile) $\lambda$max 292.0 ($\epsilon$212), 242.4 (226) nm; IR (CHCl$_3$) 3460 (br), 2940 (s), 2860 (s), 1770 (s), 1710 (s), 1610 (s), 1470 (s), 1440 (s), 1400 (s), 1370 (s), 1190 (m), 1170 (m), 1130 (m), 1050 (s), 960 (m), 890 (m), 875 (m), 790 (m), 720 (s) cm$^{-1}$; $^1$H NMR (500 MHz, CDCl$_3$) $\delta$7.72–7.70 (m, 2H), 3.69 (t, J=7.2 Hz, 1H), 3.64 (t, J=6.5 Hz, 1H), 2.17 (br s, 1H), 1.74–1.59 (m, 2H), 1.46–1.40 (m, 1H); $^{13}$C NMR (125 MHz, CDCl$_3$) $\delta$169.39, 133.78, 131.96, 123.05, 62.34, 37.74, 32.03, 28.22, 22.93; high resolution mass spectrum (Cl, NH$_3$) m/z 234.1108 [(M+H)$^+$; calcd for $C^{13}H_{15}NO_3$: 234.1129].

AG. 3,4-Di-O-Benzyl-6-O-(5-phthalimidopentyl)-D-glucal (III-34).

5-Phthalimidopentyl triflate was prepared as follows: A stirred solution of 5-phthalimido-1-pentanol (III-33) (1.32 g, 4.67 mmol) and 2,6-di-tert-butyl-4-methylpyridine (0.960 g, 4.67 mmol) in dry dichloromethane (10 ml) was treated with triflic anhydride (0.784 ml, 4.67 mmol). After 10 min at room temperature, the mixture was diluted with water (100 ml) and extracted with dichloromethane (2×200 ml). The combined extracts were washed with brine, dried over sodium sulfate, filtered, and concentrated in vacuo, affording a yellow solid which was used without purification in the next reaction. Sodium hydride (60% dispersion in oil, 0.20 g, 5.06 mmol) was added to a solution of alcohol III-32 (1.27 g, 3.89 mmol), 5-phthalimdopentyl triflate (4.67 mmol), and 15-crown-5 (20 mg, 2.3 mol %), in dichloromethane (100 ml) at 0° C. After stirring for 24 h at room temperature, the mixture was poured into water. The aqueous layer was extracted with dichloromethane (3×50 ml) and the combined extracts were washed with water, dried over magnesium sulfate and concentrated in vacuo. Flash chromatography (3% ether/dichloromethane) provided III-34 (1.82 g, 86% yield) as a colorless oil: $[\alpha]D^{25}-8.2°$ (c 0.70, CHCl$_3$); IR (CHCl$_3$) 3080 (w), 3020 (m), 3009 (m), 2959 (m), 2880 (m), 1780 (m), 1719 (s), 1652 (m), 1500 (w), 1470 (w), 1457 (m), 1440 (m), 1400 (s), 1365 (m), 1235 (m), 1110 (br, s), 1058 (br, s), 908 (w), 692 (m), cm$^{-1}$; $^1$H NMR (500 MHz, CDCl$_3$) δ7.80 (m, 2H), 7.68 (m, 2H), 7.25–7.34 (m, 10H), 6.38, (dd, J=6.1, 1.2 Hz, 1H), 4.84 (m, 2H), 4.66 (d, J=11.4 Hz, 1H), 4.63 (d, J=11.7 Hz, 1H), 4.55 (d, J=11.7 Hz, 1H), 4.19 (m, 1H), 4.00 (m, 1H), 3.81 (dd, J=8.7, 6.2 Hz, 1H), 3.64–3.74 (m, 4H), 3.40–3.50 (m, 2H), 1.60–1.70 (m, 4H), 1.40 (m, 2H); $^{13}$C NMR (62.9 MHz, CDCl$_3$) δ168.4, 144.8, 138.4, 138.3, 133.9, 132.2, 128.4, 127.9, 127.8, 127.6, 123.2, 99.9, 76.8, 75.8, 74.5, 73.8, 71.4, 70.5, 69.2, 37.9, 29.2, 28.5, 23.5; high resolution mass spectrum (Cl, NH$_3$) m/z 541.2483 (M$^+$; calcd for C$_{33}$H$_{35}$NO$_6$: 541.2464).

AH. 2-(N-phenylsulfonylindol-3-yl)ethyl 3,4-Di-O-benzyl-6-O-(5-phthalimidopentyl)-β-D-glucopyranoside (III-35).

A solution of dimethyldioxirane in acetone (1.2 equiv, ca. 0.05M) was added dropwise to glycal III-34 (1.53 g, 2.80 mmol) in dichloromethane (26 ml) at 0° C. The mixture was stirred at 0° C. for 1 h and concentrated in vacuo. To a solution of the crude epoxide and III-12 (1.15 g, 3.82 mmol) in THF (12 ml) at –78° C. was added ZnCl$_2$. (1.0M in ether, 5.6 ml, 5.6 mmol) and the mixture was allowed to stir at –78° C. for 1 h. The solution was then slowly warmed to room temperature and stirred 18 h. The mixture was poured into saturated aqueous sodium bicarbonate (50 ml) and extracted with ethyl acetate (3×50 ml) and the combined extracts were washed with water, dried over magnesium sulfate, and concentrated in vacuo. Flash chromatography (45% ethyl acetate/hexane) yielded III-35 (1.05 g, 44% yield) as a colorless oil: [α]D$^{25}$–8.1° (c 1.8 CHCl$_3$); IR (CHCl$_3$) 3069 (w), 3039 (m), 3019 (m), 2955 (m), 2879 (m), 1780 (m), 1719 (s), 1612 (w), 1472 (w), 1451 (s), 1401 (s), 1370 (s), 1175 (m), 1121 (s), 1068 (s), 695 (w), 680 (w), 596 (m), 570 (m) cm$^{-1}$; $^1$H NMR (500 MHz, CDCl$_3$) δ7.96 (dd, J=8.1, 0.6 Hz, 1H), 7.85 (dd, J=8.2, 0.9 Hz, 2H), 7.78 (m, 2H), 7.66 (m, 2H), 7.20–7.50 (m, 17H), 4.89 (d, J=11.3 Hz, 1H), 4.86 (d, J=11.0 Hz, 1H), 4.83 (d, J=11.4 Hz, 1H), 4.60 (d, J=10.9 Hz, 1H), 4.24 (d, J=7.6 Hz, 1H), 4.20 (dt, J=9.5, 6.4 Hz, 1H), 3.76 (dt, J=9.5, 7.2 Hz, 1H), 3.37–3.68 (m, 10H), 2.98 (m, 2H), 2.13 (br s, 1H), 1.57–1.68 (m, 4H), 1.38 (m, 2H); $^{13}$C NMR (62.9 MHz, CDCl$_3$) δ168.4, 138.6, 138.2, 135.1, 133.8, 133.7, 132.1, 131.0, 129.1, 128.4, 127.9, 127.8, 127.7, 126.7, 124.7, 123.5, 123.1, 119.7, 119.4, 113.7, 102.8, 84.4, 76.5, 75.1, 71.5, 69.6, 68.7, 37.8, 29.2, 28.4, 25.4, 23.5; high resolution mass spectrum (Cl, NH$_3$) m/z 662.2774 (M$^+$; calcd for C$_{35}$H$_{42}$SO$_7$: 662.2775).

AI. 2-Deoxy-3,4-di-O-benzyl-6-O-(5-phthalimido-pentyl)-β-D-glucopyranoside (III-36).

A solution of III-35 (0.455 g, 0.530 mmol) in THF (10 ml) was cooled to –78° C. and treated with carbon disulfide (27 ml, 0.583 mmol) followed by sodium bis(trimethylsilyl)amide (0.6M in toluene, 0.953 ml, 0.572 mmol). After 20 min, methyl iodide (59 ml, 0.640 mmol) was added and the solution was stirred for 5 min at –78° C. and then at room temperature for 45 min. The reaction mixture was quenched with water (50 ml) and extracted with ethyl acetate (3×50 ml). The organic layer was washed with brine, dried over sodium sulfate, filtered, and concentrated in vacuo, affording the crude xanthate as a pale yellow oil (0.462 g, 92% yield) which was used without purification in the next step.

To a solution of the crude xanthate (0.462 g, 0.487 mmol) and AIBN (10 mg) in toluene (8 ml) was added tributyltin hydride (0.214 ml, 0.795 mmol) and the reaction mixture heated to reflux for 4 h, cooled, and concentrated in vacuo. The residue was taken up in acetonitrile (30 ml) and washed with petroleum ether (5×10 ml), dried over sodium sulfate, filtered, and concentrated in vacuo to an oil. Flash chromatography (20% ethyl acetate/petroleum ether) yielded III-36 (0.296 g, 72% yield) as a colorless oil: [α]D$^{25}$–10° (c 1.1 CHCl$_3$); IR (CHCl$_3$) 3062 (w), 3031 (w), 3009 (w), 2939 (m), 2864 (m), 1777 (w), 1712 (s), 1610 (w), 1469 (w), 1449 (m), 1396 (s), 1378 (s), 1181 (m), 1171 (s), 1120 (s), 1090 (s), 990 (w), 910 (s), 692 (w), 595 (m) cm$^{-1}$; $^1$H NMR (500 MHz, CDCl$_3$) δ7.96 (d, J=7.5 Hz, 1H), 7.84 (m, 2H), 7.79 (m, 2H), 7.66 (m, 2H), 7.20–7.41 (m, 15H), 4.91 (d, J=11.0 Hz, 1H), 4.60 (m, 2H), 4.66 (d, J=11.7 Hz, 1H), 4.41 (dd, J=9.7, 1.8 Hz, 1H), 4.15 (dt, J=9.5, 6.6 Hz, 1H), 3.59–3.71 (m, 6H), 3.47 (m, 2H), 3.40 (m, 1H), 2.94 (t, J=6.6 Hz, 2H), 2.57 (ddd, J=14.2, 5.0, 3.2 Hz, 1H), 1.57–1.68 (m, 5H), 1.38 (m, 2H); $^{13}$C NMR (62.9 MHz, CDCl$_3$) δ23.5, 25.5, 28.4, 29.2, 36.7, 37.9, 68.1, 70.0, 71.4, 75.0, 75.2, 78,2, 79.3, 99.9, 113.6, 119.6, 123.1, 123.5, 124.7, 126.7, 127.7, 128.0, 128.4, 129.2, 131.1, 132.1, 133.6, 133.8, 135.1, 138.3, 138.5, 168.4; high resolution mass spectrum (Cl, NH$_3$) m/z 814.3287 (M$^+$; calcd for C$_{44}$H$_{50}$SO$_8$N$_2$: 814.3289).

AJ. 2-(1H-Indol-3-yl)ethyl2-Deoxy-3,4-di-O-benzyl-6-O-(5-aminopentyl)-β-D-glucopyranoside (III-6).

A solution of hydrazine (0.2M in MeOH, 6 ml) was added to III-36 (0.034 g, 0.043 mmol). After stirring for 16 h, the reaction mixture was concentrated in vacuo, the residue dissolved in ethanol (4 ml), and 5N NaOH (0.90 ml) added. The mixture was heated at reflux for 4 h, cooled, and extracted with dichloromethane (3×10 ml). The combined extracts were washed with brine, dried over magnesium sulfate, and concentrated in vacuo to an oil. Flash chromatography (11% methanol/dichloromethane) afforded 6 (11 mg, 44%) as a pale yellow oil: [Cα]D$^{25}$–15° (c 0.62, CHCl$_3$); IR (CHCl$_3$) 3490 (m), 3345 (br, m), 3020 (m), 2945 (s), 2882 (s), 1625 (w), 1500 (w), 1459 (m), 1370 (m), 1230 (w), 1100 (s), 695 (w) cm$^{-1}$; $^1$H NMR (500 MHz, CDCl$_3$) δ8.80 (br s, 1H), 7.49 (d, J=7.9 Hz, 1H), 7.19–7.31 (m, 11H), 7.10 (t, J=7.1 Hz, 1H), 7.00 (t, J=8.0 Hz, 1H), 6.97 (s, 1H), 4.83 (d, J=11.1 Hz, 1H), 4.59 (d, J=11.7 Hz, 1H), 4.51 (d, J=11.0 Hz), 4.50 (d, J=11.7 Hz, 1H), 4.39 (d, J=9.7 Hz, 1H), 4.00 (apparent q, J=7.3 Hz, 1H), 3.67 (apparent q, J=7.3 Hz, 1H), 3.60 (d, J=9.0 Hz, 1H), 3.56 (m, 1H), 3.46 (dd, J=10.8, 5.3 Hz), 3.31 (m, 4H), 2.98 (t, J=7.2 Hz, 2H), 2.50 (t, J=7.3 Hz, 2H), 2.28 (m, 2H), 1.57 (q, J=10 Hz, 1H), 1.42 (m, 4H), 1.19 (m, 2H); $^{13}$C NMR (62.9 MHz, CDCl$_3$) δ138.3, 138.2, 136.2, 128.4, 128.0, 127.7, 127.5, 122.3, 121.8, 119.1, 118.7, 112.0, 111.4, 99.9, 79.3, 78.2, 74.9, 71.4, 71.0, 69.9, 69.8, 39.7, 36.7, 28.8, 27.6, 25.7, 23.1; high resolution mass spectrum (FAB, m-nitrobenzyl alcohol) m/z 573.3371 [(M+H)$^+$; calcd for C$_{35}$H$_{44}$N$_2$O$_5$: 573.3328].

AK. Methyl 2,3,6-Tri-O-benzoyl-4-deoxy-α-D-glucopyranoside (III-38).

A solution of III-37 (5.00 g, 9.87 mmol) in THF (100 ml) was cooled to –78° C. and treated with carbon disulfide (0.45 ml, 7.48 mmol) followed by sodium bis(trimethylsilyl)amide (1.0M in THF, 10.5 ml, 51.8 mmol). After 20 min, methyl iodide (2.10 ml, 33.7 mmol) was added and the solution was stirred for 5 min at –78° C. and then at room temperature for 45 min. The reaction mixture was quenched with water (5 ml) and extracted with ethyl acetate. The organic layer was washed with brine, dried over sodium sulfate, filtered, and concentrated in vacuo, affording the crude xanthate as a pale yellow oil (5.70 g, 97% yield) which was used without purification in the next step. Purification of an analytical sample by flash chromatography (20% ethyl acetate/petroleum ether) gave white crystals: mp 72°–73° C.; [α]D$^{25}$ 140° (c 0.13, acetonitrile); $^{13}$C NMR (125 MHz, CDCl$_3$) δ166.10, 165.73, 165.53, 133.37, 133.13, 129.90, 129.75, 129.70, 129.21, 128.90, 128.37, 128.23, 96.94, 76.25, 71.83, 70.45, 67.36, 62.58, 55.60, 19.18; high resolution mass spectrum (FAB, m-nitrobenzyl alcohol) m/z 597.1286 [(M+H)$^+$; calcd for $C_{30}H_{28}O_9S_2$: 597.1253].

Tributyltin hydride (6.68 ml, 24.8 mmol) was added to a solution of the crude xanthate (5.70 g, 9.55 mmol) and AIBN (50 mg) in toluene (120 ml), and the reaction mixture was then heated to reflux for 4 h, cooled, and concentrated in vacuo. The residue was taken up in acetonitrile (200 ml) and extracted with petroleum ether (5×100 ml). The acetonitrile solution was dried over sodium sulfate, filtered, and concentrated in vacuo, affording a clear, colorless oil which solidified on standing. Flash chromatography (20% ethyl acetate/petroleum ether) yielded III-38 (3.60 g, 82% yield) as a white solid: mp 119°–120° C.; $[\alpha]D^{25}$+121° (c 0.17, acetonitrile); IR (CHCl$_3$) 3010 (m), 1730 (s), 1600 (w), 1580 (w), 1460 (m), 1270 (s), 1220 (s), 1110 (s), 1080 (m), 1060 (m), 1040 (m), 750 (s), 710 (s), 660 (m) cm$^{-1}$; $^1$H NMR (500 MHz, CDCl$_3$) δ8.08 (dd, J=8.3, 1.2 Hz, 2H), 8.05 (dd, J=8.3, 1.2 Hz, 2H), 8.00 (dd, J=8.4, 1.3 Hz, 2H), 7.51–7.35 (m, 9H), 5.78 (m, 1H), 5.31 (dd, J=10.2, 3.6 Hz, 1H), 5.15 (d, J=3.6 Hz, 1H), 4.45–4.43 (m, 3H), 3.44 (s, 3H), 2.47 (ddd, J=12.5, 5.2, 2.1, 1H), 1.89 (q, J=12 Hz, 1 H); $^{13}$C NMR (125 MHz, CDCl$_3$) δ166.23, 166.09, 165.81, 133.22, 133.16, 133.09, 129.84, 129.67, 129.62, 129.41, 128.42, 128.35, 128.32, 97.82, 72.57, 68.38, 66.05, 65.33, 55.32, 33.16; high resolution mass spectrum (CI, NH$_3$) m/z 536.1902 [(M+NH$_4$)$^+$; calcd for $C_{28}H_{30}N_1O_8$: 536.1919].

AL. Acetyl 2,3,6-Tri-O-benzoyl-4-deoxy-α-D-glucopyranoside (III-39).

A solution of glycoside III-38 (0.50 g, 1.1 mmol) in acetic anhydride (3.0 ml, 32 mmol) was cooled to 0° C. and treated with boron trifluoride etherate (0.1 ml). The reaction mixture was then stirred at room temperature for 4 h, diluted with ethyl acetate, and poured into ice-cold saturated sodium bicarbonate. The layers were separated and the aqueous layer was extracted with ethyl acetate. The combined extracts were washed with brine, dried over sodium sulfate, filtered, and concentrated in vacuo, affording III-39 (0.45 g, 85% yield) as a colorless oil which crystallized upon standing as white needles: mp 123°–124° C.; $[\alpha]D^{25}$+123° (c 0.19, acetonitrile); IR (CHCl$_3$) 3020 (s), 2400 (w), 1760 (m), 1730 (s), 1460 (w), 1280 (s), 1220 (s), 1110 (s), 930 (m) cm$^{-1}$; $^1$H NMR (500 MHz, CDCl$_3$) δ8.07–8.05 (m, 2H), 7.97–7.92 (m, 5H), 7.51–7.36 (m, 8H), 6.58 (d, J=3.7 Hz, 1H), 5.78 (m, 1H), 5.52 (m, 1H), 4.46 (m, 3H), 2.52 (ddd, J=12.5, 5.2, 2.1 Hz, 1H), 2.17 (s, 3H), 2.03 (m, 1H); $^{13}$C NMR (125 MHz, CDCl$_3$) δ168.87, 166.16, 165.54, 133.35, 133.29, 133.22, 129.71, 129.66, 129.58, 129.35, 129.02, 128.42, 128.39, 90.32, 71.59, 71.36, 70.78, 68.12, 68.05, 65.57, 32.76, 20.86, 20.80; high resolution mass spectrum (CI, NH$_3$) m/z 536.1902 [(M+NH$_4$)$^+$; calcd for $C_{29}H_{26}O_9$: 536.1919].

AM. 2-(N-Phenylsulfonylindol-3-yl)ethyl 2,3,6-Tri-O-benzoyl-4-deoxy-β-D-glucopyranoside (III-40).

A stirred solution of acetate III-39 (0.137 g, 0.29 mmol) in dichloromethane (3 ml) was cooled to 0° C. and treated with 30% hydrogen bromide in acetic acid (0.07 ml, 0.33 mmol). The reaction mixture was stirred at room temperature for 4 h, diluted with ethyl acetate, washed with saturated aqueous sodium bicarbonate and brine, dried over sodium sulfate, filtered, and concentrated in vacuo, furnishing a colorless oil which solidified upon standing. Recrystallization (ether/petroleum ether) yielded the bromide (0.15 g, 100% yield) as white crystals: mp 134°–135° C.; $[\alpha]D^{25}$+114° (c 0.10, acetonitrile); $^{13}$C NMR (125 MHz, CDCl$_3$) δ166.11, 165.64, 165.53, 133.65, 133.35, 133.32, 130.01, 129.78, 129.69, 129.49, 129.31, 128.75, 128.48, 128.42, 88.85, 71.54, 70.78, 68.63, 65.05, 32.16; high resolution mass spectrum (FAB, m-nitrobenzyl alcohol) m/z 539.0661 [(M+H)$^+$; calcd for $C_{27}H_{23}O_7Br$: 539.0705].

A solution of the above bromide (0.40 g, 0.814 mmol) in hexane and benzene (2:3, 17 ml) was added to a mixture of activated, powdered 4 Angstrom molecular sieves (0.83 g), protected tryptophol III-12 (0.37 g, 1.23 mmol) and silver(I) oxide (0.83 g, 3.58 mmol) in a flask wrapped with aluminum foil. The mixture was stirred at room temperature for two days, filtered through Celite, and concentrated in vacuo to furnish a colorless oil. Flash chromatography (50% ether/petroleum ether) then yielded III-40 (0.50 g, 81% yield) as a colorless solid: mp 76°–78° C.; $[\alpha]D^{25}$+28° (c 0.12, acetonitrile); UV (9.21×10$^{-5}$M, acetonitrile) λmax 237.6 (ε4.47×10$^3$), 198.8 (4.10×10$^3$) nm; IR (CHCl$_3$) 3010 (s), 1730 (s), 1455 (m), 1380 (m), 1320 (m), 1280 (s), 1220 (s), 1180 (s), 1120 (s), 1100 (m), 1075 (m), 1030 (m), 770 (s), 710 (s), 670 (s) cm$^{-1}$; $^1$H NMR (500 MHz, CDCl$_3$) δ8.03–7.10 (m, 2 5H), 5.42 (m, 2H), 4.74 (d, J=7.5 Hz, 1H), 4.47 (m, 2H), 4.16–4.05 (m, 2H), 3.82 (m, 1H), 2.91 (m, 2H), 2.47 (ddd, J=12.5, 4.6, 1.9 Hz, 1H), 1.90 (q, J=13.0 Hz, 1H); $^{13}$C NMR (125 MHz, CDCl$_3$) δ166.20, 165.89, 165.42, 135.03, 133.55, 133.24, 133.22, 133.06, 130.86, 129.72, 129.67, 129.62, 129.49, 129.32, 129.12, 128.42, 128.37, 128.31, 126.67, 124.58, 123.43, 123.06, 119.42, 119.35, 113.56, 101.42, 72.53, 71.56, 69.75, 68.80, 65.81, 33.00, 25.60; high resolution mass spectrum (FAB, m-nitrobenzyl alcohol) m/z 759.2108 (M$^+$; calcd for $C_{43}H_{37}NO_{10}S$: 759.2138).

AN. 2-(N-phenylsulfonylindol-3-yl)ethyl 4-Deoxy-β-D-glucopyranoside (III-41).

A solution of tribenzoate III-40 (120 mg, 0.158 mmol) in methanol (20 ml) was treated with sodium methoxide (0.027 g, 0.507 mmol) and then stirred for 16 h. The mixture was neutralized with Amberlyst® 15 ion exchange resin, filtered, and the filtrate was concentrated in vacuo to yield a tan solid. Flash chromatography (10% methanol/dichloromethane) yielded III-(41 (65 mg, 91% yield) as a white solid: mp 64°–65° C.; $[\alpha]D^{25}$−29° (c 0.15, acetonitrile); UV (9.21×10$^{-5}$M, acetonitrile) λmax 253.2 (ε1.55×10$^3$), 212.0 (2.58×10$^4$) nm; IR (CHCl$_3$) 3420 (w), 3010 (m), 1455 (m), 1370 (m), 1280 (w), 1220 (s), 1180 (m), 1120 (m), 1075 (m), 760 (s), 690 (w), 670 (s) cm$^{-1}$; $^1$H NMR (500 MHz, CDCl$_3$) δ7.99–7.22 (m, 10H), 4.22 (m, 2H), 3.82 (m, 1H), 3.69 (m, 2H), 3.61 (m, 2H), 3.24 (m, 1H), 2.97 (m, 2H), 2.76 (br s, 1H), 2.61 (br s, 1H), 1.89 (ddd, J=13.1, 5.1, 1.7 Hz, 1H), 1.56 (q, J=11.5 Hz, 1H); $^{13}$C NMR (125 MHz, CDCl$_3$) δ138.19, 135.14, 133.74, 131.04, 129.23, 126.70, 124.83, 123.68, 123.22, 119.74, 119.31, 113.76, 102.92, 76.09, 72.75, 70.72, 68.72, 65.04, 33.75, 25.40; high resolution mass spectrum (FAB, m-nitrobenzyl alcohol) m/z 447.1389 (M$^+$; calcd for $C_{22}H_{25}NO_7S$: 447.1352).

AO. 2-(N-Phenylsulfonylindol-3-yl)ethyl 4-Deoxy-6-O-tert-butyldimethylsilyl-β-D-glucopyranoside (III-42).

A solution of triol III-41 (0.24 g, 0.536 mmol) in DMF (6 ml) was treated with imidazole (73 mg, 1.07 mmol) followed by tert-butyldiphenylsilyl chloride (0.17 ml, 0.643 mmol). The reaction mixture was then heated at 70° C. for 48 h, cooled, quenched with methanol (5 ml), and concentrated in vacuo. The residue was extracted with ethyl acetate and the extracts were washed with brine, dried over sodium sulfate, filtered and concentrated in vacuo. The resultant pale yellow oil was purified by flash chromatography (3% methanol/dichloromethane) to give III-42 (0.36 g, 97% yield) as a colorless oil: $[\alpha]D^{25}$ −24° (c 0.37, acetonitrile); UV (1.75×10$^{-4}$M, acetonitrile) λmax 253.2 (ε1.53×10$^3$), 212.0 (2.58×10$^3$) nm; IR (CHCl$_3$) 3440 (br), 3010 (m), 2960 (w), 2940

(m), 2870 (m), 1455 (m), 1430 (m), 1380 (m), 1280 (w), 1220 (s), 1180 (s), 1120 (s), 1070 (s), 1020 (w), 760 (s), 705 (m), 690 (m), 670 (m) cm$^{-1}$; $^1$H NMR (500 MHz, CDCl$_3$) δ7.98 (d, J=8.4 Hz, 1H), 7.82 (m, 2H), 7.65 (m, 4H), 7.39–7.17 (m, 13H), 4.17 (d, J=7.7 Hz, 1H), 4.17–4.13 (m, 2H), 3.81–3.62 (m, 3H), 3.32 (t, J=8.0 Hz, 2H), 2.99–2.96 (m, 2H), 2.76 (br s, 1H), 2.59 (br s, 1H), 2.15–2.08 (ddd, J=13.1, 5.1, 1.7 Hz, 1H), 1.45 (q, J=12.7 Hz, 1H), 1.04 (s, 9H); $^{13}$C NMR (125 MHz, CDCl$_3$) δ138.22, 135.55, 135.52, 133.64, 133.33, 129.69, 129.66, 129.16, 127.65, 126.65, 124.76, 123.49, 123.15, 119.75, 119.41, 113.71, 102.80, 76.24, 72.66, 70.82, 68.64, 66.09, 34.75, 26.75, 25.48, 19.20; high resolution mass spectrum (Cl, NH$_3$) m/z 703.2929 [(M+NH$_4$)$^+$; calcd for C$_{38}$H$_4$N$_2$O$_7$SSi: 703.2873].

AP. 2-(N-Phenylsulfonylindol-3-yl)ethyl 2,3-Di-O-benzyl-4-deoxy-6-O-tert-butyldimethylsilyl-β-D-glucopyranoside (III-43).

A solution of diol III-42 (0.50 g, 0.729 mmol) in THF (7 ml) was added to a stirred suspension of sodium hydride (73.0 mg, 3.04 mmol, 60% oil dispersion) in THF (3 ml) at 0° C., and the reaction was stirred at room temperature for 30 min. The mixture was recooled to 0° C. and benzyl bromide (0.26 ml, 2.2 mmol) was added dropwise. After 3 days at room temperature, the reaction mixture was quenched with saturated aqueous ammonium chloride (10 ml) and extracted with ether. The extracts were washed with brine, dried over sodium sulfate, filtered, and concentrated in vacuo. Flash chromatography (33% ether/petroleum ether) afforded III-43 (0.73 g, 76% yield) as a colorless oil: [Cα]D$^{25}$−5.6° (c 0.16, acetonitrile); UV (1.44×10$^{-4}$M, acetonitrile) λmax 252.8 (ε2.27×10$^3$), 222.0 (2.63×10$^3$) nm; IR (CHCl$_3$) 3080 (w), 3010 (m), 2900 (m), 2850 (m), 1450 (m), 1430 (m), 1380 (m), 1220 (m), 1180 (m), 1100 (s), 750 (s), 700 (s), 660 (m) cm$^{-1}$; $^1$H NMR (500 MHz, CDCl$_3$) δ7.98 (d, J=8.3 Hz, 1H), 7.80 (dd, J=8.1, 0.83 Hz, 2H), 7.64 (m, 4H), 7.32 (m, 23H), 4.67 (m, 4H), 4.33 (d, J=7.7 Hz, 1H), 4.14 (m, 1H), 3.81–3.77 (m, 2H), 3.62 (m, 1H), 3.57–3.48 (m, 2H), 3.47–3.29 (m, 1H), 3.29 (t, J=7.8 Hz, 1H), 2.99 (t, J=7.1 Hz, 1H), 2.13 (ddd, J=12.8, 5.2, 1.6 Hz, 1H), 1.40 (q, J=11.7 Hz, 1H), 1.08 (s, 9H); $^{13}$C NMR (125 MHz, CDCl$_3$) δ138.64, 138.31, 135.58, 135.54, 135.19, 133.54, 133.46, 130.99, 129.70, 129.67, 129.10, 128.33, 128.20, 127.95, 127.66, 127.62, 127.54, 127.44, 126.62, 124.70, 123.42, 123.11, 119.74, 119.51, 113.69, 103.84, 82.95, 76.74, 74.89, 72.24, 68.55, 66.22, 33.66, 26.80, 25.80, 19.23; high resolution mass spectrum (Cl, NH$_3$) m/z 883.3898 [(M+N$_4$)$^+$; calcd for C$_{52}$H$_{59}$N$_2$O$_7$SSi: 883.3812].

AQ. 2-(N-Phenylsulfonylindol-3-yl)ethyl 2,3-Di-O-benzyl-4-deoxy-β-D-glucopyranoside (III-44).

A solution of silyl ether III-43 (0.37 g, 0.427 mmol) in THF (11 ml) was treated with tetrabutylammonium fluoride (1.33 ml, 1.0M in THF, 1.33 mmol) and stirred at room temperature for 3 h. The solution was then diluted with ethyl acetate, washed with water and brine, dried over sodium sulfate, filtered, and concentrated in vacuo. Flash chromatography (33% petroleum ether/ethyl acetate) yielded III-44 (0.43 g, 85% yield) as a colorless oil: [α]D$^{25}$−4.4° (c 0.32, acetonitrile); IR (CHCl$_3$) 3600 (w), 3480 (br), 3010 (m), 2920 (m), 2890 (m), 1450 (m), 1380 (m), 1220 (s), 1180 (m), 1120 (m), 1100 (m), 760 (s), 700 (m), 690 (m), 670 (m) cm$^{-1}$; $^1$H NMR (500 MHz, CDCl$_3$) δ7.98 (d, J=8.3 Hz, 1H), 7.83 (m, 2H), 7.52–7.04 (m, 1 2H), 4.74–4.66 (m, 5H), 4.41 (d, J=6.9 Hz, 1H), 4.19 (m, 1H), 3.88 (m, 1H), 3.67–3.50 (m, 4H), 3.31–3.27 (m, 1H), 2.99 (m, 2H), 2.08 (t, J=5.9 Hz, 1H), 1.98 (ddd, J=12.8, 5.2, 1.9 Hz, 1H), 1.56 (q, J=11.7 Hz, 1H); $^{13}$C NMR (125 MHz, CDCl$_3$) δ138.54, 138.19, 135.14, 133.61, 130.99, 129.12, 128.32, 128.20, 127.92, 127.60, 127.56, 127.49, 126.63, 124.72, 123.58, 123.13, 119.69, 119.37, 113.69, 103.84, 82.74, 78.11, 74.93, 72.29, 72.19, 68.65, 65.12, 32.61, 25.65; high resolution mass spectrum (Cl, CH$_4$) m/z 645.2675 [(M+NH$_4$)$^+$; calcd for C$_{36}$H$_{41}$N$_2$O$_7$S: 645.2634].

AR. 2-(N-Phenylsulfonylindol-3-yl)ethyl 2,3-Di-O-benzyl-4-deoxy-6-O-(5-phthalimidopentyl)-β-D-glucopyranoside (III-45).

5-Phthalimidopentyl triflate was prepared as follows: A stirred solution of 5-phthalimido-1-pentanol (III-33) (39.1 mg, 0.168 mmol) and 2,6-di-tert-butyl-4-methylpyridine (34.5 mg, 0.168 mmol) in dry dichloromethane (1.5 ml) was treated with triflic anhydride (28.3 ml, 0.168 mmol). After 10 min at room temperature, the mixture was diluted with water (25 ml) and extracted with dichloromethane (2×50 ml ). The combined extracts were washed with brine, dried over sodium sulfate, filtered, and concentrated in vacuo, affording a yellow solid which was used without purification in the next reaction. Sodium hydride (60% dispersion in oil, 51 mg, 1.3 mmol) was added to a solution of alcohol III-44 (150 mg, 0.240 mmol), 5-phthalimidopentyl triflate (1.37 mmol), and 2,6-di-tert-butyl-4-methylpyridine (282 mg, 1.39 mmol), in dichloromethane (1.5 ml) at 0° C. The reaction mixture was stirred for 48 h at room temperature, quenched with saturated aqueous ammonium chloride, and extracted with dichloromethane, and the organic layer was washed with brine, dried over sodium sulfate, filtered, and concentrated in vacuo. Flash chromatography (20% ethyl acetate/petroleum ether) gave III-45 (158 mg, 78% yield) as a colorless oil: [α]D$^{25}$−2.5° (c 0.36, acetonitrile); UV (2.14×10$^{-4}$M, acetonitrile) λmax 283.6 (ε710), 242.4 (808) nm; IR (CHCl$_3$) 2940 (m), 2860 (m), 1775 (m), 1715 (s), 1450 (m), 1400 (s), 1370 (s), 1175 (m), 1120 (s), 1090 (s), 1050 (s), 745 (m), 720 (s), 700 (m) cm$^{-1}$; $^1$H NMR (500 MHz, CDCl$_3$) δ7.96 (d, J=8.3 Hz, 1H), 7.84–7.80 (m, 4H), 7.69–7.64 (m, 2H), 7.50–7.17 (m, 12H), 4.69 (d, J=11.0 Hz, 1H), 4.67 (s, 2H), 4.64 (d, J=11.0 Hz, 1H), 4.36 (d, J=7.7 Hz, 1H), 4.21–4.17 (m, 1H), 3.86–3.81 (m, 1H), 3.66 (t, J=7.3 Hz, 2H), 3.60–3.39 (m, 6H), 3.28 (dd, J=7.8, 8.8 Hz, 1H), 3.00 (t, J=6.7 Hz, 2H), 2.12 (dd, J=5.4, 12.2 Hz, 1H), 1.71–1.58 (m, 5H), 1.47–1.36 (m, 3H); $^{13}$C NMR (125 MHz, CDCl$_3$) δ168.37, 138.61, 138.31, 135.19, 133.83, 133.56, 132.13, 131.03, 129.11, 128.31, 128.19, 127.96, 127.63, 127.51, 127.44, 126.65, 124.68, 123.51, 123.12, 119.78, 119.49, 113.70, 103.85, 82.83, 78.23, 74.90, 73.10, 72.16, 71.39, 70.95, 68.68, 37.86, 33.94, 29.67, 29.11, 28.36, 25.75, 23.41; high resolution mass spectrum (FAB, m-nitrobenzyl alcohol) m/z 865.3201 [(M+Na)$^+$; calcd for C$_{49}$H$_{50}$N$_2$O$_9$SNa: 865.3134].

AS. 2-(1H-Indol-3yl)ethyl 2,3-Di -O-benzyl-6-O-(5-aminopentyl)-β-D-glucopyranoside (III-7).

Sodium methoxide (40 mg, 0.740 mmol) was added to a solution of III-45 (150 mg, 0.178 mmol) in methanol (8 ml) and the reaction mixture was then heated at reflux for 24 h, cooled, poured into water (100 ml), and extracted with dichloromethane (2×100 ml). The combined organic layers were washed with brine, dried over sodium sulfate, filtered, and concentrated in vacuo. Flash chromatography (10% methanol/dichloromethane) afforded III-7 (72.0 mg, 71% yield) as a colorless oil: [α]D$^{25°}$3.9° (c 1.8, acetonitrile); UV (1.57×10$^{-4}$M, acetonitrile) λmax 280.0 (ε1.41×10$^3$), 224.8 (1.66×10$^3$) nm; IR (CHCl$_3$) 3350 (br), 3060 (w), 2930 (m), 2860 (m), 1630 (m), 1590 (m), 1560 (m), 1450 (m), 1400 (m), 1270 (m), 1100 (s), 740 (s), 700 (s) cm$^{-1}$; $^1$H NMR (500 MHz, CDCl$_3$) δ7.74 (br m, 1H), 7.48 (d, J=7.8 Hz, 1H), 7.36–6.93 (m, 1 5H), 4.62–4.49 (m, 4H), 4.32 (d, J=7.7 Hz, 1H), 4.11 (dt, J=9.4, 6.7 Hz, 1H), 3.78 (dt, J=9.2, 7.4 Hz, 1H), 3.52 (m, 4H), 3.26 (m, 2H), 3.22 (t, J=7.2 Hz, 1H), 3.13 (t, J=7.8 Hz, 1H), 3.00 (t, J=7.0 Hz, 2H), 2.00 (ddd, J=6.7, 5.2, 1.4 Hz, 1H), 1.29 (m, 9H); $^{13}$C NMR (125 MHz, CDCl$_3$) δ140.11, 138.10, 130.75, 130.59, 129.31, 128.92, 128.84, 128.57, 128.44, 123.70, 122.24, 119.40, 112.82, 112.31, 105.01, 84.13, 79.55, 75.76, 74.12, 73.12, 72.53, 72.18, 71.29, 41.05, 34.54, 30.38, 29.90, 27.07, 24.72; high resolution mass spectrum (Cl, NH$_3$) m/z 573.3301 [(M+H)$^+$; calcd for C$_{35}$H$_{45}$N$_2$O$_5$: 573.3328].

AT. Methyl 2,3,4-Tri-O-benzyl-6-O-(5-azidopentyl)-β-D-glucopyranoside (III-47a).

At room temperature a solution of 5-azido-1-pentanol (0.18 g, 1.40 mmol) and 2,6-di-tert-butyl-4-methylpyridine (0.3 g, 1.46 mmol) in dichloromethane (10 ml) was treated dropwise with triflic anhydride (0.240 ml, 1.43 mmol). After 15 min the mixture was diluted with dichloromethane (40 ml) and poured into saturated aqueous sodium bicarbonate. The organic phase was washed with brine (2×20 ml), dried over magnesium sulfate, filtered, and concentrated, affording a light yellow solid which was used without purification. The alcohol III-46 (0.2 g, 0.429 mmol) and the crude triflate were dissolved in dichloromethane (2 ml) and treated with sodium hydride (0.025 g, 0.625 mmol, 60% dispersion in oil). The mixture was stirred for 48 h, diluted with dichloromethane (40 ml), and poured into saturated aqueous ammonium chloride (40 ml). The aqueous phase was extracted with dichloromethane (3×20 ml) and the combined organic solutions were washed with brine, dried over magnesium sulfate, filtered, and concentrated in vacuo. Flash chromatography (15% ethyl acetate/hexane) provided III-47a (0.126 g, 51% yield) as a white solid: [α]D$^{25}$+7.7° (c 0.75, CHCl$_3$); IR 3028 (m), 2921 (m), 2863 (m), 2110 (s), 1497 (w), 1462 (m), 1421 (m), 1356 (m), 1280 (s), 1070 (s), 732 (br) cm$^{-1}$; $^1$H NMR (500 MHz, CDCl$_3$) δ7.35–7.23 (m, 15H), 4.92 (d, J=10.9 Hz, 1H), 4.91 (d, J=11.0 Hz, 1H), 4.86 (d, J=10.9 Hz, 1H), 4.78 (d, J=7.8 Hz, 1H), 3.70–3.50 (m, 6H), 3.56 (s, 3H), 3.44–3.40 (m, 3H), 3.23 (t, J=6.9 Hz, 2H), 1.63–1.40 (m, 6H); $^{13}$C NMR (125 MHz, CDCl$_3$) δ138.59, 138.53, 138.27, 128.42, 128.35, 128.33, 128.07, 127.88, 127.83, 127.76, 127.60, 127.50, 104.73, 84.63, 82.32, 77.96, 75.67, 74.97, 74.84, 74.72, 71.41, 69.70, 57.08, 51.35, 29.22, 28.69, 23.44; high resolution mass spectrum (FAB, m-nitrobenzyl alcohol) m/z 598.2880 [(M+Na)$^+$; calcd for C$_{33}$H$_{39}$N$_3$O$_6$: 598.2893].

AU. Methyl 2,3,4-Tri-O-benzyl-6-O-(5-aminopentyl)-β-D-glucopyranoside (III-8a).

Azide III-47a (0.126 g, 0.219 mmol) was dissolved in THF (12 ml) and treated with water (0.096 ml, 5.33 mmol) followed by triphenylphosphine (0.114 g, 0.44 mmol). The mixture was then heated at 60° C. for 12 h, cooled, and concentrated in vacuo. Flash chromatography (10% methanol/dichloromethane) afforded III-8a (87.3 mg, 73% yield) as a white solid: [α]D$^{25}$+6.8° (c 1.85, CHCl$_3$); IR (CH$_2$Cl$_2$) 3700 (w), 3040 (s), 2980 (s), 2920 (s), 2860 (m), 1420 (s), 1350 (m), 1310 (m), 1260 (s), 1140 (m), 1060 (s), 890 (s), 700 (br) cm$^{-1}$; $^1$H NMR (500 MHz, CDCl$_3$) δ7.35–7.25 (m, 15H), 4.92 (d, J=10.9 Hz, 1H), 4.91 (d, J=11.0 Hz, 1H), 4.85 (d, J=10.9 Hz, 1H), 4.78 (d, J=11.0 Hz, 1H), 4.70 (d, J=10.9 Hz, 1H), 4.61 (d, J=10.9 Hz, 1H), 4.29 (d, J=7.8 Hz, 1H), 3.70–3.40 (m, 8H), 3.56 (s, 3H), 2.66 (t, J=6.9 Hz, 2H), 1.61–1.56 (m, 4H), 1.46–1.35 (m, 4H); $^{13}$C NMR (125 MHz, CDCl$_3$) δ138.58, 138.52, 138.25, 128.39, 128.31, 128.05, 127.85, 127.84, 127.73, 127.58, 127.55, 104.71, 84.61, 82.30, 77.94, 75.65, 74.95, 74.83, 74.70, 71.63, 69.61, 57.07, 42.02, 33.47, 29.48, 23.45; high resolution mass spectrum (FAB, m-nitrobenzyl alcohol) m/z 572.2997 [(M+Na)+; calcd for C$_{33}$H$_{43}$O$_6$N: 572.2988].

AV. Methyl 2,3,4-Tri-O-benzyl-6-amino-6-deoxy-6-N-(5-hydroxypentyl)-β-D-glucopyranoside (III-8b).

A stirred solution of III-46 (800 mg, 1.71 mmol) and 2,6-di-tert-butyl-4-methyl pyridine (632 mg, 3.08 mmol) in dichloromethane (9 ml) was cooled to −78° C. and treated with triflic anhydride (0.345 ml, 2.05 mmol). After 15 min the mixture was warmed to room temperature over 20 min, poured into saturated aqueous sodium bicarbonate (20 ml), and extracted with ethyl acetate (50 ml). The organic layer was washed with additional bicarbonate solution and brine, dried over magnesium sulfate, filtered, and concentrated in vacuo, affording crude triflate which was used in the next step without further purification.

A solution of 5-trifluoroacetamido-1-pentanol (III-18a) (1.7 g, 8.6 mmol) in THF (35 ml) was added to a stirred suspension of sodium hydride (855 mg, 21.4 mmol, 60% oil dispersion) in THF (60 ml) at 0° C. After 10 min the suspension was warmed to room temperature, stirred for 1 h, and recooled to 0° C. A solution of the crude triflate (1.71 mmol) in dichloromethane (60 ml) was then added and stirring continued at 0° C. for 30 min and at room temperature for 24 h. The reaction mixture was quenched at 0° C. with saturated aqueous ammonium chloride and extracted with ethyl acetate, and the combined organic extracts were washed with water and brine, dried over magnesium sulfate, filtered, and concentrated in vacuo. Purification through a small plug of silica gel (30% ethyl acetate/petroleum ether) gave crude III-47b which was used immediately in the next step.

A stirred solution of the above crude III-47b in ethanol (10 ml) was treated with 5N NaOH (3 ml, 15 mmol) at room temperature and then heated at reflux for 2 h, cooled, and concentrated in vacuo. The residue was diluted with dichloromethane and washed with 2N HCl. The aqueous layer was extracted with dichloromethane (3×50 ml), and the combined organic solutions were washed with brine, dried over magnesium sulfate, filtered, and concentrated in vacuo. Recrystallization (ethyl acetate/petroleum ether) furnished pure III-Sb (675 mg, 72% yield from 46) as a white solid: mp 95°–95.5° C.; [α]D$^{25}$+9.3° (c 0.15, acetonitrile); IR (film) 3280 (m), 3095 (w), 3065 (w), 3035 (w), 2935 (s), 2915 (s), 2860 (s), 1496 (w), 1454 (m), 1404 (w), 1393 (w), 1358 (m), 1214 (m), 1115 (s), 1072 (s), 1037 (m), 1027 (m), 1009 (m), 911 (w), 826 (w), 747 (s), 696 (s) cm$^{-1}$; $^1$H NMR (500 MHz, CDCl$_3$) δ7.35–7.24 (m, 1 5H), 4.92 (d, J=7.5 Hz, 1H), 4.90 (d, J=7.6 Hz, 1H), 4.85 (d, J=11.0 Hz, 1H), 4.78 (d, J=11.0 Hz, 1H), 4.70 (d, J=11.0 Hz, 1H), 4.60 (d, J=11.0 Hz, 1H), 4.32 (d, J=7.8 Hz, 1H), 3.66–3.59 (m, 3H), 3.56 (s, 3H), 3.48–3.36 (m, 3H), 2.94 (dd, J=12.5, 2.1 Hz, 1H), 2.68 (dd, J=12.0, 6.8 Hz, 1H), 2.64–2.53 (m, 2H), 1.71 (s, 2H), 1.59–1.53 (m, 2H), 1,51–1.45 (m, 2H), 1.42–1.36 (m, 2H); $^{13}$C NMR (125 MHz, CDCl$_3$) δ138.55, 138.47, 138.17, 128.39, 128.33, 128.03, 127.95, 127.85, 127.77, 127.60, 127.57, 104.72, 84.56, 82.45, 79.74, 75.66, 75.02, 74.74, 74.16, 62.62, 57.20, 50.69, 49.72, 32.49, 29.65, 23.37; high resolution mass spectrum (Cl, NH$_3$) m/z 550.3179 [(M+H)$^+$; calcd for C$_{33}$H$_{43}$O$_6$N: 550.3168].

AW. 2-(1H-Indol-3-yl)ethyl 2,3,4-Tri-O-benzyl-β-D-glucopyranoside (III-9).

A stirred solution of III-17 (100 mg, 0.136 mmol) in ethanol (3 ml) was treated with 5N NaOH (1 ml) and then heated at reflux for 2 h, cooled, and concentrated in vacuo. The residue was diluted with dichloromethane and washed with 2N HCl, and the aqueous layer was extracted with dichloromethane. The combined organic solutions were washed with brine, dried over magnesium sulfate, filtered, and concentrated in vacuo. Flash chromatography (25% ethyl acetate/petroleum ether) furnished III-9 (68 mg, 85% yield) as a colorless oil: $[\alpha]_D^{25}$ –2.5° (c 1.37, acetonitrile); UV (2.89×10$^{-4}$M, acetonitrile) λmax 289.6 (ε3.56×10$^3$), 281.2 (4.24×10$^3$), 222.4 (1.01×10$^4$) nm; IR (film) 3575 (sh), 3435 (m), 3085 (sh), 3065 (w), 3035 (w), 2925 (m), 2880 (m), 1500 (w), 1455 (m), 1360 (w), 1310 (w), 1150 (sh), 1085 (s), 1030 (s), 920 (w), 810 (w), 740 (s), 700 (s) cm$^{-1}$; $^1$H NMR (500 MHz, CDCl$_3$) δ7.83 (s, 1H), 7.59 (d, J=7.8 Hz, 1H), 7.33–7.24 (m, 1 5H), 7.20–7.17 (m, 2H), 7.11 (t, J=7.8 Hz, 1H), 7.01 (d, J=1.8 Hz, 1H), 4.91 (d, J=10.9 Hz, 1H), 4.85 (d, J=10.9 Hz, 1H), 4.80 (d, J=10.9 Hz, 1H), 4.79 (d, J=11.0 Hz, 1H), 4.64 (d, J=11.0 Hz, 1H), 4.63 (d, J=11.0 Hz, 1H), 4.49 (d, J=7.8 Hz, 1H), 4.22 (ddd, J=9.4, 6.7, 6.7 Hz, 1H), 3.90–3.82 (m, 2H), 3.72–3.67 (m, 1H), 3.65 (apparent t, J=9.1 Hz, 1H), 3.56 (apparent t, J=9.3 Hz, 1H), 3.42 (apparent t, J=8.1 Hz, 1H), 3.35 (ddd, J=9.5, 4.3, 2.8 Hz, 1H), 3.11 (t, J=7.0 Hz, 2H), 1.87 (dd, J=7.6, 5.9 Hz, 1H); $^{13}$C NMR (500 MHz, CDCl$_3$) δ138.52, 138.44, 137.98, 136.17, 128.46, 128.36, 128.29, 128.05, 128.00, 127.89, 127.86, 127.60, 127.57, 127.45, 122.09, 122.01, 119.34, 118.68, 112.60, 111.13, 103.69, 84.49, 82.34, 77.57, 75.64, 75.04, 75.01, 74.75, 70.25, 62.04, 25.86; high resolution mass spectrum (Cl, NH$_3$) m/z 611.3043 [(M+NH$_4$)$^+$; calcd for C$_{37}$H$_{39}$O$_6$N: 611.3121].

AX. Methyl 2,3-Di-O-benzyl-4,6-di-O-isopropylidene-β-D-glucopyranoside (III-50).

A solution of glucoside III-49 (2.5 g, 10.7 mmol) in THF (100 ml) was added to a suspension of sodium hydride (0.94 g, 23.5 mmol) in THF (50 ml) at 0° C. The reaction was stirred at room temperature for 1 h and cooled to 0° C., and benzyl bromide (2.8 ml, 24 mmol) was then added dropwise, followed by tetrabutylammonium iodide (100 mg). The mixture was stirred at room temperature for 24 h, quenched with saturated aqueous ammonium chloride, extracted with ether, and the extracts washed with brine, dried over sodium sulfate, filtered, and concentrated in vacuo. Flash chromatography (10% ethyl acetate/petroleum ether) afforded III-50 as a colorless oil (4.02 g, 91% yield): $[\alpha]_D^{25}$ –2.0° (c 0.15, acetonitrile); UV (6.01×10$^{-4}$M, acetonitrile) λmax 257.6 (ε508) nm; IR (film) 3060 (m), 3000 (m), 2980 (m), 2900 (m), 1460 (m), 1390 (m), 1380 (m), 1310 (w), 1270 (s), 1210 (m), 1180 (m), 1100 (s), 1080 (s), 1050 (m), 1030 (m), 860 (m), 740 (s), 705 (s) cm$^{-1}$; $^1$H NMR (500 MHz, CDCl$_3$) δ7.35–7.23 (m, 10H), 4.84 (d, J=11.3 Hz, 2H), 4.74 (dd, J=11.4, 9.2 Hz, 1H), 4.36 (d, J=7.6 Hz, 1H), 3.93 (dd, J=10.8, 5.4 Hz, 1H), 3.76 (t, J=10.5 Hz, 1H), 3.69 (t, J=9.3 Hz, 1H), 3.57 (m, 4H), 3.37 (t, J=8.3 Hz, 1H), 3.23 (m, 1H), 1.48 (s, 3H), 1.42 (s, 3H); $^{13}$C NMR (125 MHz, CDCl$_3$) δ138.81, 138.54, 128.26, 128.17, 127.98, 127.85, 127.58, 127.46, 105.16, 99.24, 82.14, 81.27, 75.19, 74.77, 74.27, 69.79, 62.25, 57.32, 29.14, 19.09; high resolution mass spectrum (Cl, NH$_3$) m/z 415.2137 [(M+H)$^+$; calcd for C$_{24}$H$_{31}$O$_6$: 415.2120].

AY. Methyl 2,3-Di-O-benzyl-β-D-glucopyranoside (III-51).

Amberlyst® 15 ion exchange resin (0.5 g) was added to a solution of III-50 (1.00 g, 2.4 mmol) in methanol (50 ml) and the mixture was stirred at room temperature for 4 h, filtered, and concentrated in vacuo. Flash chromatography (6% methanol/dichloromethane) yielded III-51 (0.75 g, 83% yield) as a white foam: $[\alpha]_D^{25}$ +16° (c 0.15, acetonitrile); UV (2.00×10$^{-4}$ M, acetonitrile) λmax 257.6 (ε385.0) nm; IR (film) 3590 (w), 3410 (br), 3080 (m), 2910 (w), 2890 (w), 1500 (w), 1455 (m), 1270 (s), 1210 (m), 1065 (s), 1030 (s), 1000 (m), 900 (m), 740 (s), 700 (s) cm$^{-1}$; $^1$H NMR (500 MHz, CDCl$_3$) δ7.34–7.23 (m, 10H), 4.91 (dd, J=15.6, 11.5 Hz, 2H), 4.69 (dd, J=11.5 , 8.7 Hz, 2H), 4.34 (d, J=7.7 Hz, 1H), 3.87–3.83 (m, 1H), 3.77–3.72 (m, 1H), 3.58–3.54 (m, 4H), 3.44 (t, J=9.1 Hz, 1H), 3.37 (t, J=7.6 Hz, 1H), 3.31–3.27 (m, 1H), 2.84 (br s, 1H), 2.48 (br s, 1H); $^{13}$C NMR (125 MHz, CDCl$_3$) δ138.48, 138.34, 128.49, 128.46, 128.30, 127.99, 127.83, 127.76, 127.62, 104.85, 83.82, 81.87, 75.13, 74.90, 74.57, 70.18, 62.30, 57.20; high resolution mass spectrum (Cl, NH$_3$) m/z 392.2043 [(M+NH$_4$)$^+$; calcd for C$_{21}$H$_{30}$NO$_6$: 392.2072].

BA. Methyl 2,3-Di-O-benzyl-6-O-tert-butyldiphenylsilyl-β-D-glucopyranoside (III-52).

A solution of III-51 (3.30 g, 8.81 mmol) and imidazole (0.84 g, 12.3 mmol) in a mixture of THF (150 ml) and DMF (25 ml) was treated with tert-butyldiphenylsilyl chloride (2.80 ml, 10.6 mmol) and heated at 50° C. for 24 h. The reaction mixture was quenched with methanol (5 ml) and concentrated in vacuo. The resultant oil was taken up in ethyl acetate and the solution was washed with water and brine, dried over sodium sulfate, filtered, and concentrated in vacuo. Flash chromatography (10% ethyl acetate/petroleum ether) furnished III-52 (5.40 g, 100% yield) as a colorless oil: $[\alpha]_D^{25}$ +7.3° (c 0.22, acetonitrile); UV (1.79×10$^{-4}$M, acetonitrile) λmax 258.8 (ε836) nm; IR (film) 3500 (br), 3080 (w), 3030 (w), 2940 (m), 2860 (m), 1450 (w), 1430 (m), 1390 (w), 1360 (w), 1310 (w), 1270 (w), 1220 (w), 1190 (w), 1120 (s), 1070 (s), 830 (m), 805 (w), 740 (s), 700 (s) cm$^{-1}$; $^1$H NMR (500 MHz, CDCl$_3$) δ7.71–7.69 (m, 4H), 7.42–7.25 (m, 1 6H), 4.93 (d, J=11.5 Hz, 2H), 4.76 (d, J=11.4 Hz, 1H), 4.71 (d, J=11.1 Hz, 1H), 4.32 (d, J=7.6 Hz, 1H), 3.94–3.88 (m, 2H), 3.69–3.64 (m, 1H), 3.66 (s, 3H), 3.47 (t, J=9.1 Hz, 1 H), 3.41–3.34 (m, 2H), 2.57 (br s, 1H), 1.06 (s, 9H); $^{13}$C NMR (125 MHz, CDCl$_3$) δ138.71, 138.62, 135.69, 135.61, 129.73, 128.50, 128.34, 128.03, 127.99, 127.78, 127.72, 127.69, 127.62, 104.68, 84.22, 81.93, 75.30, 74.89, 74.67, 71.62, 64.44, 56.86, 26.79, 19.25; high resolution mass spectrum (Cl, NH$_3$) m/z 630.3296 [(M+NH$_4$)$^+$; calcd for C$_{37}$H$_{48}$NO$_6$Si: 630.3251].

BB. Methyl 2,3-Di-O-benzyl-4-deoxy-6-O-tert-butyldiphenylsilyl-β-D-glucopyranoside (III-53).

A solution of III-52 (0.33 g, 0.54 mmol) in THF (20 ml) was cooled to –78° C. and treated with sodium bis(trimethylsilyl)amide (0.66 ml, 1.0M in THF, 0.66 mmol) followed by carbon disulfide (46 ml, 0.77 mmol). After 15 min, methyl iodide (137 ml, 2.20 mmol) was added, and the solution was stirred 15 min further at –78° C. and then at room temperature for 45 min. The reaction mixture was quenched with water (2 ml) and extracted with ether. The organic layer was washed with brine, dried over sodium sulfate, filtered, and concentrated in vacuo affording the crude xanthate as a yellow oil which was used without purification.

A solution of crude xanthate (6.06 g, 8.62 mmol) and a catalytic amount of AIBN (ca. 50 mg) in toluene (350 ml) was treated with tributyltin hydride (7.0 ml, 26 mmol) and then heated at reflux for 3 h, cooled, and concentrated in vacuo. The residue was taken up in acetonitrile and extracted with petroleum ether (5×100 ml). The acetonitrile layer was dried over sodium sulfate, filtered, and concentrated in vacuo. Flash chromatography (8% ethyl acetate/petroleum ether) yielded III-53 (3.60 g, 78% yield for two steps) as a colorless oil: $[\alpha]_D^{25}$ +2.7° (c 0.15, acetonitrile); UV (1.26×10$^{-4}$M, acetonitrile) λmax 258.4 (ε976) nm; IR (film) 3080 (m), 2990 (w), 2880 (w), 1430 (w), 1270 (s), 1110 (m), 900 (w), 740 (s), 710 (s) cm$^{-1}$; $^1$H NMR (500 MHz, CDCl$_3$) δ7.68–7.66 (m, 4H), 7.43–7.21 (m, 1 6H), 4.89 (d, J=11.1 Hz, 1H), 4.75 (d, J=10.2 Hz, 1H), 4.67 (dd, J=18.2, 11.9 Hz, 2H), 4.22 (d, J=7.6 Hz, 1H), 3.80 (dd, J=10.5, 5.7 Hz, 1H), 3.63 (dd, J=10.4, 5.4 Hz, 1H), 3.59–3.44 (m, 5H), 3.29 (t, J=8.9 Hz, 1H), 2.11 (ddd, J=12.8, 5.1, 1.5 Hz, 1H), 1.41 (q, J=11.8 Hz, 1H), 1.06 (s, 9H); $^{13}$C NMR (125 MHz, CDCl$_3$) δ138.91, 138.65, 135.60, 135.55, 133.48, 133.44, 129.66, 128.29, 128.22, 127.95, 127.63, 127.60, 127.49, 127.43, 104.81, 82.99, 78.32, 74.82, 72.20, 72.15, 66.22, 56.73, 33.62, 26.78, 19.22; high resolution mass spectrum (Cl, NH$_3$) m/z 614.3256 [(M+NH$_4$)$^+$; calcd for C$_{37}$H$_{48}$NO$_5$Si: 614.3301].

BC. Methyl 2,3-Di-O-benzyl-4-deoxy-β-D-glucopyranoside (III-54).

A solution of III-53 (3.60 g, 6.02 mmol) in THF (125 ml) was treated with tetrabutylammonium fluoride (1.0M in THF, 6.1 mmol, 6.1 ml) at room temperature, stirred for 4 h, poured into water, and extracted with ethyl acetate. The organic layer was dried over sodium sulfate, filtered, and concentrated in vacuo. Flash chromatography (50% ethyl acetate/petroleum ether) afforded III-54 (2.03 g, 94% yield) as a colorless oil: [α]D$^{25}$+8.0° (c 0.15, acetonitrile); UV (2.09×10$^{-4}$M, acetonitrile) λmax 257.6 (ε177) nm; IR (film) 3450 (br), 3095 (w), 3060 (w), 3030 (w), 2920 (m), 2880 (m), 1500 (w), 1450 (m), 1380 (m), 1360 (m), 1300 (w), 1260 (w), 1210 (m), 1180 (w), 1070 (br), 910 (m), 740 (m), 700 (m) cm$^{-1}$; $^1$H NMR (500 MHz, CDCl$_3$) δ7.38–7.25 (m, 10H), 4.89 (d, J=11.1 Hz, 1H), 4.76 (d, J=11.1 Hz, 1H), 4.67 (m, 2H), 4.28 (d, J=7.7 Hz, 1H), 3.73–3.49 (m, 7H), 3.29 (t, J=7.9 Hz, 1H), 2.08 (br s, 1H), 1.97 (ddd, J=12.9, 5.3, 1.9 Hz, 1H), 1.49 (dd, J=24.4, 11.7 Hz, 1H); $^{13}$C NMR (500 MHz, CDCl$_3$) δ138.71, 138.47, 128.33, 128.28, 128.00, 127.62, 127.58, 127.55, 104.95, 82.81, 78.07, 74.92, 72.26, 72.13, 65.20, 57.19, 32.65; high resolution mass spectrum (Cl, NH$_3$) m/z 359.1827 [(M+H)$^+$; calcd for C$_{21}$H$_{27}$O$_5$: 359.1858].

BD. Methyl 2,3-Di-O-benzyl-4-deoxy-6-O-(5-phthalimidopentyl)-β-D-glucopyranoside (III-55).

A solution of 5-phthalimido-1-pentanol (0.66 g, 2.83 mmol) and 2,6-di-tert-butyl-4-methylpyridine (0.58 g, 2.83 mmol) in dry dichloromethane (21 ml) was treated with triflic anhydride (0.48 ml, 2.83 mmol) at room temperature, stirred for 10 min, poured into water, and extracted with dichloromethane. The organic layer was dried over sodium sulfate, filtered, and concentrated in vacuo. The freshly generated triflate was then dissolved in dry dichloromethane (21 ml ), 2,6-di-tert-butyl-4-methylpyridine (0.58 g, 2.83 mmol) was added, and the solution was cooled to 0° C. A solution of III-54 (1.0 g, 2.79 mmol) in dichloromethane (21 ml) was introduced, followed after 20 min by sodium hydride (60% oil dispersion, 0.25 g, 6.25 mmol). The reaction mixture was stirred at room temperature for 24 h, quenched with saturated aqueous ammonium chloride, extracted with dichloromethane, and the combined extracts were washed with brine, dried over sodium sulfate, filtered, and concentrated in vacuo. Flash chromatography (50% ethyl acetate/petroleum ether) yielded III-55 (1.42 g, 89% yield) as a colorless oil: [Cα]D$^{25}$+11° (c 0.11, acetonitrile); UV (9.60×10$^{-5}$M, acetonitrile) λmax 290.8 (ε3.20×103), 257.6 (2.20×10$^3$), 241.2 (1.69×10$^4$) nm; IR (film) 3480 (br), 3090 (w), 3040 (w), 3010 (w), 2940 (s), 2860 (s), 2250 (m), 1770 (m), 1715 (s), 1500 (w), 1470 (w), 1450 (m), 1430 (m), 1400 (s), 1370 (m), 1340 (w), 1300 (w), 1260 (m), 1210 (m), 1190 (m), 1170 (w), 1100 (br), 1000 (w), 910 (s), 730 (s), 720 (s), 700 (s), 650 (m) cm$^{-1}$; $^1$H NMR (500 MHz, CDCl$_3$) δ7.84–7.68 (m, 4H), 7.38–7.24 (m, 10H), 4.88 (d, J=11.1 Hz, 1H), 4.75 (d, J=11.1 Hz, 1H), 4.67 (s, 2H), 4.24 (d, J=7.6 Hz, 1H), 3.68 (t, J=7.3 Hz, 2H), 3.61–3.41 (m, 9H), 3.28 (t, J=8.5 Hz, 1H), 2.10 (dd, J=12.6, 5.3 Hz, 1H), 1.73–1.59 (m, 5H), 1.45–1.37 (m, 2 H); $^{13}$C NMR (125 MHz, CDCl$_3$) δ168.38, 138.87, 138.64, 133.84, 132.17, 128.30, 128.25, 128.02, 127.63, 127.48, 123.14, 104.85, 82.91, 78.24, 74.86, 73.15, 72.19, 71.42, 70.92, 56.97, 37.90, 33.94, 29.15, 28.38, 23.44; high resolution mass spectrum (Cl, NH$_3$) m/z 591.3014 [(M+NH$_4$)$^+$; calcd for C$_{34}$H$_2$: 591.3070].

BE. Methyl2,3-Di-O-benzyl-4-deoxy-6-O-(5-aminopentyl)-β-D-glucopyranoside (III-10).

A solution of phthalimide III-55 (0.79 g, 1.38 mmol) in methanol (100 ml) was treated with sodium methoxide (0.23 g, 4.26 mmol), heated at reflux for 4 h, cooled, and concentrated in vacuo. The residue was taken up in water and extracted with dichloromethane, and the organic layer was washed with brine, dried over sodium sulfate, filtered, and concentrated in vacuo. Flash chromatography (10% methanol/dichloromethane) furnished III-10 (0.46 g, 75% yield) as a white foam: [α]D$^{25}$+8.9° (c 0.18, acetonitrile); UV (2.03×10$^{-4}$M, acetonitrile) λmax 276.4 (ε1.54×103), 257.6 (2.26×10$^3$)nm; IR (film) 3330 (br), 3080 (w), 3020 (w), 2930 (s), 2870 (s), 1650 (s), 1550 (m), 1450 (m), 1370 (m), 1300 (s), 1210 (m), 1185 (m), 1100 (br), 1000 (w), 900 (w), 740 (s), 700 (s), 670 (w), 640 (w) cm$^{-1}$; $^1$H NMR (500 MHz, CD$_3$OD) δ7.76–7.74 (m, 1H), 7.35–7.13 (m, 9H), 4.74–4.49 (m, 4H), 4.14 (d, J=7.7 Hz, 1H), 3.53–3.36 (m, 9H), 3.20 (m, 2H), 3.07 (t, J=7.8 Hz, 1H), 1.99 (ddd, J=2.8, 5.3, 1.7 Hz, 1H), 1.50–1.18 (m, 9H); $^{13}$C NMR (125 MHz, CD$_3$OD) δ140.18, 139.99, 138.83, 131.94, 130.83, 130.49, 129.28, 129.18, 128.99, 128.83, 128.69, 128.55, 128.49, 105.98, 84.04, 79.56, 75.73, 74.05, 73.04, 72.49, 72.12, 57.24, 40.94, 34.53, 30.30, 29.81, 24.64; high resolution mass spectrum (Cl, NH$_3$) m/z 444.2783 [(M+H)$^+$; calcd for C$_{26}$H$_{38}$NO$_5$: 444.2749].

EXAMPLE 12

The affinity of a variety of compounds for the substance p receptor was determined employing the following procedure.

A. Receptor Expression in COS

To express the cloned human neurokinin-1 receptor (NK1R) transiently in COS, the cDNA for the human NK1R was cloned into the expression vector pCDM9 which was derived from pCDM8 (Invitrogen) by inserting the ampicillin resistance gene (nucleotide 1973 to 2964 from Bluescript SK+) into the Sac II site. Transfection of 20 μg of the plasmid DNA into 10 million COS cells was achieved by electroporation in 800 μl of the transfection buffer (135 mM CaCl$_2$, 1.2 mM MgCl$_2$, 2.4 mM K$_2$HPO$_4$, 0.6 mM KH2PO4, 10 nM glucose, 10 mM HEPES pH 7.4) at 260 V and 950 μF using the IBI Genezapper (IBI, New Haven, Conn.). The cells were incubated in 10% fetal calf serum, 2 mM glutamine, 100 U/ml penicillin-streptomycin, and 90% DMEM media (Gibco, Grand Island, N.Y.) in 5% CO$_2$ at 37° C. for three days before the binding assay.

B. Assay Protocol using COS

The binding assay of human NK1R expressed in COS cells is based on the use of $^{125}$I-substance P ($^{125}$I-SP, from DuPont, Boston, Mass.) as a radioactively labeled ligand which competes with unlabeled substance P or any other ligand for binding to the human NK1R. Monolayer cell cultures of COS were dissociated by the non-enzymatic solution (Specialty Media, Lavallette, N.J.) and resuspended in appropriate volume of the bind buffer (50 mM Tris pH 7.5, 5 mM MnCl$_2$, 150 mM NaCl, 0.04 mg/ml bacitracin, 0.004 mg/ml leupeptin, 0.2 mg/ml BSA, 0.01 mM phosphoramidon) such that 200 μl of the cell suspension would give rise to about 10,000 cpm of specific $^{125}$I-SP binding (approximately 50,000 to 200,000 cells). In the binding assay, 200 μl of cells were added to a tube containing 20 μl of 1.5 to 2.5 nM of $^{125}$I-SP and 20 μl of unlabeled substance P or any other test compound. The tubes were incubated at 4° C. or at room temperature for 1 hour with gentle shaking. The bound radioactivity was separated from unbound radioactivity by GF/C filter (Brandel, Gaithersburg, Md.) which was pre-wetted with 0.1 polyethylenimine. The filter was washed with 3 ml of wash buffer (50 Tris pH 7.5, 5 mM MnCl$_2$, 150 mM NaCl) three times and its radioactivity was determined by gamma counter.

A variety of compounds were tested according to the COS cell procedure. The concentration of compound required to inhibit the binding of substance P to the human neurokinin-1 receptor by 50% was measured. The following data were obtained:

| Compound | IC$_{50}$ |
|---|---|
| 1 | 120 nM |
| 2 | 180 nM |
| 7 | 56 nM |
| 8 | 840 nM |
| 9 | 400 nM |
| 11 | 400 nM |
| 13 | 1000 nM |

EXAMPLE 13

The affinity of a variety of compounds for the SRIF receptor was determined by studying the displacement of $^{125}$I-CGP- 23996 from ART-20 cells using the method generally in accordance with Raynor and Reisine, *Journal of Pharmacology and Experimental Therapeutics*, 1989, 251;2, 510. The following data were obtained:

| Compound | IC$_{50}$ |
|---|---|
| 1 | 9500 nM |
| 2 | 1300 nM |
| 8 | 40000 nM |
| 13 | does not bind |
| SRIF | 9.3 nM |
| MK 678 | 60 nM |
| L-363,301 | 18.7 nM |

EXAMPLE 14

The affinity of a 2-(1-phenylsulfonyl-indol-3yl)ethyl-6-O-(5-aminopentyl)-2,3,4 -tri-O-benzyl-β-D-glucopyranoside, structure (1) and methyl 6-O-(5-aminopentyl)-2,3,4-Tri-O-benzyl-β-D-glucopyranoside, structure (8 ) for a variety of G-protein-linked receptors was determined by studying the displacement of a variety of radioligands from AtT-20 and brain cells using the method disclosed by Reisine, et al., *Brain Research*, 1979, 117, 241. The following data was obtained ($^{125}$I-CYP=$^{125}$I-cyanopindolol; $^3$H-QNB=quinuclidinyl benzilate):

| Receptor | Radioligand | Compound | Binding Inhibition | Tissue |
|---|---|---|---|---|
| β-Adrenergic | $^{125}$I-CYP (0.1 nM) | 1 | 70% | AtT-20 |
|  |  | 1 | 45 | Brain |
|  |  | 8 | 0 | AtT-20 |
| Opiate Receptor | $^3$H-naloxone (0.5 nM) | 1 | 55 | Brain |
| Dopamine Receptor | $^3$H-spiperone (0.1 nM) | 1 | 82 | Brain |
| Muscarinic cholingeric | $^3$H-QNB 0.1 (nM) | 1 | 20 | AtT-20 |
|  |  | 1 | 83 | Brain |

As can be seen from Examples 9–11, the peptide analogs of the present invention are selectively bound by certain receptors. For example, structure (1) exhibits approximately 14-fold greater selectivity than structure (8) for the substance P receptor, while structure (8) is bound by the substance P and SRIF receptors but does not bind the β-adrenergic receptor.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having the structure:

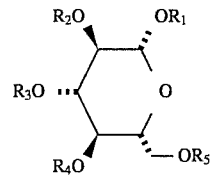

wherein:
  (a) R$_1$ is —(CH$_2$)$_2$(3-indole); R$_2$, R$_3$, and R$_4$ are benzyl; and R$_5$ is —(CH$_2$)$_5$NHC(O)CH$_3$; or
  (b) R$_1$ is —CH$_3$; R$_2$, R$_3$, and R$_4$ are benzyl; and R$_5$ is —(CH$_2$)$_5$NH$_2$; or
  (c) R$_1$ is —CH$_3$; R$_2$, R$_3$, and R$_4$ are benzyl; and R$_5$ is —(CH$_2$)$_5$NHC(O)CH$_3$; or
  (d) R$_1$ is —(CH$_2$)$_2$(3-indole); R$_2$ and R$_3$ are benzyl; R$_4$ is —H; and R$_5$ is —(CH$_2$)OH; or
  (e) R$_1$ is —(CH$_2$)$_2$(3-indole); R$_2$, R$_3$ and R$_4$ are benzyl; and R$_5$ is —(CH$_2$)OH; or
  (f) R$_1$ is —CH$_3$; R$_2$, R$_3$ and R$_4$ are benzyl; and R$_5$ is —(CH$_2$)OH.

2. The compound of claim 1 wherein R$_1$ is —(CH$_2$)$_2$(3-indole); R$_2$, R$_3$, and R$_4$ are benzyl; and R$_5$ is —(CH$_2$)$_5$NHC(O)CH$_3$.

3. The compound of claim 1 wherein R$_1$ is —CH$_3$; R$_2$, R$_3$, and R$_4$ are benzyl; and R$_5$ is —(CH$_2$)$_5$NH$_2$.

4. The compound of claim 1 wherein R$_1$ is —CH$_3$; R$_2$, R$_3$, and R$_4$ are benzyl; and R$_5$ is —(CH$_2$)$_5$NHC(O)CH$_3$.

5. A compound having the structure:

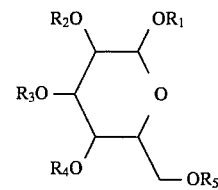

wherein R$_1$ is —(CH$_2$)$_2$(3-indole); R$_2$ and R$_3$ are benzyl; R$_4$ is —H; and R$_5$ is —(CH$_2$)$_5$NH$_2$.

6. The compound of claim 1 wherein R$_1$ is —(CH$_2$)$_2$(3-indole); R$_2$ and R$_3$ are benzyl; R$_4$ is —H; and R$_5$ is —(CH$_2$)OH.

7. The compound of claim 1 wherein R$_1$ is —(CH$_2$)$_2$(3-indole); R$_2$, R$_3$ and R$_4$ are benzyl; and R$_5$ is —(CH$_2$)OH.

8. The compound of claim 1 wherein R$_1$ is —CH$_3$; R$_2$, R$_3$ and R$_4$ are benzyl; and R$_5$ is —(CH$_2$)OH.

9. A compound having the structure:

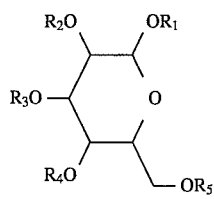

wherein:
(a) $R_1$ is —$(CH_2)_2$(3-indole); $R_2$, $R_3$, and $R_4$ are benzyl; and $R_5$ is —$(CH_2)_5NHC(O)CH_3$; or
(b) $R_1$ is —$CH_3$; $R_2$, $R_3$, and $R_4$ are benzyl; and $R_5$ is —$(CH_2)_5NH_2$; or
(c) $R_1$ is —$CH_3$; $R_2$, $R_3$, and $R_4$ are benzyl; and $R_5$ is —$(CH_2)_5NHC(O)CH_3$; or
(d) $R_1$ is —$(CH_2)_2$(3-indole); $R_2$ and $R_3$ are benzyl; $R_4$ is —H; and $R_5$ is —$(CH_2)OH$; or
(e) $R_1$ is —$(CH_2)_2$(3-indole); $R_2$, $R_3$ and $R_4$ are benzyl; and $R_5$ is —$(CH_2)OH$; or
(f) $R_1$ is —$CH_3$; $R_2$, $R_3$ and $R_4$ are benzyl; and $R_5$ is —$(CH_2)OH$.

10. The compound of claim 9 wherein $R_1$ is —$(CH_2)_2$(3-indole); $R_2$, $R_3$, and $R_4$ are benzyl; and $R_5$ is —$(CH_2)_5NHC(O)CH_3$.

11. The compound of claim 9 wherein $R_1$ is —$CH_3$; $R_2$, $R_3$, and $R_4$ are benzyl; and $R_5$ is —$(CH_2)_5NH_2$.

12. The compound of claim 9 wherein $R_1$ is —$CH_3$; $R_2$, $R_3$, and $R_4$ are benzyl; and $R_5$ is —$(CH_2)_5NHC(O)CH_3$.

13. A compound having the structure:

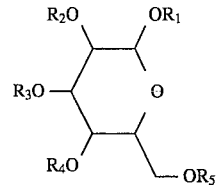

wherein $R_1$ is —$(CH_2)_2$(3-indole); $R_2$ and $R_3$ are benzyl; $R_4$ is —H; and $R5$ is —$(CH_2)_5NH_2$.

14. The compound of claim 1 wherein $R_1$ is —$(CH_2)_2$(3-indole); $R_2$ and $R_3$ are benzyl; $R_4$ is —H; and $R_5$ is —$(CH_2)OH$.

15. The compound of claim 9 wherein $R_1$ is —$(CH_2)_2$(3-indole); $R_2$, $R_3$ and $R_4$ are benzyl; and $R_5$ is —$(CH_2)OH$.

16. The compound of claim 9 wherein $R_1$ is —$CH_3$; $R_2$, $R_3$ and $R_4$ are benzyl; and $R_5$ is —$(CH_2)OH$.

* * * * *

UNITED STATES PATENT AND TRADEMARK OFFICE
CERTIFICATE OF CORRECTION

PATENT NO. : 5,552,534
DATED : September 3, 1996
INVENTOR(S) : Ralph F. Hirschmann et al Page 1 of 2

It is certified that error appears in the above-indentified patent and that said Letters Patent is hereby corrected as shown below:

Col. 13, line 42, manuacturing" should be --manufacturing--.
Col. 14, line 35, "form" should be --from--.

Col. 34, line 7, "ptroleum" should be --petroleum--.
Col. 34, line 31, "ptroleum" should be --petroleum--.
Col. 34, line 56, "ptroleum" should be --petroleum--.
Col. 34, line 61, "57o" should be --570--.
Col. 35, line 27, "ptroleum" should be --petroleum--
Col. 36, line 1, "04.5" should be --104.5--
Col. 44, line 14, "{C$\alpha$}" should be  [$\alpha$]--
Col. 48, line 55, after "was" insert --heated to reflux for 16 h, diluted with saturated aqueous sodium --.
Col. 53, line 25, "cmpound" should be --compound--
Col. 53, line 25, "Ii-1a" should be --II-1a--.
Col. 54, line 5, "stirrred" should be --stirred--.
Col. 54, line 49, "[C$\alpha$]" should be --[$\alpha$]--.
Col. 55, line 13, "72.58" should be --72.5%--.

UNITED STATES PATENT AND TRADEMARK OFFICE
CERTIFICATE OF CORRECTION

PATENT NO. : 5,552,534
DATED : September 3, 1996
INVENTOR(S) : Ralph F. Hirschmann It is certified that error appears in the above-indentified patent and that said Letters Patent is hereby corrected as shown below:

Col. 56, line 13, "[C$\alpha$]" should be --[$\alpha$]--.

Col. 72, line 43, "[C$\alpha$]" should be --[$\alpha$]--.

Col. 76, line 37, "7.2-7.16" should be --7.27-7.16--.

Col. 77, line 13, "inseperable" should be --inseparable--.

Col. 77, line 62, "inseperable" should be --inseparable--.

Col. 80, line 31, "[C$\alpha$]" should be --[$\alpha$]--.

Col. 83, line 30, "[C$\alpha$]" should be --[$\alpha$]--.

Signed and Sealed this

Third Day of November, 1998

Attest:

*Attesting Officer*

BRUCE LEHMAN
*Commissioner of Patents and Trademarks*